(12) United States Patent
Thirring et al.

(10) Patent No.: US 9,701,628 B2
(45) Date of Patent: Jul. 11, 2017

(54) 12-EPI PLEUROMUTILINS

(71) Applicant: NABRIVA THERAPEUTICS AG, Vienna (AT)

(72) Inventors: Klaus Thirring, Vienna (AT); Werner Heilmayer, Zillingtal (AT); Rosemarie Riedl, Vienna (AT); Hermann Kollmann, Linz (AT); Zrinka Ivezic-Schoenfeld, Korneuburg (AT); Wolfgang Wicha, Bruck an der Leitha (AT); Susanne Paukner, Vienna (AT); Dirk Strickmann, Purkersdorf (AT)

(73) Assignee: Nabriva Therapeutics AG, Vienna (AT)

( * ) Notice: Subject to any disclaimer, the term of this patent is extended or adjusted under 35 U.S.C. 154(b) by 0 days.

(21) Appl. No.: 15/111,390

(22) PCT Filed: Jan. 21, 2015

(86) PCT No.: PCT/EP2015/051159
§ 371 (c)(1),
(2) Date: Jul. 13, 2016

(87) PCT Pub. No.: WO2015/110481
PCT Pub. Date: Jul. 30, 2015

(65) Prior Publication Data
US 2016/0332963 A1 Nov. 17, 2016

(30) Foreign Application Priority Data

Jan. 22, 2014 (EP) .................................... 14152107

(51) Int. Cl.
*C07C 323/52* (2006.01)
*A61K 31/22* (2006.01)
(Continued)

(52) U.S. Cl.
CPC .......... *C07C 323/52* (2013.01); *A61K 31/216* (2013.01); *A61K 31/22* (2013.01);
(Continued)

(58) Field of Classification Search
CPC .. C07C 323/52; C07D 249/14; C07D 473/38; C07D 213/56; C07D 213/32; C07D 223/06; C07D 211/20; C07D 473/24; A61K 31/216; A61K 31/44; A61K 31/4458; A61K 31/4468; A61K 31/5375; A61K 31/4196
See application file for complete search history.

(56) References Cited

U.S. PATENT DOCUMENTS 8,222,447 B2 7/2012 Mang et al.
2008/0221330 A1 9/2008 Takadoi et al.
(Continued)

FOREIGN PATENT DOCUMENTS

EP 2321272 A1 5/2011
EP 1896405 B1 8/2011
(Continued)

OTHER PUBLICATIONS

English Translation of the International Preliminary Report on Patentability and Written Opinion for International Application No. PCT/EP2015/051159 issued Jul. 26, 2016.
Bacque et al., "A flexible strategy for the divergent modification of pleuromutilin", Chemical Communications—ChemCom; Royal Society of Chemistry, GB, vol. 20, Jan. 1, 2002, p. 2312-2313, XP002997534.
Sato et al. Science of Synthesis, 2005, vol. 18, pp. 821-968.
(Continued)

*Primary Examiner* — Sudhakar Katakam
(74) *Attorney, Agent, or Firm* — Fitzpatrick, Cella, Harper & Scinto

(57) ABSTRACT

A compound selected from 14-O-[((Alkyl-, cycloalkyl-, heterocycloalkyl-, heteoroaryl-, or aryl)-sulfanyl)-acetyl]-12-epi-mutilins, or 14-O-[((Alkyl-, cycloalkyl-, heterocycloalkyl-, heteoroaryl-, or aryl)-oxy)-acetyl]-12-epi-mutilins, wherein 12-epi-mutilin is characterized in that the mutilin ring at position 12 is substituted by two substituents, the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom and all other substituents of the mutilin ring having the same stereochemistry compared with the stereochemistry of the substituents at the corresponding positions in the naturally occurring pleuromutilin ring; optionally in the form of a salt and/or solvate, wherein the naturally occurring pleuromutilin is of formula

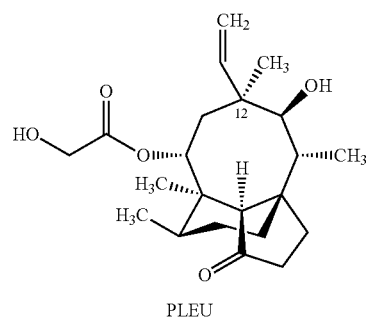

PLEU processes for the preparation of such compounds and their use as pharmaceuticals.

17 Claims, No Drawings

(51) Int. Cl.

| | | |
|---|---|---|
| *A61K 31/4409* | (2006.01) | |
| *A61K 31/445* | (2006.01) | |
| *A61K 31/4465* | (2006.01) | |
| *A61K 31/495* | (2006.01) | |
| *A61K 31/52* | (2006.01) | |
| *C07C 323/62* | (2006.01) | |
| *C07D 211/26* | (2006.01) | |
| *C07D 295/13* | (2006.01) | |
| *C07D 211/54* | (2006.01) | |
| *C07D 211/58* | (2006.01) | |
| *C07D 295/192* | (2006.01) | |
| *C07D 213/36* | (2006.01) | |
| *C07D 213/40* | (2006.01) | |
| *C07D 213/70* | (2006.01) | |
| *C07D 223/06* | (2006.01) | |
| *C07D 473/24* | (2006.01) | |
| *C07D 211/20* | (2006.01) | |
| *A61K 31/216* | (2006.01) | |
| *A61K 31/4196* | (2006.01) | |
| *A61K 31/44* | (2006.01) | |
| *A61K 31/4458* | (2006.01) | |
| *A61K 31/4468* | (2006.01) | |
| *A61K 31/5375* | (2006.01) | |
| *C07D 213/32* | (2006.01) | |
| *C07D 213/56* | (2006.01) | |
| *C07D 249/14* | (2006.01) | |
| *C07D 473/38* | (2006.01) | |

(52) U.S. Cl.
CPC .......... *A61K 31/4196* (2013.01); *A61K 31/44* (2013.01); *A61K 31/445* (2013.01); *A61K 31/4409* (2013.01); *A61K 31/4458* (2013.01); *A61K 31/4465* (2013.01); *A61K 31/4468* (2013.01); *A61K 31/495* (2013.01); *A61K 31/52* (2013.01); *A61K 31/5375* (2013.01); *C07C 323/62* (2013.01); *C07D 211/20* (2013.01); *C07D 211/26* (2013.01); *C07D 211/54* (2013.01); *C07D 211/58* (2013.01); *C07D 213/32* (2013.01); *C07D 213/36* (2013.01); *C07D 213/40* (2013.01); *C07D 213/56* (2013.01); *C07D 213/70* (2013.01); *C07D 223/06* (2013.01); *C07D 249/14* (2013.01); *C07D 295/13* (2013.01); *C07D 295/192* (2013.01); *C07D 473/24* (2013.01); *C07D 473/38* (2013.01); *C07C 2101/02* (2013.01); *C07C 2101/14* (2013.01); *C07C 2103/82* (2013.01)

(56) References Cited

U.S. PATENT DOCUMENTS

| | | | | |
|---|---|---|---|---|
| 2008/0287442 A1* | 11/2008 | Thirring | ................ | C07C 323/52 514/238.2 |
| 2009/0306203 A1* | 12/2009 | Mang | .................... | C07C 323/52 514/510 |
| 2010/0160266 A1 | 6/2010 | Ascher | | |
| 2010/0197909 A1 | 8/2010 | Fukuda et al. | | |

FOREIGN PATENT DOCUMENTS

| | | |
|---|---|---|
| JP | 2006306727 A | 11/2006 |
| JP | 2008280297 A | 11/2008 |
| JP | 2009040709 A | 2/2009 |
| JP | 2010100582 A | 5/2010 |
| WO | 0071560 A1 | 11/2000 |
| WO | 2006070671 A1 | 7/2006 |
| WO | 2007000001 A2 | 1/2007 |
| WO | 2008117796 A1 | 10/2008 |
| WO | 2008143343 A1 | 11/2008 |
| WO | 2009009813 A1 | 1/2009 |
| WO | 2010025482 A1 | 3/2010 |

OTHER PUBLICATIONS

Stahl, et al., Handbook of Pharmaceutical Salts: Properties, Selection, and Use, Helvetica Chimica Acta/Wiley-VCH, 2001.
Berner H et al: "Chemie der Pleuromutiline, II. Mitt.1: Konfigurationsumkehr der Vinylgruppe am Kohlenstoff 12 durch reversible Retro-En-Spaltung / Inversion of Configuration of the Vinylgroup at Carbon 12 by Reversible Retro-En-Cleavage", Monatshefte für Chemie, Springer Verlag Wien, AT, vol. 117, No. 8/09, Aug. 1, 1986, p. 1073-1080, XP009067495.
Schindler, S., "Funktionalisierung des tricyclischen Gerüstes des Antibioticums Pleuromutilin", University of Vienna, 2003, p. 26 and 31.
Berner, et al., "Synthese AB-Trans-Anellierter Derivate Des Tricyclischen Diterpens Pleuromutilin Durch Intramolekulare 1,5-Hydrid-Verschiebung", Tetrahedron 1980, vol. 36, 1807-1811.

* cited by examiner

12-EPI PLEUROMUTILINS

BACKGROUND OF THE INVENTION

Field of the Invention

The present invention relates to organic compounds, namely pleuromutilins.

Pleuromutilin, a compound of formula

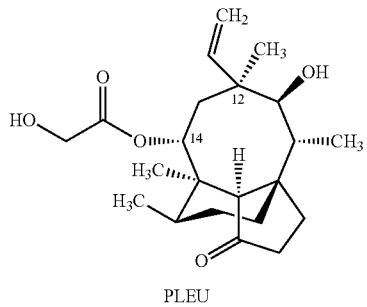 [SMILES: C=C[C@]1(C)C[C@@H](OC(=O)CO)[C@]2(C)[C@H](C)CC[C@]3(CCC(=O)[C@H]32)[C@@H](C)[C@@H]1O]

PLEU is a naturally occurring antibiotic, e.g. produced by the basidiomycetes *Pleurotus mutilus* and *P. passeckerianus*, see e.g. The Merck Index, 13th edition, item 7617. A number of further pleuromutilins being substituted at the hydroxy group of the C-14 side chain and otherwise having the principle ring structure of pleuromutilin have been developed, e.g. as antimicrobials, such as

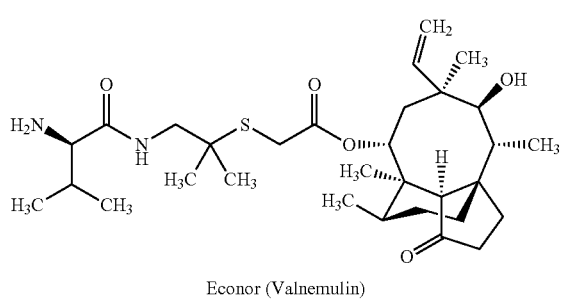

Econor (Valnemulin)

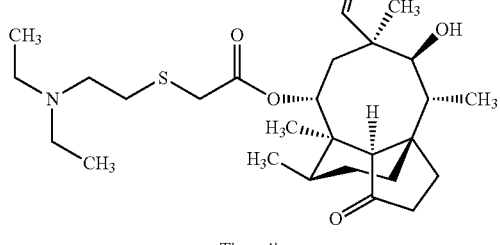

Tiamulin

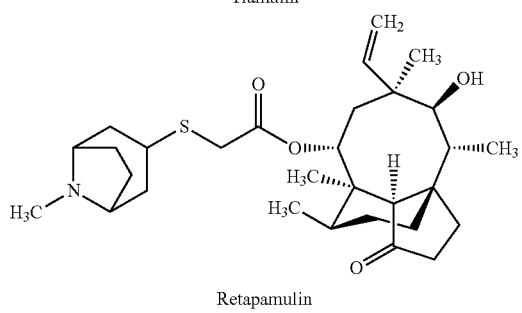

Retapamulin

From patent filings JP2006306727, JP2008280297, JP2009040709, JP2010100582, US20080221330, US20100197909, WO2006070671, WO2008117796, WO2008143343 and WO2000071560 and from E. Bacqué et al. Chem. Comm., 2002, 20, 2312-2313 and S. Sato et al. Science of Synthesis, 2005, Vol 18, 821-968, compounds of formula

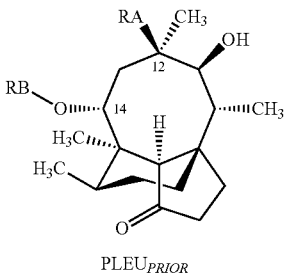

PLEU$_{PRIOR}$ wherein RA and RB have various meanings and thus comprising C-12 substituted pleuromutilins are known and their antimicrobial activity is described. It is noted that in all of these publications the stereochemistry of the methyl group at the C-12 position in the mutilin ring is the same as in the naturally occurring pleuromutilin.

In H. Berner et al., Monatshefte für Chemie, 1986, 117, 1073-1080, a pleuromutilin derivative is described in which the methyl at position 12 of the mutilin ring has the inverse stereochemistry than in the naturally occurring pleuromutilin. Mutilins in which the methyl at position 12 of the mutilin ring have the inverse stereochemistry than that in the naturally occurring pleuromutilin are herein also designated as "12-epi-mutilin(s)". The 12-epi mutilin of Berner et al. has as second substituent a vinyl group in position 12 of the mutilin ring.

12-epi-Mutilins are also disclosed in the Dissertation of S. Schindler, "Funktionalisierung des tricyclischen Gerüstes des Antibioticums Pleuromutilin", University of Vienna, 2003, page 26 and 31, namely the compounds of formula

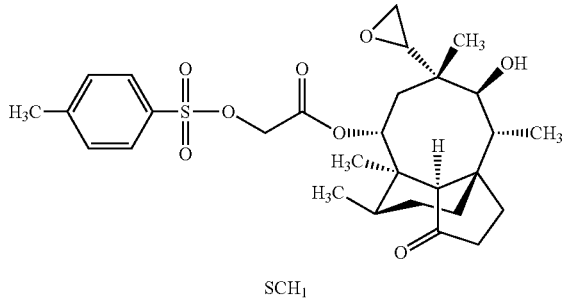

SCH$_1$ and of formula

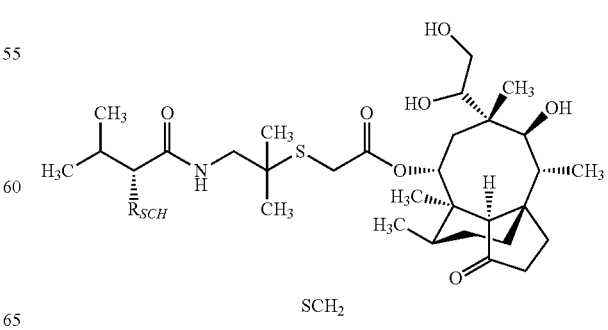

SCH$_2$ wherein R$_{SCH}$ is —NH-BOC, —NH$_2$, or NH$_3^+$Cl$^-$.

We have now found surprisingly that epi-pleuromutilins, wherein in addition to the inverted methyl group in C-12, the second substituent in C-12 comprising at least one nitrogen atom, do have interesting activity against Gram negative and Gram positive bacteria, in particular improved activity against Gram negative bacteria, in particular activity against *Escherichia coli*.

In one aspect the present invention provides a compound selected from 14-O-[((Alkyl-, cycloalkyl-, heterocycloalkyl-, heteoroaryl-, or aryl)-sulfanyl)-acetyl]-12-epi-mutilins, or
14-O-[((Alkyl-, cycloalkyl-, heterocycloalkyl-, heteoroaryl-, or aryl)-oxy)-acetyl]-12-epi-mutilins,
wherein 12-epi-mutilin is characterized in that
the mutilin ring at position 12 is substituted by two substituents, the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom, and all other substituents of the mutilin ring having the same stereochemistry compared with the stereochemistry of the substituents at the corresponding positions in the naturally occurring pleuromutilin ring; optionally in the form of a salt and/or solvate, in particular in the form of a salt,
wherein the naturally occurring pleuromutilin is of formula

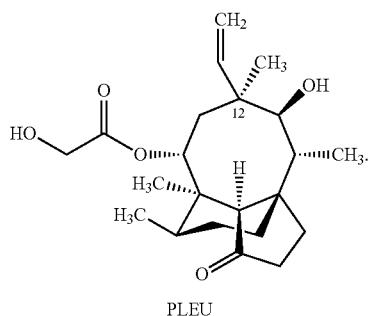

PLEU

Compounds provided by the present invention hereinafter also are referred to as "Compound(s) of (according to) the present invention".

In another aspect the present invention provides a compound of the present invention which is of formula

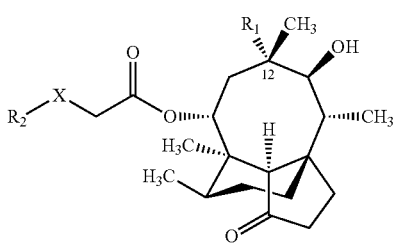

I wherein
the methyl group at position 12 of the mutilin ring has the inverse stereochemistry compared with the stereochemistry of the methyl group at position 12 of the naturally occurring pleuromutilin ring, all other substituents of the mutilin ring having the same stereochemistry compared with the stereochemistry of the substituents at the corresponding positions in the naturally occurring pleuromutilin ring, $R_1$ is a hydrocarbon group comprising 1 to 16, in particular 1 to 12 carbon atoms comprising one N atom, optionally comprising one or more additional heteroatoms selected from N, O, S, halogen, in particular N, X is sulfur or oxygen, in particular sulfur, and $R_2$ is a hydrocarbon group comprising 1 to 22 carbon atoms, optionally comprising heteroatoms selected from N, O, S, halogen, in particular N or O.

In a further aspect the present invention provides a compound of formula I, wherein
X and $R_2$ are as defined above, and
$R_1$ is either $(C_{1-16})$alkyl or $(C_{2-16})$alkenyl, substituted by $(C_{1-13})$heterocyclyl, including aliphatic heterocyclyl and aromatic heterocyclyl comprising 1 to 4 heteroatoms selected from N, O, S, with the proviso that at least one heteroatom is a nitrogen atom, or
$R_1$ is a group of formula

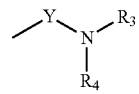

wherein Y—N($R_3R_4$) is
$(C_{1-16})$alkyl-N($R_3R_1$),
in particular $(C_{1-12})$alkyl-N($R_3R_4$),
$(C_{1-16})$alkyl-$(C_{6-14})$aryl-N($R_3R_4$),
$(C_{1-16})$alkyl-$(C_{6-14})$aryl-$(C_{1-16})$alkyl-N($R_3R_4$),
in particular $(C_{1-4})$alkyl-phenyl-$(C_{1-6})$alkyl-N($R_3R_4$),
$(C_{1-16})$alkyl-$(C_{1-13})$heterocyclyl —N($R_3R_4$),
$(C_{1-16})$alkyl-$(C_{1-13})$heterocyclyl-$(C_{1-16})$alkyl-N($R_3R_4$),
carbonyl-N($R_3R_4$),
$(C_{1-4})$alkyl-carbonyl-N($R_3R_4$),
$(C_{2-16})$alkenyl-N($R_3R_4$),
$(C_{2-16})$alkenyl-$(C_{6-14})$aryl-N($R_3R_4$),
in particular $(C_{2-4})$alkenyl-phenyl-N($R_3R_4$),
in particular ethenyl-phenyl-N($R_3R_4$),
$(C_{2-16})$alkenyl-$(C_{6-14})$aryl-$(C_{1-16})$alkyl-N($R_3R_4$),
in particular $(C_{2-16})$alkenyl-phenyl-$(C_{1-16})$alkyl-N($R_3R_4$),
$(C_{2-16})$alkenyl-$(C_{1-13})$heterocyclyl-N($R_3R_4$),
$(C_{2-16})$alkenyl-$(C_{1-13})$heterocyclyl-$(C_{1-16})$alkyl-N($R_3R_4$),
wherein heterocyclyl includes aliphatic and aromatic heterocyclyl comprising at least one heteroatom selected from N, O, S and wherein alkyl, aryl, heterocyclyl or alkenyl is optionally substituted comprising substituents which optionally having heteroatoms selected from O, N, S, halogen;

in particular $R_1$ is
aminomethyl, amino(-ethyl-, -propyl-, -butyl-, -pentyl-, -hexyl-, -octyl-, -decyl-)-aminomethyl, amino-propoxy-propyl-aminomethyl, guanidino(-butyl-, -hexyl-)-aminomethyl, dimethylamino-propyl-aminomethyl, amino(-propyl-, -hexyl-)-aminoethyl, guanidino-ethyl, bis-aminomethyl-methyl-aminomethyl,
aminomethyl-phenyl-aminomethyl, aminophenyl-methyl-aminomethyl, aminomethyl-phenyl-methyl-aminomethyl wherein phenyl optionally is further substituted by one or more halogen, in particular by one or more fluoro,
aminomethyl-phenyl-propyl-aminomethyl, guanidino-methyl-phenyl-methyl-aminomethyl, amido-ethyl-phenyl-methyl-aminomethyl, optionally substituted by amino, wherein the amido nitrogen optionally is substituted by one or two $(C_{1-4})$alkyl, amido-phenyl-methyl-aminomethyl, aminopropyl-aminocarbonyl-phenyl-methyl-aminomethyl, aminomethyl-phenyl-methyl-aminoethyl wherein phenyl optionally is further substituted by one or more halogen, in particular by one or more fluoro, (aminoethoxy-phenyl-methyl-amino)-methyl and -ethyl, aminomethyl-phenyl-methyl-aminocarbonyl, aminopropyl-aminocarbonyl, phenyl-methyl-aminomethyl, pyridyl-ethyl-aminomethyl, hexyl-aminomethyl, allyl-aminomethyl, hydroxyhexyl-aminomethyl, dihydroxypropyl-aminomethyl, aminobutyl-aminomethyl wherein amino is substituted by $(C_{1-4})$alkyl-carbonyl and aminobutyl, dimethylamido-pentyl-aminomethyl, ethoxycarbonyl-pentyl-aminomethyl optionally substituted by amino, piperidino-aminomethyl, morpholino-N-propyl-aminomethyl, amino-cyclohexyl-aminomethyl, aminomethyl-cyclohexyl-methyl-aminomethyl, aminomethyl-phenyl-carbonyl-aminoethyl, aminomethyl-phenyl-propyl, aminohexyl, aminooctyl, aminoethyl-aminomethyl-phenyl-ethyl, aminomethyl-phenyl-ethyl, pyridinyl-ethenyl, aminoethyl-aminomethyl-phenyl-ethenyl wherein phenyl is optionally substituted by halogen, in particular by fluoro;

$R_3$ and $R_4$ independently of each other are hydrogen, $(C_{1-16})$alkyl, $(C_{2-16})$alkenyl, hydroxy$(C_{1-16})$alkyl, amino-$(C_{1-16})$alkyl, mono or di-$(C_{1-6})$alkylamino-$(C_{1-16})$alkyl, guanidino$(C_{1-16})$alkyl, ureido$(C_{1-16})$alkyl or thioureido $(C_{1-16})$alkyl, amino$(C_{1-6})$alkyl-$(C_{6-14})$aryl-$(C_{1-16})$alkyl, amino$(C_{1-6})$alkyl-$(C_{6-14})$aryl, guanidino$(C_{1-6})$alkyl-$(C_{6-14})$aryl-$(C_{1-6})$alkyl, amino-$(C_{1-6})$alkyloxy-$(C_{1-6})$alkyl, amino $(C_{3-8})$cycloalkyl, amino$(C_{1-6})$alkyl-$(C_{3-8})$cycloalkyl, amino $(C_{3-8})$cycloalkyl-$(C_{1-6})$alkyl, amino$(C_{1-6})$alkyl-$(C_{3-8})$ cycloalkyl-$(C_{1-6})$alkyl, $(C_{1-13})$ heterocyclyl-$(C_{1-16})$alkyl, $(C_{6-14})$aryl-$(C_{1-6})$alkyl, $(C_{1-13})$heterocyclyl, amino-$(C_{6-14})$ aryl-$(C_{1-16})$alkyl, amino-$(C_{1-6})$alkyloxy-$(C_{6-14})$aryl-$(C_{1-16})$ alkyl, amino$(C_{1-6})$alkyl-$(C_{6-12})$aryl-carbonyl, amino$(C_{1-6})$ alkyl-amido-$(C_{6-12})$aryl$(C_{1-6})$alkyl, $(C_{1-4})$alkylcarbonyl, carbamimidoyl, carbamoyl, thiocarbamoyl, wherein heterocyclyl includes aliphatic and aromatic heterocyclyl comprising at least one heteroatom selected from N, O, S, and wherein alkyl, cycloalkyl, heterocyclyl, alkenyl or aryl is optionally further substituted, in particular once or twice, by amino$(C_{1-4})$alkyl, amido, mono or di-$(C_{1-4})$alkyl-amido, $(C_{1-6})$alkyloxy-carbonyl, halogen, oxo, hydroxy; in particular by fluoro; hydroxy, oxo.

In a preferred embodiment $R_2$ in a compound of formula I is $(C_{1-6})$alkyl, in particular $(C_{1-4})$alkyl, $(C_{3-12})$cycloalkyl, in particular $(C_{5-7})$cycloalkyl, in particular cyclohexyl, $(C_{1-13})$heterocyclyl, $(C_{6-14})$aryl, wherein heterocyclyl includes aliphatic and aromatic heterocyclyl comprising at least one heteroatom selected from N, O, S, and wherein alkyl, cycloalkyl, aryl, heterocyclyl is unsubstituted or substituted by substituents which optionally having a heteroatom selected from O, N, S, halogen.

In another preferred embodiment of the present invention in a compound of formula I, $R_2$ is alkyl, in particular $(C_{1-4})$alkyl, optionally substituted by hydroxy or amino, $(C_{3-12})$cycloalkyl wherein the cycloalkyl group is optionally further substituted by amino or amino$(C_{1-4})$alkyl wherein the amino or aminoalkyl group is optionally further substituted by amino$(C_{1-6})$alkylcarbonyl and optionally $(C_{1-4})$alkyl, $(C_{1-13})$heterocyclyl, wherein a nitrogen in the ring as a heteroatom optionally is further substituted by amino$(C_{1-16})$ alkylcarbonyl, cycloalkyl, in particular $(C_{3-12})$cycloalkyl, optionally substituted by amino$(C_{1-4})$alkyl, wherein the amino group is optionally further substituted by amino$(C_{1-6})$alkylcarbonyl, hydroxy, amino, wherein the amino group is optionally further substituted by amino$(C_{1-6})$alkylcarbonyl and optionally $(C_{1-4})$alkyl, amino and hydroxy, wherein the amino group is optionally further substituted by amino$(C_{1-6})$alkylcarbonyl and optionally $(C_{1-4})$alkyl, $(C_{1-4})$alkylamino, wherein alkyl is optionally further substituted by one or more halogen;

aliphatic heterocyclyl, in particular $(C_{2-13})$heterocyclyl, comprising 1 to 4 heteroatoms selected from N, O, S, in particular nitrogen, wherein the nitrogen heteroatom optionally is further substituted by $(C_{1-4})$alkyl, amino$(C_{1-6})$alkylcarbonyl, aryl, in particular $(C_{6-14})$aryl, particularly phenyl, optionally substituted by hydroxy, halogen, amino, hydroxy$(C_{1-4})$alkyl, bis-(hydroxy$(C_{1-4})$alkyl), amino$(C_{1-4})$alkyl, bis-(amino$(C_{1-4})$ alkyl), wherein the amino group in amino$(C_{1-4})$alkyl optionally is further substituted, particularly substituted by $(C_{3-6})$cycloalkyl, $(C_{2-6})$alkenyl, amino$(C_{1-6})$alkyl, $(C_{6-14})$ aryl$(C_{1-4})$alkyl, wherein aryl optionally is further substituted by amino$(C_{1-4})$alkyl, aminocarbonyl, wherein the nitrogen optionally is substituted by amino$(C_{1-12})$alkyl, bis-(amino$(C_{1-12})$alkyl), hydroxy $(C_{1-6})$alkyl, bis-(hydroxy$(C_{1-6})$alkyl) or diamino$(C_{1-6})$alkyl, $(C_{1-12})$alkyl, which alkyl optionally is substituted by amino, which amino optionally is acylated, particularly amino substituted by formyl, $(C_{1-4})$alkylcarbonyl, saturated or unsaturated heterocyclyl comprising 1 to 3 heteroatoms, particularly N, and 4 to 8, particularly 5 to 6 ring members, $(C_{6-14})$aryl, particularly phenyl, which aryl optionally is substituted by amino$(C_{1-4})$alkyl, or the nitrogen of the aminocarbonyl group is part of $(C_{3-8})$ heterocyclyl, including aliphatic and aromatic heterocyclyl, comprising one or more heteroatoms selected from N, O, S preferably N, wherein the heterocycle is optionally further substituted by amino$(C_{1-4})$alkyl;

$(C_{1-6})$alkyl, which $(C_{1-6})$alkyl group is optionally substituted by aminocarbonyl wherein the nitrogen of the aminocarbonyl group is optionally further substituted by amino $(C_{1-12})$alkyl, diamino-$(C_{1-12})$alkyl, bis-(amino$(C_{1-12})$alkyl), hydroxy$(C_{1-6})$alkyl, bis-(hydroxy$(C_{1-6})$alkyl) or the nitrogen of the aminocarbonyl group is acylated by amino$(C_{1-4})$alkyl, particularly wherein the acyl group includes $(C_{1-4})$alkylcarbonyl, wherein alkyl optionally is further substituted by amino, phenyl, particularly including amino$(C_{1-4})$alkylphenyl, hydroxyphenyl, aromatic heterocyclyl, in particular $(C_{1-13})$heterocyclyl, comprising 1 to 4 heteroatoms, in particular N, wherein the aromatic heterocyclyl is optionally substituted by $(C_{1-6})$alkyl, amino or hydroxy wherein the alkyl group is optionally further substituted by halogen or amino or the aromatic heterocyclyl is optionally substituted by aminocarbonyl wherein the amino group is optionally further substituted by amino$(C_{1-12})$alkyl, bis-(amino$(C_{1-12})$ alkyl), hydroxy$(C_{1-6})$alkyl, bis-(hydroxy$(C_{1-6})$alkyl) or diamino$(C_{1-6})$alkyl.

In a further preferred embodiment of the present invention in compound of formula I, $R_2$ is amido-phenyl, amido $(C_{1-4})$alkyl-phenyl, wherein the nitrogen of the amido group is unsubstituted or substituted by amino$(C_{1-8})$alkyl, in which alkyl optionally is further substituted.

In a further preferred embodiment of the present invention in compound of formula I, $R_2$ is amino $(C_{3-12})$cycloalkyl, amino$(C_{1-4})$alkyl$(C_{3-12})$cycloalkyl, amino$(C_{3-12})$cycloalkyl $(C_{1-4})$alkyl, or amino$(C_{1-4})$alkyl$(C_{3-12})$cycloalkyl$(C_{1-4})$ alkyl, wherein the amino group is unsubstituted or substituted by amino$(C_{1-6})$alkylcarbonyl, or amino$(C_{1-6})$ alkylcarbonyl and $(C_{1-4})$alkyl.

In a further preferred embodiment of the present invention in compound of formula I, $R_2$ is $(C_{2-11})$heterocyclyl, in particular aliphatic heterocyclyl, comprising 1 to 4 heteroatoms selected from N, O, S, in particular nitrogen, wherein a nitrogen in the ring as heteroatom is unsubstituted, or optionally further substituted by $(C_{1-6})$alkyl or amino$(C_{1-6})$ alkylcarbonyl.

In another preferred embodiment of the present invention in a compound of formula I, $R_2$ is selected from aminoethyl-amidomethyl-phenyl, aminopropyl-amidomethyl-phenyl, hydroxyphenyl-(amino)ethyl-amidomethyl-phenyl, aminomethyl-phenyl-(amino)ethyl-amidomethyl-phenyl, aminopropyl-amidophenyl, aminomethyl-phenylmethyl-amidophenyl, aminomethyl-phenyl, aminoacetyl-aminomethyl-phenyl, bis(aminomethyl)phenyl, bisaminopropyl-amidomethyl-phenyl, (2-amino)-aminopropyl-amidomethyl-phenyl, aminoethyl-aminomethyl-phenyl, aminopropyl-aminomethyl-phenyl, allyl-aminomethyl-phenyl, aminomethyl-phenylmethyl-aminomethyl-phenyl, hydroxymethyl-phenyl, bis(hydroxymethyl)-phenyl, (tetrafluoro-hydroxymethyl)-phenyl, amino-hydroxy-cyclohexyl, hydroxyethyl, aminoethyl, piperazinocarbonyl-phenyl, aminomethyl-piperidine-carbonyl-phenyl, piperidine-ylmethyl-amido-phenyl, pyridine-ylmethyl-amido-phenyl, acetyl-aminopropyl-amido-phenyl, formyl-aminopropyl-amido-phenyl, amido-phenyl, aminohexyl-amidophenyl, aminoethyl-amidophenyl, (5-Amino)-4H-[1,2,4]triazol-3-yl, pyridinyl, hydroxyphenyl, fluorophenyl, purinyl, aminophenyl, acetyl-aminomethyl-phenyl, cyclopropyl-aminomethyl-phenyl, aminopropyl-amidopyridinyl, hydroxypropyl-amidophenyl, amino-purinyl, difluoroethylamino-cyclohexyl, amino-hydroxy-cyclohexyl, azepanyl, aminomethylcyclohexylmethyl, N-methyl-piperidinyl, piperidinyl, aminomethylcyclohexyl, aminopropylphenyl, phenyl, N-aminomethylcarbonyl-piperidinyl, N-aminoethylcarbonyl-piperidinyl, N-aminomethylcarbonyl-piperidinylmethyl, aminomethylamidomethylcyclohexyl, aminomethyl-pyridinyl, aminomethylamidocyclohexyl.

In a further aspect the present invention provides a compound according to the present invention which is of formula

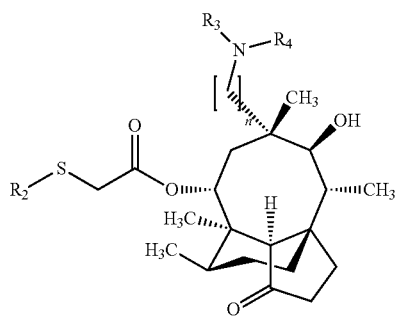

wherein $R_2$ is as defined above, n is 1 to 12 and $R_3$ is H, aminoethyl, aminopropyl, aminobutyl, aminopentyl, aminohexyl, aminooctyl, aminodecyl, dimethylaminopropyl, dimethylamidopentyl, guanidinobutyl, guanidinohexyl, carbamimidoyl, aminomethylcylcohexylmethyl, aminopropoxypropyl, aminocyclohexyl, hydroxyhexyl, dihydroxypropyl, aminomethylphenylmethyl, guanidinomethylphenylmethyl, phenylmethyl, morpholinopropyl, piperidinyl, hexyl, pyridinylethyl, allyl, amido-benzyl, aminopropyl-amidobenzyl, (2-amino)-amidoethyl-benzyl, (2-amino)-dimethylamidoethyl-benzyl, 2-amino-1-aminomethyl-ethyl, 5-amino-5-ethoxycarbonyl-pentyl, aminomethylphenylpropyl, aminomethylphenyl, aminophenymethyl, aminoethoxyphenylmethyl, aminomethyl-fluorophenyl-methyl, aminomethyl-di-fluorophenyl-methyl, and $R_4$ is H, $(C_{1-4})$alkylcarbonyl or aminomethylphenylcarbonyl.

In a further preferred embodiment of the present invention in compound of formula I, $R_1$ is aminomethylphenylpropyl, aminoethylaminomethylphenylethenyl, aminoethylaminomethylphenylethyl, aminomethylphenylethyl, aminomethylphenylethyl, pyridinylethenyl, aminoethylamino-fluorophenyl-ethenyl.

In one particular aspect the present invention provides a compound of the present invention which is of formula

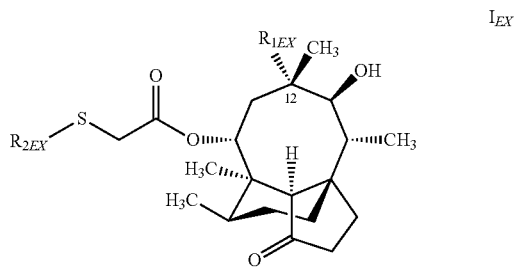

wherein $R_{1EX}$ and $R_{2EX}$ are as set out in Examples 1 to 160 below.

If not otherwise specifically defined herein

Any group (substituent) defined herein may comprise 1 to 22 carbon atoms, e.g. 1 to 18, such as 1 to 16, for example alkyl e.g. includes $(C_{1-16})$alkyl, such as $(C_{1-12})$alkyl, e.g. $(C_{1-4})$alkyl;

alkenyl e.g. includes $(C_{2-16})$alkenyl, such as $(C_{2-12})$alkenyl; e.g. $(C_{2-6})$alkenyl;

cycloalkyl e.g. includes $(C_{3-12})$cycloalkyl, such as $(C_{3-7})$ cycloalkyl, e.g. $(C_{5-6})$cycloalkyl;

alkoxy e.g. includes $(C_{1-16})$alkoxy, such as $(C_{1-12})$alkoxy, e.g. $(C_{1-4})$alkoxy;

aryl includes $(C_{6-14})$aryl, e.g. phenyl, naphthyl, phenanthrenyl, such as phenyl;

alkylaryl e.g. includes $(C_{1-16})$alkyl$(C_{6-14})$aryl, such as $(C_{1-12})$alkylphenyl;

arylalkyl e.g. includes $(C_{6-14})$aryl$(C_{1-16})$alkyl, such as phenyl$(C_{1-12})$alkyl; heterocyclyl includes aliphatic heterocyclyl and aromatic heterocyclyl, heterocyclyl having 1 to 13, such as 4 to 8 ring members, heterocyclyl having 1 to 4 heteroatoms selected from N, O and/or S, heterocyclyl optionally alleviated with another ring (system), e.g. anellated with aryl;

e.g. or anellated with a heterocyclic ring (system);

halogen includes F, Cl, Br, I, such as F;

amine includes unsubstituted amine and amine substituted by alkyl, alkenyl, cycloalkyl, aryl, arylalkyl, alkylaryl, heterocyclyl.

Any group defined herein may be unsubstituted or substituted, e.g. one or morefold.

Alkyl, alkenyl, cycloalkyl, aryl and heterocyclyl include unsubstituted or substituted alkyl, alkenyl, cycloalkyl, aryl and heterocyclyl, e.g. substituted by groups which are conventional in organic chemistry. Substituents include alkyl, alkenyl, alkoxy, hydroxy, oxo, carboxyl, alkylcarbonyl, amido, ureido, guanidino, thioureido, amino, halogen.

A compound of the present invention includes a compound in any form, e.g. in free form, in the form of a salt, in the form of a solvate and in the form of a salt and a solvate.

According to another aspect, the present invention provides a compound of the present invention in the form of a salt; e.g. and/or solvate.

The salts include preferably pharmaceutically acceptable salts, although pharmaceutically unacceptable salts are included, e.g. for preparation/isolation/purification purposes.

A salt of a compound of the present invention includes an acid addition salt. Pharmaceutically acceptable acid addition salts include salts of a compound of the present invention with an acid, e.g. fumaric acid, tartaric acid, sulphuric acid, p-toluene sulphonic acid, methane sulphonic acid, phosphoric acid, citric acid, L-malic acid, hippuric acid, D-gluconic acid, L-lactic acid, benzoic acid, hydrogenmaleic acid, hydrogen sulphuric acid, hydrogenphosphoric acid, hydrogen tartaric acid, hydrogen fumaric acid, hydrogen malic acid, hydrogen succinic acid, ethane-1,2-disulphonic acid, maleic acid, naphthalin-1,5-sulphonic acid, acetic acid, succinic acid, salicylic acid, azelaic acid, 2-[(2,6-dichlorophenyl)amino]benzene acetic acid, trifluoro acetic acid, hydrochloric acid, deuterochloric acid, preferably hydrochloric acid.

Pharmaceutically acceptable alts are described in e.g. Stahl, P. H., Wermuth, C. G. *Handbook of Pharmaceutical Salts: Properties, Selection, and Use*, Helvetica Chimica Acta/Wiley-VCH, 2001.

A compound of the present invention in free form may be converted into a corresponding compound in the form of a salt, and vice versa. A compound of the present invention in free form or in the form of a salt and/or in the form of a solvate may be converted into a corresponding compound in free form or in the form of a salt in non-solvated form, and vice versa.

A compound of the present invention may exist in the form of isomers and mixtures thereof, e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates or diastereomeric mixtures. Any asymmetric carbon atom may be present in the (R)-, (S)- or (R,S)-configuration, preferably in the (R)- or (S)-configuration.

The configuration of substituents attached to asymmetric carbon atoms of the mutilin-tricyclus is preferably the same as in natural pleuromutilin except for the methyl substituent at position C-12 of the mutilin ring which is present in the inverted stereochemistry compared to the stereochemistry of the methyl group in the natural pleuromutilin ring.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

Any compound described herein, e.g. a compound of the present invention and intermediates may be prepared as appropriate, e.g. according, e.g. analogously, to a method as conventional, e.g. or as specified herein.

A compound of the present invention e.g. may be prepared according to the following Reaction Scheme 1:

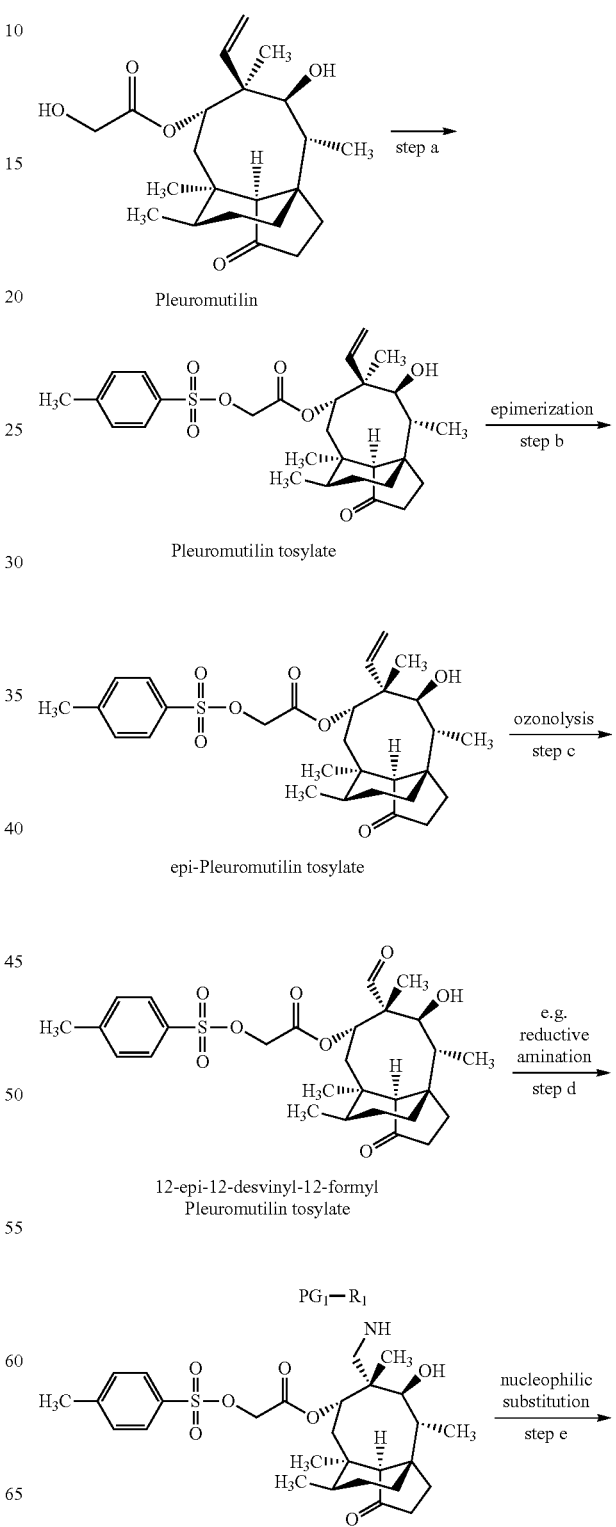

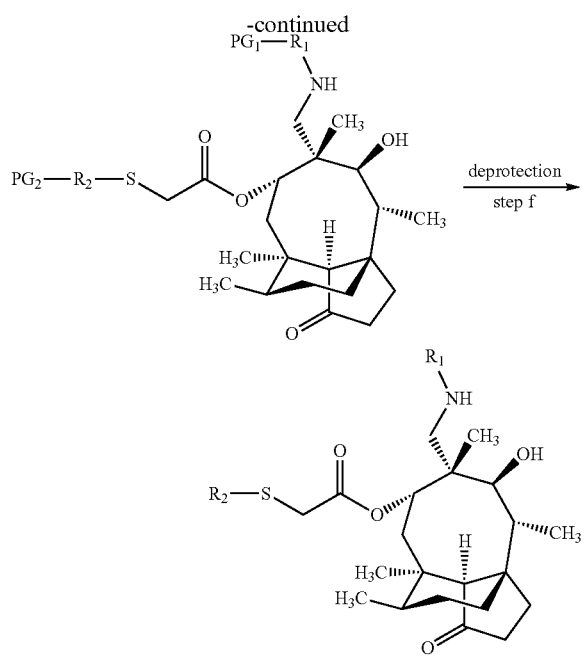

wherein PG₁ and PG₂ are protecting groups.

In another aspect the present invention provides a process for the production of a compound of the present invention, e.g. of formula I, comprising the steps a) providing a pleuromutilin wherein the hydroxy group of the side chain in position 14 is activated e.g. activated as a tosylate, b) epimerizing the methyl group attached in position 12 of the mutilin ring in a mutilin obtained in step a) to obtain the inverse stereochemistry of said methyl group, e.g. and of the vinyl group at the same position, c) subjecting the epimerized mutilin of step b) to ozonolysis in order to obtain the aldehyde from the vinyl group, d) subjecting the aldehyde obtained in step c) to further reactions in order to obtain a desired side chain, e.g. wherein reactive groups are protected, e) reacting the activated hydroxy group of the side chain in position 14 with a desired side chain, optionally in protected and/or activated form, in order to replace the activated hydroxy group by the desired side chain, f) removing the protecting groups optionally present in the side chains attached in position 14 and in position 12, and g) isolating a compound of the present invention from the reaction mixture.

An activated pleuromutilin according to step a), e.g. the pleuromutilin tosylate, is known or can easily be provided and the preparation of pleuromutilin tosylate is also described in Example 1 of the present invention.

Epimerization according to step b) can e.g. be carried out by reacting the protected pleuromutilin of step a) with diethyl zinc in an organic solvent and isolating the desired product.

Ozonolysis of a double bond according to step c) is a known procedure and can easily be carried out by a person skilled in the art.

Numerous procedures for reacting an aldehyde in order to obtain a desired side chain in position 12 according to step d) are known, or described herein.

Numerous procedures are known for step e) from prior art, or are described herein.

Numerous methods for removing (e.g. selectively) protecting groups according to step f) are known as well.

Alternatively, a compound of the present invention e.g. may be prepared according to the following Reaction Schemes 2-4:

Reaction Scheme 2

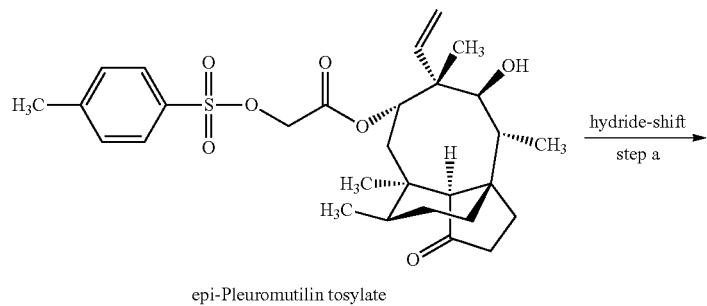

epi-Pleuromutilin tosylate

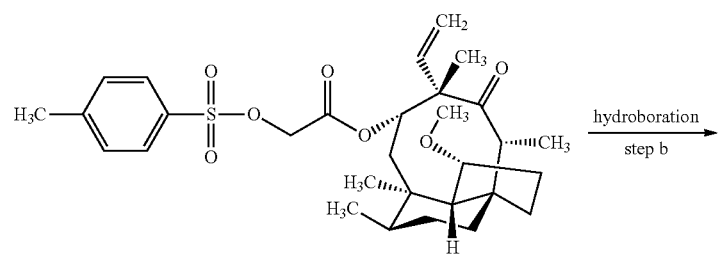

H-shift-epi-Pleuromutilin tosylate 13 14

-continued

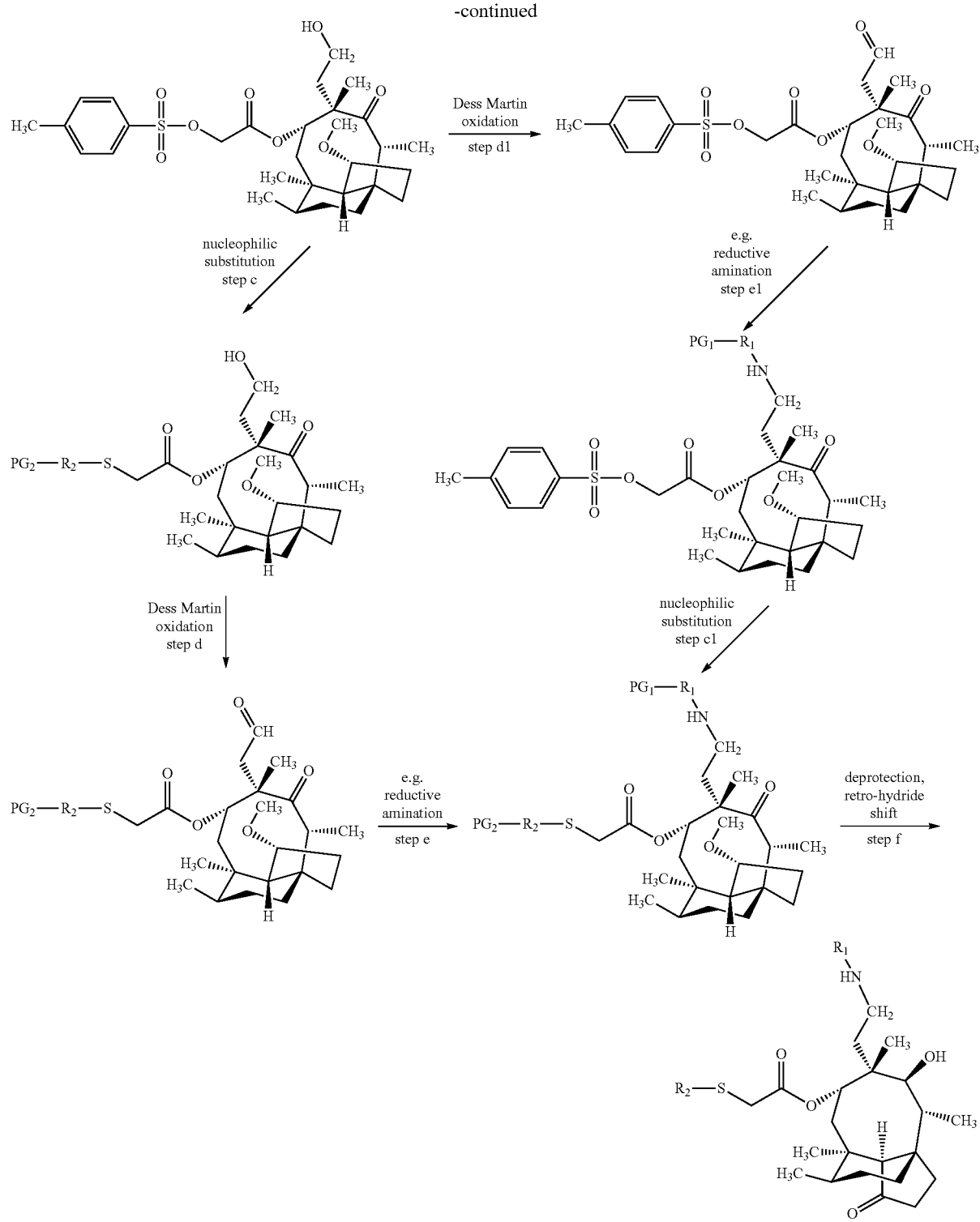

wherein PG$_1$ and PG$_2$ are protecting groups.

In another aspect the present invention provides a process for the production of a compound of the present invention, e.g. of formula I, comprising the steps a) subjecting the epimerized mutilin (Reaction Scheme 1) to acidic conditions resulting in a hydride-shifted 4-epi-3-methoxy-pleuromutilin derivative, b) hydroxylating the vinyl group of the product obtained in step c) via hydroboration, c) reacting the activated hydroxy group of the side chain in position 14 with a desired side chain, optionally in protected and/or activated form, in order to replace the activated hydroxy group by the desired side chain, d) oxidizing the primary hydroxyl group of the side chain in position 12 to the corresponding aldehyde using Dess-Martin conditions e) subjecting the aldehyde obtained in step f) to further reactions in order to obtain a desired side chain, e.g. wherein reactive groups are protected, f) removing the protecting groups optionally present in the side chains attached in position 14 and in position 12 together with concomitant retro-hydride shift, and g) isolating a compound of the present invention from the reaction mixture.

Hydride shift according to step a) is a known procedure as e.g. disclosed in: Tetrahedron, 36, 1807 (1980), and can easily be carried out by a person skilled in the art.

Numerous procedures for hydroxylating an olefin in order to obtain a desired alcohol according to step b) are known, or described herein.

Numerous procedures are known for step c) from prior art, or are described herein.

Numerous procedures for oxidizing an alcohol in order to obtain an aldehyde according to step d) are known, or described herein.

Numerous procedures for reacting an aldehyde in order to obtain a desired side chain in position 12 according to step e) are known, or described herein.

Numerous methods for removing (e.g. selectively) protecting groups according to step f) are known as well. The concomitant retro-hydride shift according to step f) is a known procedure as e.g. disclosed in: Tetrahedron, 36, 1807 (1980), and can easily be carried out by a person skilled in the art.

Alternatively, the order of the reaction sequence [a→b→c→d→e→f] can be altered, e.g. [a→b→d→e→c→f].

Reaction Scheme 3

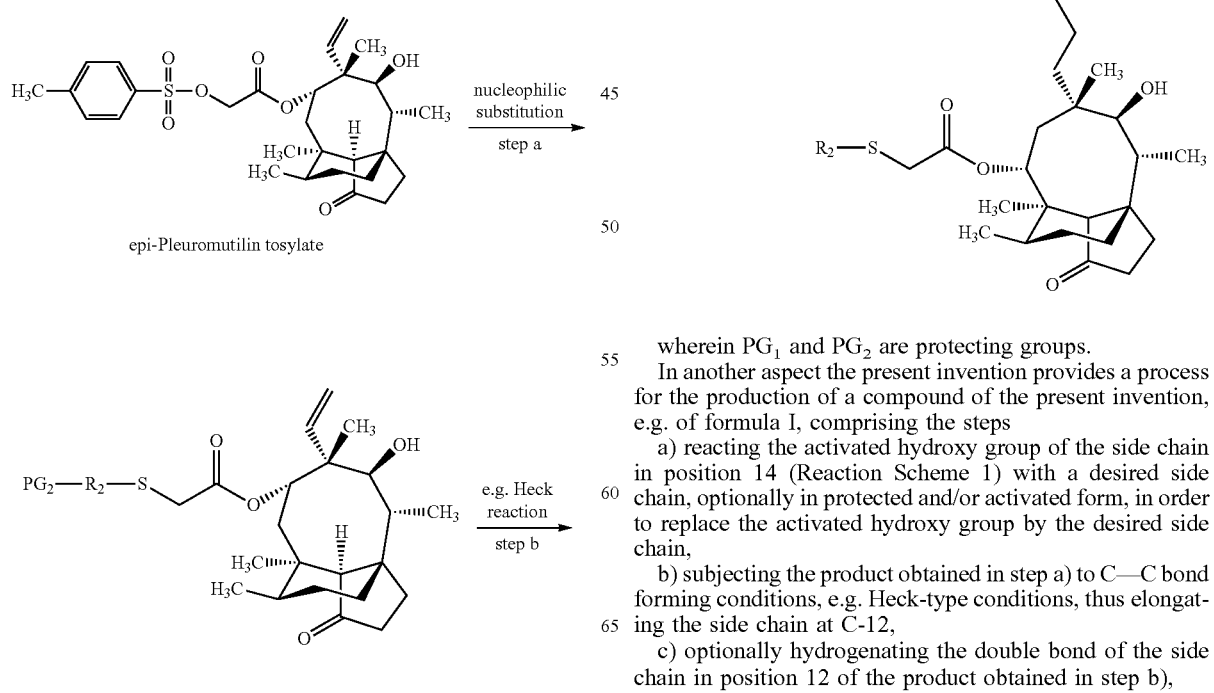

epi-Pleuromutilin tosylate

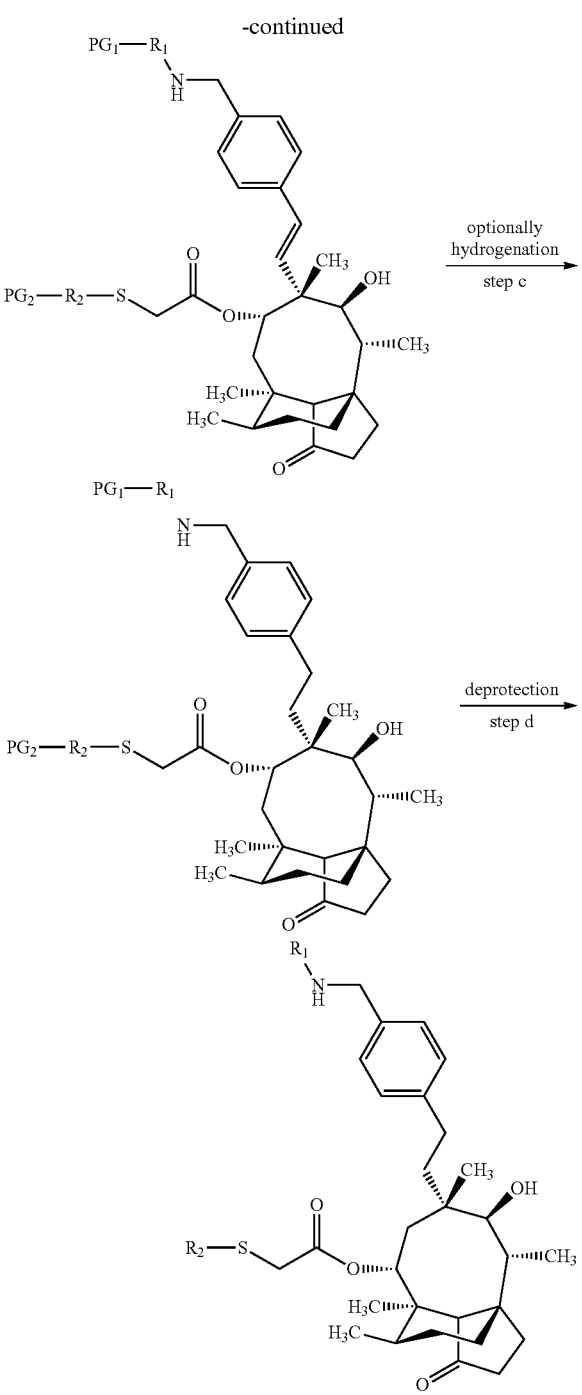

wherein $PG_1$ and $PG_2$ are protecting groups.

In another aspect the present invention provides a process for the production of a compound of the present invention, e.g. of formula I, comprising the steps a) reacting the activated hydroxy group of the side chain in position 14 (Reaction Scheme 1) with a desired side chain, optionally in protected and/or activated form, in order to replace the activated hydroxy group by the desired side chain, b) subjecting the product obtained in step a) to C—C bond forming conditions, e.g. Heck-type conditions, thus elongating the side chain at C-12, c) optionally hydrogenating the double bond of the side chain in position 12 of the product obtained in step b), d) removing the protecting groups optionally present in the side chains attached in position 14 and in position 12, and e) isolating a compound of the present invention from the reaction mixture.

Numerous procedures are known for step a) from prior art, or are described herein.

Numerous procedures for reacting an olefin in order to obtain a desired side chain in position 12 according to step b) are known, or described herein.

Numerous procedures for hydrogenating an olefin in order to obtain a desired side chain in position 12 according to step c) are known, or described herein.

Numerous methods for removing (e.g. selectively) protecting groups according to step d) are known as well.

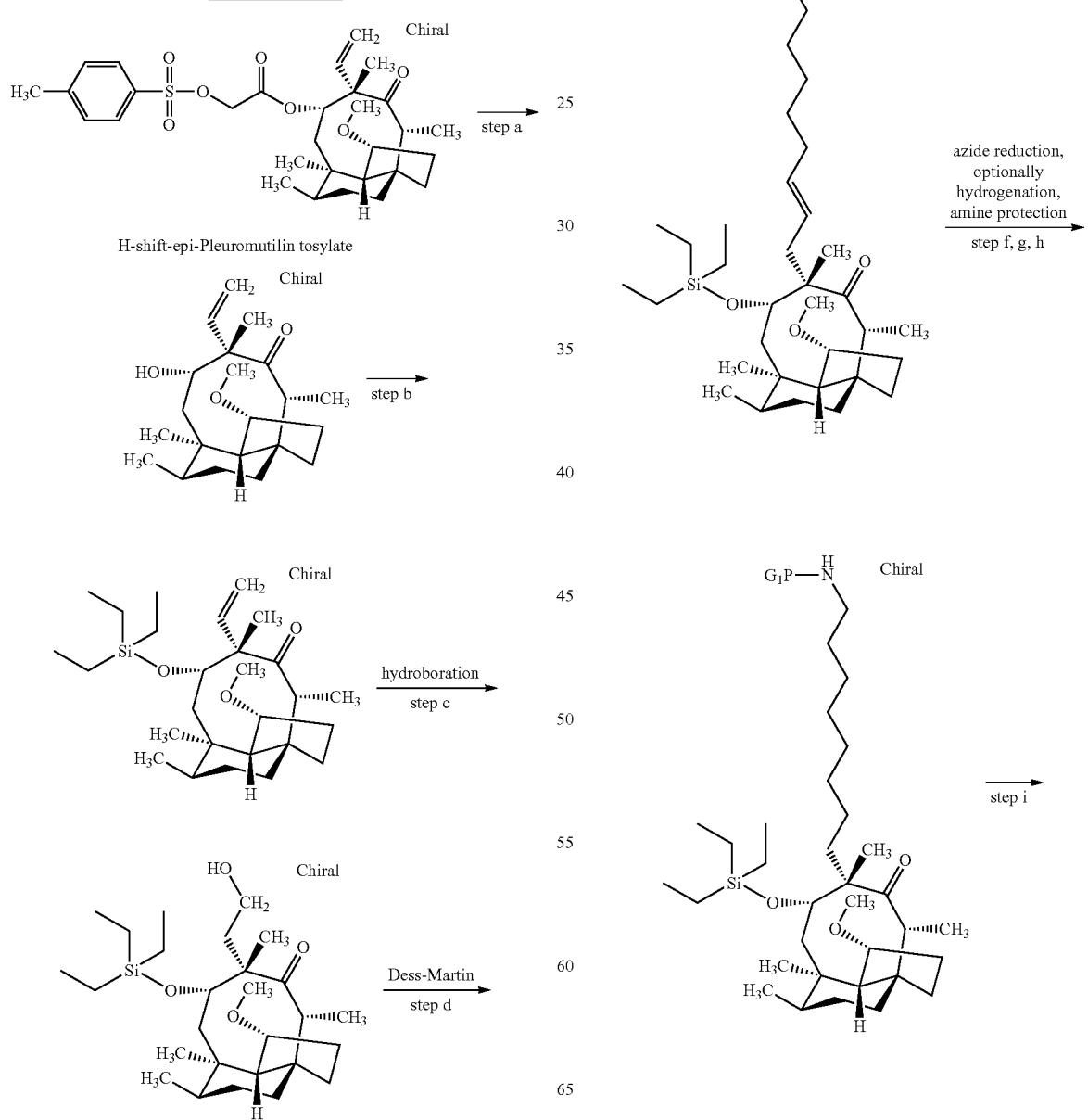

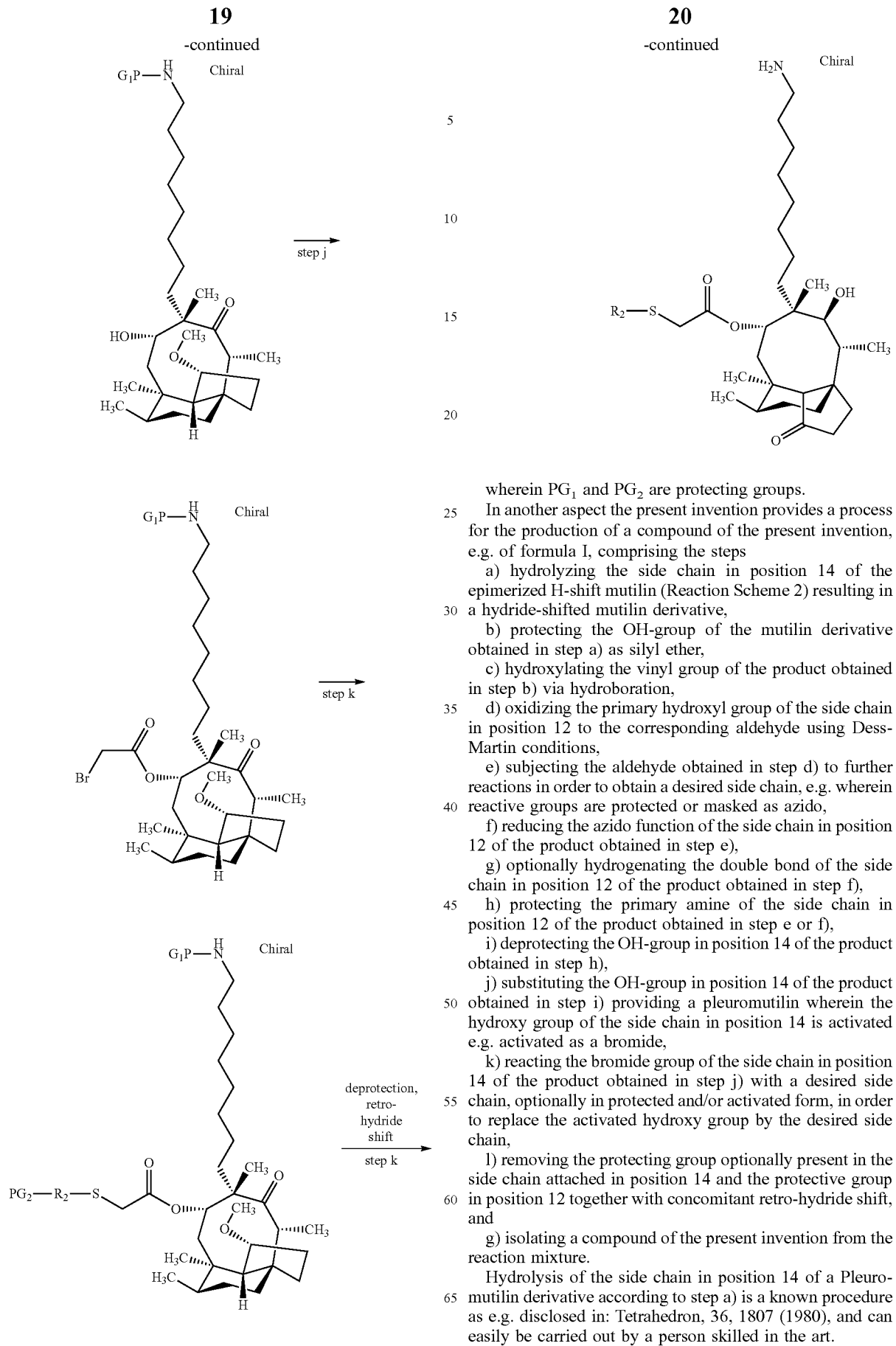

wherein PG$_1$ and PG$_2$ are protecting groups.

In another aspect the present invention provides a process for the production of a compound of the present invention, e.g. of formula I, comprising the steps a) hydrolyzing the side chain in position 14 of the epimerized H-shift mutilin (Reaction Scheme 2) resulting in a hydride-shifted mutilin derivative, b) protecting the OH-group of the mutilin derivative obtained in step a) as silyl ether, c) hydroxylating the vinyl group of the product obtained in step b) via hydroboration, d) oxidizing the primary hydroxyl group of the side chain in position 12 to the corresponding aldehyde using Dess-Martin conditions, e) subjecting the aldehyde obtained in step d) to further reactions in order to obtain a desired side chain, e.g. wherein reactive groups are protected or masked as azido, f) reducing the azido function of the side chain in position 12 of the product obtained in step e), g) optionally hydrogenating the double bond of the side chain in position 12 of the product obtained in step f), h) protecting the primary amine of the side chain in position 12 of the product obtained in step e or f), i) deprotecting the OH-group in position 14 of the product obtained in step h), j) substituting the OH-group in position 14 of the product obtained in step i) providing a pleuromutilin wherein the hydroxy group of the side chain in position 14 is activated e.g. activated as a bromide, k) reacting the bromide group of the side chain in position 14 of the product obtained in step j) with a desired side chain, optionally in protected and/or activated form, in order to replace the activated hydroxy group by the desired side chain, l) removing the protecting group optionally present in the side chain attached in position 14 and the protective group in position 12 together with concomitant retro-hydride shift, and g) isolating a compound of the present invention from the reaction mixture.

Hydrolysis of the side chain in position 14 of a Pleuromutilin derivative according to step a) is a known procedure as e.g. disclosed in: Tetrahedron, 36, 1807 (1980), and can easily be carried out by a person skilled in the art.

Numerous procedures for protecting an OH-group in order to obtain a desired silyl ether according to step b) are known, or described herein.

Numerous procedures for hydroxylating an olefin in order to obtain a desired alcohol according to step c) are known, or described herein.

Numerous procedures for oxidizing an alcohol in order to obtain an aldehyde according to step d) are known, or described herein.

Numerous procedures for reacting an aldehyde in order to obtain a desired side chain in position 12 according to step e) are known, or described herein.

Numerous procedures for reducing an azido function according to step f) are known, or are described herein.

Numerous procedures for hydrogenating an olefin in order to obtain a desired side chain in position 12 according to step g) are known, or described herein.

Numerous procedures for protecting an amine in order to obtain a protected amino function in the side chain in position 12 according to step h) are known, or described herein.

Numerous methods for removing (e.g. selectively) a silyl ether according to step i) are known, or described herein.

Numerous procedures for substituting an OH-group in order to obtain an activated acetoxy derivative according to step j) are known, or described herein.

Numerous procedures are known for stop k) from prior art, or are described herein.

Numerous methods for removing (e.g. selectively) protecting groups according to step 1) are known as well. The concomitant retro-hydride shift is described in Reaction Scheme 2.

A compound of formula I thus obtained may be converted into another compound of formula I, e.g. or a compound of formula I obtained in free form may be converted into a salt of a compound of formula I and vice versa.

Intermediates (starting materials) in the production of a compound of the present invention are known or may be prepared according, e.g. analogously, to a method as conventional or as specified herein.

The compounds of the present invention exhibit pharmacological activity and are therefore useful as pharmaceuticals.

For example, the compounds of the present invention show antimicrobial, e.g. antibacterial, activity against Gram-negative bacteria, such as Enterobacteriaceae, e.g. *Escherichia coli, Salmonella typhimurium, Citrobacter freundii, Klebsiella pneumoniae*, and *Enterobacter cloacae*, as well as *Haemophilus influenzae, Haemophilus parainfluenzeae, Moraxella catarrhalis, Acinetobacter lwoffii* and *Acinetobacter baumannii* and against Gram-positive bacteria such as staphylococci, e.g. *Staphylococcus aureus*, as well as streptococci, e.g. *Streptococcus pneumoniae*, and *Enterococcus faecium*. The compounds also show activity against Gram-positive obligatory anaerobes such as Clostridia e.g. *Clostridium difficile* and *Clostridium perfringens*, such as *Eubacterium lentum*, and Peptostreptococci, e.g. *Peptostreptococcus anaerobius, Finegoldia magna, Anaerococcus prevotii, Peptoniphilus assaccharolyticus*, as well as Gram-negative obligatory anaerobic organisms such as Fusobacteria e.g. *Fusobacterium fusiforme, Fusobacterium necrophorum, Fusobacterium mortiferum* and *Fusobacterium varium, Prevotella* spp., e.g. *Prevotella buccae* and *Prevotella oris*, and *Porphyromonas* spp., e.g. *Porphyromonas gingivalis, Porphyromonas asaccharolytica*.

The in vitro activity against aerobic bacteria was determined by Broth Microdilution Test according to the Clinical and Laboratory Standards Institute (CLSI, former NCCLS) Document M7-A9 Vol 32, No 2 "Methods for Dilution Antimicrobial Susceptibility Tests for Bacteria that Grow Aerobically; Approved Standard—Ninth Edition (2012)"; and the test against anaerobic bacteria was performed by Agar Dilution Test according to the Clinical and Laboratory Standards Institute (CLSI, former NCCLS), Document, M11-A8, Vol. 32, No. 5: "Methods for Antimicrobial Susceptibility Testing of Anaerobic Bacteria; Approved Standard—Eighth Edition (2012)". Performance standards and interpretive criteria followed the CLSI Document, M100-S23: "Performance Standards for Antimicrobial Susceptibility Testing; Twenty-Third Informational Supplement" (2013). The in vivo activity was tested by the septicaemia mouse model against *Staphylococcus aureus* and *Escherichia coli*.

Compounds of the present invention are therefore suitable for the treatment and prevention of diseases which are mediated by microbes, e.g. by bacteria, e.g. potential indications for the compounds of the present invention are acute bacterial skin and skin structure infections (ABSSSI), respiratory tract infections (RTI) such as community-acquired pneumonia (CABP), Hospital-Acquired Bacterial Pneumonia (HABP) and Ventilator-Associated Bacterial Pneumonia (VABP); urinary tract infections (UTI), complicated intra-abdominal infections (cIAI) and other indications which might include sexually transmitted infections (STI) such as gonorrhea or STI caused by *Chlamydia*, Mycoplasms or anaerobic organi, bone and joint infections, eye and blood stream infections. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from *staphylococci, streptococci, enterococci;* diseases mediated by bacteria, e.g. selected from *Moraxella, Haemophilus, Legionella*, Neisseriaceae;

diseases mediated by bacteria, e.g. Enterobacteriaceae diseases mediated by *Helicobacter;* diseases mediated by *Mycobacterium tuberculosis;* e.g. diseases mediated by *Mycoplasma, Chlamydia* and obligatory anaerobes;

and for the treatment of acne.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention conveniently administered, for example, in divided doses up to four times a day. Administration may also include continuous infusion if the compound is given intravenously.

A compound of the present invention may be administered by any conventional route, for example enterally, e.g. including nasal, buccal, rectal, oral administration; parenterally, e.g., including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in free form or in the form of a pharmaceutically acceptable salt and/or in the form of a solvate in association with at least one pharmaceutical, excipient, e.g. carrier or diluent, e.g. including fillers, binders, disintegrators, flow conditioners, flow enhancers, glidants, lubricants, sugars and sweeteners, fragrances, taste maskers, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 2000 mg, such as 10 mg to about 1500 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

According to the present invention it was found that the inversion of the stereochemistry of the methyl group in position C-12 of the mutilin ring compared to the stereochemistry of the methyl group in position C-12 of the naturally occurring pleuromutilin and the introduction of a substituent in C-12 comprising at least one nitrogen atom increased surprisingly and remarkably the activity against Enterobacteriaceae, e.g. *Escherichia coli*.

The compounds of the following Examples 1 to 160 exhibit surprising activity against Gram positive and Gram negative bacteria i.e. *Staphylococcus aureus* ATCC 49951 and *Escherichia coli* ATCC 25922. Especially the improved activity against Gram negative bacteria, in particular *Escherichia coli*, is very surprising which is linked in one aspect to the inversion of the stereochemistry of the methyl group in position C-12 of the mutilin ring compared to the stereochemistry of the methyl group in position C-12 of the naturally occurring pleuromutilin, and in another aspect to the second C-12 substituent comprises at least one nitrogen atom. Moreover, the activity against *Staphylococcus aureus* was confirmed to be retained. All exemplified compounds exhibit MICs≤2 µg/mL against *Staphylococcus aureus* ATCCC 49951 and MICs≤16 µg/mL against *Escherichia coli* ATCC 25922.

In still a further aspect the present invention provides

A) A compound selected from 14-O-[((Alkyl-, cycloalkyl-, heterocycloalkyl-, heteroaryl-, or aryl)-sulfanyl)-acetyl]-12-epi-mutilins, or 14-O-[((Alkyl-, cycloalkyl-, heterocycloalkyl-, heteroaryl-, or aryl)-oxy)-acetyl]-12-epi-mutilins, wherein 12-epi-mutilin is characterized in that there is a substituent other than the natural occurring vinyl group in position 12 of the mutilin ring;

the methyl group in position 12 of the mutilin ring has the inverse stereochemistry compared with the methyl group in position 12 in the natural pleuromutilin ring, and all other substituents of the mutilin ring having the same stereochemistry compared with the stereochemistry of the corresponding substituents in the natural pleuromutilin ring, for use in the treatment of diseases mediated by Gram negative bacteria, in particular *Escherichia coli*.

B) 14-O-[((Alkyl-, cycloalkyl-, heterocycloalkyl-, heteoroaryl-, or aryl)-sulfanyl)-acetyl]-12-epi-mutilins, or 14-O-[((Alkyl-, cycloalkyl-, heterocycloalkyl-, heteroaryl-, or aryl)-oxy)-acetyl]-12-epi-mutilins, wherein 12-epi-mutilin is characterized in that there is a substituent other than the natural occurring vinyl group in position 12 of the mutilin ring;

the methyl group in position 12 of the mutilin ring has the inverse stereochemistry compared with the methyl group in position 12 in the natural pleuromutilin ring,
and
all other substituents of the mutilin ring having the same stereochemistry compared with the stereochemistry of the corresponding substituents in the natural pleuromutilin ring,
with the proviso that the compounds

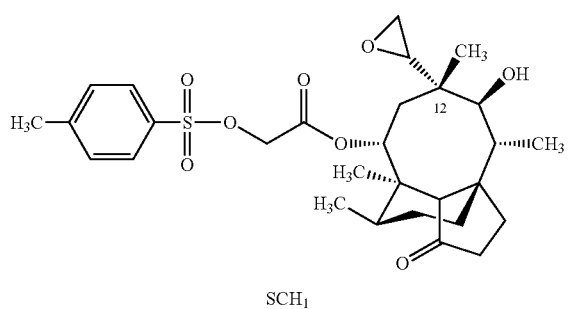

SCH₁ and

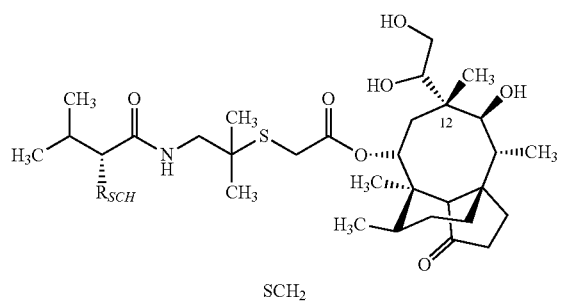

SCH₂ wherein $R_{SCH}$ is —NH—BOC, —NH₂, or NH₃⁺Cl⁻ are excluded;
which compounds are designated herein also as "priority compounds".

C) A priority compound as defined under B) wherein in the side chain attached to the mutilin ring in position 12 a nitrogen atom is present.

D) A priority compound of formula

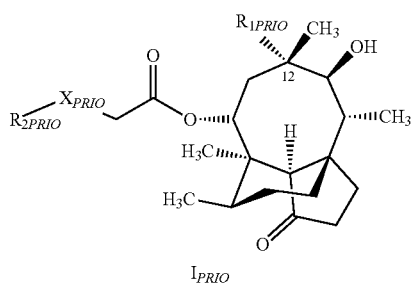

I$_{PRIO}$ wherein the methyl group in position 12 of the mutilin ring has the inverse stereochemistry compared with the methyl group in position 12 in the natural pleuromutilin ring,
all other substituents of the mutilin ring having the same stereochemistry compared with the stereochemistry of the corresponding substituents in the natural pleuromutilin ring.

$R_{1PRIO}$ is a hydrocarbon group comprising 1 to 16, in particular 1 to 12 carbon atoms, optionally comprising one or more heteroatoms selected from N, O, S, halogen, in particular N, and being other than the natural occurring vinyl group,
$X_{PRIO}$ is sulfur or oxygen, preferably sulfur, and
$R_{2PRIO}$ is a hydrocarbon group comprising 1 to 22 carbon atoms, optionally comprising heteroatoms selected from N, O, S, halogen, in particular N or O,
with the proviso, that the compounds of formula SCH₁ and SCH₂ wherein $R_{SCH}$ is as defined above are excluded.

E) A Priority compound of formula I$_{PRIO}$ as defined under D), wherein
$X_{PRIO}$ is defined as under D), $R_{1PRIO}$ is a group of formula

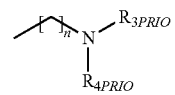

n is 1 to 12, $R_{2PRIO}$ is $(C_{1-16})$alkyl, $(C_{3-12})$cycloalkyl, $(C_{6-12})$aryl, heterocyclyl, comprising 3 to 12 ring members, including aliphatic and aromatic heterocyclyl, comprising a heteroatom selected from N, O, and/or S,
wherein alkyl, aryl or cycloalkyl, heteroaryl or aliphatic heterocyclyl is substituted or unsubstituted, comparing substituents which optionally having a heteroatom selected from O, N, S, halogen, and
$R_{3PRIO}$ and $R_{4PRIO}$ independently of each other are hydrogen,
$(C_{1-16})$alkyl or $(C_{2-16})$ alkenyl, optionally substituted by a hydrocarbon group comprising 1 to 12 carbon atoms,
which hydrocarbon group optionally comprises substituents, optionally having a heteroatom selected from N, O, S, halogen,
carbamimidoyl, carbamoyl, thiocarbamoyl,
$(C_{3-8})$cycloalkyl,
$(C_{6-12})$aryl, optionally comprising a heteroatom selected from N, O, S,
aliphatic heterocyclyl comprising 3 to 8 ring members, and 1 to 3 heteroatoms selected from N, O, S,
which cycloalkyl, aryl, heteroaryl or aliphatic heterocyclyl optionally comprises substituents, which optionally having a heteroatom selected from O, N, S, halogen;

F) A Priority compound of formula I$_{PRIO}$ as defined under D), wherein
$X_{PRIO}$ and $R_{2PRIO}$ are as defined above, and $R_{1PRIO}$ is $(C_{1-16})$alkyl or $(C_{1-16})$ alkenyl comprising at least one heteroatom selected from N, O, S, either within the chain, or in a terminal position, which alkyl or alkenyl optionally is substituted by
$(C_{3-8})$cycloalkyl,
aliphatic heterocyclyl comprising 3 to 8 ring members, in and 1 to 4 heteroatoms selected from N, O, S,
$(C_{6-12})$aryl, optionally comprising a heteroatom selected from N, O, S,
which alkyl, alkenyl, cycloalkyl, aryl, heteroaryl or aliphatic heterocyclyl optionally comprises substituents, optionally having a heteroatom selected from N, O, S, halogen.

G) A compound of formula I as defined under D),
wherein $X_{PRIO}$ and $R_{1PRIO}$ are as defined above,
$R_{2PRIO}$ is
alkyl, such as $(C_{1-4})$alkyl, optionally substituted by hydroxy, amino;

cycloalkyl, such as (C$_{3-12}$)cycloalkyl, optionally substituted by amino, (C$_{1-4}$)alkylamino, hydroxy, (C$_{1-4}$)alkyl;

aryl, such as (C$_{5-12}$)aryl, e.g. phenyl, optionally substituted by hydroxy, halogen, amino, hydroxy(C$_{1-4}$)alkyl, bis-(hydroxy(C$_{1-4}$)alkyl), amino(C$_{1-4}$)alkyl, bis-(amino(C$_{1-4}$)alkyl), e.g. wherein the amino group in amino(C$_{1-4}$)alkyl optionally is further substituted, e.g. by (C$_{3-6}$)cycloalkyl, (C$_{2-6}$)alkenyl, amino(C$_{1-6}$)alkyl, (C$_{5-12}$)aryl(C$_{1-4}$)alkyl wherein aryl optionally is further substituted by amino(C$_{1-4}$)alkyl, aminocarbonyl, wherein the nitrogen optionally is substituted by amino(C$_{1-12}$)alkyl, bis-(amino(C$_{1-12}$)alkyl), hydroxy (C$_{1-6}$)alkyl, bis-(hydroxy(C$_{1-6}$)alkyl), (C$_{1-6}$)alkyl, which alkyl optionally is substituted by amino, which amino optionally is acylated, e.g. substituted by formyl, (C$_{1-4}$)alkylcarbonyl, saturated or unsaturated heterocyclyl comprising 1 to 3 heteroatoms, e.g. N, and 4 to 8, such as 5 to 6 ring members, (C$_{5-12}$)aryl, e.g. phenyl, which aryl optionally is substituted by amino(C$_{1-4}$)alkyl or the nitrogen of the aminocarbonyl group is part of (C$_{3-8}$) heterocyclyl, e.g. saturated or unsaturated, containing one or more heteroatoms selected from N, O, S preferable N, wherein the heterocycle is optionally further substituted by amino(C$_1$-C$_4$)alkyl;

(C$_{1-6}$)alkyl, which (C$_{1-6}$)alkyl group is optionally substituted by aminocarbonyl wherein the nitrogen of the aminocarbonyl group is optionally further substituted by amino (C$_{1-12}$)alkyl, bis-(amino(C$_{1-12}$)alkyl), hydroxy(C$_{1-6}$)alkyl, bis-(hydroxy(C$_{1-16}$)alkyl)

acylated amino(C$_{1-4}$)alkyl, e.g. wherein the acyl group includes (C$_{1-4}$)alkylcarbonyl, wherein alkyl optionally is further substituted by amino, phenyl, e.g. including amino (C$_{1-4}$)alkylphenyl, hydroxyphenyl, saturated and unsaturated (C$_{3-12}$)heterocyclyl, comprising 1 to 4 heteroatoms, preferably N, e.g. heterocyclyl optionally annellated with another ring (system), which heterocyclyl is optionally substituted by (C$_{1-6}$)alkyl, amino or hydroxy wherein the alkyl group is optionally further substituted by halogen or amino.

H) A compound of formula I$_{PRIO}$ as defined under D), wherein X$_{PRIO}$ and R$_{1PRIO}$ are as defined in any one of the definitions under D) to G), R$_{2PRIO}$ is amido(C$_{0-4}$)alkyl-phenyl, wherein the nitrogen of the amido group is unsubstituted or substituted by amino (C$_{1-8}$)alkyl, in which alkyl optionally is further substituted.

J) A compound of formula X$_{PRIO}$ as defined under D), wherein X$_{PRIO}$ is S and R$_{1PRIO}$ is as defined in any one of the definitions under D) to H), and R$_{2PRIO}$ is aminoethyl-amidomethyl-phenyl, aminopropyl-amidomethyl-phenyl, hydroxyphenyl-(amino)ethyl-amidomethyl-phenyl, aminomethyl-phenyl-(amino)ethyl-amidomethyl-phenyl, aminopropyl-amidophenyl, aminomethyl-phenylmethyl-amido-phenyl, aminomethyl-phenyl, aminoacetyl-aminomethyl-phenyl, bis(aminomethyl)phenyl, bisaminopropyl-amidomethyl-phenyl, (2-amino)-aminopropyl-amidomethyl-phenyl, aminoethyl-aminomethyl-phenyl, aminopropyl-aminomethyl-phenyl, allyl-aminomethyl-phenyl, aminomethyl-phenylmethyl-aminomethyl-phenyl, hydroxymethyl-phenyl, bis(hydroxymethyl)-phenyl, (tetrafluoro)(hydroxymethyl)-phenyl, amino-hydroxy-cyclohexyl, hydroxyethyl, aminoethyl, piperazincarbonyl-phenyl, aminomethyl-piperidine-carbonyl-phenyl, piperidine-ylmethyl-amido-phenyl, pyridine-ylmethyl-amido-phenyl, acetyl-aminopropyl-amido-phenyl, formyl-aminopropyl-amido-phenyl, amidophenyl, aminohexyl-amidophenyl, aminoethyl-amidophenyl, (5-Amino)-4H-[1,2,4]triazol-3-yl, pyridinyl, hydroxyphenyl, fluorophenyl, purinyl, aminophenyl, acetyl-aminomethyl-phenyl, cyclopropyl-aminomethyl-phenyl, aminopropyl-amidopyridinyl, hydroxypropyl-amidophenyl, amino-purinyl, difluoroethylamino-cyclohexyl, amino-hydroxy-cyclohexyl, azepanyl.

K) A priority compound of formula

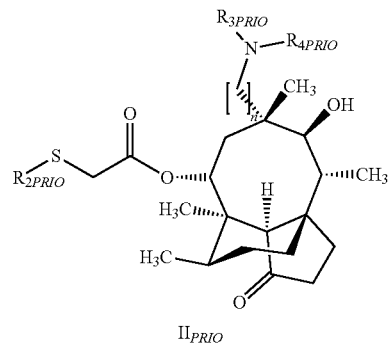

II$_{PRIO}$ wherein n and R$_{2PRIO}$ are is as defined in any one of the definitions under D) to J), R$_{3PRIO}$ is H, or aminoethyl, aminopropyl, aminobutyl, aminopentyl, aminohexyl, aminooctyl, aminodecyl, dimethylaminopropyl, dimethylamidopentyl, guanidinobutyl, guanidinohexyl, carbamimidoyl, aminomethylcylcohexylmethyl, aminopropoxypropyl, aminocyclohexyl, hydroxyhexyl, dihydroxypropyl, aminomethylphenylmethyl, guanidinomethylphenylmethyl, phenylmethyl, morpholinopropyl, piperidinyl, hexyl, pyridinylethyl, allyl, amido-benzyl, aminopropyl-amidobenzyl, (2-amino)-amidoethyl-benzyl, (2-amino)-dimethylamidoethyl-benzyl, 2-amino-1-aminomethyl-ethyl, 5-amino-5-ethoxycarbonyl-pentyl, and R$_{4PRIO}$ is H or (C$_{1-4}$)alkylcarbonyl.

L) A compound according to the definitions under D) which is of formula

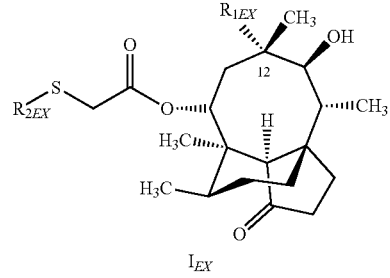

I$_{EX}$ wherein R$_{1EX}$ and R$_{2EX}$ are as set out in Examples 1 to 42, 49 to 73, 85 to 97, 104 and 106 to 132.

M) A Priority compound as defined under any one under A) to L)

in the form of a salt and/or solvate, for use as a pharmaceutical drug substance, in a pharmaceutical composition, additionally comprising at least one pharmaceutical excipient, optionally further comprising another pharmaceutically active agent, in a method of treatment of diseases mediated by microbes.

The trivial name mutilin refers to the IUPAC systematic name (1S, 2R, 3S, 4S, 6R, 7R, 8R, 14R)-3,6-dihydroxy-2,4,7,14-tetramethyl-4-vinyl-tricyclo[5.4.3.0$^{1,8}$]tetradecan-9-one.

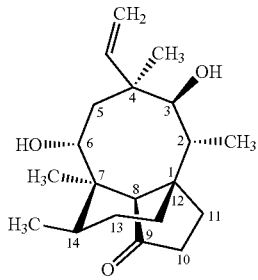

In the following examples, pleuromutilin derivatives are numbered in analogy to the mutilin numbering system described by H. Berner (Berner, H.; Schulz, G.; Schneider H. *Tetrahedron* 1980, 36, 1807-1811):

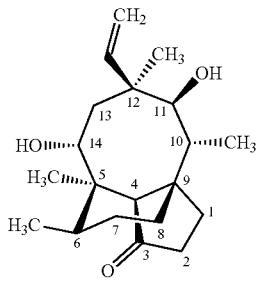

In the compounds of the present invention, e.g. in the compounds of Examples 1 to 160, the stereochemistry of the methyl group at position 12 (and in turn also the stereochemistry of the second group attached in position 12 of the mutilin ring) is inverted (epi-mutilin derivatives) and in addition the vinyl group is altered and various substituents instead of vinyl have been introduced:

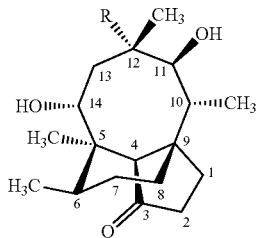

Pleuromutilin tosylate is a compound of formula:

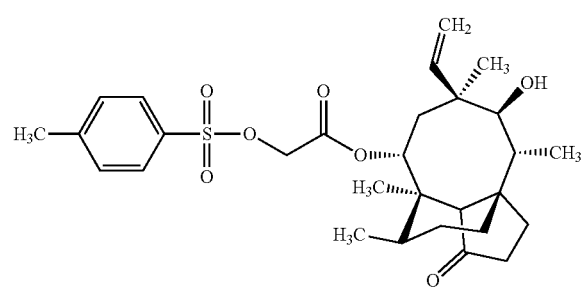

12-Epi-pleuromutilin and 12-epi-pleuromutilin tosylate are compounds of formula:

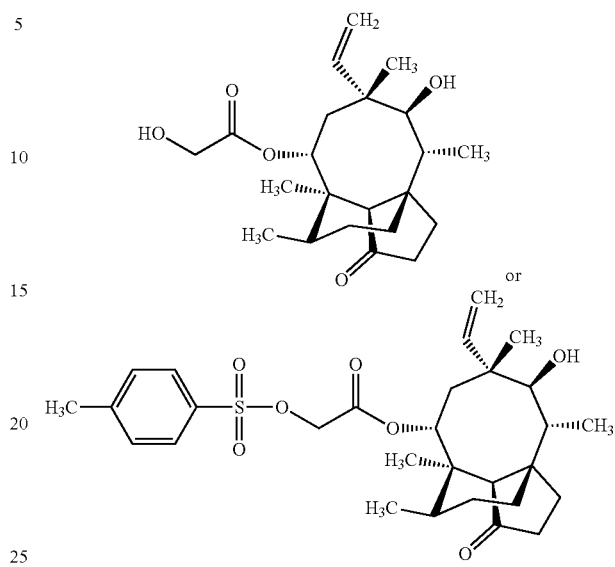

respectively.

Herein, including the examples and the reaction scheme the following abbreviations are used:

$^1$H-NMR proton nuclear magnetic resonance spectroscopy
approx. approximately
C degrees Celsius
BOC tert-butoxycarbonyl
conc. concentrated
BOC$_2$O di-tert-butyl dicarbonate
d days
DCM CH$_2$Cl$_2$
DBU 1,8-diazabicyclo[5.4.0]undec-7-ene
DCC N,N'-dicyclohexylcarbodiimide
DIEA Diisopropylethylamine
DIPEA Ethyl-diisopropyl-amine
DMAP 4-dimethylaminopyridine
DMA N,N-dimethylacetmamide
DMF N,N-dimethylformamide
DMSO dimethylsulfoxide
DPPA diphenylphosphoryl azide
dppf 1,1'-Bis(diphenylphosphino)ferrocene
DTT 1,4-dithio-DL-threitol
eq equivalents
EtOAc ethyl acetate
EtOH ethanol
h hours
HATU 1-[Bis(dimethylamino)methylene]-1H-1,2,3-triazolo[4,5-b]pyridinium 3-oxid hexafluorophosphate
heptane n-heptane
HOBt 1-hydroxybenzotriazol
HPLC High Performance Liquid Chromatography
LAH Lithium Aluminum Hydride
M molarity
MeOH methanol
min minutes
MS mass spectrometry
MsCl methanesulfonyl chloride
MTBE Methyl tert-butyl ether
m/z mass/charge ratio Na₂SO₄ sodium sulfate
NMM N-Methylmorpholine
Pd₂(dba)₃ Tris(dibenzylideneacetone)dipalladium(0)
PE Petroleum ether
PG protecting group
rt room temperature
sat. saturated
TLC thin layer chromatography
TFA Trifluoroacetic acid
TEA, Et₃N triethylamine
THF tetrahydrofuran
TLC thin layer chromatography
wt weight
w/w weight/weight

EXAMPLE 1

12-epi-12-desvinyl-14-O-{{4-[(3-Amino-propylcarbamoyl)-methyl]-phenylsulfanyl}-acetyl}-12-[(3-amino-propylamino)-methyl] mutilin trihydrochloride Step 1: Pleuromutilintosylate To a solution of 18.63 g of pleuromutilin and 9.39 g of toluenesulfonylchloride in 1400 mL of methylethylketone a solution of 4.98 g of triethylamine in 300 mL of methylethylketone is slowly added at rt. The mixture obtained is stirred for 24 h at rt, the formed precipitate is filtered off and to the filtrate obtained 2800 mL of water is added. The solution obtained is extracted 3 times with EtOAc and the organic phase obtained is dried over Na₂SO₄ and evaporated to dryness under reduced pressure. The crude product is used for the next step without further purification.

¹H-NMR (400 MHz, DMSO-d₆, δ, ppm, characteristic signals): 0.49 (d, 3H, J=7 Hz, CH₃-16); 0.8 (d, 3H, J=7 Hz, CH₃-17); 1.02 (s, 3H, CH₃-18), 1.29 (s, 3H, CH₃-15); AB-system (v$_A$=4.75, v$_B$=4.62, J=50 Hz, CH₂-22); 5.00 (m, 2H, H-20); 5.52 (d, 1H, J=8 Hz, H-14); 6.04 (dd, 1H, J=11, 18 Hz, H-19), 7.46 (d, 2H, J=8 Hz, arom.); 7.79 (d, 2H, J=8 Hz, arom.).

Step 2: 12-epi-Pleuromutilintosylate 20 g of Pleuromutilin tosylate was dissolved in 100 mL of THF and the solution obtained was heated to reflux. 20 mL of Diethylzinc (1M in heptane) was carefully added during 10 minutes and the reaction was kept at reflux for 7 hours. HPLC showed then a 46:53 ratio of Pleuromutilin tosylate: 12-epi-Pleuromutilin tosylate by area. The batch was cooled to approx. 50° C., 2 mL of water was added; the resulting precipitate was filtered off and the organic phase was evaporated to dryness. The evaporation residue obtained was subjected to chromatography over silica gel using toluene/acetone 80:1 as eluent.

¹H-NMR (200 MHz, DMSO-d₆): 7.79 (d, 2H, arom., J=8 Hz), 7.45 (d, 1H, arom., J=8 Hz), 5.9 (dd, 1H, H-19, J$_E$=18 Hz, J$_Z$=12 H$_Z$), 5.49 (d, 1H, H-14, J=7.8 Hz), 4.92-4.85 (m, 2H, H-20), AB (2H, H-22, v$_A$=4.76, v$_B$=4.61, J=16 Hz), 4.25 (d, 1H, 11-OH, J=5.8 Hz), 2.40 (s, 3H, —CH₃), 1.31 (s, 3H, H-15), 0.99 (s, 3H, H-18), 0.80 (d, 3H, H-17, J=6.6 Hz), 0.52 (d, 3H, H-16, J=6.2 Hz).

MS m/e: 550 [M⁺+NH₄].

Step 3: 12-epi-12-desvinyl-14-O-{(Toluene-4-sulfonyloxy)-acetyl}-12-formyl mutilin 1 g of 12-epi-Pleuromutilin tosylate was dissolved in 25 mL of MeOH and 10 mL of EtOAc, cooled to −78° C. (carbon dioxide/acetone) and the mixture obtained was subjected to ozonisation at a flow rate of 70 L/h until a blue coloration persisted (ca. 10 minutes). To the still cold mixture was added 0.85 g of potassium iodide in 2.3 mL of water, 1.3 mL of acetic acid and 8 mL of MeOH in a manner that the internal temperature did not exceed −50° C. After addition the flask remained in the cooling bath and was left to warm up to about 0° C. At 0° C. 10 mL of 20% aqueous sodium thiosulfate solution was added to the mixture obtained and stirring was continued for 30 min. The reaction mixture was poured on 100 mL of water and extracted with 3×50 mL EtOAc. The combined organic layers obtained were washed with 5% NaHCO₃ solution, dried over Na₂SO₄ and evaporated to dryness. The evaporation residue was subjected to chromatography over silica gel using cyclohexane/EtOAc 3:1 as eluent.

¹H-NMR (200 MHz, DMSO-d₆): 9.59 (s, 1H, —CHO), 7.80 (d, 2H, arom., J=8 Hz), 7.47 (d, 1H, arom., J=8 Hz), 5.34 (d, 1H, H-14, J=8.2 Hz), 4.83 (d, 1H, 11-OH, J=6.6 Hz), AB (2H, H-22, v$_A$=4.76, v$_B$=4.61, J=16 Hz), 3.57-3.5 (m, 1H, H-11), 2.41 (s, 3H, —CH₃), 1.30 (s, 3H, H-15), 1.07 (s, 3H, H-18), 0.93 (d, 3H, H-17, J=6.6 Hz), 0.50 (d, 3H, H-16, J=6.6 Hz).

MS m/e: 552 [M⁺+NH₄].

The ozonolysis of 11-Oxo pleuromutilin to give 12-desvinyl-12-formyl-11-oxo pleuromutilin using the same procedure is e.g. disclosed in: Tetrahedron, 37, 915 (1981).

Step 4: 12-epi-12-desvinyl-14-O-{(Toluene-4-sulfonyloxy)-acetyl}-12-[(3-tert-butoxycarbonylamino-propylamino)-methyl] mutilin of formula 620 mg of 12-epi-12-desvinyl-14-O-{(toluene-4-sulfonyloxy)-acetyl}-12-formyl mutilin was dissolved in dichloroethane, 202 mg of N-BOC-diaminopropane dissolved in a minimum volume of dichloroethane was added and the mixture obtained was stirred at rt for one h. To the mixture obtained 541 mg of sodium trisacetoxyborohydride was added and the resulting slurry was stirred for another h at rt. HPLC then indicated the absence of the starting material. The mixture obtained was quenched with 5% aqueous NaHCO$_3$ solution, the aqueous phase obtained was washed with DCM; the combined organic phases were dried over Na$_2$SO$_4$ and evaporated to dryness. The evaporation residue was subjected to chromatography over silica gel using EtOAc/triethylamine 100:1 as eluent.

$^1$H-NMR (200 MHz, DMSO-d$_6$): 7.80 (d, 2H, arom., J=8 Hz), 7.47 (d, 1H, arom., J=8.2 Hz), 6.87 (bs, 1H, BOC-NH), 5.50 (d, 1H, H-14, J=7.2 Hz), AB (2H, H-22, v$_A$=4.74, v$_B$=4.62, J=16 Hz), 3.66 (bs, 1H, H-11), 2.41 (s, 3H, —CH$_3$), 1.36 (s, 9H, 3×CH$_3$), 1.30 (s, 3H, H-15), 0.91 (s, 3H, H-18), 0.80 (d, 3H, H-17, J=5.6 Hz), 0.51 (d, 3H, H-16, J=5.8 Hz).

MS m/e: 693 [M$^+$+H].

Step 5: 12-epi-12-desvinyl-14-O-{{4-[(3-tert-Butoxycarbonylamino-propylcarbamoyl)-methyl]-phenylsulfanyl}-acetyl}-12-[(3-tert-butoxycarbonylamino-propylamino)-methyl] mutilin 440 mg of tert-Butyl N-{3-[2-(4-mercapto-phenyl)-acetylamino]-propyl}-carbamate was dissolved in 20 mL of acetonitrile, 152 mg of potassium tert-butoxide was added followed by addition of 892 mg of 12-epi-12-desvinyl-14-O-[(toluene-4-sulfonyloxy)-acetyl]-12-[(3-tert-butoxycarbonylamino-propylamino)-methyl] mutilin in one portion. The resulting slurry was stirred at rt for 1 h, diluted with 60 mL of water and extracted with DCM (4×). The combined organic phases were washed 2× with aqueous 2N NaOH solution, water, dried over Na$_2$SO$_4$ and evaporated to dryness. The evaporation residue obtained subjected to chromatography EtOAc/MeOH 8/1 to yield colourless crystals.

$^1$H-NMR (200 MHz, DMSO-d$_6$): 8.03 (t, 1H, CO—NH, J=6 Hz), 7.27 (d. 2H. arom. J=8 Hz), 7.17 (d, 1H, arom., J=8.2 Hz), 6.83-6.74 (m, 2H, 2×BOC-NH), 5.47 (d, 1H, H-14, J=7.2 Hz), 3.76 (s, 2H, H-22), 3.40 (bs, 1H, H-11), 1.36 (s, 9H, 3×CH$_3$), 1.30 (s, 3H, H-15), 0.80-0.76 (m, 6H, H-18, H-17), 0.57 (d, 3H, H-16, J=5.6 Hz).

Step 6: 12-epi-12-desvinyl-14-O-{{4-[(3-Aminopropylcarbamoyl)-methyl]-phenylsulfanyl}-acetyl}-12-[(3-amino-propylamino)-methyl] mutilin trihydrochloride 654 mg of 12-epi-12-desvinyl-14-O-{{4-[(3-tert-butoxycarbonylamino-propylcarbamoyl)-methyl]-phenylsulfanyl}-acetyl}-12-[(3-tert-butoxycarbonylamino-propylamino)-methyl] mutilin was dissolved in 2 mL of DCM, 11.5 mL of 1N HCl in diethyl ether was added and the mixture obtained was stirred at rt for 1 h. A precipitate formed and was collected with suction, washed 5× with diethyl ether and dried in a high vacuum overnight. The title compound was obtained in the form of a trihydrochloride.

NMR: $^1$H-NMR (200 MHz, DMSO-d$_6$): 7.29 (d, 2H, arom., J=8.4 Hz), 7.21 (d, 2H, arom., J=8.4 Hz), 5.44 (d, 1H, H-14, J=6 Hz), 5.36 (d, 11-OH, J=4 Hz), 1.35 (s, 3H, H-15), 0.57 (d, 3H, H-16, J=5.2 Hz).

MS m/e: 645 [M$^+$+H].

Preparation of step 5—Intermediate tert-Butyl N-[3-[[2-(4-Sulfanylphenyl)-acetyl]-amino]-propyl]-carbamate Step a: 2-(4-Acetylsulfanylphenyl)-acetic acid 605 mg of 4-mercaptophenylacetic acid and 1.44 g of diisopropylethylamine was dissolved in 10 mL of DCM under an argon atmosphere, and the mixture obtained was cooled in an ice bath and treated with 532 mg of acetic anhydride. The mixture obtained was stirred 10 min with cooling and then 45 min at rt. To the mixture obtained 10 mL of 1N HCl was added and vigorous stirring was maintained for 10 min, the phases obtained were separated, the aqueous phase obtained was washed once with DCM and the combined organic phases were dried over $Na_2SO_4$ and evaporated to dryness. The title compound was obtained in the form of pale yellow crystals (containing residual solvent).

Step b: S-[4-[2-[3-(tert-Butoxycarbonylamino)-propylamino]-2-oxo-ethyl]-phenyl]-ethanethioate 770 mg of 2-(4-acetylsulfanylphenyl)-acetic acid, 638 mg of N-BOC-1,3-diaminopropane and 560 mg of HOBt was dissolved in 15 mL DCM, stirred for 20 min at rt, cooled in an ice bath and treated with 755 mg of DCC. The cooling bath was removed and resulting slurry was stirred at rt for 1 hour and filtered from dicyclohexylurea. The filtrate obtained was washed with aqueous 10% $K_2CO_3$, 0.1N HCl and 5% $NaHCO_3$, dried over $Na_2SO_4$ and evaporated to dryness. The evaporation residue obtained was triturated with 10 mL of acetonitrile, filtered from insoluble material and brought to dryness. The title compound in the form of pale yellow soft crystals was obtained.

Step c: tert-Butyl N-[3-[[2-(4-sulfanylphenyl)-acetyl]-amino]-propyl]-carbamate 560 mg (1.53 mmol) of S-[4-[2-[3-(tert-butoxycarbonylamino)-propylamino]-2-oxo-ethyl]-phenyl]-ethanethioate was dissolved in 10 mL of MeOH, 422 mg (3.06 mmol) of potassium carbonate in 4 mL of water was added and the resulting yellow solution was stirred at ambient temperature for 1 hour, followed by dilution with 40 mL of water plus 7 mL of 1N HCl and extraction with 10 mL of dichloromethane. The aqueous phase was washed with dichloromethane (2×), the combined organic phases washed with 5% $NaHCO_3$, dried over $Na_2SO_4$ and evaporated to dryness. The title compound was obtained in the form of pale yellow crystals which were used in the next step without further purification.

According, e.g. analogously, to a method as conventional, or according, e.g. analogously to a method as set out under Example 1 above, but using appropriate starting materials the compounds of formula

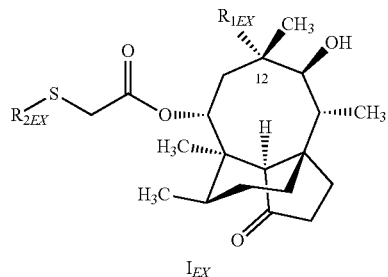

$I_{EX}$ wherein $R_{1EX}$ and $R_{2EX}$ are as defined in Table 1 are prepared. Chemical characterisation data are also set out in Table 1.

TABLE 1

| Example | | $R_{2EX}$ | $R_{1EX}$ |
|---|---|---|---|
| 2 | 12-epi-12-desvinyl-14-O-{{4-[(2-Amino-ethylcarbamoyl)-methyl]-phenylsulfanyl}-acetyl}-12-[(3-amino-propylamino)-methyl] mutilin trihydrochloride<br>$^1$H-NMR (200 MHz, DMSO-d6): 7.29 (d, 2H, arom., J = 7.2 Hz), 7.23 (d, 2H, arom., J = 9 Hz), 5.44 (d, 1H, H-14, J = 8 Hz), 3.81 (s, 2H, H-22), 1.36 (s, 3H, H-15), 0.84 (s, 3H, H-18) 0.58 (d, 3H, H-16, J = 4.8 Hz)<br>MS m/e: 631 [M$^+$ + H] | | |

TABLE 1-continued

| Example | | $R_{2EX}$ | $R_{1EX}$ |
|---|---|---|---|
| 3 | 12-epi-12-desvinyl-14-O-{{4-([Bis-(3-amino-propyl)-carbamoyl]-methyl}-phenylsulfanyl)-acetyl}-12-[(3-amino-propylamino)-methyl] mutilin tetrahydrochloride<br>MS m/e: 702 [M⁺ + H] | *(structure)* | *(structure)* |
| 4 | 12-epi-12-desvinyl-14-O-{{4-[(2,3-Diamino-propylcarbamoyl)-methyl]-phenylsulfanyl}-acetyl}-12-[(3-amino-propylamino)-methyl] mutilin tetrahydrochloride<br>MS m/e: 694 [M⁻ + Cl]<br>The required [2-Amino-1-(tert-butoxycarbonylamino-methyl)-ethyl]-carbamic acid tert-butyl ester is e.g. described in U.S. Pat. No. 4,933,470 | *(structure)* | *(structure)* |
| 5 | 12-epi-12-desvinyl-14-O-{{4-[(2-Amino-ethylcarbamoyl)-methyl]-phenylsulfanyl}-acetyl}-12-[(2-amino-ethylamino)-methyl] mutilin trihydrochloride<br>¹H-NMR (200 MHz, DMSO-d6): 7.29 (d, 2H, arom., J = 8 Hz), 7.22 (d, 2H, arom., J = 8 Hz), 5.44 (d, 1H, H-14, J = 5.6 Hz), 3.80 (s, 2H H-22), 1.36 (s, 3H, H-15), 0.82 (s, 3H, H-18), 0.80 (d, 3H, H-17, J = 5.8 Hz), 0.57 (d, 3H, H-16, J = 5.4 Hz)<br>MS m/e: 617 [M⁺ + H]. | *(structure)* | *(structure)* |
| 6 | 12-epi-12-desvinyl-14-O-{{4-[(3-Amino-propylcarbamoyl)-methyl]-phenylsulfanyl}-acetyl}-12-[(2-amino-ethylamino)-methyl] mutilin trihydrochloride<br>¹H-NMR (200 MHz, DMSO-d6): 7.29 (d, 2H, arom., J = 8 Hz), 7.21 (d, 2H, arom., J = 8.2 Hz), 5.44 (d, 1H, H-14, J = 5.8 Hz), 1.36 (s, 3H, H-15), 0.86 (s, 3H, H-18), 0.80 (d, 3H, H-17, J = 5.4 Hz), 0.57 (d, 3H, H-16, J = 5.8 Hz)<br>MS m/e: 631 [M⁺ + H] | *(structure)* | *(structure)* |

TABLE 1-continued

| Example | | R₂ₑₓ | R₁ₑₓ |
|---|---|---|---|
| 7 | 12-epi-12-desvinyl-14-O-{{4-[(3-Amino-propylcarbamoyl)-methyl]-phenylsulfanyl}-acetyl}-12-[(4-amino-butylamino)-methyl] mutilin trihydrochloride<br>¹H-NMR (200 MHz, DMSO-d6): 8.45 (t, 1H, CO—NH, J = 6 Hz), 7.99 (bs, 6 H, NH₃⁺), 7.28 (d, 2H, arom., J = 8 Hz), 7.21 (d, 2H, arom., J = 8 Hz), 5.44 (d, 1H, H-14, J = 6.4 Hz), 1.34 (s, 3H, H-15), 0.85-0.79 (m, 6H, H-17, H-18), 0.57 (d, 3H, H-16, J = 5.2 Hz)<br>MS m/e: 659 [M⁺ + H] | | |
| 8 | 12-epi-12-desvinyl-14-O-{{4-[(3-Amino-propylcarbamoyl)-methyl]-phenylsulfanyl}-acetyl}-12-[(5-amino-pentylamino)-methyl] mutilin trihydrochloride<br>¹H-NMR (200 MHz, DMSO-d6): 8.41 (t, 1H, CO—NH, J = 6 Hz), 8.0 (bs, 6 H, NH₃⁺), 7.29 (d, 2H, arom., J = 8 Hz), 7.21 (d, 2H, arom., J = 8 Hz), 5.42 (bs, 1H, H-14), 1.35 (s, 3H, H-15), 0.85-0.79 (m, 6H, H-17, H-18), 0.57 (d, 3H, H-16, J = 5.4 Hz)<br>MS m/e: 673 [M⁺ + H] | | |
| 9 | 12-epi-12-desvinyl-14-O-{{4-[(3-Amino-propylcarbamoyl)-methyl]-phenylsulfanyl}-acetyl}-12-[(4-aminomethyl-benzylamino)-methyl] mutilin trihydrochloride<br>¹H-NMR (200 MHz, DMSO-d6): 7.68 (d, 2H, arom., J = 8 Hz), 7.55 (d, 2H, arom., J = 8.2 Hz), 7.26 (d, 2H, arom., J = 8 Hz), 7.18 d, 2H, arom., J = 8.2 Hz), 5.42 (d, 1H, H-14, J = 7.2 Hz), 1.34 (s, 3H, H-15), 0.56 (d, 3H, H-16, J = 5.6 Hz)<br>MS m/e 707 [M⁺ + H] | | |
| 10 | 12-epi-12-desvinyl-14-O-{{4-[(3-Amino-propylcarbamoyl)-methyl]-phenylsulfanyl}-acetyl}-12-[(6-amino-hexylamino)-methyl] mutilin trihydrochloride<br>¹H-NMR (200 MHz, DMSO-d₆): 7.28 (d, 2H, arom., J = 8 Hz), 7.21 (d, 2H, arom., J = 8 Hz), 5.44 (d, 1H, H-14, J = 7.2 Hz), 3.8 (s, 2H, H-22), 1.35 (s, 3H, H-15), 0.57 (d, 3H, H-16, J = 4.6 Hz)<br>MS m/e: 687 [M⁺ + H] | | |

TABLE 1-continued

| Example | | $R_{2EX}$ | $R_{1EX}$ |
|---|---|---|---|
| 11 | 12-epi-12-desvinyl-14-O-{{4-[(3-Amino-propylcarbamoyl)-methyl]-phenylsulfanyl}-acetyl}-12-[(6-guanidino-hexylamino)-methyl] mutilin trihydrochloride<br>$^1$H-NMR (200 MHz, DMSO-d$_6$): 7.28 (d, 2H, arom., J = 8 Hz), 7.21 (d, 2H, arom., J = 8 Hz), 5.44 (d, 1H, H-14, J = 7 Hz), 1.35 (s, 3H, H-15), 0.85 (s, 3H, H-18), 0.80 (d, 3H, H-17, J = 6.4 Hz), 0.57 (d, 3H, H-16, J = 5.4 Hz)<br>MS m/e: 730 [M$^+$ + H]<br>The required tert-Butyl (NE)-N-[(6-aminohexylamino)-(tert-butoxycarbonylamino)-methylene]-carbamate was prepared according to: Journal of Medicinal Chemistry, 44(18), 2950; 2001 | | |
| 12 | 12-epi-12-desvinyl-14-O-{{4-[(3-Amino-propylcarbamoyl)-methyl]-phenylsulfanyl}-acetyl}-12-[(4-guanidino-butylamino)-methyl] mutilin trihydrochloride<br>$^1$H-NMR (200 MHz, DMSO-d$_6$): 7.32 (d, 2H, arom., J = 8 Hz), 7.25 (d, 2H, arom., J = 8 Hz), 5.43 (d, 1H, H-14, J = 7.4 Hz), 4.44 (s, 2H, Ph—CH$_2$), 3.87 (s, 2H H-22), 1.35 (s, 3H, H-15), 0.86 (s, 3H, H-18), 0.80 (d, 3H, H-17, J = 5.8 Hz), 0.57 (d, 3H, H-16, J = 5.8 Hz)<br>MS m/e: 702 [M$^+$ + 2H] | | |
| 13 | 12-epi-12-desvinyl-14-O-{{4-[(3-Amino-propylcarbamoyl)-methyl]-phenylsulfanyl}-acetyl}-12-[(allylamino)-methyl] mutilin dihydrochloride<br>MS m/e: 672 [M + formate] | | |

EXAMPLE 14

12-epi-12-desvinyl-14-O-{{4-[(3-Amino-propylcarbamoyl)-methyl]-phenylsulfanyl}-acetyl}-12-aminomethyl mutilin dihydrochloride

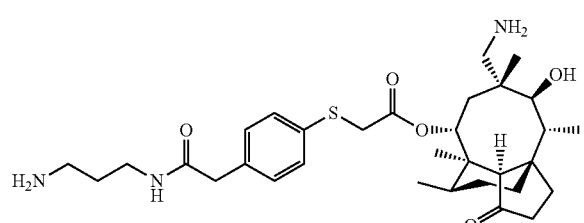

Step 1: 12-cpi-12-desvinyl-14-O-{{4-[(3-tert-Butoxycarbonylamino-propylcarbamoyl)-methylphenylsulfanyl]}-acetyl}-12-aminomethyl mutilin 120 mg of N,N'-Dimethylbarbituric acid and 6 mg of tetrakis(triphenylphosphine) palladium (0) was placed under a positive argon stream in a three necked round bottom flask together with a stirrer. 187 mg (0.257 mmol) of 12-epi-12-desvinyl-14-O-{{4-[(3-tert-Butoxycarbonylamino-propylcarbamoyl)-methylphenylsulfanyl]}-acetyl}-12-[(allylamino)methyl]mutilin (compound of Example 13 prior to BOC-deprotection) was dissolved in 5 mL of DCM and degassed in a ultrasonic bath for 15 min and then added to the reaction flask via syringe and septum. The mixture was stirred for 6 hours under an inert atmosphere. HPLC indicated that there was still starting material left, hence 120 mg of N,N'-Dimethylbarbituric acid and 6 mg of tetrakis(triphenylphosphine) palladium (0) were added to the mixture obtained and stirring was continued overnight until the reaction was deemed complete. The mixture obtained was diluted with DCM and washed with 10% $K_2CO_3$ (2×), the combined aqueous phases were washed with DCM and the combined organic layers obtained were dried over $Na_2SO_4$ and evaporated to dryness. An orange residue was obtained which was subjected to column chromatography (EtOAc/ $Et_3N$ 50:1 and EtOH). The title compound was obtained in the form of orange-red crystals.

Step 2: 12-epi-12-desvinyl-14-O-{{4-[(3-Amino-propylcarbamoyl)-methyl]-phenylsulfanyl}-acetyl}-12-aminomethyl mutilin dihydrochloride 100 mg of 12-epi-12-desvinyl-14-O-{{4-[(3-tert-Butoxy-carbonylamino-propylcarbamoyl)-methylphenylsulfanyl]}-acetyl}-12-aminomethyl mutilin was dissolved in 0.5 mL of DCM, treated with 5 mL of 1N HCl in diethyl ether and stirred at rt for 1 h. A precipitate formed and was collected with suction filtration, washed 5× with diethyl ether, dried 1 h at a rotary evaporator and purified via reverse chromatography with acetonitrile/$H_2O$ (0-75%). The according fractions were identified by HPLC, freed from organic solvent and lyophilized overnight. The title compound was obtained in the form of colourless crystals.

MS m/e: 588 [M$^+$+H].

According, e.g. analogously, to a method as conventional, or according, e.g. analogously to a method as set out under Example 1 above, but using appropriate starting materials, the compounds of formula $I_{EX}$, wherein $R_{1EX}$ and $R_{2EX}$ are as defined in Table 2 are prepared. Chemical characterisation data are also set out in Table 2.

TABLE 2

| Example | | $R_{2EX}$ | $R_{1EX}$ |
|---|---|---|---|
| 15 | 12-epi-12-desvinyl-14-O-{{4-[(3-Amino-propylcarbamoyl)-methyl]-phenylsulfanyl}-acetyl}-12-[(benzylamino)-methyl] mutilin dihydrochloride<br>$^1$H-NMR (200 MHz, DMSO-d$_6$): 7.29 (d, 2H, arom., J = 8 Hz), 7.21 (d, 2H, arom., J = 8 Hz), 5.41 (d, 1H, H-14, J = 7 Hz), 3.78 (s, 2H H-22), 1.34 (s, 3H, H-15), 0.86 (s, 3H, H-18), 0.80 (d, 3H, H-17, J = 5.8 Hz), 0.56 (d, 3H, H-16, J = 5.4 Hz)<br>MS m/e: 678 [M$^+$ + H] | | |
| 16 | 12-epi-12-desvinyl-14-O-{{4-[(3-Amino-propylcarbamoyl)-methyl]-phenylsulfanyl}-acetyl}-12-[(4-guanidinomethyl-benzylamino)-methyl] mutilin trihydrochloride<br>MS m/e: 750 [M$^+$ + H]<br>The required tert-Butyl (NE)-N-[[[4-(aminomethyl)phenyl]-methylamino]-(tert-butoxycarbonylamino)-methylene]-carbamate was prepared in analogy to: J. Med. Chem, 44(18), 2950; 2001 | | |
| 17 | 12-epi-12-desvinyl-14-O-{{4-[(3-Amino-propylcarbamoyl)-methyl]-phenylsulfanyl}-acetyl}-12-[(6-hydroxy-hexylamino)-methyl] mutilin dihydrochloride<br>$^1$H-NMR (200 MHz, DMSO-d$_6$): 7.29 (d, 2H, arom., J = 8 Hz), 7.20 (d, 2H, arom., J = 8 Hz), 5.44 (d, 1H, H-14, J = 7 Hz), 3.80 (s, 2H H-22), 1.35 (s, 3H, H-15), 0.85 (s, 3H, H-18), 0.80 (d, 3H, H-17, J = 6.2 Hz), 0.58 (d, 3H, H-16, J = 5.6 Hz)<br>MS m/e: 688 [M$^+$ + H] | | |

TABLE 2-continued

| Example | | $R_{2EX}$ | $R_{1EX}$ |
|---|---|---|---|
| 18 | 12-epi-12-desvinyl-14-O-{{4-[(3-Amino-propylcarbamoyl)-methyl]-phenylsulfanyl}-acetyl}-12-[(2,3-dihydroxypropylamino)-methyl] mutilin dihydrochloride<br>$^1$H-NMR (200 MHz, DMSO-$d_6$): 7.28 (d, 2H, arom., J = 8 Hz), 7.18 (d, 2H, arom., J = 8 Hz), 3.80 (s, 2H, H-22), 1.33 (s, 3H, H-15), 0.80 (d, 3H, H-17, J = 5 Hz), 0.58 (d, 3H, H-16, J = 5.6 Hz)<br>MS m/e: 662 [M$^+$ + H]<br>(2,2-Dimethyl-[1,3]dioxolan-4-yl)-methylamine was used as intermediate for step 4 | | |
| 19 | 12-epi-12-desvinyl-14-O-{{4-[(3-Amino-propylcarbamoyl)-methyl]-phenylsulfanyl}-acetyl}-12-[(4-piperidylamino)-methyl] mutilin trihydrochloride<br>MS m/e: 671 [M$^+$ + H] | | |
| 20 | 12-epi-12-desvinyl-14-O-{{4-[(3-Amino-propylcarbamoyl)-methyl]-phenylsulfanyl}-acetyl}-12-[(3-morpholin-4-yl-propylamino)-methyl] mutilin trihydrochloride<br>MS m/e: 715 [M$^+$ + H] | | |

TABLE 2-continued

| Example | | $R_{2EX}$ | $R_{1EX}$ |
|---|---|---|---|
| 21 | 12-epi-12-desvinyl-14-O-{{4-[(3-Amino-propylcarbamoyl)-methyl]-phenylsulfanyl}-acetyl}-12-[(3-dimethylamino-propylamino)-methyl] mutilin trihydrochloride<br>MS m/e: 673 [M$^+$ + H] | *(4-substituted phenyl with -CH$_2$-C(O)-NH-(CH$_2$)$_3$-NH$_2$)* | *(-CH$_2$-NH-(CH$_2$)$_3$-N(CH$_3$)$_2$)* |
| 22 | 12-epi-12-desvinyl-14-O-{{4-[(3-Amino-propylcarbamoyl)-methyl]-phenylsulfanyl}-acetyl}-12-[(S)-5-amino-5-ethoxycarbonyl-pentylamino-methyl] mutilin trihydrochloride<br>MS m/e: 745 [M$^+$ + H]<br>The necessary Lysine-(N$^2$—BOC)-ethyl ester was prepared from N$^2$—BOC-Lysine using EtOH/1.1 eq of sulfuric acid | *(4-substituted phenyl with -CH$_2$-C(O)-NH-(CH$_2$)$_3$-NH$_2$)* | *(lysine ethyl ester linked via -CH$_2$-NH-)* |

EXAMPLE 23

12-epi-12-desvinyl-14-O-{[4-(4-Aminomethyl-benzylcarbamoyl)-phenylsulfanyl]-acetyl}-12-[(6-amino-hexylamino)-methyl] mutilin trihydrochloride

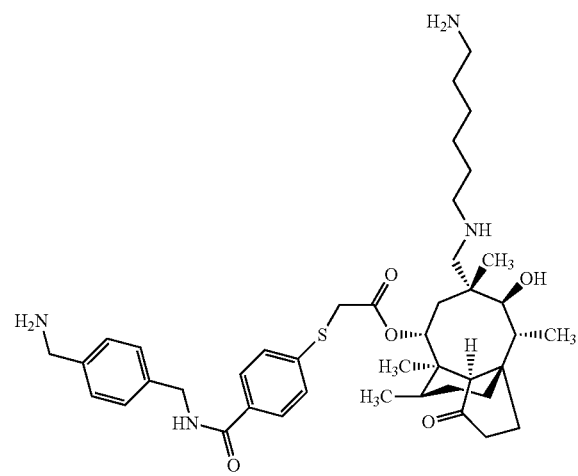 [SMILES: C[C@@H]1CC[C@@]23CCC(=O)[C@H]2[C@]1(C)[C@H](OC(=O)CSc1ccc(C(=O)NCc2ccc(CN)cc2)cc1)C[C@](C)(CNCCCCCCN)[C@@H](O)[C@@H]3C]

was obtained similarly and in analogy to a method as set out in Example 1, but using appropriate starting materials.

$^1$H-NMR (200 MHz, DMSO-d$_6$): 7.86 (d, 2H, arom., J=8 Hz), 7.44-7.31 (m, 6H, arom.), 5.46 (d, 1H, H-14, J=6.6 Hz), 5.36 (d, 1H, 11-OH, J=5.6 Hz), 4.44 (d, 2H, Ph-CH$_2$—CO—, J=5.2 Hz), 3.97 (s, 2H, H-22), 1.35 (s, 3H, H-15), 0.87 (s, 3H, H-18), 0.80 (d, 3H, H-17, J=6.2 Hz), 0.59 (d, 3H, H-16, J=5.6 Hz).

MS m/e: 735 [M$^+$+H].

Preparation of the intermediate Thioacetic acid S-{4-[4-(tert-butoxycarbonylamino-methyl)-benzyl-carbamoyl]-phenyl} ester Step a: Thioacetic acid S-(4-chlorocarbonyl-phenyl) ester 4.48 g of 4-acetylsulfanylbenzoic acid was dissolved in 50 mL of DCM, treated with 5.8 mL of oxalyl chloride and one drop of DMF and the mixture obtained was stirred at rt for 90 min. The volatiles were distilled off in vacuo leaving the title compound as residue, Step b: Thioacetic acid S-{4-[4-(tert-butoxycarbonylamino-methyl)-benzylcarbamoyl]-phenyl} ester 820 mg of tert-butyl N-[[4-(aminomethyl)-phenyl]-methyl]-carbamate and 421 mg of TEA was dissolved in 10 mL of DCM, cooled in an ice bath and 725 mg of thioacetic acid S-(4-chlorocarbonyl-phenyl) ester, dissolved in 5 mL of DCM, was slowly added. The mixture obtained was stirred for 30 min at rt, the phases were separated, the organic phase obtained was washed successively with 2N HCl and 5% aqueous NaHCO$_3$ solution, dried over Na$_2$SO$_4$ and evaporated to dryness. The title compound was obtained in the form of pale brown crystals.

According, e.g. analogously, to a method as conventional, or according, e.g. analogously to a method as set out under Examples 1 and 23 above, but using appropriate starting materials, the compounds of formula $I_{EX}$, wherein $R_{1EX}$ and $R_{2EX}$ are as defined in Table 3 are prepared. Chemical characterisation data are also set out in Table 3.

TABLE 3

| Example | | $R_{2EX}$ | $R_{2EX}$ |
|---|---|---|---|
| 24 | 12-epi-12-desvinyl-14-O-{[4-(4-Aminomethylbenzylcarbamoyl)-phenylsulfanyl]-acetyl}-12-[(6-guanidino-hexylamino)-methyl] mutilin trihydrochloride<br>$^1$H-NMR (200 MHz, DMSO-d$_6$): 9.23 (t, 1H, NH, J = 5.2 Hz), 7.86 (d, 2H, arom., J = 8 Hz), 7.44-7.24 (m, 6H, arom.), 5.46 (d, 1H, H-14, J = 6.8 Hz), 1.36 (s, 3H, H-15), 0.86 (s, 3H, H-18), 0.78 (d, 3H, H-17, J = 6 Hz), 0.58 (d, 3H, H-16, J = 5 Hz)<br>MS m/e: 777 [M$^+$ + H] | | |
| 25 | 12-epi-12-desvinyl-14-O-{[(4-Piperazinylcarbamoyl)-phenylsulfanyl]-acetyl}-12-[(6-guanidino-hexylamino)-methyl] mutilin trihydrochloride<br>MS m/e: 727 [M$^+$ + H] | | |
| 26 | 12-epi-12-desvinyl-14-O-{[4-(4-Aminomethyl-piperidine-1-carbonyl)-phenylsulfanyl]-acetyl}-12-[(6-guanidino-hexylamino)-methyl] mutilin trihydrochloride<br>$^1$H-NMR (200 MHz, DMSO-d$_6$): 7.40 (d, 2H, arom., J = 8 Hz), 7.38 (d, 2H, arom., J = 8 Hz), 5.45 (d, 1H, H-14, J = 7 Hz), 3.93 (s, 2H, H-22), 1.34 (s, 3H, H-15), 0.86 (s, 3H, H-18), 0.80 (d, 3H, H-17, J = 6.4 Hz), 0.55 (d, 3H, H-16, J = 5.6 Hz)<br>MS m/e: 755 [M++ H] | | |
| 27 | 12-epi-12-desvinyl-14-O-{(4-[(Piperidin-4-ylmethyl)-carbamoyl]-phenylsulfanyl)-acetyl}-12-[(6-guanidino-hexylamino)-methyl] mutilin trihydrochloride<br>$^1$H-NMR (200 MHz, DMSO-d$_6$): 7.82 (d, 2H, arom., J = 8 Hz), 7.38 (d, 2H, arom., J = 8 Hz), 4.95 (d, 1H, H-14, J = 6.6 Hz), 5.37 (d, 1H, 11-OH, J = 5.4 Hz), 1.35 (s, 3H, H-15), 0.87 (s, 3H, H-18), 0.80 (d, 3H, H-17, J = 5.8 Hz), 0.58 (d, 3H, H-16, J = 5.5 Hz)<br>MS m/e: 755 [M$^+$ + H] | | |

TABLE 3-continued

| Example | | $R_{2EX}$ | $R_{2EX}$ |
|---|---|---|---|
| 28 | 12-epi-12-desvinyl-14-O-{(4-[(Pyridin-4-ylmethyl)-carbamoyl]-phenylsulfanyl)-acetyl}-12-[(6-amino-hexylamino)-methyl] mutilin trihydrochloride<br>$^1$H-NMR (200 MHz, DMSO-d$_6$): 9.53 (bs, 1H, —CO—NH), 7.99-7.89 (m, 6H, arom.), 7.42 (d, 1H, arom., J = 8 Hz), 5.47 (d, 1H, H-14, J = 6.8 Hz), 3.98 (s, 2H, H-22), 1.36 (s, 3H, H-15), 0.90 (s, 3H, H-18), 0.80 (d, 3H, H-17, J = 6 Hz), 0.59 (d, 3H, H-16, J = 5.2 Hz)<br>MS m/e: 707 [M$^+$ + H] | | |
| 29 | 12-epi-12-desvinyl-14-O-{[3-(3-Aminopropylcarbamoyl)-phenylsulfanyl]-acetyl}-12-[(6-guanidino-hexylamino)-methyl] mutilin trihydrochloride<br>$^1$H-NMR (200 MHz, DMSO-d$_6$): 7.70 (d, 1H, arom., J = 8 Hz), 7.50-7.37 (m, 3H, arom.), 5.45 (d, 1H, H-14, J = 6.8 Hz), 5.34 (bs, 1H, 11-OH), 3.93 (s, 2H, H-22), 3.72 (bs, 1H, H-11), 1.33 (s, 3H, H-15), 0.86 (s, 3H, H-18), 0.80 (d, 3H, H-17, J = 6.2 Hz), 0.56 (d, 3H, H-16, J = 5.4 Hz)<br>MS m/e: 715 [M$^+$ + H] | | |
| 30 | 12-epi-12-desvinyl-14-O-{[4-(3-Acetylamino-propylcarbamoyl)-phenylsulfanyl]-acetyl}-12-[(3-amino-propylamino)-methyl] mutilin dihydrochloride<br>$^1$H-NMR (200 MHz, DMSO-d$_6$): 7.81 (d, 2H, arom., J = 8 Hz), 7.39 (d, 2H, arom., J = 8 Hz), 5.47 (d, 1H, H-14, J = 8 Hz), 5.34 (bs, 1H, 11-OH), 3.96 (s, 2H, H-22), 1.36 (s, 3H, H-15), 0.89 (s, 3H, H-18), 0.81 (d, 3H, H-17, J = 5.8 Hz), 0.59 (d, 3H, H-16, J = 5.8 Hz)<br>MS m/e: 673 [M$^+$ + H] | | |
| 31 | 12-epi-12-desvinyl-14-O-{[4-(3-Formylamino-propylcarbamoyl)-phenylsulfanyl]-acetyl}-12-[(3-amino-propylamino)-methyl] mutilin dihydrochloride<br>$^1$H-NMR (200 MHz, DMSO-d$_6$): 8.82 (bs, 1H, —CO—NH), 7.81 (d, 2H, arom., J = 8 Hz), 7.38 (d, 2H, arom., J = 8 Hz), 5.46 (d, H, H-14, J = 6.8 Hz), 5.36 (bs, 1H, 11-OH), 3.96 (s, 2H, H-22), 1.36 (s, 3H, H-15), 0.88 (s, 3H, H-18), 0.82 (bs, 3H, H-17), 0.59 (d, 3H, H-16, J = 5.4 Hz).<br>MS m/e: 659 [M$^+$ + H] | | |

TABLE 3-continued

| Example | | $R_{2EX}$ | $R_{2EX}$ |
|---|---|---|---|
| 32 | 12-epi-12-desvinyl-14-O-{[4-(3-Amino-propylcarbamoyl)-phenylsulfanyl]-acetyl}-12-[(3-amino-propylamino)-methyl] mutilin trihydrochloride<br>$^1$H-NMR (200 MHz, DMSO-d$_6$): 7.85 (d, 2H, arom., J = 8 Hz), 7.39 (d, 2H, arom., J = 8 Hz), 5.46 (d, 1H, H-14, H = 6 Hz), 1.36 (s, 3H, H-15), 0.88 (s, 3H, H-18), 0.81 (d, 3H, H-17, J = 6 Hz), 0.59 (d, 3H, H-16, J = 5.6 Hz)<br>MS m/e: 665 [M$^-$ + Cl] | | |
| 33 | 12-epi-12-desvinyl-14-O-{(4-[(3-Aminopropylcarbamoyl)-phenylsulfanyl)-acetyl}-12-[(4-aminomethyl-benzylamino)-methyl] mutilin trihydrochloride<br>$^1$H-NMR (200 MHz, DMSO-d$_6$): 7.84 (d, 2H, arom., J = 8 Hz), 7.68 (d, 2H, arom., J = 6 Hz), 7.55 (d, 2 H, arom., J = 10 Hz), 7.37 (d, 2H, arom., J = 8 Hz), 5.43 (d, 1H, H-14, J = 7 Hz), 5.31 (bs, 1H, 11-OH), 1.34 (s, 3H, H-15), 0.83-0.77 (m, 6H, H-17, H-18), 0.57 (d, 3H, H-16, J = 5.4 Hz).<br>MS m/e: 693 [M$^+$ + H] | | |
| 34 | 12-epi-12-desvinyl-14-O-{(4-[(3-Aminopropylcarbamoyl)-phenylsulfanyl]-acetyl}-12-[(6-amino-hexylamino)-methyl] mutilin trihydrochloride<br>$^1$H-NMR (200 MHz, DMSO-d$_6$): 7.84 (d, 2H, arom., J = 8 Hz), 7.38 (d, 2H, arom., J = 8 Hz), 5.46 (d, 1H, H-14, J = 6 Hz), 5.35 (bs, 1H, 11-OH), 1.35 (s, 3H, H-15), 0.88 (s, 3H, H-18), 0.80 (d, 3H, H-17, J = 5.4 Hz), 0.58 (d, 3H, H-16, J = 5.4 Hz).<br>MS m/e: 673 [M$^+$ + H] | | |
| 35 | 12-epi-12-desvinyl-14-O-{[4-(3-Aminopropylcarbamoyl)-phenylsulfanyl]-acetyl}-12-[(6-guanidino-hexylamino)-methyl] mutilin trihydrochloride<br>$^1$H-NMR (200 MHz, DMSO-d$_6$): 8.81 (t, 1H, CO—NH, J = 5.4 Hz), 7.84 (d, 2H, arom., J = 8 Hz), 7.38 (d, 2H, arom., J = 8 Hz), 5.46 (d, 1H, H-14, J = 6.8 Hz), 3.96 (s, 2H, H-22), 1.35 (s, 3H, H-15), 0.88 (s, 3H, H-18), 0.80 (d, 3H, H-17, J = 5.8 Hz), 0.58 (d, 3H, H-16, J = 5.6 Hz)<br>MS m/e: 715 [M$^+$ + H] | | |

TABLE 3-continued

| Example | | R$_{2EX}$ | R$_{2EX}$ |
|---|---|---|---|
| 36 | 12-epi-12-desvinyl-14-O-{[4-(3-Aminopropylcarbamoyl)-phenylsulfanyl]-acetyl}-12-[(8-amino-octylamino)-methyl]mutilin trihydrochloride<br>$^1$H-NMR (200 MHz, DMSO-d$_6$): 7.84 (d, 2H, arom., J = 8 Hz), 7.38 (d, 2H, arom., J = 8 Hz), 5.45 (d, 1H, H-14, J = 6.6 Hz), 3.96 (s, 2H, H-22), 1.35 (s, 3H, H-15), 0.87 (s, 3H, H-18), 0.79 (d, 3H, H-17, J = 5 Hz), 0.58 (d, 3H, H-16, J = 5 Hz).<br>MS m/e: 701 [M$^+$ + H]<br>The reductive amination was done as described in Example 1, step 4 using 10 eq of 1,8-diaminooctane | | |
| 37 | 12-epi-12-desvinyl-14-O-{[4-(3-Aminopropylcarbamoyl)-phenylsulfanyl]-acetyl}-12-[(10-amino-decylamino)-methyl] mutilin trihydrochloride<br>$^1$H-NMR (200 MHz, DMSO-d$_6$): 7.84 (d, 2H, arom., J = 8 Hz), 7.38 (d, 2H, arom., J = 8 Hz), 5.45 (d, 1H, H-14, J = 7 Hz), 3.96 (s, 2H, H-22), 1.35 (s, 3H, H-15), 0.87 (s, 3H, H-18), 0.79 (d, 3H, H-17, J = 5 Hz), 0.58 (d, 3H, H-16, J = 5 Hz).<br>MS m/e: 729 [M$^+$ + H]<br>The reductive amination was done as described in Example 1, step 4 using 10 eq of 1,10-diaminodecane | | |
| 38 | 12-epi-12-desvinyl-14-O-{(4-Carbamoyl-phenylsulfanyl)-acetyl}-12-[(6-guanidino-hexylamino)-methyl] mutilin dihydrochloride<br>$^1$H-NMR (200 MHz, DMSO-d$_6$): 7.82 (d, 2H, arom., J = 8 Hz), 7.37 (d, 2H, arom., J = 8 Hz), 5.44 (d, 1H, H-14, J = 7 Hz), 3.96 (s, 2H, H-22), 1.35 (s, 3H, H-15), 0.87 (s, 3H, H-18), 0.80 (d, 3H, H-17, J = 6 Hz), 0.58 (d, 3H, H-16, J = 5.6 Hz).<br>MS m/e: 658 [M$^+$ + H]<br>The required 4-mercapto-benzamide is e.g. described in: WO 2003/062235 | | |
| 39 | 12-epi-12-desvinyl-14-O-{[4-(3-Amino-propylcarbamoyl)-phenylsulfanyl]-acetyl}-12-{[3-(3-amino-propoxy)-propylamino)]-methyl} mutilin trihydrochloride<br>$^1$H-NMR (200 MHz, DMSO-d$_6$): 7.83 (d, 2H, arom., J = 8 Hz), 7.38 (d, 2H, arom., J = 8 Hz), 5.44 (bs, 2H, H-14, 11-OH), 3.96 (s, 2H, H-22), 1.35 (s, 3H, H-15), 0.91 (s, 3H, H-18), 0.80 (d, 3H, H-17, J = 6 Hz), 0.58 (d, 3H, H-16, J = 5.4 Hz);<br>MS m/e: 689 [M$^+$ + H] | | |

TABLE 3-continued

| Example | | $R_{2EX}$ | $R_{2EX}$ |
|---|---|---|---|
| 40 | 12-epi-12-desvinyl-14-O-{[4-(3-Amino-propylcarbamoyl)-phenylsulfanyl]-acetyl}-12[(2-pyridin-4-yl-ethylamino)-methyl] mutilin trihydrochloride<br>MS m/e: 679 [M⁺ + H] | | |
| 41 | 12-epi-12-desvinyl-14-O-{[4-(6-Amino-hexylcarbamoyl)-phenylsulfanyl]-acetyl}-12-[(6-guanidino-hexylamino)-methyl] mutilin trihydrochloride<br>$^1$H-NMR (200 MHz, DMSO-d$_6$): 7.76 (d, 2H, arom., J = 8 Hz), 7.38 (d, 2H, arom., J = 8 Hz), 5.45 (d, 1H, H-14, J = 7.6 Hz), 3.95 (s, 2H, H-22), 1.34 (s, 3H, H-15), 0.87 (s, 3H, H-18), 0.81 (d, 3H, H-17, J = 5.8 Hz), 0.58 (d, 3H, H-16, J = 5.6 Hz).<br>MS m/e: 757 [M⁺ + H] | | |
| 42 | 12-epi-12-desvinyl-14-O-{[4-(2-Amino-ethylcarbamoyl)-phenylsulfanyl]-acetyl}-12-[(6-guanidino-hexylamino)-methyl] mutilin trihydrochloride<br>$^1$H-NMR (200 MHz, DMSO-d$_6$): 7.79 (d, 2H, arom., J = 8 Hz), 7.40 (d, 2H, arom., J = 8 Hz), 5.46 (d, 1H, H-14, J = 7.2 Hz), 3.96 (s, 2H, H-22), 1.34 (s, 3H, H-15), 0.94 (s, 3H, H-18), 0.81 (d, 3H, H-17, J = 6.4 Hz), 0.58 (d, 3H, H-16, J = 5.6 Hz).<br>MS m/e: 701 [M⁺ + H] | | |
| 43 | 12-epi-12-desvinyl-14-O-{[4-(3-Aminopropylcarbamoyl)-phenylsulfanyl]-acetyl}-12-{[3-(4-aminomethyl-phenyl)-propylamino]-methyl} mutilin trihydrochloride<br>MS m/e: 721 [M⁺ + H]<br>The required [4-(3-Amino-propyl)-benzyl]-carbamic acid tert-butyl ester is described in:<br>Bioorganic & Medicinal Chemistry Letters, 16(11), 2986-2990; 2006 | | |

According, e.g. analogously, to the method as set out under Example 100 below, but using appropriate starting materials, the compounds of formula $I_{EX}$, wherein $R_{1EX}$ and $R_{2EX}$ are as defined in Table 4 are prepared. Chemical characterisation data are also set out in Table 4.

$^1$H-NMR (200 MHz, DMSO-$d_6$): 5.47 (d, 1H, H-14, J=7.8 Hz), 1.40 (s, 3H, H-15), 0.98 (s, 3H, H-18), 0.82 (d, 3H, H-17, J=5.8 Hz), 0.64 (d, 3H, H-16, J=5 Hz)

MS m/e: 608 [M$^+$+H]

TABLE 4

| Example | | $R_{2EX}$ | $R_{1EX}$ |
|---|---|---|---|
| 44 | 12-epi-12-desvinyl-14-O-{[(4-Aminomethyl-cyclohexyl)-methylsulfanyl]-acetyl}-12-[(6-amino-hexylamino)-methyl] mutilin trihydrochloride $^1$H-NMR (200 MHz, DMSO-$d_6$): 5.46 (d, 1H, H-14, J = 6.6 Hz), 5.39 (bs, 1H, 11-OH), 1.39 (s, 3H, H-15), 0.96 (s, 3H, H-18), 0.81 (d, 3H, H-17, J = 5.8 Hz), 0.64 (d, 3H, H-16, J = 5.2 Hz) MS m/e: 622 [M$^+$ + H] | | |
| 45 | 12-epi-14-O-[(1-Methyl-piperidin-4-ylsulfanyl)-acetyl}-12-[(6-guanidino-hexylamino)-methyl] mutilin trihydrochloride MS m/e: 638 [M + NH$_4$$^+$] The required 1-Methyl-piperidine-4-thiol is described in: J.Med.Chem., 36(22), 3251-64; 1993 | | |
| 46 | 12-epi-14-O-[(Piperidin-4-ylsulfanyl)-acetyl]-12-[(6-amino-hexylamino)-methyl] mutilin trihydrochloride $^1$H-NMR (200 MHz, DMSO-$d_6$): 5.48 (d, 1H, H-14, J = 6.2 Hz), 5.35 (bs, 1H, 11-OH), 1.41 (s, 3H, H-15), 0.99 (s, 3H, H-18), 0.83 (d, 3H, H-17, J = 6 Hz), 0.65 (d, 3H, H-16, J = 5 Hz) MS m/e: 580 [M$^+$ + H] | | |

EXAMPLE 47

12-epi-12-desvinyl-14-O-{[(4-Aminomethyl-cyclohexyl)-sulfanyl]-acetyl}-12-[(6-amino-hexylamino)-methyl] mutilin trihydrochloride

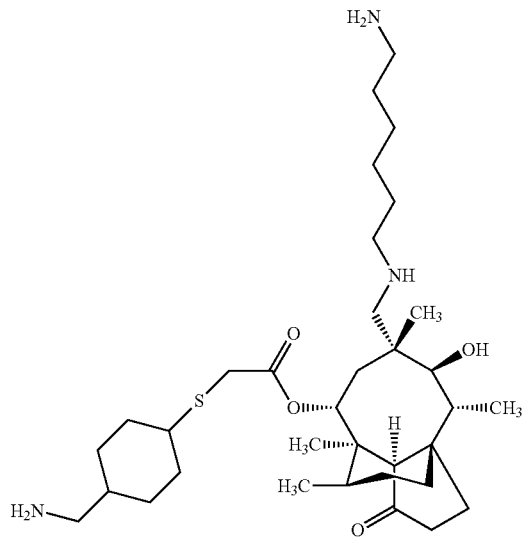 [SMILES: C[C@@H]1CC[C@@]23CCC(=O)[C@H]2[C@]1(C)[C@H](OC(=O)CSC1CCC(CN)CC1)C[C@](C)(CNCCCCCCN)[C@@H](O)[C@@H]3C]

was obtained similarly and in analogy to a method as set out in Example 1, but using appropriate starting materials.

Preparation of the required Thioacetic acid S-[4-(tert-butoxycarbonylamino-methyl)-cyclohexyl] ester Step a: Methanesulfonic acid 4-(tert-butoxycarbonylamino-methyl)-cyclohexyl ester To a solution of 71 g of (4-Hydroxy-cyclohexylmethyl)-carbamic acid tert-butyl ester and 93.9 g of TEA in 1500 mL of DCM was added dropwise 34.1 g of MsCl at 0° C. over 30 min. After addition, the mixture was allowed to warm to rt and stirred at this temperature for 2.5 h. The reaction mixture was quenched by addition of water, the resulting mixture was extracted 3× with DCM. The combined organic layers were washed 3× with 0.5 M citric acid, 2× with a saturated solution of NaHCO$_3$, water and dried over Na$_2$SO$_4$. After filtration, the filtrate was concentrated under reduced pressure to afford the title compound as yellow oil, and the crude product was used directly for the next step.

Step b: Thioacetic acid S-[4-(tert-butoxycarbonylamino-methyl)-cyclohexyl]ester

A suspension of 52 g of methanesulfonic acid 4-(tert-butoxycarbonylamino-methyl)-cyclohexyl ester and 48.3 g of potassium thioacetate in 1 L of dry DMF was heated to 50° C. under N$_2$ and stirred for 16 h. TLC showed the reaction was completed. The reaction mixture was cooled to 25° C. and poured into ice-water, the resulting mixture was extracted 5× with MTBE. The combined organic layers were washed 3× with citric acid, 2× with saturated solution of NaHCO$_3$, 2× with brine and dried over Na$_2$SO$_4$. After filtration, the filtrate was concentrated under reduce pressure to afford the crude product as red oil. The crude product was purified by silica gel chromatography (PE/EtOAc=40:1 to 15:1) to afford the title compound as red solid.

EXAMPLE 48

12-epi-12-desvinyl-14-O-{[4-(3-Amino-propyl)-phenylsulfanyl]-acetyl}-12-[(6-amino-hexylamino)-methyl] mutilin trihydrochloride Step 2: 12-epi-12-desvinyl-14-O-{{4-[3-(2,2,2-Trifluoro-acetylamino)-propyl]-phenylsulfanyl}-acetyl}-12-[(6-amino-hexylamino)-methyl] mutilin dihydrochloride

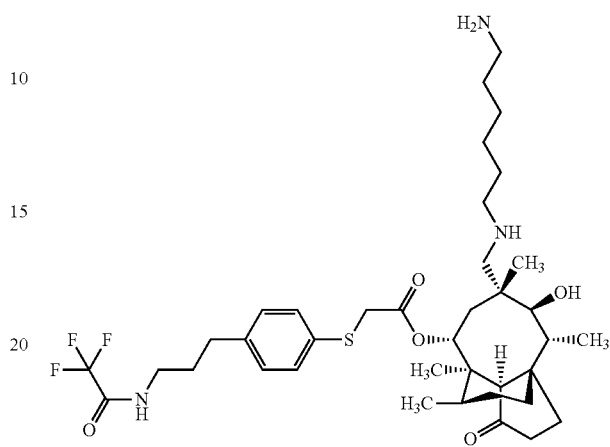

The compound was prepared in analogy to compound 1, step 6.

Step 3: 12-epi-12-desvinyl-14-O-{[4-(3-Amino-propyl)-phenylsulfanyl]-acetyl}-12-[(6-amino-hexylamino)-methyl] mutilin trihydrochloride

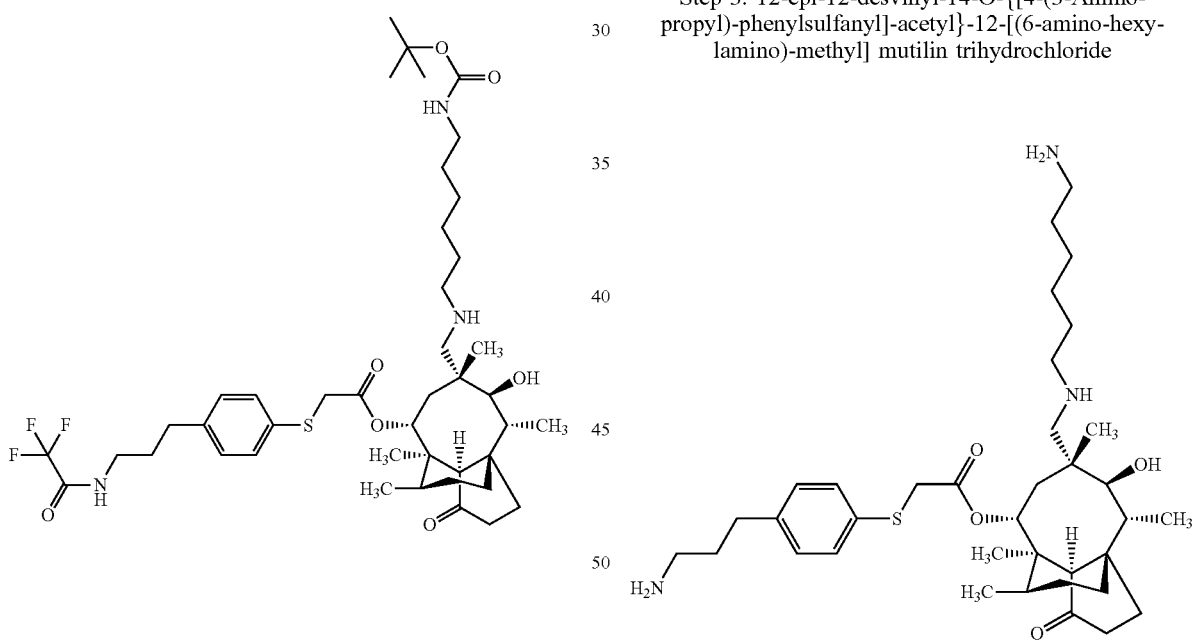

246 mg of 12-epi-12-desvinyl-14-O-{{4-[3-(2,2,2-Trifluoro-acetylamino)-propyl]-phenylsulfanyl}-acetyl}-12-[(6-amino-hexylamino)-methyl] mutilin was dissolved in 10 mL of MeOH/H$_2$O under ice-cooling and 0.51 mL of 1N NaOH was added. The reaction was stirred for 1 h under ice-cooling, poured into water and extracted with 3× with EtOAc. The organic phase was washed with brine, dried over Na$_2$SO$_4$ and evaporated to dryness. The resulting colorless foam was purified by reversed phase chromatography (eluant: acetonitrile in 1N HCl 0-35%) yielding the title compound.

$^1$H-NMR (200 MHz, DMSO-d$_6$): 7.58 (d, 2H, arom., J=5.6 Hz), 7.49 (d, 2H, arom., J=14 Hz), 4.43 (d, 1H, H-14, Step 1: 12-epi-12-desvinyl-14-O-{{4-[3-(2,2,2-Trifluoro-acetylamino)-propyl]-phenylsulfanyl}-acetyl}-12-[(6-tert-butoxycarbonylamino-hexylamino)-methyl]mutilin The compound was prepared in analogy to compound 1, step 5 using 2,2,2-Trifluoro-N-[3-(4-mercapto-phenyl)-propyl]-acetamide as intermediate.

J=6.6 Hz), 1.34 (s, 3H, H-15), 0.84 (s, 3H, H-18), 0.79 (d, 3H, H-17, J=5.4 Hz), 0.54 (d, 3H, H-16, J=5.6 Hz)

MS m/e: 630 [M$^+$+H]

Preparation of the required 2,2,2-Trifluoro-N-[3-(4-mercapto-phenyl)-propyl]-acetamido Step a:
2,2,2-Trifluoro-N-(3-phenyl-propyl)-acetamide To a solution of 50 g of benzenepropanamine in 600 mL of MeOH was added dropwise 300 mL of CF$_3$COOEt over a period of 0.5 h at 0° C. After stirring at 20° C. for 16 h, the solvent was removed under reduced pressure. The crude product was washed with PE to give the title compound as white solid.

Step b: 4-[3-(2,2,2-Trifluoro-acetylamino)-propyl]-benzenesulfonyl chloride

To a solution of 32 g of 2,2,2-Trifluoro-N-(3-phenyl-propyl)-acetamide in 32 mL of DCM was added dropwise 200 mL of ClSO$_3$H below −10° C. Then the reaction mixture was warmed to 15° C. and stirred for 20 h. The reaction mixture was poured into ice water at 05° C. and extracted 2× with DCM. The organic phase was washed with brine, dried over Na$_2$SO$_4$ and concentrated to give the crude product which was purified by silica gel chromatography (PE/EtOAc=10:1) to afford the title compound as yellow solid.

Step c: 2,2,2-Trifluoro-N-[3-(4-mercapto-phenyl)-propyl]-acetamide

To a solution of 100 mL of H$_2$SO$_4$ in 600 mL of water was added slowly at 0° C. 102 g of Zinc dust and a solution of 49 g of 4-[3-(2,2,2-Trifluoro-acetylamino)-propyl]-benzenesulfonyl chloride in 50 mL of THF. Then the reaction mixture was heated to 60° C. and stirred for 4 h after which it was cooled and poured into DCM. The mixture was filtered and separated. The organic phase was washed with brine, dried over Na$_2$SO$_4$ and concentrated to give the crude product which was washed with PE/EtOAc=40:1 to afford the title compound as white solid.

EXAMPLE 49

12-epi-12-desvinyl-14-O-{(4-[(3-Amino-propylcarbamoyl)-methyl]-phenylsulfanyl)-acetyl}-12-{[(3-amino-propyl)-acetylamino]-methyl} mutilin dihydrochloride was prepared analogously to the method as set out under Example 1, step 6, but using the appropriate starting materials.

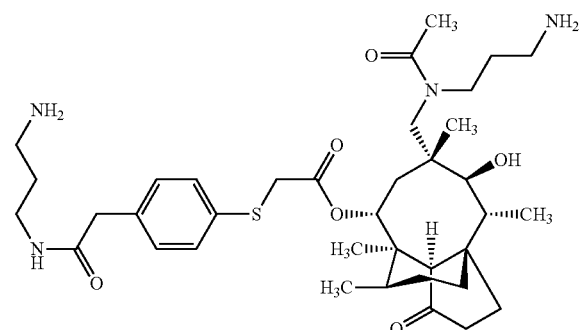

$^1$H-NMR (200 MHz, DMSO-d$_6$): 7.29-7.22 (m, 4H, arom.), 5.44 (d, 1H, H-14, J=5.6 Hz), 3.78 (s, 2H H-22), 2.05 (s, 3H, N-acetyl), 1.30 (s, 3H, H-15)

MS m/e: 687 [M$^+$+H]

Preparation of the intermediate 12-epi-12-desvinyl-14-O-{([4-(3-tert-Butoxycarbonylamino-propylcarbamoyl)-methyl]-phenylsulfanyl)-acetyl}-12-{[(3-tert-butoxycarbonylamino-propyl)-acetylamino]-methyl} mutilin 500 mg of 12-epi-12-desvinyl-14-O-{([4-(3-tert-Butoxycarbonylamino-propylcarbamoyl)-methyl]-phenylsulfanyl)-acetyl}-12-[(3-tert-butoxycarbonylamino-propylamino)-methyl] mutilin (Example 1, step 5) was dissolved in 7 mL of DCM. To the mixture obtained 134 μl of diisopropylethylamine was added and the mixture obtained was cooled in an ice bath, treated with 61.5 μl of f acetic anhydride in 1 mL of DCM and stirring at rt was maintained for 1 h. To the mixture obtained 12 μl of base and 6 μl of acetic anhydride was added and stirring was continued for 30 min and the reaction was deemed to be complete. The mixture obtained was washed with 5% NaHCO$_3$, the aqueous phase was back-extracted with DCM, the combined organic phases obtained were washed with water and brine, dried over Na$_2$SO$_4$ and evaporated to dryness to yield the title compound.

EXAMPLE 50

12-epi-12-desvinyl-14-O-{(4-[(3-Amino-propylcarbamoyl)-methyl]-phenylsulfanyl)-acetyl}-12-(3-amino-propylcarbamoyl) mutilin dihydrochloride Step 1: Pleuromutilintosylate-12-epi-12-desvinyl-12-carboxylic acid

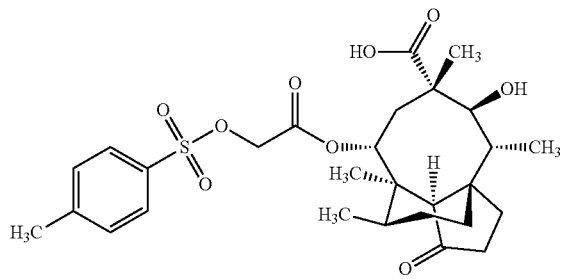

2.5 g of 12-epi-2-desvinyl-14-O-[(toluene-4-sulfonyloxy)-acetyl]-12-formyl mutilin (Example 1, step 3) was dissolved in 50 mL of DMF, 14.4 g of oxone was added and the resulting slurry was stirred at rt for 4 d. The mixture obtained was diluted with 300 mL of water, 50 mL 2N HCl was added and the mixture obtained was extracted with EtOAc (2×). The phases obtained were separated and the combined organic phases were washed with water, dried over Na$_2$SO$_4$, brought to dryness (semisolid residue) and subjected to column chromatography (eluent: EtOAc/toluene=2:1). The title compound was obtained in the form of colourless crystals.

$^1$H-NMR (200 MHz, DMSO-d$_6$): 7.79 (d, 2H, arom., J=8 Hz), 7.44 (d, 2H, arom., J=8 Hz), 5.41 (d, 1H, H-14, J=7.2 Hz), 4.70 AB-system (2H, H-22, $v_A$=4.78, $v_B$=4.70, J=16

Hz), 2.4 (s, 3H, tosyl-CH$_3$), 1.30 (s, 3H, H-15), 1.08 (s, 3H, H-18), 0.80 (d, 3H, H-17, J=5 Hz), 0.52 (d, 3H, H-16, J=5.6 Hz).

Step 2: 12-epi-12-desvinyl-14-O-[(Toluene-4-sulfonyloxy)-acetyl]-12-(3-tert-butoxycarbonylaminopropylcarbamoyl) mutilin

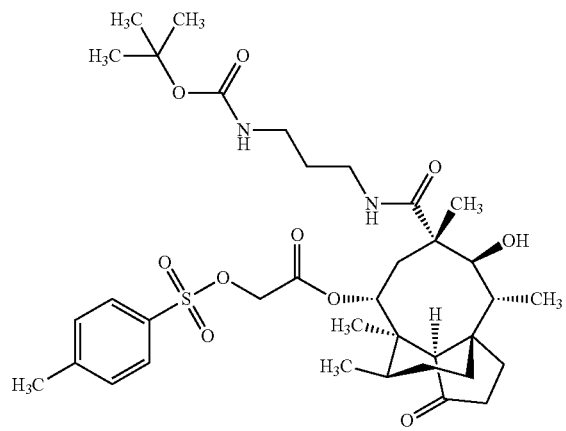

500 mg of pleuromutilintosylate-12-epi-12-desvinyl-12-carboxylic acid, 158 mg of N-BOC-1,3-diaminopropane, 139 mg of HOBt and 174 mg of N-(3-dimethylaminopropyl)-N'-ethylcarbodiimide hydrochloride was dissolved in 10 mL of DCM and the mixture obtained was stirred at rt for 2 h. From the mixture obtained the phases were separated and the organic phase obtained was washed successively with 10% aqueous K$_2$CO3, (2×), 1N HCl (1×) and 5% aqueous NaHCO$_3$ solution (1×), dried over Na$_2$SO$_4$, evaporated to dryness and the evaporation residue obtained was subjected to chromatography over silica gel with toluene/EtOAc=2:1, 1:1, 1:2, 1:5 and EtOAc. The title compound was obtained in the form of a colourless foam.
MS m/e: 729 [M+Na]

Step 3: 12-epi-14-O-{{[(3-tert-Butoxycarbonylamino-propylcarbamoyl)-methyl]-phenylsulfanyl}-acetyl}-12-(3-tert-butoxycarbonylamino-propylcarbamoyl) motilin

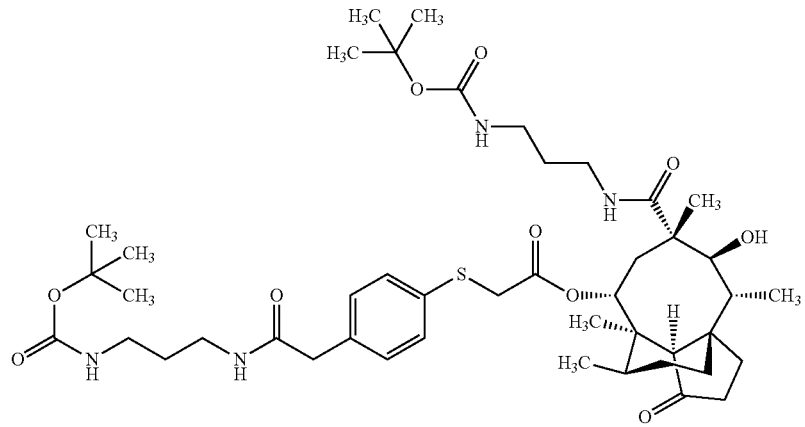 [SMILES: C[C@@H]1CC[C@@]23CCC(=O)[C@H]2[C@]1(C)[C@H](OC(=O)CSc1ccc(CC(=O)NCCCNC(=O)OC(C)(C)C)cc1)C[C@](C)(C(=O)NCCCNC(=O)OC(C)(C)C)[C@@H](O)[C@@H]3C]

314 mg of S-{4-[(3-tert-butoxycarbonylamino-propylcarbamoyl)-methyl]-phenyl} thioacetic acid ester was dissolved in 10 mL of MeOH/H$_2$O 4:1, 229 µl of 5 M aqueous K$_2$CO$_3$ solution was added and after 5 minutes 404 mg of 12-epi-12-desvinyl-14-O-[(Toluene-4-sulfonyloxy)-acetyl]-12-(3-tert-butoxycarbonylamino-propylcarbamoyl) mutilin. The mixture obtained was stirred for 15 min, diluted with 75 mL of water and extracted with EtOAc (2×). The combined organic layers obtained were washed with 2N NaOH (2×), 1N HCl and 5% NaHCO$_3$, dried over Na$_2$SO$_4$ and evaporated to dryness. Pale yellow crystals were obtained which were subjected to chromatography (eluent: EtOAc/toluene=2:1). The title compound was obtained in the form of colourless crystals.
MS m/e: 859 [M$^+$+H].

Step 4: 12-epi-12-desvinyl-14-O-{{4-[(3-Amino-propylcarbamoyl)-methyl]-phenylsulfanyl}-acetyl}-12-{[(3-amino-propylcarbamoyl) mutilin dihydrochloride

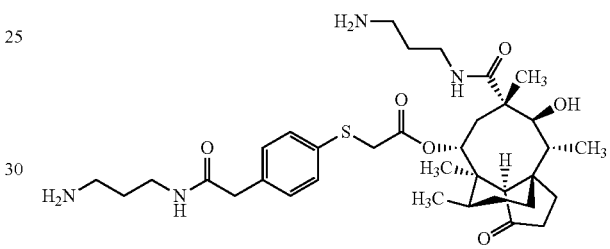

BOC-deprotection was carried out as described in Example 1, Step 6.
$^1$H-NMR (200 MHz, DMSO-d$_6$): 8.38 (t, 1H, CO—NH, J=4 Hz), 7.25 (d, 2H, arom., J=8 Hz), 7.17 (d, 2H, arom., J=8 Hz), 5.39 (d, 1H, H-14, J=7.4 Hz), 1.31 (s, 3H, H-15), 1.04 (s, 3H, H-18), 0.79 (d, 3H, H-17, J=6 Hz), 0.57 (d, 3H, H-16, J=5.8 Hz);
MS m/e: 659 [M$^+$+H].

According, e.g. analogously, to the method as set out under Example 50 above, but using appropriate starting materials, the compound of formula $I_{EX}$, wherein $R_{1EX}$ and $R_{2EX}$ are as defined in Table 5 is prepared. Chemical characterisation data are also set out in Table 5.

TABLE 5

| Example | | $R_{2EX}$ | $R_{1EX}$ |
|---|---|---|---|
| 51 | 12-epi-12-desvinyl-14-O-{[4-(3-Amino-propylcarbamoyl)-phenylsulfanyl]-acetyl}-12-(4-aminomethyl-benzylcarbamoyl) mutilin dihydrochloride<br>$^1$H-NMR (200 MHz, DMSO-$d_6$): 8.74 (t, 1H, Ph—CO—NH, J = 6 Hz), 8.17 (bs, 1H, —CO—NH), 7.79 (d, 2H, arom., J = 8 Hz), 7.41-7.35 (m, 4H, arom.), 7.26 (d, 2H, arom., J = 8 Hz), 5.44 (d, 1H, H-14, J = 6.8 Hz), 4.62 (d, 1H, 11-OH, J = 6.8 Hz), 4.40-4.04 (m, 2H, Ph—CH$_2$), 1.31 (s, 3H, H-15), 1.12 (s, 3H, H-18), 0.81 (d, 3H, H-17, J = 6 Hz), 0.59 (d, 3H, H-16, J = 5.2 Hz)<br>MS m/e: 707 [M$^+$ + H] | | |

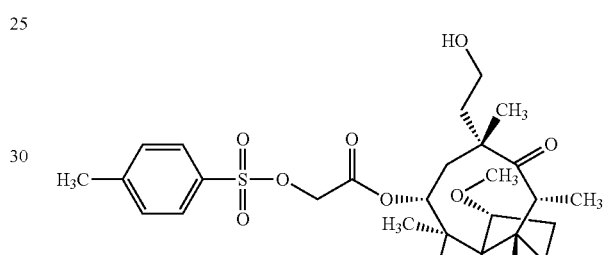

EXAMPLE 52

12-epi-12-desvinyl-14-O-{{4-[(3-Amino-propylcarbamoyl)-methyl]-phenylsulfanyl}-acetyl}-12-[2-(3-amino-propylamino)-ethyl] mutilin trihydrochloride Step 1: 4-epi-12-epi-3-deoxo-11-deoxy-3-methoxy-11-oxo-14-O-[(toluene-4-sulfonyloxy)-acetyl] mutilin

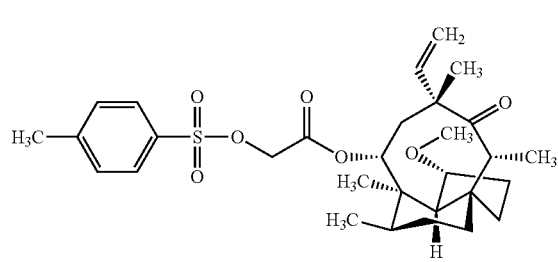

59.1 g of 12-epi-Pleuromutilintosylate was dissolved/suspended in 1 L of MeOH, 66.8 mL of trimethylorthoformate was added and the mixture obtained was cooled in an ice-bath. 13.15 mL of H$_2$SO$_4$ conc. was added while keeping the temperature below 10° C. The mixture obtained was stirred for further 30 min at this temperature, the ice bath was removed and the mixture obtained was stirred for a further 120 h. 21.5 g of solid NaHCO$_3$ was added followed by addition of water until there was no more gas evolution. A precipitate formed and was filtered off, washed with water and the mother liquors obtained were extracted with DCM. The precipitate and the extracts were combined and dried.

The synthesis of 4-epi-3-methoxy-pleuromutilin is e.g. disclosed in: Tetrahedron, 36, 1807 (1980).

Step 2: 4-epi-12-epi-3-deoxo-11-deoxy-12-desvinyl-12-(2-hydroxy-ethyl)-3-methoxy-11-oxo-14-O-[(toluene-4-sulfonyloxy)-acetyl] mutilin 1.5 g of 4-epi-12-epi-3-deoxo-11-deoxy-3-methoxy-11-oxo-14-O-[(toluene-4-sulfonyloxy)-acetyl] mutilin was dissolved in 15 mL of dry THF and 10.8 mL of 0.5 M 9-Borabicyclo[3.3.1]nonane was added at rt. The resulting mixture was refluxed for 5 min, cooled to rt over 30 min and, eventually in an ice bath; 600 µl of 35% H$_2$O$_2$ and 600 µl of 3N NaOH was added. The mixture obtained was allowed to warm to rt over 30 min and the resulting slurry was partitioned between water and EtOAc. The phases were separated, the organic phase obtained was washed with water, dried over Na$_2$SO$_4$, evaporated to dryness and the evaporation residue was subjected to chromatography (eluent: toluene/acetone=10:1). The title compound in the form of a colourless solid was obtained.

$^1$H-NMR (200 MHz, DMSO-$d_6$): 7.83 (d, 2H, arom., J=8 Hz), 7.48 (d, 2H, arom., J=8 Hz), 4.76, AB-system (2H, H-22, $v_A$=4.80, $v_B$=4.71, J=16 Hz), 4.40-4.35 (m, —OH), 2.41 (s, 3H, tosyl-CH$_3$), 1.18 (s, 3H, H-15), 1.08 (s, 3H, H-18), 0.88 (d, 3H, H-17, J=6 Hz), 0.63 (d, 3H, H-16, J=6.2 Hz).

Step 3: 4-epi-12-epi-14-O-{{4-[(3-tert-butoxycarbonylamino-propylcarbamoyl)-methyl]-phenylsulfanyl}-acetyl}-3-deoxo-11-deoxy-12-desvinyl-12-(2-hydroxy-ethyl)-3-methoxy-11-oxo mutilin

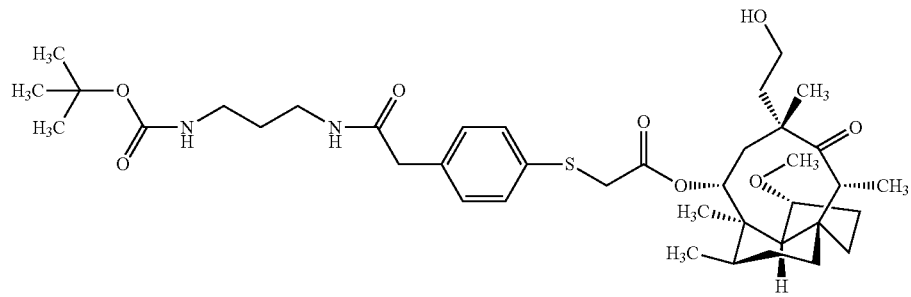

430 mg of S-{4-[(3-tert-butoxycarbonylamino-propylcarbamoyl)-methyl]-phenyl} thioacetic acid ester was dissolved in 10 mL of MeOH, 470 µl of 5 M aqueous $K_2CO_3$ solution was added and stirring was maintained for 10 min. To the mixture obtained 663 mg 4-epi-12-epi-3-deoxo-11-deoxy-12-desvinyl-12-(2-hydroxy-ethyl)-3-methoxy-11-oxo-14-O-[(toluene-4-sulfonyloxy)-acetyl] mutilin in 2 mL of MeOH was added and the resulting yellow mixture was stirred for 2 h. From the mixture obtained solvent was evaporated and the evaporation residue was partitioned between EtOAc and brine. The phases were separated, the organic phase obtained was dried over $Na_2SO_4$ and evaporated to dryness. The title compound was obtained in the form of a yellow foam.

$^1$H-NMR (200 MHz, DMSO-$d_6$): 8.06-8.02 (m, 1H, —CO—NH—), 7.29 (d, 2H, arom., J=8 Hz), 7.18 (d, 2H, arom., J=8 Hz), 5.63 (d, 1H, H-14, J=10 Hz), 4.39-4.35 (m, 1H, —OH), 3.84 (bs, 2H, H-22), 1.10 (s, 3H, H-18), 0.87 (d, 3H, H-17, J=5.8 Hz), 0.67 (d, 3H, H-16, J=6.4 Hz).

Step 4: 4-epi-12-epi-14-O-{{4-[(3-tert-butoxycarbonylamino-propylcarbamoyl)-methyl]-phenylsulfanyl}-acetyl}-3-deoxo-11-deoxy-12-desvinyl-3-methoxy-11-oxo-12-(2-oxo-ethyl) mutilin

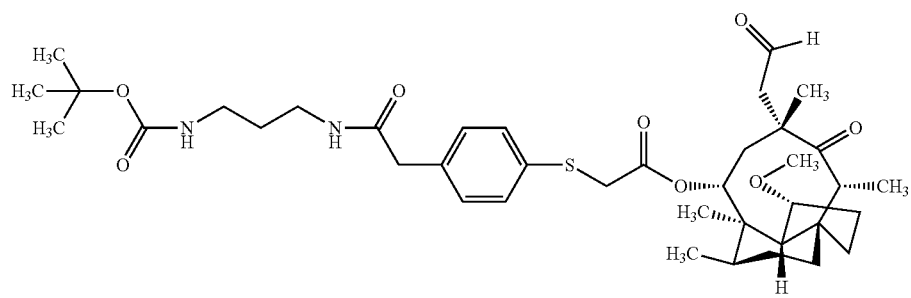

200 mg of 4-epi-12-epi-14-O-{{4-[(3-tert-butoxycarbonylamino-propylcarbamoyl)-methyl]-phenylsulfanyl}-acetyl}-3-deoxo-11-deoxy-12-desvinyl-12-(2-hydroxy-ethyl)-3-methoxy-11-oxo mutilin was dissolved in 10 mL of DCM with stirring, 118 mg Dess-Martin-periodinane was added and stirring was maintained overnight. From the mixture obtained the phases were separated, the organic phase was washed with 5% aqueous $NaHCO_3$ solution, dried over $Na_2SO_4$ and brought to dryness. The title compound in the form of colourless foamy crystals was obtained which was used without purification for the next step.

Step 5: 4-epi-12-epi-14-O-{{4-[(3-tert-butoxycarbo-
nylamino-propylcarbamoyl)-methyl]-phenylsulfa-
nyl}-acetyl}-12-[2-(3-tert-butoxycarbonylamino-
propylamino)-ethyl]-3-deoxo-11-deoxy-12-desvinyl-
3-methoxy-11-oxo mutilin

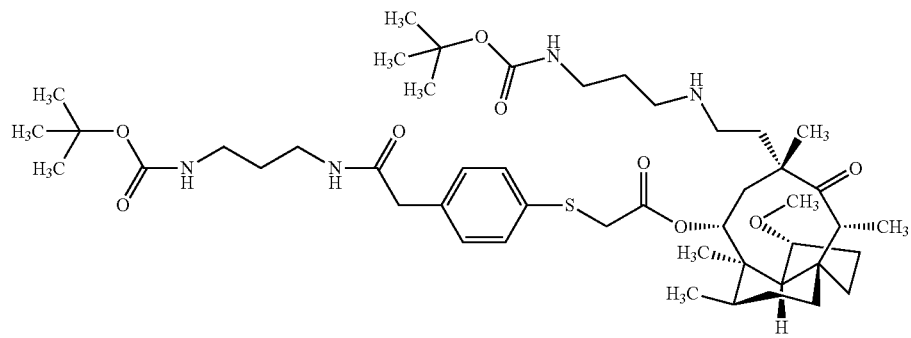

200 mg of 4-epi-12-epi-14-O-{{4-[(3-tert-butoxycarbo-nylamino-propylcarbamoyl)-methyl]-phenylsulfanyl}-acetyl}-3-deoxo-11-deoxy-12-desvinyl-3-methoxy-11-oxo-12-(2-oxo-ethyl) mutilin and 50 mg of N-BOC-1,3-diaminopropane were dissolved in 5 mL of DCM, 0.5 g of molecular sieves was added and stirring was maintained for 3 h. To the mixture obtained 150 mg of sodium triacetoxyborohydride was added and stirring was continued overnight. From the mixture obtained the phases were separated, the organic phase obtained was diluted with DCM, washed with 5% aqueous $NaHCO_3$ solution, dried over $Na_2SO_4$ and evaporated to dryness. The title compound was obtained in the form of colourless crystals which were used without purification for the next step. MS m/e: 874 [M$^+$+H].

Step 6: 12-epi-12-desvinyl-14-O-{{4-[(3-amino-propylcarbamoyl)-methyl]-phenylsulfanyl}-acetyl}-12-[2-(3-amino-propylamino)-ethyl] mutilin trihydrochloride

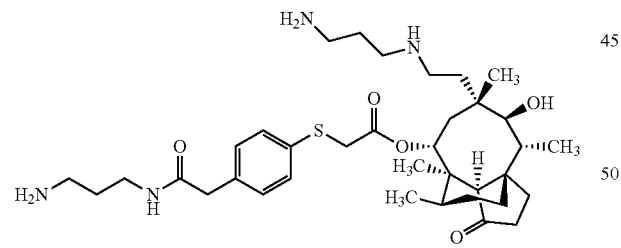

BOC-deprotection of the product obtained in step 5, which resulted also in methyl ether cleavage and retro hydride shift as described in Tetrahedron, 36, 1807 (1980), was carried out as described in Example 1, Step 6.

$^1$H-NMR (200 MHz, DMSO-d$_6$): 7.28 (d, 2H, arom., J=8 Hz), 7.23 (d, 2H, arom., J=8 Hz), 5.44 (d, 1H, H-14, J=7 Hz), 4.71 (d, 1H, 11-OH, J=4.4 Hz), 1.33 (s, 3H, H-15), 0.78 (bs, 6H, H-17, H-18), 0.58 (d, 3H, H-16, J=5.8 Hz); MS m/e: 659 [M$^+$+H].

According, e.g. analogously, to a method as set out under Example 1, but using appropriate starting materials, the compounds of formula I$_{EX}$, wherein R$_{1EX}$ and R$_{2EX}$ are as defined in Table 6 are prepared. Chemical characterisation data are also set out in Table 6.

TABLE 6

| Example | | $R_{2EX}$ | $R_{1EX}$ |
|---|---|---|---|
| 53 | 12-epi-12-desvinyl-14-O-[(3-Hydroxymethyl-phenylsulfanyl)-acetyl]-12-[(3-amino-propylamino)-methyl] mutilin dihydrochloride<br>$^1$H-NMR (200 MHz, DMSO-d$_6$): 7.31-7.12 (m, 4 H, arom.), 5.45 (d, 1H, H-14, J = 6.6 Hz), 4.45 (s, 2H, Ph—CH$_2$), 3.82 (s, 2H, H-22), 1.36 (s, 3H, H-15), 0.88 (s, 3H, H-18), 0.81 (d, 2H, H-17, J = 5.6 Hz), 0.58 (d, 3H, H-16, J = 4.8 Hz)<br>MS m/e: 561 [M$^+$ + H] | | |
| 54 | 12-epi-12-desvinyl-14-O-[(3-Hydroxymethyl-phenylsulfanyl)-acetyl]-12-[(6-amino-hexylamino)-methyl] mutilin dihydrochloride<br>$^1$H-NMR (200 MHz, DMSO-d$_6$): 7.31-7.11 (m, 4 H, arom.), 5.44 (d, 1H, H-14, J = 7.8 Hz), 4.45 (s, 2H, Ph—CH$_2$), 3.82 (s, 2H, H-22), 1.36 (s, 3H, H-15), 0.87 (s, 3H, H-18), 0.78 (d, 2H, H-17, J = 6.6 Hz), 0.58 (d, 3H, H-16, J = 5.6 Hz)<br>MS m/e: 603 [M$^+$ + H] | | |
| 55 | 12-epi-12-desvinyl-14-O-[(3-Hydroxymethyl-phenylsulfanyl)-acetyl]-12-[(4-aminomethyl-benzylamino)-methyl] mutilin dihydrochloride<br>$^1$H-NMR (200 MHz, DMSO-d$_6$): 7.30-7.08 (m, 8H arom.), 5.47 (d, 1H, H-14, J = 7 Hz), 4.42 (s, 2H, Ph—CH$_2$—OH), 1.31 (s, 3H, H-15), 0.80 (s, 3H, H-18), 0.80-0.77 (6H, H-17, H-18), 0.59 (d, 3H, H-16, J = 5.8 Hz)<br>MS m/e: 623 [M$^+$ + H] | | |
| 56 | 12-epi-12-desvinyl-14-O-[(3-Hydroxymethyl-phenylsulfanyl)-acetyl]-12-[(6-guanidino-hexylamino)-methyl] mutilin dihydrochloride<br>$^1$H-NMR (200 MHz, DMSO-d$_6$): 7.39-7.11 (m, 4 H, arom.), 5.44 (d, 1H, H-14, J = 7.6 Hz), 4.45 (s, 2H, Ph—CH$_2$), 3.82 (s, 2H, H-22), 1.36 (s, 3H, H-15), 0.87 (s, 3H, H-18), 0.80 (d, 2H, H-17, J = 6.4 Hz), 0.58 (d, 3H, H-16, J = 5.6 Hz).<br>MS m/e: 645 [M$^+$ + H] | | |
| 57 | 12-epi-12-desvinyl-14-O-[(4-Hydroxymethyl-phenylsulfanyl)-acetyl]-12-[(3-amino-propylamino)-methyl] mutilin dihydrochloride<br>$^1$H-NMR (200 MHz, DMSO-d$_6$): 7.32 (d, 2H, arom., J = 8.4 Hz), 7.25 (d, 2H, J = 8.4 Hz), 5.44 (d, 1H, H-14, J = 6 Hz), 4.45 (s, 2H, Ph—CH$_2$), 3.8 (s, 2H, H-22), 1.36 (s, 3H, H-15), 0.87 (s, 3H, H-18) 0.58 (d, 3H, H-16, J = 5.4 Hz).<br>MS m/e: 561 [M$^+$ + H] | | |
| 58 | 12-epi-12-desvinyl-14-O-[(4-Hydroxymethyl-phenylsulfanyl)-acetyl]-12-[(4-aminomethyl-benzylamino)-methyl] mutilin dihydrochloride<br>$^1$H-NMR (200 MHz, DMSO-d$_6$): 7.66 (d, 2H, arom., J = 8 Hz), 7.53 (d, 2H, arom., J = 8 Hz), 7.30 (d, 2H, arom., J = 8 Hz), 7.23 (d, 2H, arom., J = 8.2 Hz), 5.41 (d, 1H, H-14, J = 6.8 Hz), 1.34 (s, 3H, H-15), 0.56 (d, 3H, H-16, J = 5.8 Hz).<br>MS m/e: 623 [M$^+$ + H] | | |

TABLE 6-continued

| Example | | $R_{2EX}$ | $R_{1EX}$ |
|---|---|---|---|
| 59 | 12-epi-12-desvinyl-14-O-[(4-Hydroxymethyl-phenylsulfanyl)-acetyl]-12-[(6-amino-hexylamino)-methyl] mutilin dihydrochloride<br>$^1$H-NMR (200 MHz, DMSO-d$_6$): 7.32 (d, 2H, arom., J = 8 Hz), 7.25 (d, 2H, arom., J = 8 Hz), 5.43 (d, 1H, H-14, J = 7.4 Hz), 4.44 (s, 2H, Ph—CH$_2$), 3.87 (s, 2H H-22), 1.35 (s, 3H, H-15), 0.86 (s, 3H, H-18), 0.80 (d, 3H, H-17, J = 5.8 Hz), 0.57 (d, 3H, H-16, J = 5.8 Hz)<br>MS m/e: 603 [M$^+$ + H] | 4-hydroxymethylphenyl group | 6-aminohexylamino group |
| 60 | 12-epi-12-desvinyl-14-O-[(3,5-Bis-hydroxymethyl-phenylsulfanyl)-acetyl]-12-[(3-amino-propylamino)-methyl] mutilin dihydrochloride<br>$^1$H-NMR (200 MHz, DMSO-d$_6$): 5.45 (d, 1H, H-14, J = 6.6 Hz), 4.44 (s, 4H, 2 Ph—CH$_2$), 1.40 (s, 3H, H-15), 3.81 s (H-22), 1.37 (s, 3H, H-15), 0.90 (s, 3H, H-18), 0.81 (d, 2H, H-17, J = 5.4 Hz), 0.59 (d, 3H, H-16, J = 5.4 Hz).<br>MS m/e: 591 [M$^+$ + H]<br>The required intermediate (3-Hydroxymethyl-5-mercapto-phenyl)-methanol was prepared in analogy to the synthesis of (3-Hydroxymethyl-4-mercapto-phenyl)-methanol as described in J. Antibiot. 51 (8), 722; (1998) | 3,5-bis(hydroxymethyl)phenyl group | 3-aminopropylamino group |
| 61 | 12-epi-12-desvinyl-14-O-{[(2,3,5,6-Tetrafluoro-4-hydroxymethyl)-phenylsulfanyl]-acetyl}-12-[(4-aminomethyl-benzylamino)-methyl]-mutilin dihydrochloride<br>$^1$H-NMR (200 MHz, DMSO-d$_6$): 7.67 (d, 2H arom., H = 8 Hz), 7.54 (d, 2H arom., J = 8 Hz), 5.40 (d, 1H, H-14, J = 6.4 Hz), 4.56 (s, 2H, Ph—CH$_2$—OH), 1.33 (s, 3H, H-15), 0.86 (s, 3H, H-18), 0.80 (d, 3H, H-17, J = 5.6 Hz), 0.53 (d, 3H, H-16, J = 6.2 Hz).<br>MS m/e: 695 [M$^+$ + H]<br>The required intermediate (2,3,5,6-Tetrafluoro-4-mercapto-phenyl)-methanol was prepared by LAH-reduction of 2,3,5,6-Tetrafluoro-4-mercaptobenzoic acid | tetrafluoro-hydroxymethylphenyl group | 4-aminomethylbenzylamino group |
| 62 | 12-epi-12-desvinyl-14-O-{[(1R,2R,4R)-4-Amino-2-hydroxy-cyclohexylsulfanyl]-acetyl}-12-[(3-amino-propylamino)-methyl] mutilin trihydrochloride<br>$^1$H-NMR (200 MHz, DMSO-d$_6$): 7.31-7.12 (m, 4 H, arom.), 5.48 (d, 1H, H-14, J = 7.8 Hz), 1.40 (s, 3H, H-15), 1.00 (s, 3H, H-18), 0.83 (d, 2H, H-17, J = 6.2 Hz), 0.64 (d, 3H, H-16, J = 4.8 Hz).<br>MS m/e: 568 [M$^+$ + H]<br>The required intermediate [3-((1R,3R,4R)-3-Hydroxy-4-mercapto-cyclohexylamino)-propyl]-carbamic acid tert-butyl ester is described in EP2399904 | 4-amino-2-hydroxycyclohexyl group | 3-aminopropylamino group |
| 63 | 12-epi-12-desvinyl-14-O-{[(1R,2R,4R)-4-Amino-2-hydroxy-cyclohexylsulfanyl]-acetyl}-12-[(4-aminomethyl-benzylamino)-methyl] mutilin trihydrochloride<br>$^1$H-NMR (200 MHz, DMSO-d$_6$): 7.67 (d, 2H, arom., J = 8 Hz), 7.53 (d, 2H, arom., J = 8 Hz), 5.45 (d, 1H, H-14, H = 7.4 Hz), 1.39 (s, 3H, H-15), 0.93 (s, 3H, H-18), 0.81 (d, 3H, H-17, J = 6 Hz), 0.63 (d, 3H, H-16, J = 5.4 Hz)<br>MS m/e: 630 [M$^+$ + H] | 4-amino-2-hydroxycyclohexyl group | 4-aminomethylbenzylamino group |

| Example | | $R_{2EX}$ | $R_{1EX}$ |
|---|---|---|---|
| 64 | 12-epi-12-desvinyl-14-O-[(2-Hydroxy-ethylsulfanyl)-acetyl]-12-[(4-aminomethyl-benzylamino)-methyl] mutilin dihydrochloride<br>$^1$H-NMR (200 MHz, DMSO-$d_6$): 7.67 (d, 2H arom., J = 8 Hz), 7.54 (d, 2H arom., J = 8 Hz), 5.46 (d, 1H, H-14, J = 7 Hz), 1.40 (s, 3H, H-15), 0.93 (s, 3H, H-18), 0.82 (d, 3H, H-17, J = 6.2 Hz), 0.65 (d, 3H, H-16, J = 5.2 Hz)<br>MS m/e: 561 [M$^+$ + H] | HO–CH$_2$CH$_2$– | 4-(H$_2$N-CH$_2$)-C$_6$H$_4$-CH$_2$-NH-CH$_2$- |
| 65 | 12-epi-12-desvinyl-14-O-[(2-Amino-ethylsulfanyl)-acetyl]-12-[(4-aminomethyl-benzylamino)-methyl] mutilin trihydrochloride<br>$^1$H-NMR (200 MHz, DMSO-$d_6$): 7.69 (d, 2H arom., J = 8 Hz), 7.54 (d, 2H arom., J = 8 Hz), 5.47 (d, 1H, H-14, J = 6.8 Hz), 1.41 (s, 3H, H-15), 0.95 (s, 3H, H-18), 0.81 (d, 3H, H-17, J = 5.8 Hz), 0.65 (d, 3H, H-16, J = 5.6 Hz)<br>MS m/e: 560 [M$^+$ + H] | H$_2$N-CH$_2$CH$_2$– | 4-(H$_2$N-CH$_2$)-C$_6$H$_4$-CH$_2$-NH-CH$_2$- |
| 66 | 12-epi-12-desvinyl-14-O-{[(5-Amino-4H-1,2,4-triazol-3-yl)-sulfanyl]-acetyl}-12-[(6-amino-hexylamino)-methyl] mutilin trihydrochloride<br>$^1$H-NMR (200 MHz, DMSO-$d_6$): 5.47 (d, 1H, H-14, J = 7 Hz), 5.33 (bs, 1H, 11-OH), 3.93 (s, 2H, H-22), 1.38 (s, 3H, H-15), 0.90 (s, 3H, H-18), 0.81 (d, 3H, H-17, J = 6.2 Hz), 0.60 (d, 3H, H-16, J = 5.2 Hz).<br>MS m/e: 579 [M$^+$ + H] | 5-amino-4H-1,2,4-triazol-3-yl | H$_2$N-(CH$_2$)$_6$-NH-CH$_2$- |
| 67 | 12-epi-12-desvinyl-14-O-[(2-Amino-ethylsulfanyl)-acetyl]-12-[(6-amino-hexylamino)-methyl] mutilin trihydrochloride<br>$^1$H-NMR (200 MHz, DMSO-$d_6$): 5.49 (d, 1H, H-14, J = 6.6 Hz), 3.77 (s, 2H, H-22), 1.42 (s, 3H, H-15), 1.01 (s, 3H, H-18), 0.83 (d, 3H, H-17, J = 6.2 Hz), 0.66 (d, 3H, H-16, J = 5.6 Hz).<br>MS m/e: 540 [M$^+$ + H] | H$_2$N-CH$_2$CH$_2$– | H$_2$N-(CH$_2$)$_6$-NH-CH$_2$- |
| 68 | 12-epi-12-desvinyl-14-O-[(Pyridin-4-ylsulfanyl)-acetyl]-12-[(6-amino-hexylamino)-methyl] mutilin trihydrochloride<br>$^1$H-NMR (200 MHz, DMSO-$d_6$): 8.36 (d, 2H, arom., J = 5.4 Hz), 7.27 (d, 2H, arom., J = 5.2 Hz), 5.52 (d, 1H, H-14, J = 6.6 Hz), 4.02 (s, 2H, H-22), 1.31 (s, 3H, H-15), 0.85 (s, 3H, H-18), 0.77 (d, 3H, H-17, J = 6.2 Hz), 0.60 (d, 3H, H-16, J = 5.4 Hz).<br>MS m/e: 574 [M$^+$ + H] | pyridin-4-yl | H$_2$N-(CH$_2$)$_6$-NH-CH$_2$- |
| 69 | 12-epi-12-desvinyl-14-O-[(Pyridin-4-ylsulfanyl)-acetyl]-12-[(6-guanidino-hexylamino)-methyl] mutilin trihydrochloride<br>$^1$H-NMR (200 MHz, DMSO-$d_6$): 8.39 (d, 2H, arom., J = 3.8 Hz), 7.29 (d, 2H, arom., J = 5 Hz), 5.50 (d, 1H, H-14, J = 6.8 Hz), 4.06 (s, 2H, H-22), 1.37 (s, 3H, H-15), 0.91 (s, 3H, H-18), 0.81 (d, 3H, H-17, J = 6.4 Hz), 0.61 (d, 3H, H-16, J = 5.4 Hz).<br>MS m/e: 616 [M$^+$ + H] | pyridin-4-yl | H$_2$N-C(=NH)-NH-(CH$_2$)$_6$-NH-CH$_2$- |

TABLE 6-continued

| Example | | $R_{2EX}$ | $R_{1EX}$ |
|---|---|---|---|
| 70 | 12-epi-12-desvinyl-14-O-[(3-Hydroxy-phenylsulfanyl)-acetyl]-12-[(6-amino-hexylamino)-methyl] mutilin dihydrochloride<br>$^1$H-NMR (200 MHz, DMSO-d$_6$): 7.07 (m, 1H, arom.), 7.71 (m, 2H, arom.), 6.57 (m, 1H, arom.), 5.48 (d, 1H, H-14, J = 7 Hz), 3.73 (s, 2H, H-22), 1.30 (s, 3H, H-15), 0.83 (s, 3H, H-18), 0.77 (d, 3H, H-17, J = 6.6 Hz), 0.58 (d, 3H, H-16, J = 5.2 Hz).<br>MS m/e: 589 [M$^+$ + H] | | |
| 71 | 12-epi-12-desvinyl-14-O-[(4-Fluoro-phenylsulfanyl)-acetyl]-12-[(6-amino-hexylamino)-methyl] mutilin dihydrochloride<br>$^1$H-NMR (200 MHz, DMSO-d$_6$): 7.44 (m, 2H, arom.), 7.17 (m, 2H, arom.), 5.46 (d, 1H, H-14, J = 7.8 Hz), 3.79 (m, 2H, H-22), 1.28 (s, 3H, H-15), 0.83 (s, 3H, H-18), 0.78 (d, 3H, H-17, J = 6.6 Hz), 0.56 (d, 3H, H-16, J = 5.6 Hz).<br>MS m/e: 591 [M$^+$ + H] | | |
| 72 | 12-epi-12-desvinyl-14-O-{[(7H-Purin-6-yl)-sulfanyl]-acetyl}-12-[(6-amino-hexylamino)-methyl] mutilin dihydrochloride<br>MS m/e: 615 [M$^+$ + H] | | |
| 73 | 12-epi-12-desvinyl-14-O-[(3-Amino-phenylsulfanyl)-acetyl]-12-[(3-amino-propylamino)-methyl] mutilin trihydrochloride<br>MS m/e: 546 [M$^+$ + H] | | |
| 74 | 12-epi-12-desvinyl-14-O-(Phenylsulfanyl-acetyl)-12-[(4-aminomethyl-benzylamino)-methyl] mutilin trihydrochloride<br>$^1$H-NMR (200 MHz, DMSO-d$_6$): 7.68 (d, 2H, arom., J = 8 Hz), 7.56 (d, 2H, arom., J = 8 Hz), 7.33-7.23 (m, 5H, arom.), 5.42 (d, 1H, H-14, J = 6.4 Hz), 3.83 (bs, 2H, H-22), 1.34 (s, 3H, H-15), 0.79 (bs, 6H, H-18, H-17), 0.55 (d, 3H, H-16, J = 5.8 Hz)<br>MS m/e: 593 [M$^+$ + H] | | |
| 75 | 12-epi-12-desvinyl-14-O-[(4-Fluoro-phenylsulfanyl)-acetyl]-12-[(4-aminomethyl-benzylamino)-methyl] mutilin trihydrochloride<br>MS m/e: 611 [M$^+$ + H] | | |

TABLE 6-continued

| Example | | $R_{2EX}$ | $R_{1EX}$ |
|---|---|---|---|
| 76 | 12-epi-12-desvinyl-14-O-[(Pyridin-2-ylsulfanyl)-acetyl]-12-[(4-aminomethyl-benzylamino)-methyl] mutilin trihydrochloride<br>$^1$H-NMR (200 MHz, DMSO-$d_6$): 8.32-8.30 (m, 1H, arom., J = 4.4 Hz), 7.70-7.54 (m, 5H, arom.), 7.36-7.32 (m, 1H, arom.), 7.12-7.06 (m, 1H, arom.), 5.45 (d, 1H, H-14, J = 7.8 Hz), 5.31 (bs, 1H, 11-OH), 3.94 (bs, 2H, H-22), 1.37 (s, 3H, H-15), 0.84-0.78 (m, 6H, H-18, H-17), 0.62 (d, 3H, H-16, J = 5.8 Hz)<br>MS m/e: 594 [M$^+$ + H] | | |
| 77 | 12-epi-12-desvinyl-14-O-[(Pyridin-4-ylsulfanyl)-acetyl]-12-[(4-aminomethyl-benzylamino)-methyl] mutilin trihydrochloride<br>$^1$H-NMR (200 MHz, DMSO-$d_6$): 8.56 (m, 2H, arom.), 7.67 (d, 2H, arom., J = 8 Hz), 7.54 (d, 2H, arom., J = 8 Hz), 7.48-7.45 (m, 2H, arom.), 5.46 (d, 1H, H-14, J = 7.2 Hz), 5.28 (d, 1H 11-OH, J = 4.8 Hz), 4.14 (bs, 2H, H-22), 1.34 (s, 3H, H-15), 0.85 (s, 3H, H-18), 0.78 (d, 3H, H-17, J = 6.4 Hz), 0.58 (d, 3H, H-16, J = 6 Hz)<br>MS m/e: 594 [M$^+$ + H] | | |

EXAMPLE 78

12-epi-12-desvinyl-14-O-{[1-(2-Amino-acetyl)-piperidin-4-yl-sulfanyl)]-acetyl}-12-[(4-aminomethyl-benzylamino)-methyl] mutilin trihydrochloride was obtained similarly and in analogy to a method as set out in Example 1, but using appropriate starting materials.

$^1$H-NMR (200 MHz, DMSO-$d_6$): 7.68 (d, 2H, arom., J=8 Hz), 7.54 (d, 2H, J=8 Hz), 5.46 (d, 1H, H-14, J=7.2 Hz), 5.32 (d, 1H, 11-OH, J=4 Hz), 1.37 (s, 3H, H-15), 0.92 (s, 3H, H-18), 0.81, (d, 3H, H-17, J=6.2 Hz), 0.64 (d, 3H, H-16, J=6 Hz)

MS m/e: 657 [M$^+$+H]

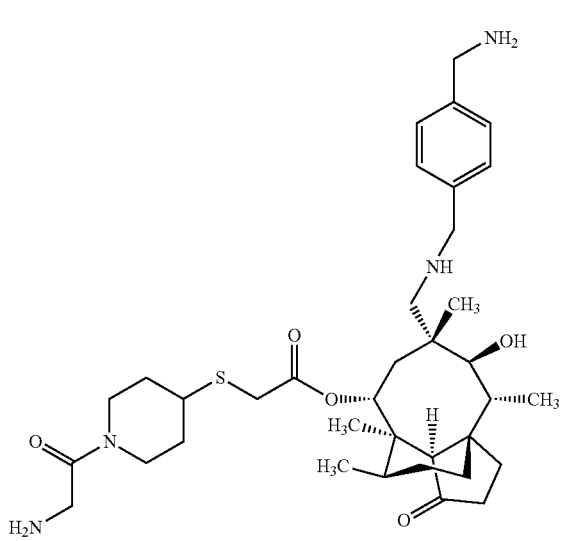 [SMILES: C[C@@H]1CC[C@@]23CCC(=O)[C@H]2[C@]1(C)[C@H](OC(=O)CSC1CCN(C(=O)CN)CC1)C[C@](C)(CNCc1ccc(CN)cc1)[C@@H](O)[C@@H]3C]

Preparation of the required Thioacetic acid S-[1-(2-tert-butoxycarbonylamino-acetyl)-piperidin-4-yl] ester Step a: 4-Methanesulfonyloxy-piperidine-1-carboxylic acid tert-butyl ester To a mixture of 10 g of 4-hydroxy-piperidine-1-carboxylic acid tert-butyl ester nd 12.57 g of TEA in 100 mL of DCM was added 7.09 g of MsCl dropwise at 0° C. under N$_2$. After addition, the resulting mixture was stirred at 20° C. for 4 hours. TLC showed the reaction was complete. The mixture was washed 2× with brine, dried over Na$_2$SO$_4$, filtered and concentrated to afford the title compound as white solid.

Step b: 4-Acetylsulfanyl-piperidine-1-carboxylic acid tert-butyl ester

To a solution of 13.50 g of 4-methanesulfonyloxy-piperidine-1-carboxylic acid tert-butyl ester in 140 mL of DMF was added 11.04 g of potassium ethanethioate in one portion at 20° C. under N$_2$. The mixture was stirred at 20° C. for 10 min. Then the reaction mixture heated to 60° C. and stirred for 16 hours. TLC showed the reaction was complete. The mixture was cooled to 20° C. and poured into ice-water and stirred for 20 min. The aqueous phase was extracted 2× with MTBE. The combined organic phase was washed 2× with brine, dried over Na$_2$SO$_4$, filtered and concentrated. The residue was purified by silica gel chromatography (PE/EtOAc=30/1, 20/1) to afford the title compound as red oil.

Step c: Thioacetic acid S-piperidin-4-yl ester hydrochloride

A solution of 6.5 g of 4-acetylsulfanyl-piperidine-1-carboxylic acid tert-butyl ester in 100 mL of EtOAc was acidified by adding a solution of HCl/EtOAc dropwise at 20° C. over a period of 30 min. under N$_2$. The resulting mixture was stirred at 20° C. for 0.5 h after which a solid formed. TLC (PE:EtOAc=10:1) showed the reaction was complete. The reaction mixture was filtered to afford the title compound as off-white solid.

Step d: Thioacetic acid S-[1-(2-tert-butoxycarbonylamino-acetyl)-piperidin-4-yl]ester To a mixture of 4.70 g of thioacetic acid S-piperidin-4-yl ester hydrochloride, 3.84 g of N-BOC-Glycine and 7.29 g of DIPEA in 50 mL DMF was added 10.96 g of HATU in one portion at 20° C. under $N_2$. The mixture was stirred at 20° C. for 16 h. The residue was poured into ice-water and stirred for 20 min. The aqueous phase was extracted 3× with MTBE. The combined organic phase was washed 2× with brine, dried over $Na_2SO_4$, filtered and concentrated. The residue was purified by chromatography (PE/EtOAc=30/1, 20/1) to give the title compound as yellow oil.

According, e.g. analogously, to a method as set out under Example 78 above, but using appropriate starting materials, the compounds of formula $I_{EX}$, wherein $R_{1EX}$ and $R_{2EX}$ are as defined in Table 7 are prepared. Chemical characterisation data are also set out in Table 7.

TABLE 7

| Example | | $R_{2EX}$ | $R_{1EX}$ |
|---|---|---|---|
| 79 | 12-epi-12-desvinyl-14-O-{[1-(3-Amino-propionyl)-piperidin-4-yl-sulfanyl)]-acetyl}-12-[(4-aminomethyl-benzylamino)-methyl] mutilin trihydrochloride<br>$^1$H-NMR (200 MHz, DMSO-$d_6$): 7.67 (d, 2H, arom., J = 8 Hz), 7.53 (d, 2H, arom., J = 8 Hz), 5.46 (d, 1H, H-14, J = 7 Hz), 5.31 (d, 1H 11-OH, J = 4.6 Hz), 1.40 (s, 3H, H-15), 0.92 (s, 3H, H-18), 0.81 (d, 3H, H-17, J = 5 Hz), 0.64 (d, 3H, H-16, J = 5.4 Hz)<br>MS m/e: 611 [M$^+$ + H]<br>The required Thioacetic acid S-[1-(3-tert-butoxycarbonylamino-propionyl)-piperidin-4-yl] ester was prepared in analogy to the procedure described in Example 78 using the appropriate starting materials | | |
| 80 | 12-epi-12-desvinyl-14-O-{[1-(3-Amino-propionyl)-piperidin-4-yl-sulfanyl]-acetyl}-12-[(6-amino-hexylamino)-methyl] mutilin trihydrochloride<br>$^1$H-NMR (200 MHz, DMSO-$d_6$): 5.48 (d, 1H, H-14, J = 7 Hz), 5.37 (bs, 11-OH), 1.41 (s, 3H, H-15), 0.98 (s, 3H, H-18), 0.83 (d, 3H, H-17, J = 6 Hz), 0.65 (d, 3H, H-16, J = 5.2 Hz)<br>MS m/e: 325 [M/2$^+$ + H]<br>The required Thioacetic acid S-[1-(3-tert-butoxycarbonylamino-propionyl)-piperidin-4-yl] ester was prepared in analogy to the procedure described in Example 78 using the appropriate starting materials | | |
| 81 | 12-epi-12-desvinyl-14-O-{[1-(2-Amino-acetyl)-piperidin-4-yl-methylsulfanyl]-acetyl}-12-[(4-aminomethyl-phenylamino)-methyl] mutilin trihydrochloride<br>$^1$H-NMR (200 MHz, DMSO-$d_6$): 5.51 (d, 1H, H-14, J = 5.8 Hz), 1.39 (s, 3H, H-15), 0.99 (s, 3H, H-18), 0.85 (d, 3H, H-17, J = 6.4 Hz), 0.65 (d, 3H, H-16, J = 6.4 Hz)<br>MS m/e: 691 [M$^-$ + Cl]<br>The required Thioacetic acid S-[1-(2-tert-butoxycarbonylamino-acetyl)-piperidin-4-ylmethyl] ester was prepared in analogy to the procedure described in Example 78 using the appropriate starting materials | | |
| 82 | 12-epi-12-desvinyl-14-O-{[1-(2-Amino-acetyl)-piperidin-4-yl-methylsulfanyl]-acetyl}-12-[(4-amino-benzylamino)-methyl] mutilin trihydrochloride<br>MS m/e: 656 [M$^+$ + H]<br>For the reductive amination N-(4-Aminomethyl-phenyl)-2,2,2-trifluoro-acetamide (obtained in 2 steps from (4-Amino-benzyl)-carbamic acid tert-butyl ester) was used. In the subsequent nucleophilic displacement reaction (e.g. Example 1, step 5) using $K_2CO_3$ instead of potassium tert-butoxide as base the N-trifluoroacetyl group was concomitantly cleaved | | |

EXAMPLE 83

12-epi-12-desvinyl-14-O-{[1-(2-Amino-acetyl)-piperidin-4-yl-sulfanyl]-acetyl}-12{2-[4-(2-amino-ethoxy)-benzylamino]-methyl} mutilin trihydrochloride was obtained similarly and in analogy to a method as set out in Example 1 and 78, but using appropriate starting materials.

$^1$H-NMR (200 MHz, DMSO-$d_6$): 7.57 (d, 2H, arom., J=8 Hz), 7.00 (d, 2H, arom., J=8 Hz), 5.45 (d, 1H, H-14, J=6.2 Hz), 1.39 (s, 3H, H-15), 0.93 (s, 3H, H-18), 0.81 (d, 3H, H-17, J=6 Hz), 0.64 (d, 3H, H-16, J=5.4 Hz)

MS m/e: 687 [M$^+$+H]

Preparation of the required
[2-(4-Aminomethyl-phenoxy)-ethyl]-carbamic acid
tert-butyl ester

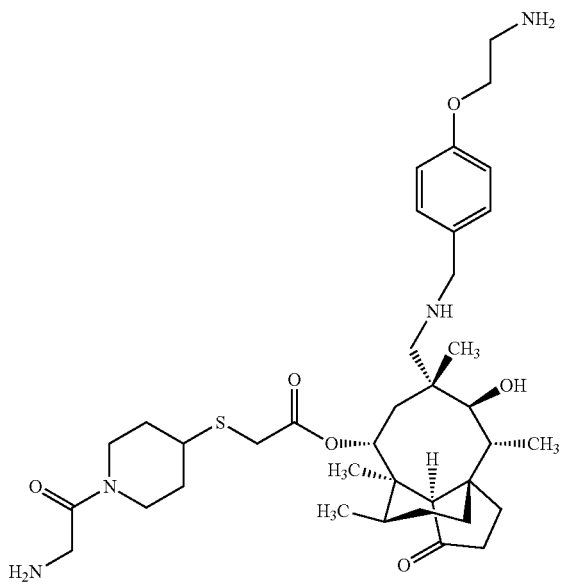 [SMILES: C[C@@H]1CC[C@@]23CCC(=O)[C@H]2[C@]1(C)[C@H](OC(=O)CSC1CCN(C(=O)CN)CC1)C[C@](C)(CNCc1ccc(OCCN)cc1)[C@@H](O)[C@@H]3C]

Step a: (4-Hydroxy-benzyl)-carbamic acid benzyl ester 10 g of 4-Aminomethyl-phenol was dissolved in 200 mL DMF, the solution was cooled to 0° C., 13.6 mL of triethylamine followed by 11.6 mL of benzyl chloroformate was added and stirring was continued at rt overnight. The reaction mixture was diluted with water and extracted 2× with EtOAc, the combined organic layers were washed 2× with 2N hydrochloric acid, 5% sodium bicarbonate solution, dried over Na$_2$SO$_4$ and evaporated to dryness to give an almost colourless oil. The product was chromatographed over silica gel (eluant: toluene/EtOAc=10:1) and yielded the title compound as almost colourless oil.

Step b: {2-[4-(Benzyloxycarbonylamino-methyl)-phenoxy]-ethyl}-carbamic acid tert-butyl ester 3.25 g of (4-Hydroxy-benzyl)-carbamic acid benzyl ester, 3.11 g of (2-bromo-ethyl)-carbamic acid tert-butylester, 4.10 g of cesium carbonate and 209 mg of potassium iodide was refluxed in 20 mL 2-butanone for 24 hours. The solvent was removed in vacuo, the residue partitioned between water and EtOAc. The aqueous phase was washed with EtOAc, the combined organic layers with 2N sodium hydroxide solution and finally with brine. After drying over anhydrous Na$_2$SO$_4$ and evaporation of the solvent a yellowish oil was obtained which was chromatographed over silica gel (eluant: toluene/EtOAc=10:1) to yield an almost colorless viscous oil.

Step c: [2-(4-Aminomethyl-phenoxy)-ethyl]-carbamic acid tert-butyl ester 2.0 g of {2-[4-(Benzyloxycarbonylamino-methyl)-phenoxy]-ethyl}-carbamic acid tert-butyl ester, dissolved in 120 mL ethanol, was hydrogenated in an H-cube apparatus over 10% Pd/C at 10 bar and 50° C. for 3 days. The solvent was evaporated and the title compound (containing residual solvent) was obtained as a slowly crystallizing oil.

EXAMPLE 84

12-epi-12-desvinyl-14-O-{{4-[(2-Amino-acetylamino)-methyl]-cyclohexylsulfanyl}-acetyl}-12-[{4-[(2-amino-ethoxy)-benzylamino]-methyl}mutilin trihydrochloride was obtained similarly and in analogy to a method as set out in Example 1 and 83, but using appropriate starting materials.

MS m/e: 715 [M$^+$+H]

The required Thioacetic acid S-{4-[(2-tert-butoxycarbonylamino-acetylamino)-methyl]-cyclohexyl} ester was prepared in analogy to the procedure described in Example 78 using the appropriate starting materials.

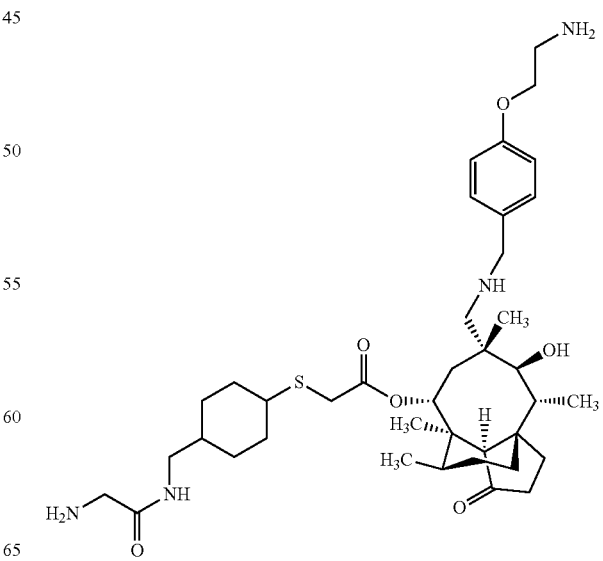

EXAMPLE 85

12-epi-12-desvinyl-14-O-[(4-Aminomethyl-phenyl-sulfanyl)-acetyl]-12-[(3-amino-propylamino)-methyl] mutilin trihydrochloride Step 1: 12-epi-12-desvinyl-14-O-[(4-Azidomethyl-phenylsulfanyl)-acetyl]-12-[(3-tert-butoxycarbonylamino-propylamino)-methyl] mutilin

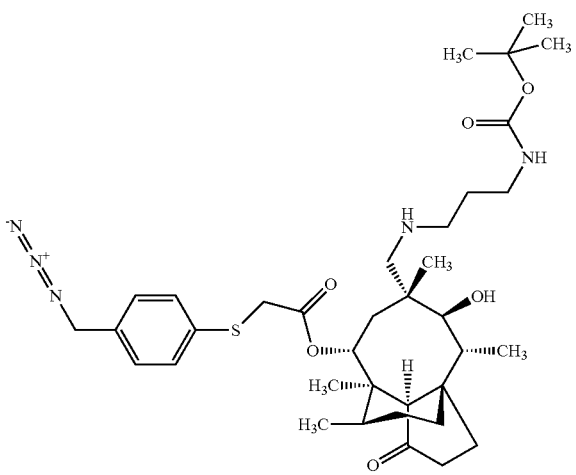

264 mg of 12-epi-12-desvinyl-14-O-[(4-hydroxymethyl-phenylsulfanyl)-acetyl]-12-[(3-tert-butoxycarbonylamino-propylamino)-methyl] mutilin (Example 57, prior to BOC-deprotection) was dissolved in 4 mL of THF and the flask cooled in an ice bath. To the mixture obtained 122 mg of DPPA was added, followed by 76 mg of DBU in 3 mL of THF over five minutes. The cooling bath was removed, the mixture obtained was stirred at rt overnight and 45 mg of DPPA and 30.5 mg of DBU was further added.

The mixture obtained was stirred for another 6 h. HPLC revealed still some starting material left; thus 56.8 mg of DPPA and 38.1 mg of DBU was again added, stirring was continued overnight and the reaction was deemed to be complete. About 40 mL of water was added and the mixture obtained was extracted with EtOAc (2×), the combined organic phases were washed with 2N NaOH and water, dried over $Na_2SO_4$, evaporated to dryness and subjected to column chromatography over silica gel (eluent: EtOAc/$Et_3N$=80:1). The title compound was obtained in the form of a foamy residue.

Step 2: 12-epi-12-desvinyl-14-O-[(4-Aminomethyl-phenylsulfanyl)-acetyl]-12-[(3-tert-butoxycarbonylamino-propylamino)-methyl] mutilin

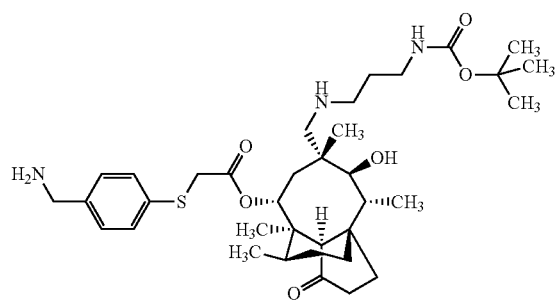 [SMILES: C[C@@H]1CC[C@@]23CCC(=O)[C@H]2[C@]1(C)[C@H](OC(=O)CSc1ccc(CN)cc1)C[C@](C)(CNCCCNC(=O)OC(C)(C)C)[C@@H](O)[C@@H]3C]

155 mg of 12-epi-12-desvinyl-14-O-[(4-azidomethyl-phenylsulfanyl)-acetyl]-12-[(3-tert-butoxycarbonylamino-propylamino)-methyl] mutilin was dissolved in 4 mL of EtOH and 1.3 mL of water in an ultrasonic bath and 32.3 mg of $NH_4Cl$ and 20 mg of zinc powder was added. The mixture obtained was refluxed for 10 min. Since the reaction was not complete, 164 mg of $NH_4Cl$ and 100 mg of zinc powder was added and the mixture obtained was stirred at rt overnight. To the mixture obtained 75 mL of EtOAc and 5 mL of 25% ammonia solution was added, the formed precipitate was filtered off and the filtrate obtained was treated with brine, stirred for 5 min and from the mixture obtained the phases were separated. The organic phase obtained was dried over $Na_2SO_4$, evaporated to dryness and the evaporation residue was subjected to silica gel chromatography (eluent: EtOAc/EtOH/25% ammonia=100:2:0.5). The title compound was obtained in the form of colourless foamy crystals.

Step 3: 12-epi-12-desvinyl-14-O-[(4-Aminomethyl-phenylsulfanyl)-acetyl]-12-[(3-amino-propylamino)-methyl] mutilin trihydrochloride BOC-deprotection of the product of step 2 above was carried out as described in Example 1, Step 6.

$^1$H-NMR (200 MHz, DMSO-$d_6$): 7.45 (d, 2H, arom., J=8.2 Hz), 7.23 (d, 2H, arom., J=8.2 Hz), 5.46 (d, 1H, H-14, J=7 Hz), 3.88 (s, 2H, H-22), 1.37 (s, 3H, H-15), 0.89 (s, 3H, H-18), 0.81 (d, 3H, H-17, J=6.2 Hz), 0.59 (d, 3H, H-16, J=5.2 Hz)

MS m/e: 594 [M$^-$+Cl]

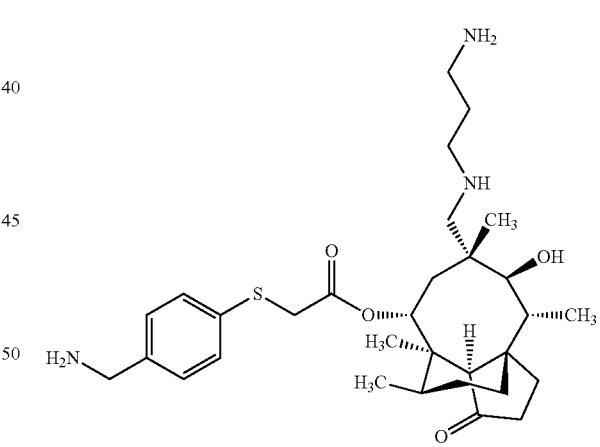

According, e.g. analogously, to a method as set out under Example 85 above, but using appropriate starting materials, the compounds of formula $I_{EX}$, wherein $R_{1EX}$ and $R_{2EX}$ are as defined in Table 8 are prepared. Chemical characterisation data are also set out in Table 8.

TABLE 8

| Example | | $R_{2EX}$ | $R_{1EX}$ |
|---|---|---|---|
| 86 | 12-epi-12-desvinyl-14-O-[(3-Aminomethyl-phenylsulfanyl)-acetyl]-12-[(3-amino-propylamino)-methyl] mutilin trihydrochloride<br>$^1$H-NMR (200 MHz, DMSO-d$_6$): 7.54 (s, 1H, arom.), 7.36-7.24 (m, 4H, 3H arom., 1H, —NH), 5.46 (d, 1H, H-14, J = 6.4 Hz), 5.32 (bs, 1H, 11-OH), 3.93 (s, 2H, H-22), 1.35 (s, 3H, H-15), 0.90 (s, 3H, H-18), 0.81 (d, 3H, H-17, J = 5.8 Hz), 0.59 (d, 3H, H-16, J = 5.4 Hz)<br>MS m/e: 560 [M$^+$ + H] | | |
| 87 | 12-epi-12-desvinyl-14-O-[(3-Aminomethyl-phenylsulfanyl)-acetyl]-12-[(6-guanidino-hexylamino)-methyl] mutilin trihydrochloride<br>MS m/e: 645 [M$^+$ + H] | | |
| 88 | 12-epi-12-desvinyl-14-O-[(4-Aminomethyl-phenylsulfanyl)-acetyl]-12-[(4-aminomethyl-benzylamino)-methyl] mutilin trihydrochloride<br>$^1$H-NMR (200 MHz, DMSO-d$_6$): 7.68 (d, 2H arom., J = 8 Hz), 7.55 (d, 2H arom., J = 8 Hz), 7.49 (d, 2H arom., J = 8 Hz), 7.33 (d, 2 H arom., J = 8 Hz), 1.36 (s, 3H, H-15), 0.83 (s, 3H, H-18), 0.57 (d, 3H, H-16, J = 3.6 Hz)<br>MS m/e: 622 [M$^+$ + H] | | |
| 89 | 12-epi-12-desvinyl-14-O-[(4-Aminomethyl-phenylsulfanyl)-acetyl]-12-[(6-amino-hexylamino)-methyl] mutilin trihydrochloride<br>$^1$H-NMR (200 MHz, DMSO-d$_6$): 7.46 (d, 2H arom., J = 8 Hz), 7.36 (d, 2H arom., J = 8 Hz), 5.48-5.39 (m, 2H, H-14, 11-OH), 1.38 (s, 3H, H-15), 0.90 (s, 3H, H-18), 0.81 (d, 3H, H-17, J = 6.2 Hz), 0.60 (d, 3H, H-16, J = 5.4 Hz);<br>MS m/e: 602 [M$^+$ + H] | | |
| 90 | 12-epi-12-desvinyl-14-O-[(3-Aminomethyl-phenylsulfanyl)-acetyl]-12-[((4-aminomethyl-cyclohexyl)-methylamino)-methyl] mutilin trihydrochloride<br>$^1$H-NMR (200 MHz, DMSO-d$_6$): 7.54 (s, 1H arom.), 7.34 (bs, 3H arom.), 5.48 (d, 1H, H-14, J = 7.2 Hz), 1.36 (s, 3H, H-15), 0.95 (s, 3H, H-18), 0.82 (d, 3H, H-17, J = 6.2 Hz), 0.60 (d, 3H, H-16, J = 5.6 Hz)<br>MS m/e: 628 [M$^+$ + H] | | |
| 91 | 12-epi-12-desvinyl-14-O-[(4-Aminomethyl-phenylsulfanyl)-acetyl]-12-{[(4-aminocyclohexyl)-amino]-methyl} mutilin trihydrochloride<br>$^1$H-NMR (200 MHz, DMSO-d$_6$): 7.30-7.16 (m, 4H arom.), 7.54 (d, 2H arom., J = 8 Hz), 5.48 (d, 1H, H-14, J = 7.4 Hz), AB (2H, H-22, v$_A$ = 3.85, v$_B$ = 3.76, J = 16 Hz), 1.29 (s, 3H, H-15), 0.83 (s, 3H, H-18), 0.77 (d, 3H, H-17, J = 6.4 Hz), 0.59 (d, 3H, H-16, J = 5.8 Hz)<br>MS m/e: 600 [M$^+$ + H] | | |

TABLE 8-continued

| Example | | $R_{2EX}$ | $R_{1EX}$ |
|---|---|---|---|
| 92 | 12-epi-12-desvinyl-14-O-[(4-Aminomethyl-phenylsulfanyl)-acetyl]-12-[(hexylamino)-methyl] mutilin dihydrochloride<br>MS m/e: 587 [M$^+$ + H] | 4-(aminomethyl)phenyl group | hexylaminomethyl group (CH$_3$(CH$_2$)$_5$NH-CH$_2$-) |
| 93 | 12-epi-12-desvinyl-14-O-[(4-Aminomethyl-phenylsulfanyl)-acetyl]-12-[(4-carbamoylphenyl)-methylamino)-methyl] mutilin dihydrochloride<br>$^1$H-NMR (200 MHz, DMSO-d$_6$): 7.83 (d, 2H, arom., J = 8 Hz), 7.38 (d, 2H, arom., J = 8 Hz), 7.32-7.13 (m, 4H, arom.), 5.49 (bs, 1H, H-14), 1.31 (s, 3H, H-15), 0.79 (bs, 6H, H-17, H-18), 0.60 (bs, 3H, H-16)<br>MS m/e: 636 [M$^+$ + H] | 4-(aminomethyl)phenyl group | (4-carbamoylphenyl)methylaminomethyl group |

EXAMPLE 94

12-epi-12-desvinyl-14-O-[(4-Aminomethyl-phenylsulfanyl)-acetyl]-12-{[4-(3-amino-propylcarbamoyl)-benzylamino]-methyl} mutilin trihydrochloride was obtained similarly and in analogy to a method as set out in Example 85, but using appropriate starting materials.

MS m/e: 727 [M$^+$+H]

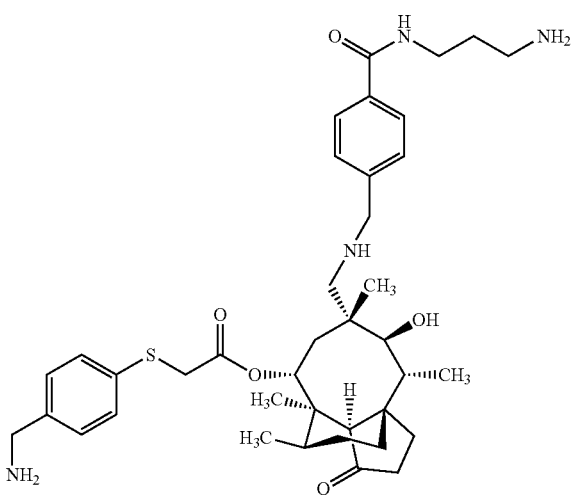 [SMILES: C[C@@H]1CC[C@@]23CCC(=O)[C@H]2[C@]1(C)[C@H](OC(=O)CSc1ccc(CN)cc1)C[C@](C)(CNCc1ccc(C(=O)NCCCN)cc1)[C@@H](O)[C@@H]3C]

Preparation of the intermediate tert-butyl N-[3-[[4-(aminomethyl)-benzoyl]-amino]-propyl]-carbamate Step a:
[3-(4-Cyanobenzoylamino)-propyl]-carbamic acid tert-butyl ester A mixture of 1.47 g of 4-cyanobenzoic acid, 5.7 g of HATU and 2.58 g DIEA in 25 mL of DMF was stirred at 25° C. for 45 min. To the mixture obtained 3.48 g (3-Amino-propyl)-carbamic acid tert-butyl ester was added slowly and the mixture obtained was stirred at rt for another 2 h. The mixture obtained was quenched with water and extracted with EtOAc (30 mL*3). The phases obtained were separated and the organic phase was washed with water and brine, dried over Na$_2$SO$_4$, concentrated and the concentration residue was subjected to chromatography (DCM/MeOH=10:1) yielding the title compound.

Step b:
[3-(4-Aminomethyl-benzoylamino)-propyl]-carbamic acid tert-butyl ester

A mixture of 1 g of [3-(4-cyanobenzoylamino)-propyl]-carbamic acid tert-butyl ester and Pd/C (100 mg) in 25 mL of THF was stirred at 25° C. under hydrogen for 5 h. The mixture obtained was filtered and concentrated. The concentration residue was subjected to chromatography (DCM/MeOH=10:1) yielding the title compound.

EXAMPLE 95

12-epi-12-desvinyl-14-O-[(4-Aminomethyl-phenylsulfanyl)-acetyl]-12-[(5-dimethylcarbamoyl-pentylamino)-methyl] mutilin dihydrochloride was obtained similarly and in analogy to a method as set out in Example 85, but using appropriate starting materials.

$^1$H-NMR (200 MHz, DMSO-d$_6$): 7.45 (d, 2H, arom., J=8 Hz), 7.34 (d, 2H, arom., J=8 Hz), 5.46 (d, 1H, H-14, J=6.4 Hz), 1.37 (s, 3H, H-15), 0.88 (s, 3H, H-18), 0.80 (d, 3H, H-17, J=6.4 Hz), 0.59 (d, 3H, H-16, J=5.6 Hz)

MS m/e: 678 [M$^+$+H].

93

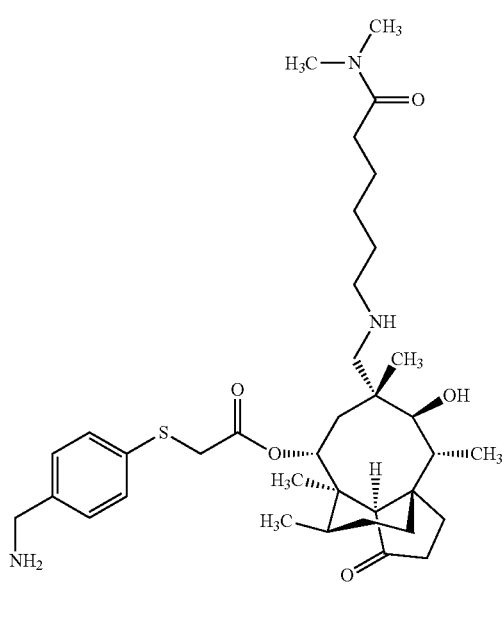 [SMILES: C[C@@H]1CC[C@@]23CCC(=O)[C@H]2[C@]1(C)[C@H](OC(=O)CSc1ccc(CN)cc1)C[C@](C)(CNCCCCCC(=O)N(C)C)[C@@H](O)[C@@H]3C]

Preparation of the intermediate 6-Amino-hexanoic acid dimethylamide

Step a: A solution of 305 mg of Me$_2$NH.HCl and 970 mg of DIPEA in 10 mL of DMF was stirred at rt for 30 min and 500 mg of N-benzyloxycarbonyl-6-aminocaproic acid and 1.07 g of HATU was added and the mixture obtained was stirred at rt overnight. The mixture obtained was extracted 3× with 10 mL EtOAc and the combined organic phases were washed with brine, dried and concentrated.

Step b: 400 mg of the crude product of step a was dissolved in 15 mL of MeOH and Pd/C (wet, 100 mg) was added. The mixture obtained was stirred at rt under 30 Psi H$_2$-pressure overnight. TLC showed that the reaction was completed. The mixture obtained was filtered and the filtrate was concentrated. The title compound in the form of a white solid was obtained and used without further purification.

EXAMPLE 96

12-epi-12-desvinyl-4-O-[(4-Aminomethyl-phenylsulfanyl)-acetyl]-12-{[4-(2-amino-2-carbamoyl-ethyl)-benzylamino]-methyl} mutilin trihydrochloride was obtained similarly and in analogy to a method as set out in Example 85, but using appropriate starting materials.

MS m/e: 679 [M++H]

94

Preparation of the intermediate tert-butyl N-[2-Amino-1-[[4-(aminomethyl)-phenyl]-methyl]-2-oxo-ethyl]-carbamate

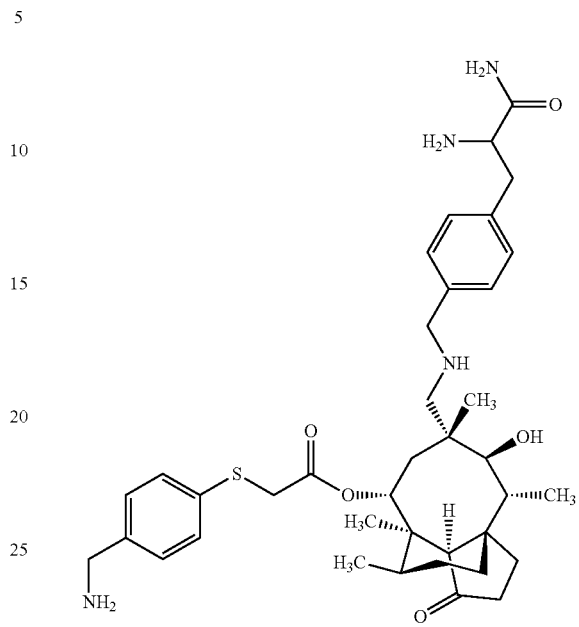

Step a: 2-tert-Butoxycarbonylamino-3-(4-cyano-phenyl)-propionic acid methyl ester A mixture of 8.4 g of 4-cyano-phenylalanine methylester (prepared in analogy to JACS, 129(1), 14-15; 2007), 9 g of BOC$_2$O and 50 mg of DMAP in 150 m, of THF was stirred at rt for 3.5 h, diluted with water, extracted with EtOAc and subjected to column chromatography (DCM/MeOH=100:4) yielding the title compound.

Step b: 2-tert-Butoxycarbonylamino-3-(4-cyano-phenyl)-propionic acid

A mixture of 1.91 g of 2-tert-butoxycarbonylamino-3-(4-cyano-phenyl)-propionic acid methyl ester and 0.38 g NaOH in 30 mL of THF and 15 mL of water was stirred at rt for 2 h, concentrated to removed THF, extracted with EtOAc, acidified by HCl to pH 3, extracted with EtOAc and concentrated to yield the title compound.

Step c: [1-Carbamoyl-2-(4-cyano-phenyl)-ethyl]-carbamic acid tert-butyl ester

A mixture of 0.9 g of 2-tert-Butoxycarbonylamino-3-(4-cyano-phenyl)-propionic acid, 1.413 g of HATU, and 1.6 g of DIPEA in 60 mL of DMF was stirred at rt for 2 h and 9.3 mmol of NH$_4$Cl was added. The mixture was stirred at rt for 2 h, diluted with water, extracted with EtOAc and subjected to column chromatography (DCM/MeOH=100:5) yielding the title compound.

Step d: tert-butyl N-[2-Amino-1-[[4-(aminomethyl)-phenyl]-methyl]-2-oxo-ethyl]-carbamate A mixture of 1.58 mmol [1-carbamoyl-2-(4-cyano-phenyl)-ethyl]-carbamic acid tert-butyl ester, 50 mg of Ni and 50 mg of NH$_3$H$_2$O in 50 mL of MeOH was stirred at rt under H$_2$ for 4 h, filtered and concentrated to yield the title compound.

EXAMPLE 97

12-epi-12-desvinyl-14-O-[(4-Aminomethyl-phenylsulfanyl)-acetyl]-12-{[4-(2-amino-2-dimethylcarbamoyl-ethyl)-benzylamino]-methyl} mutilin trihydrochloride was obtained similarly and in analogy to a method as set out in Example 85, but using appropriate starting materials.

MS m/e: 707 [M$^+$+H]

Preparation of the intermediate tert-butyl N-[1-[[4-(Aminomethyl)-phenyl]-methyl]-2-(dimethylamino)-2-oxo-ethyl]-carbamate

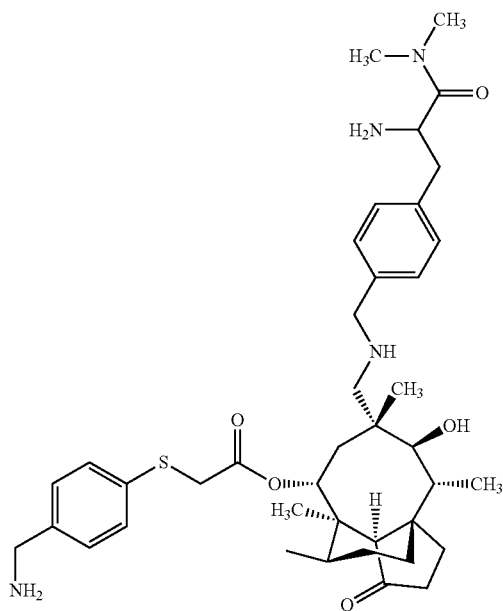 [SMILES: C[C@@H]1CC[C@@]23CCC(=O)[C@H]2[C@]1(C)[C@H](OC(=O)CSc1ccc(CN)cc1)C[C@](C)(CNCc1ccc(CC(N)C(=O)N(C)C)cc1)[C@@H](O)[C@@H]3C]

Step a: A solution of 305 mg Me$_2$NH.HCl and 970 mg in 10 mL of DMF was stirred at rt for 30 min. To the mixture obtained 545 mg of 2-tert-butoxycarbonylamino-3-(4-cyano-phenyl)-propionic acid (see example 96) and 1.07 g of HATU were added and the mixture obtained was stirred at rt overnight. The mixture obtained was extracted 3× with 10 mL EtOAc, the combined organic phases were washed with brine, dried over Na$_2$SO$_4$, concentrated and used for the next step without further purification.

Step b: A mixture 458 mg of the residue of step a, 50 mg of Ni and 50 mg of NH$_3$H$_2$O in 50 mL of MeOH was stirred at rt under H$_2$ for 4 h, filtered and concentrated to yield the title compound.

EXAMPLE 98

12-epi-12-desvinyl-14-O-{[5-Aminomethyl-pyridin-2-yl-sulfanyl)]-acetyl}-12-[(4-aminomethyl-benzylamino)-methyl] mutilin tetrahydrochloride was obtained similarly and in analogy to a method as set out in Example 1, but using appropriate starting materials.

$^1$H-NMR (200 MHz, DMSO-d$_6$): 7.83-7.78 (m, 1H, arom.), 7.70 (d, 2H, arom., J=8 Hz), 7.55 (d, 2H, arom., J=8 Hz), 7.41-7.37 (m, 1H, arom.), 5.45 (bs, 2H, H-14, 11-OH), 3.92 (s, 2H, H-22), 1.37 (s, 3H, H-15), 0.89 (s, 3H, H-18), 0.79 (s, 3H, H-17, J=6 Hz), 0.64 (d, 3H, H-16, J=5.6 Hz)

MS m/e: 623 [M$^+$+H]

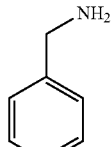

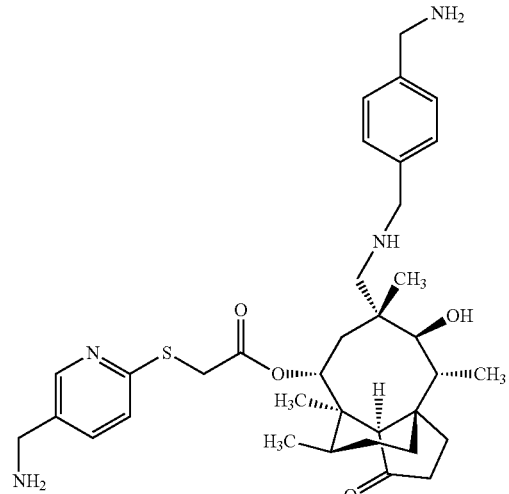

Preparation of the required Thioacetic acid S-[5-(tert-butoxycarbonylamino-methyl)-pyridin-2-yl] ester Step a: (6-Mercapto-pyridin-3-ylmethyl)-carbamic acid tert-butyl ester To a mixture of 12 g 6-mercapto-nicotinamide (described in PCT Int. Appl., 2011039259) in 250 mL THF was added 46.7 mL of BH$_3$-Me$_2$S (dropwise at 25° C. under N$_2$. The mixture was stirred at 70° C. for 12 hr. The mixture was cooled to 0° C., 100 mL of 1N HCl) was added to the reaction and stirred at 45° C. for 1 h, the aqueous phase was extracted 3× with EtOAc, the aqueous phase was adjusted to pH=13 with 1N NaOH. To the solution was added 21.23 g of BOC$_2$O and the mixture was stirred at 25° C. for 12 h. The aqueous phase was extracted 3× with EtOAc. The combined organic phase was washed 2× with brine, dried over Na$_2$SO$_4$, filtered and concentrated. The residue was purified by silica gel chromatography (PE/EtOAc=10:1 to 1:3) to afford the title compound as yellow solid.

Step b: Thioacetic acid S-[5-(tert-butoxycarbonylamino-methyl)-pyridin-2-yl]ester A mixture of 2.5 g of (6-mercapto-pyridin-3-ylmethyl)-carbamic acid tert-butyl ester in 25 mL DCM, was added 4.21 g of TEA at 0° C. under N$_2$. The reaction was stirred at 0° C. for 10 min and 1.63 g of acetyl chloride was added drop-wise at 0° C. under N$_2$. The mixture was stirred at 0° C. for 20 min. The mixture was poured into ice-water and stirred for 10 min. The aqueous phase was extracted 3× with DCM. The combined organic phase was washed with 2× brine, dried over Na$_2$SO$_4$, filtered and concentrated under reduced pressure. The residue was purified by silica gel chromatography (PE/EtOAe—1:1) to afford the title compound as yellow solid.

EXAMPLE 99

12-epi-12-Desvinyl-14-O-{[5-aminomethyl-pyridin-2-yl-sulfanyl)]-acetyl}-12-[(4-aminomethyl-3-fluoro-benzylamino)-methyl] mutilin tetrahydrochloride was obtained similarly and in analogy to a method as set out in Example 98, but using appropriate starting materials.

MS m/e: 641 [M$^+$+H]

Preparation of the required (4-Aminomethyl-2-fluoro-benzyl)-carbamic acid tert-butyl ester

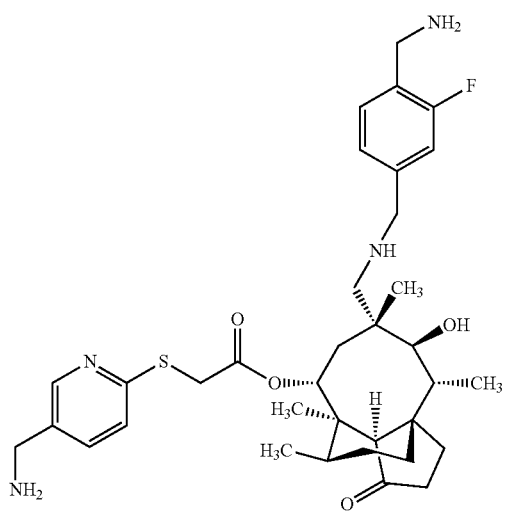 [SMILES: C[C@@H]1CC[C@@]23CCC(=O)[C@H]2[C@]1(C)[C@H](OC(=O)CSc1ccc(CN)cn1)C[C@](C)(CNCc1ccc(CN)c(F)c1)[C@@H](O)[C@@H]3C]

Step a: (4-Cyano-2-fluoro-benzyl)-carbamic acid tert-butyl ester

To a mixture of 16 g of tert-butyl N-[(4-bromo-2-fluorophenyl)methyl]carbamate in 480 mL of DMF was added 12.35 g of Zn(CN), 5.83 g of dppf, 687.98 mg of Zn and 4.82 g of Pd$_2$(dba)$_3$ under N$_2$. The reaction mixture was heated to 120-128° C. and stirred for 5 hours. TLC showed the reaction was complete. The mixture was cooled to 25° C. and poured into ice-water and stirred for 20 min. The aqueous phase was extracted 3× with EtOAc. The combined organic phase was washed 2× with brine, dried over Na$_2$SO$_4$, filtered and concentrated. The residue was purified by silica gel chromatography (silica gel, PE/EtOAc=30/1 to 5/1) to afford the product as yellow solid.

Step b: (4-Aminomethyl-2-fluoro-benzyl)-carbamic acid tert-butyl ester

To a solution of 9.00 g tert-butyl N-[(4-cyano-2-fluorophenyl)methyl]carbamate in 150 mL of MeOH—NH$_3$ was added 1.80 g of Raney Nickel under N$_2$. The suspension was degassed in vacuum and purged with H$_2$ several times. The mixture was stirred at 25° C. under H$_2$ (50 psi) for 8 hours. TLC (PE/EtOAc=5:1) showed the starting material was consumed completely. The reaction mixture was filtered and the filtrate was concentrated in vacuum. The residue was purified by silica gel chromatography eluted with DCM/MeOH=100:1 to 10:1 to give the title compound as brown solid.

EXAMPLE 100

12-epi-12-desvinyl-14-O-{[(4-Aminomethyl-cyclohexyl)-methyl sulfanyl)-acetyl]{[(4-Aminomethyl-cyclohexyl)-methylsulfanyl]-acetyl}-12-[(4-aminomethyl-benzylamino)-methyl] mutilin trihydrochloride was obtained similarly and in analogy to a method as set out in Example 1 and 85, but using appropriate starting materials.

$^1$H-NMR (200 MHz, DMSO-d$_6$): 7.69 (d, 2H, arom., J=7.6 Hz), 7.57 (d, 2H, arom., J=7.4 Hz), 5.47 (d, 1H, H-14, J=4.8 Hz), 5.34 (bs, 1H, 11-OH), 1.41 (s, 3H, H-15), 0.93 (s, 3H, H-18), 0.84 (bs, 3H, H-17), 0.66 (bs, 3H, H-16)

MS m/e: 642 [M$^+$+H]

Preparation of the required Thioacetic acid S-(4-azidomethyl-cyclohexylmethyl) ester

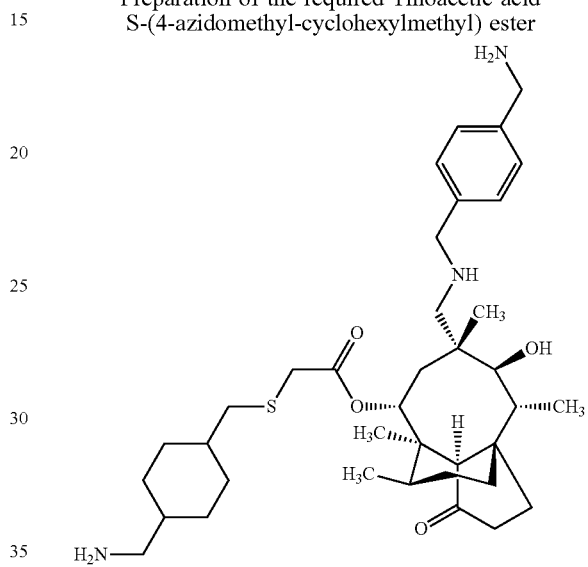

Step a: Thioacetic acid S-(4-methanesulfonyloxymethyl-cyclohexylmethyl) ester 5 g of Methanesulfonic acid 4-methanesulfonyloxymethyl-cyclohexylmethyl ester (described in JOC, 22, 994-5; 1957) was dissolved in 100 mL of DMF, 2.9 g of potassium thioacetate was added and the reaction mixture heated to 110° C. for 2 h. The reaction was quenched by pouring into water, extracted 3× with EtOAc, the organic phase washed with brine, dried over Na$_2$SO$_4$ and evaporated to dryness yielding a brown oil which was chromatographed on silica using cyclohexane/EtOAc=2:1 as eluent. The title compound was obtained as brown oil.

Step b: Thioacetic acid S-(4-azidomethyl-cyclohexylmethyl) ester 2.2 g of Thioacetic acid S-(4-methanesulfonyloxymethyl-cyclohexylmethyl) ester was dissolved in 100 mL of DMF, 2.1 g of sodium azide was added and the reaction mixture stirred at 70° C. for 16 h. The reaction mixture was poured into water, extracted 3× with EtOAc, the organic phase washed with brine, dried over Na$_2$SO$_4$ and evaporated to dryness yielding a brown oil which was used for the next step without further purification.

Accordingly, e.g. analogously, to a method as set out under Example 99 above, but using appropriate starting materials, the compounds of formula I$_{EX}$, wherein R$_{1EX}$ and R$_{2EX}$ are as defined in Table 9 are prepared. Chemical characterisation data are also set out in Table 9

TABLE 9

| Example | | $R_{2EX}$ | $R_{1EX}$ |
|---|---|---|---|
| 101 | 12-epi-12-desvinyl-14-O-{1-(2-Amino-acetyl)-piperidin-4-yl-sulfanyl]-acetyl}-12-[(4-aminomethyl-3-fluoro-benzylamino)-methyl] mutilin trihydrochloride<br>MS m/e: 675 [M⁺ + H] | | |
| 102 | 12-epi-12-Desvinyl-14-O-{{4-[(2-Amino-acetylamino)-methyl]-cyclohexylsulfanyl}-acetyl}-12-[(4-aminomethyl-3-fluoro-benzylamino)-methyl] mutilin tetrahydrochloride<br>MS m/e: 703 [M⁺ + 2H] | | |
| 103 | 12-epi-12-desvinyl-14-O-{[5-Aminomethyl-pyridin-2-yl-sulfanyl]-acetyl}-12-[(4-aminomethyl-2,5-difluoro-benzylamino)-methyl] mutilin tetrahydrochloride<br>MS m/e: 659 [M⁺ + H]<br>The required [4-(aminomethyl)-2,5-difluoro-phenyl]methanamine can be obtained byreaction of 1,4-bis(bromomethyl)-2,5-difluoro-benzene with excess NH₃/THF at rt. The reductive amination was done as described in Example 1, step 4 using 6 eq of the diamine | | |

According, e.g. analogously, to a method as set out under Example 85 above, but using appropriate starting materials, the compounds of formula $I_{EX}$, wherein $R_{1EX}$ and $R_{2EX}$ are as defined in Table 10 are prepared. Chemical characterisation data are also set out in Table 10

TABLE 10

| Example | | $R_{2EX}$ | $R_{1EX}$ |
|---|---|---|---|
| 104 | 12-epi-12-desvinyl-14-O-[(4-Aminomethyl-phenylsulfanyl)-acetyl]-12-[(2-amino-1-aminomethyl-ethylamino)-methyl] mutilin tetrahydrochloride<br>¹H-NMR (200 MHz, DMSO-d₆): 7.45 (d, 2H, arom., J = 8 Hz), 7.36 (d, 2H, arom., J = 8 Hz), 5.47 (d, 1H, H-14, J = 7 Hz), 1.36 (s, 3H, H-15), 0.95 (s, 3H, H-18), 0.82 (d, 3H, H-17, J = 5.8), 0.59 (d, 3H, H-16, J = 5.6 Hz).<br>[0256] MS m/e: 575 [M⁺ + H]<br>The intermediate (2-Amino-3-tert-butoxycarbonylamino-propyl)-carbamic acid tert-butyl ester is e.g. described in ChemMedChem, 4(7), 1182-1188; 2009 | | |
| 105 | 12-epi-12-Desvinyl-14-O-[(5-aminomethyl-pyridin-2-yl-sulfanyl)-acetyl]-12-[(6-amino-hexylamino)-methyl] mutilin tetrahydrochloride<br>¹H-NMR (200 MHz, DMSO-d₆): 7.82-7.77 (m, 1H, arom.), 7.42-7.38 (m, 1H, arom.), 5.47 (bs, 2H, H-14, 11-OH), 3.93 (s, 2H, H-22), 1.38 (s, 3H, H-15), 0.95 (s, 3H, H-18), 0.81 (d, 3H, H-17, J = 6 Hz), 0.65 (d, 3H, H-16, J = 5.6 Hz)<br>MS m/e: 603 [M⁺ + H] | | |

EXAMPLE 106

12-epi-12-desvinyl-14-O-{(4-[(2-Amino-acetylamino)-methyl]-phenylsulfanyl)-acetyl}-12-[(3-amino-propylamino)-methyl] mutilin trihydrochloride Step 1: 12-epi-12-desvinyl-14-O-{(4-[(2-tert-Butoxycarbonylamino-acetylamino)-methyl]-phenylsulfanyl)-acetyl}-12-[(3-tert-butoxycarbonylamino-propylamino)-methyl] motilin

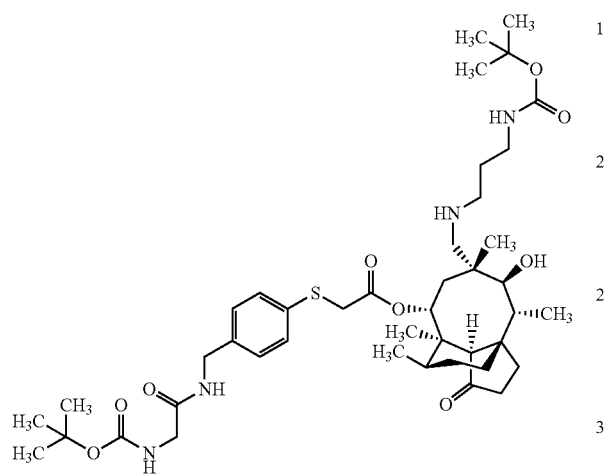

A mixture of 0.3 mmol of BOC-Glycine, 0.45 mmol of HATU and 0.6 mmol of DIPEA in 15 mL of THF was stirred at 25° C. for 45 min. To the mixture obtained 0.3 mmol of 12-epi-12-desvinyl-14-O-[(4-Aminomethyl-phenylsulfanyl)-acetyl]-12-[(3-tert-butoxycarbonylamino-propylamino)-methyl]mutilin (Example 85, step 2) was added slowly. The mixture obtained was stirred at rt for another 2 h, quenched with water and extracted with EtOAc. The organic phase obtained was washed with water, brine, dried over $Na_2SO_4$, concentrated and the concentration residue was subjected to chromatography (DCM/MeOH=10:1) yielding the title compound.

Step 2; 12-epi-12-desvinyl-14-O-{(4-[(7-Amino-acetylamino)-methyl]phenylsulfanyl)-acetyl}-12-[(3-amino-propylamino)-methyl] mutilin trihydrochloride BOC-deprotection of the compound obtained in step 1 was carried out as described in Example 1, Step 6.

$^1$H-NMR (200 MHz, DMSO-$d_6$): 7.32 (d, 2H, arom., J=8 Hz), 7.25 (d, 2H, arom., J=8 Hz), 5.45 (d, 1H, H-14, J=5.4 Hz), 1.37 (s, 3H, H-15), 0.88 (s, 3H, H-18), 0.82 (d, 3H, H-17, J=5 Hz), 0.59 (d, 3H, H-16, J=5.2 Hz);

MS m/e: 617 [M$^+$+H].

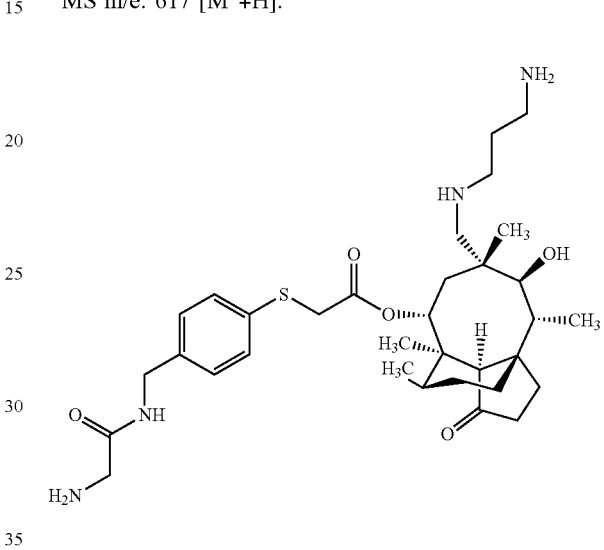

According, e.g. analogously, to a method as set out under Example 106 above, but using appropriate starting materials, the compounds of formula $I_{EX}$, wherein $R_{1EX}$ and $R_{2EX}$ are as defined in Table 11 are prepared. Chemical characterisation data are also set out in Table 11.

TABLE 11

| Example | | $R_{2EX}$ | $R_{1EX}$ |
|---|---|---|---|
| 107 | 12-epi-12-desvinyl-14-O-{(4-[(2-Amino-3-(4-hydroxy-phenyl)-propionylamino)-methyl]-phenylsulfanyl)-acetyl}-12-[(3-amino-propylamino)-methyl] mutilin trihydrochloride <br> $^1$H-NMR (200 MHz, DMSO-d6): 7.27 (d, 2H, arom., J = 8 Hz), 6.70 (d, 2H, arom., J = 8 Hz), 7.06-6.99 (m, 4H, arom.), 5.45 (d, 1H, H-14, J = 4.6 Hz), 1.37 (s, 3H, H-15), 0.89 (s, 3H, H-18), 0.81 (d, 3H, H-17, J = 4.6 Hz), 0.58 (d, 3H, H-16, J = 3 Hz) <br> MS m/e: 723 [M$^+$ + H] | | |

TABLE 11-continued

| Example | | R$_{2EX}$ | R$_{1EX}$ |
|---|---|---|---|
| 108 | 12-epi-12-desvinyl-14-O-{(4-[(3-Amino-propionylamino)-methyl]-phenylsulfanyl)-acetyl}-12-[(3-amino-propylamino)-methyl] mutilin trihydrochloride<br>$^1$H-NMR (200 MHz, DMSO-d$_6$): 7.32 (d, 2H, arom., J = 8 Hz), 7.22 (d, 2H, arom., J = 8 Hz), 5.45 (d, 1H, H-14, J = 6.2 Hz), 1.37 (s, 3H, H-15), 0.87 (s, 3H, H-18), 0.82 (d, 3H, H-17, J = 5.2 Hz), 0.58 (d, 3H, H-16, J = 5.4 Hz)<br>MS m/e: 631 [M$^+$ + H] | | |
| 109 | 12-epi-12-desvinyl-14-O-{(4-[(2-Amino-acetylamino)-methyl]-phenylsulfanyl)-acetyl}-12-[4-aminomethyl-benzylamino-methyl] mutilin trihydrochloride<br>$^1$H-NMR (200 MHz, DMSO-d$_6$): 7.29 (d, 2H arom., J = 8 Hz), 7.21 (d, 2H arom., J = 8 Hz), 5.41 (bs, 2H, H-14, 11-OH), 1.35 (s, 3H, H-15), 0.82 (bs, 6H, H-17, H-18), 0.56 (d, 3H, H-16, J = 3.2 Hz)<br>MS m/e: 679 [M$^+$ + H] | | |
| 110 | 12-epi-12-desvinyl-14-O-{(4-[(2-Amino-acetylamino)-methyl]-phenylsulfanyl)-acetyl}-12-(6-amino-hexylamino-methyl) mutilin trihydrochloride<br>MS m/e: 659 [M$^+$ + H] | | |

EXAMPLE 111

12-epi-12-desvinyl-14-O-{[(3-Acetylamino-methyl)-phenylsulfanyl]-acetyl}-12-[(3-amino-propylamino)-methyl] mutilin dihydrochloride

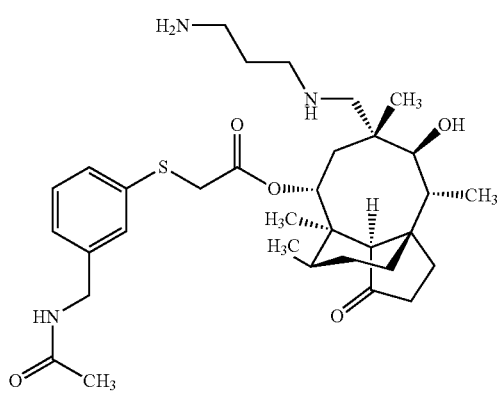 [SMILES: CC(=O)NCc1cccc(SCC(=O)O[C@@H]2C[C@](C)(CNCCCN)[C@@H](O)[C@H](C)[C@]34CCC(=O)[C@H]3[C@@]2(C)[C@H](C)CC4)c1]

was obtained similarly and in analogy to a method as set out in Example 1, but using appropriate starting materials. MS m/e: 602 [M$^+$+H].

Preparation of the intermediate N-(3-Mercapto-benzyl)-acetamide

Step a: [3-(3-Hydroxymethyl-phenyldisulfanyl)-phenyl]-methanol 2 g of 3-mercaptobenzyl alcohol was dissolved in 20 mL of MeOH. 1.8 g of iodine was added in portions with cooling until the colour of iodine persisted. The mixture obtained was diluted with EtOAc, washed with brine; the organic phase was dried over Na$_2$SO$_4$, brought to dryness and the brown oil obtained was used without purification in the next step.

Step b: Methanesulfonic acid 3-(3-methanesulfonyloxymethyl-phenyldisulfanyl)-benzyl ester 2 g of [3-(3-hydroxymethyl-phenyldisulfanyl)-phenyl]-methanol was dissolved in 20 mL of THF, 2.7 mL of N-methylmorpholine was added followed by 3.2 g of methanesulfonic anhydride and stirring was maintained overnight at rt. The mixture obtained was diluted with EtOAc, washed with brine, dried over Na$_2$SO$_4$, evaporated to dryness and dried in high vacuum for 30 min. The brown oil obtained was used without purification in the next step.

Step c: 3-(3-Aminomethyl-phenyldisulfanyl)-benzylamine 3.1 g of methanesulfonic acid 3-(3-methanesulfonyloxymethyl-phenyldisulfanyl)-benzyl ester was taken up in 50 mL of MeOH/25% ammonia solution 1:1 and stirred at rt overnight. The mixture obtained was partitioned between brine and DCM; the organic phase obtained was dried over Na$_2$SO$_4$ and brought to dryness. The colourless crystals obtained were used without purification in the next step.

Step d: N-{3-[3-(Acetylamino-methyl)-phenyldisulfanyl]-benzyl}-acetamide 1.2 g of 3-(3-aminomethyl-phenyldisulfanyl)-benzylamine was dissolved in 20 mL of DCM; cooled to 0-5° C. and 3.1 mL of DIPEA and 1.7 mL of acetic anhydride were added. The mixture obtained was stirred at rt overnight, diluted with EtOAc and washed with 1N HCl. The aqueous phase obtained was washed with EtOAc, and the combined organic layers were treated with brine, dried over Na$_2$SO$_4$ and evaporated to dryness. The colourless crystals obtained were used without purification in the next step.

Step e: N-(3-Mercapto-benzyl)-acetamide 1.55 g of N-{3-[3-(acetylamino-methyl)-phenyldisulfanyl]-benzyl}-acetamide was dissolved in 20 mL of DMF and 860 mg of DTT was added and stirring was maintained for 2 h. The mixture obtained was partitioned between EtOAc and brine, the organic phase was dried over Na$_2$SO$_4$, the solvent was evaporated to dryness and the residue obtained was dried in high vacuum for 10 min. The title compound was obtained in the form of a colourless oil.

EXAMPLE 112

12-epi-12-desvinyl-14-O-{(4-{[2-Amino-3-(4-aminomethyl-phenyl)-propionylamino]-methyl}-phenylsulfanyl)-acetyl}-12-[(3-amino-propylamino)-methyl] mutilin tetrahydrochloride was obtained similarly and in analogy to a method as set out in Example 106, but using appropriate starting materials.

$^1$H-NMR (200 MHz, DMSO-d$_6$): 7.44 (d, 2H arom., J=8 Hz), 7.28 (4H arom.), 7.12 (d, 2H arom. J=8 Hz), 5.46 (d, 1H, H-14, J=6.2 Hz), 1.37 (s, 3H, H-15), 0.89 (s, 3H, H-18), 0.81 (d, 3H, H-17, J=6.2 Hz), 0.58 (d, 3H, H-16, J=5.6 Hz); MS m/e: 736 [M$^+$+H].

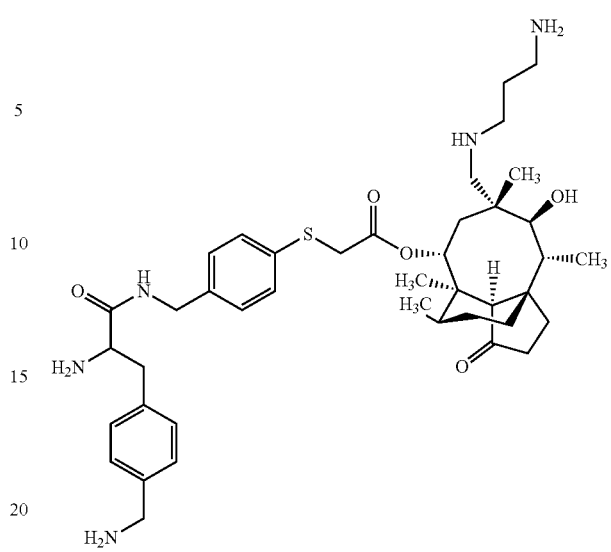

Preparation of the intermediate 2-tert-Butoxycarbonylamino-3-[4-(tert-butoxycarbonylamino-methyl)-phenyl]-propanoic acid Step a: 2-Amino-3-(4-cyano-phenyl)-propanoic acid A mixture of 3.9 g of 4-bromomethyl-benzonitrile, 5.34 g of (benzhydrylidene-amino)-acetic acid ethyl ester, 522 mg of Bu$_4$NBr and 5.16 g K$_2$CO$_3$ in 100 mL of CH$_3$CN was stirred at 25° C. for 24 h. The mixture obtained was filtered and the filtrate obtained was concentrated. The concentration residue obtained was treated with 50 mL of 2N HCl and 50 mL THF within 12 h. The mixture obtained was extracted with EtOAc (50 mL*3) and the pH of the aqueous phase was adjusted to pH=8 with Na$_2$CO$_3$. The mixture obtained was extracted 3× with 50 mL EtOAc, the organic phase obtained was washed with water, brine, dried over Na$_2$SO$_4$ and concentrated. The crude product obtained was used without purification in the next step.

Step b: Ethyl 2-(tert-butoxycarbonylamino)-3-[4-[(tert-butoxycarbonylamino)-methyl]-phenyl]-propanoate A mixture of 3 g of 2-amino-3-(4-cyano-phenyl)-propanoic acid, 7.2 g of BOC$_2$O and 500 mg of Pd/C in 100 mL of THF was stirred at rt for 16 h. The mixture obtained was filtered and the filtrate obtained was concentrated in vacuo. The crude product obtained was used without purification in the next step.

Step c: 2-tert-Butoxycarbonylamino-3-[4-(tert-butoxycarbonylamino-methyl)-phenyl]-propanoic acid A mixture of 6 g of ethyl 2-(tert-butoxycarbonylamino)-3-[4-[(tert-butoxycarbonylamino)-methyl]-phenyl]-propanoate and 1.1 g of NaOH in 40 mL of THF and 20 mL of water was stirred at rt for 16 h. From the mixture obtained THF was removed in vacuo and the residue was extracted 3× with 50 mL EtOAc. The aqueous phase's pH was adjusted to pH=8 with Na$_2$CO$_3$. The mixture obtained was extracted 3× with 50 mL EtOAc. The organic phase obtained was

EXAMPLE 113

12-epi-12-desvinyl-14-O-{{4-[(3-Amino-propylamino)-methyl]-phenylsulfanyl}-acetyl}-12-[(3-amino-propylamino)-methyl] mutilin tetrahydrochloride Step 1: 12-epi-12-desvinyl-14-O-[(4-Formyl-phenylsulfanyl)-acetyl]-12-[(3-tert-butoxycarbonylamino-propylamino)-methyl] mutilin Step 2: 12-epi-12-desvinyl-14-O-{{4-[(3-tert-Butoxycarbonylamino-propylamino)-methyl]-phenylsulfanyl}-acetyl}-12-[(3-tert-butoxycarbonylamino-propylamino)-methyl] mutilin

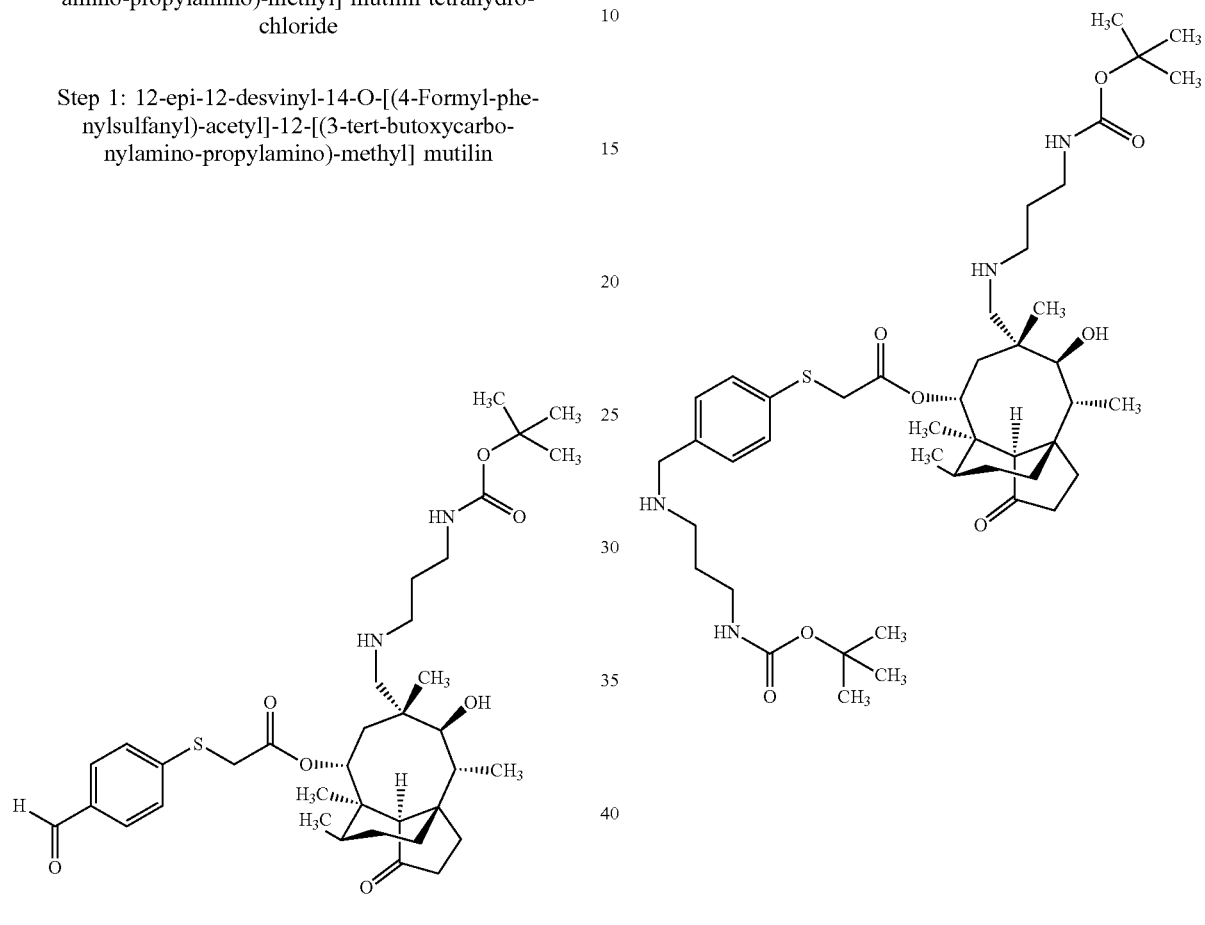

A mixture 0.92 g of 12-epi-12-desvinyl-14-O-[(4-Hydroxymethyl-phenylsulfanyl)-acetyl]-12-[(3-tert-butoxycarbonylamino-propylamino)-methyl]mutilin (Example 57 prior to BOC-deprotection) and 1.18 g of Dess-Martin reagent in 40 mL of DCM was stirred at rt for 2 h, diluted with water and extracted with DCM. The organic phase obtained was dried over Na₂SO₄, evaporated to dryness and subjected to column chromatography (DCM/MeOH=100/5). After concentration the title compound was obtained in the form of a white foam.

A mixture of 12-epi-12-desvinyl-14-O-[(4-Formyl-phenylsulfanyl)-acetyl]-12-[(3-tert-butoxycarbonylamino-propylamino)-methyl] mutilin (0.25 g) and (3-Amino-propyl)-carbamic acid tert-butyl ester (0.38 mmol) in dichloroethane (40 mL) was stirred at rt for 1 h. To the mixture obtained 161 mg of sodium triacetoxyborohydride was added and the mixture obtained was stirred at rt for 2 h, quenched with NaHCO₃, and extracted with DCM. The organic phase obtained was dried over Na₂SO₄, evaporated to dryness and the evaporation residue obtained was subjected to column chromatography (DCM/MeOH/aq. NH₃=10:1:0.1). After concentration the title compound was obtained in the form of a white foam.

Step 3: 12-epi-12-desvinyl-14-O-{{4-[(3-Amino-propylamino)-methyl]-phenylsulfanyl}-acetyl}-12-[(3-amino-propylamino)-methyl] mutilin tetrahydrochloride

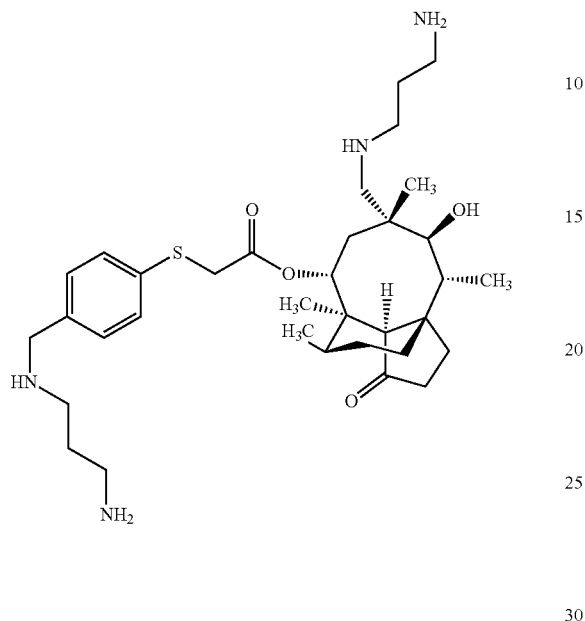

BOC-deprotection of the compound obtained in step 2 was carried out as described in Example 1, Step 6.

$^1$H-NMR (200 MHz, DMSO-d$_6$): 7.56 (d, 2H, arom., J=8 Hz), 7.37 (d, 2H, arom., J=8 Hz), 5.47 (d, 1H, H-14, J=7.2 Hz), 1.36 (s, 3H, H-15), 1.0 (s, 3H, H-18), 0.82 (d, 3H, H-17, J=4.8 Hz), 0.60 (d, 3H, H-16, J=4 Hz)

MS m/e: 614 [M$^+$+H].

According, e.g. analogously, to a method as set out under Example 113 above, but using appropriate starting materials, the compounds of formula I$_{EX}$, wherein R$_{1EX}$ and R$_{2EX}$ are as defined in Table 12 are prepared. Chemical characterisation data are also set out in Table 12.

TABLE 12

| Example | | R$_{2EX}$ | R$_{1EX}$ |
|---|---|---|---|
| 114 | 12-epi-12-desvinyl-14-O-{{3-[(3-Amino-propylamino)-methyl]-phenylsulfanyl}-acetyl}-12-[(3-amino-propylamino)-methyl] mutilin tetrahydrochloride MS m/e: 617 [M$^+$ + H] | (3-aminopropylaminomethyl-phenyl group) | (aminopropylaminomethyl group) |

TABLE 12-continued

| Example | | $R_{2EX}$ | $R_{1EX}$ |
|---|---|---|---|
| 115 | 12-epi-12-desvinyl-14-O-{{4-[(4-Aminomethyl-benzylamino)-methyl]-phenylsulfanyl}-acetyl}-12-[(3-amino-propylamino)-methyl] mutilin tetrahydrochloride<br>MS m/e: 679 [M+ + H] | | |
| 116 | 12-epi-12-desvinyl-14-O-[(3-Allylaminomethyl-phenylsulfanyl)-acetyl]-12-[(3-amino-propylamino)-methyl] mutilin trihydrochloride<br>$^1$H-NMR (200 MHz, DMSO-d$_6$): 7.38 (s, 4H, arom.), 1.35 (s, 3H, H-15), 0.90 (s, 3H, H-18), 0.81 (d, 3H, H-17, J = 5.4 Hz), 0.59 (d, 3H, H-16, J = 4.6 Hz)<br>MS m/e: 600 [M+ + H] | | |
| 117 | 12-epi-12-desvinyl-14-O-{{4-[(3-Amino-propylamino)-methyl]-phenylsulfanyl}-acetyl}-12-{[3-(3-amino-propoxy)-propylamino]-methyl} mutilin tetrahydrochloride<br>$^1$H-NMR (200 MHz, DMSO-d$_6$): 7.56 (d, 2H arom., J = 8 Hz), 7.37 (d, 2H arom., J = 8 Hz), 5.46 (bs, 2H, H-14, 11-OH), 1.36 (s, 3H, H-15), 0.93 (s, 3H, H-18), 0.82 (d, 3H, H-17, J = 6.2 Hz), 0.60 (d, 3H, H-16, J = 5.6 Hz)<br>MS m/e: 675 [M+ + H] | | |
| 118 | 12-epi-12-desvinyl-14-O-[(4-Cyclopropylaminomethyl-phenylsulfanyl)-acetyl]-12-[(3-amino-propylamino)-methyl] mutilin trihydrochloride<br>MS m/e: 600 [M+ + H] | | |
| 119 | 12-epi-12-desvinyl-14-O-[(4-Cyclopropylaminomethyl-phenylsulfanyl)-acetyl]-12-[(6-amino-hexylamino)-methyl] mutilin trihydrochloride<br>$^1$H-NMR (200 MHz, DMSO-d$_6$): 7.53 (d, 2H, arom., J = 8 Hz), 7.36 (d, 2H, arom., J = 8 Hz), 3.91 (s, 2H, H-22), 1.37 (s, 3H, H-15), 0.91 (s, 3H, H-18), 0.81 (d, 3H, H-17, J = 6.4 Hz), 0.59 (d, 3H, H-16, J = 5.6 Hz)<br>MS m/e: 642 [M+ + H] | | |

TABLE 12-continued

| Example | | $R_{2EX}$ | $R_{1EX}$ |
|---|---|---|---|
| 120 | 12-epi-12-desvinyl-14-O-{{4-[(4-Aminomethyl-benzylamino)-methyl]-phenylsulfanyl}-acetyl}-12-[(6-amino-hexylamino)-methyl] mutilin tetrahydrochloride<br>$^1$H-NMR (200 MHz, DMSO-d$_6$): 7.64-7.54 m (6H arom.), 7.37 (d, 2H arom., J = 8 Hz), 5.45 (bs, 2H, H-14, 11-OH), 1.38 (s, 3H, H-15), 0.89 (s, 3H, H-18), 0.81 (d, 3H, H-17, J = 5.4 Hz), 0.60 (d, 3H, H-16, J = 5.6 Hz)<br>MS m/e: 721 [M$^+$ + H] | | |
| 121 | 12-epi-12-desvinyl-14-O-{{4-[(4-Aminomethyl-benzylamino)-methyl]-phenylsulfanyl}-acetyl}-12-[(4-aminomethyl-benzylamino)-methyl]- mutilin tetrahydrochloride<br>MS m/e: 741 [M$^+$ + H] | | |

EXAMPLE 122

12-epi-12-desvinyl-14-O-[5-(3-Amino-propylcarbamoyl)-pyridin-2-ylsulfanyl]-acetyl-12-[(6-amino-hexylamino)-methyl] mutilin trihydrochloride was obtained similarly and in analogy to a method as set out in Example 1, but using appropriate starting materials.

$^1$H-NMR (200 MHz, DMSO-d$_6$): 7.47 (d, 1H, arom., J=8.4 Hz), 5.47 (d, 1H, H-14, J=5.8 Hz), 4.01 (s, 2H, H-22), 1.37 (s, 3H, H-15), 0.92 (s, 3H, H-18), 0.81 (d, 3H, H-17, J=6 Hz), 0.64 (d, 3H, H-16, J=5.4 Hz)
MS m/e: 674 [M$^+$+H].

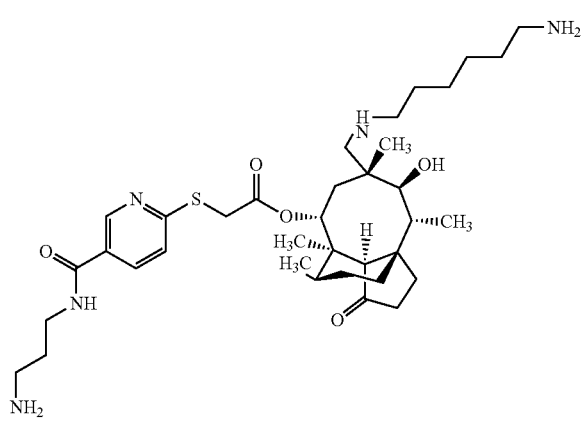 [SMILES: C[C@@H]1CC[C@@]23CCC(=O)[C@H]2[C@]1(C)[C@H](OC(=O)CSc1ccc(C(=O)NCCCN)cn1)C[C@](C)(CNCCCCCCN)[C@@H](O)[C@@H]3C]

Preparation of the intermediate tert-Butyl N-[3-[(6-sulfanylpyridine-3-carbonyl)-amino]-propyl]-carbamate Step a: 6-[(5-Chlorocarbonyl-2-pyridyl)-disulfanyl]-pyridine-3-carbonyl chloride 200 mg of 6,6'-dithiodinicotinic acid was refluxed in 5 mL of thionyl chloride for 1 h and the solvent was removed azeotropically with CHCl$_3$ on a rotary evaporator. The crude dichloride obtained was used immediately in the next step.

Step b: tert-Butyl N-[3-[[6-[[5-[3-(tert-butoxycarbonylamino)-propylcarbamoyl]-2-pyridyl]-disulfanyl]-pyridine-3-carbonyl]-amino]-propyl]-carbamate 222 mg of (3-Amino-propyl)-carbamic acid tert-butyl ester was dissolved in 10 mL of DCM, 445 µl of TEA was added followed by dropwise addition of 220 mg of 6-[(5-chlorocarbonyl-2-pyridyl)-disulfanyl]-pyridine-3-carbonyl chloride in 5 mL of DCM with external cooling (ice bath). After 30 min the mixture obtained was diluted with water and brine and filtered biphasically. The filter residue was sucked reasonably dry and dried in high vacuum overnight yielding the title compound as a light brown powder.

Step c: tert-Butyl N-[3-[(6-sulfanylpyridine-3-carbonyl)-amino]-propyl]-carbamate 174 mg of tert-Butyl N-[3-[[6-[[5-[3-(tert-butoxycarbonylamino)-propylcarbamoyl]-2-pyridyl]-disulfanyl]-pyridine-3-carbonyl]-amino]-propyl]-carbamate and 58 mg of DTT were dissolved in 20 mL of DMF and the mixture obtained was stirred at rt for 30 min. The mixture obtained was diluted with EtOAc, washed with 1N HCl and water, dried over Na$_2$SO$_4$ and brought to dryness yielding the title compound in the form of a pale brown powder.

EXAMPLE 123

12-epi-12-desvinyl-14-O-[(2,5-Bis-aminomethyl-phenylsulfanyl)-acetyl]-12-[(3-amino-propylamino)-methyl] mutilin tetrahydrochloride Step 1: 12-epi-12-desvinyl-14-O-[(2,5-Bis-hydroxymethyl-phenylsulfanyl)-acetyl]-12-[(3-tert-butoxycarbonylamino-propylamino)-methyl] mutilin

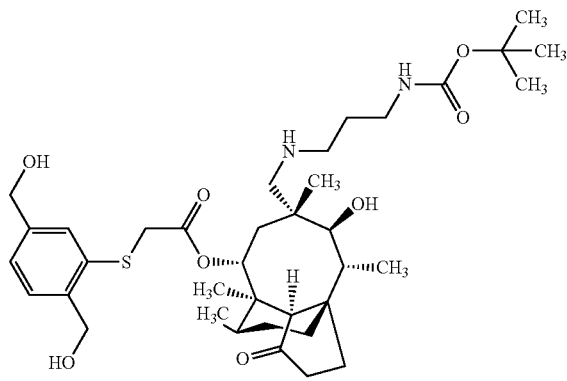 [SMILES: C[C@@H]1CC[C@@]23CCC(=O)[C@H]2[C@]1(C)[C@H](OC(=O)CSc1cc(CO)ccc1CO)C[C@](C)(CNCCCNC(=O)OC(C)(C)C)[C@@H](O)[C@@H]3C]

81 mg of (4-hydroxymethyl-2-mercapto-phenyl)-methanol was dissolved in 4 mL of CH$_3$CN, 53.4 mg of potassium tert-butoxide was added followed by 300 mg of 12-epi-12-desvinyl-14-O-[(toluene-4-yl-sulfonyloxy)-acetyl]-12-[(3-tert-butyloxycarbonylamino-propylamino)methyl] mutilin (Example 1 stop 1) in 2 mL of CH$_3$CN and stirring for 20 min. To the mixture obtained 5 mg of potassium tert-butoxide and 7 mg of the thiol was added and stirring was continued for another 35 min where upon the reaction was deemed to be complete by HPLC determination. The mixture obtained was diluted with water and extracted 4× with EtOAc, the combined organic phases were washed with 2N NaOH, water, dried over Na$_2$SO$_4$ and evaporated to dryness. The colourless foam obtained was used for the next step without further purification.

Step 2: 12-epi-12-desvinyl-14-O-[(2,5-Bis-azidomethyl-phenylsulfanyl)-acetyl]-12-[(3-tert-butoxycarbonylamino-propylamino)-methyl] motilin

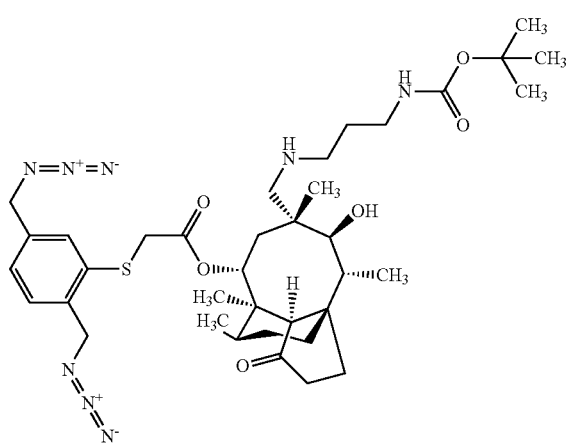 [SMILES: C[C@@H]1CC[C@@]23CCC(=O)[C@H]2[C@]1(C)[C@H](OC(=O)CSc1cc(CN=[N+]=[N-])ccc1CN=[N+]=[N-])C[C@](C)(CNCCCNC(=O)OC(C)(C)C)[C@@H](O)[C@@H]3C]

295 mg of 12-epi-12-desvinyl-14-O-[(2,5-Bis-hydroxymethyl-phenylsulfanyl)-acetyl]-12-[(3-tert-butoxycarbonylamino-propylamino)-methyl]mutilin was dissolved in 4.5 mL of THF, 267 mg of DPPA was added with external cooling, then 169 mg of DBU in 2 mL of CH$_3$CN over 10 min. The cooling bath was removed and the mixture obtained was stirred at rt overnight. To the mixture obtained ca. 20 mL water was added, the resulting slurry was extracted with EtOAc (2×), the combined organic phases were washed with water (2×) and brine, dried over Na$_2$SO$_4$, brought to dryness and the dry residue obtained was subjected to chromatography (eluent: EtOAc/Et$_3$N=100:1). The title compound was obtained in the form of colourless foamy crystals.

Step 3: 12-epi-12-desvinyl-14-O-[(2,5-Bis-aminomethyl-phenylsulfanyl)-acetyl]-12-[(3-tert-butoxycarbonylamino-propylamino)-methyl] motilin

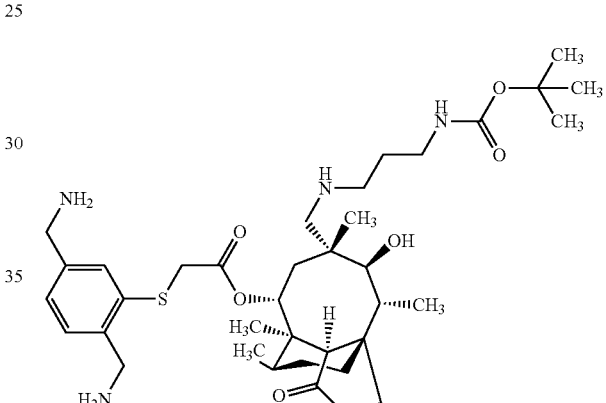

184 mg of 12-epi-12-desvinyl-14-O-[(2,5-Bis-azidomethyl-phenylsulfanyl)-acetyl]-12-[(3-tert-butoxycarbonylamino-propylamino)-methyl]mutilin was dissolved in 4 mL of EtOH, 1.35 mL of water was added and the mixture obtained was sonicated to obtain a clear solution. To the solution obtained 62.1 mg of NH$_4$Cl and 43.4 mg of zinc powder were added and the mixture obtained was heated to reflux for 10 min and cooled to rt. To the mixture obtained 2 mL of 25% NH$_4$OH was added and the phases were separated. The aqueous phase obtained was washed with EtOAc (2×), the combined organic phases were dried, brought to dryness and the dry residue was subjected to chromatography over silica gel (eluent: EtOAc/EtOH/NH$_4$OH=90:10:2). The title compound was obtained in the form of a colourless foam.

Step 4: 12-epi-12-desvinyl-14-O-[(2,5-Bis-aminomethyl-phenylsulfanyl)-acetyl]-12-[(3-amino-propylamino)-methyl] mutilin tetrahydrochloride

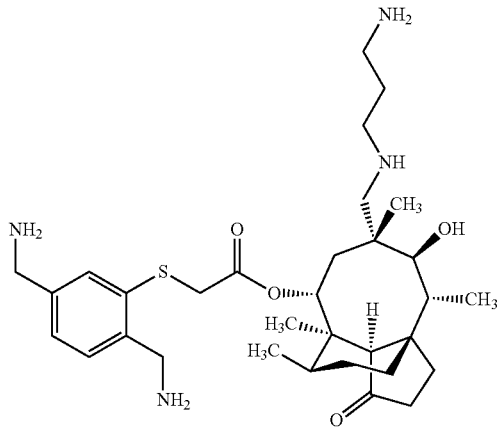 [SMILES: C[C@@H]1CC[C@@]23CCC(=O)[C@H]2[C@]1(C)[C@H](OC(=O)CSc1cc(CN)ccc1CN)C[C@](C)(CNCCCN)[C@@H](O)[C@@H]3C]

BOC-deprotection of the compound obtained in step 3 was carried out as described in Example 1, Step 6.

$^1$H-NMR (200 MHz, DMSO-d$_6$): 7.77 (s, 1H, H-2, arom.), AB-system (v$_A$=7.54, 2H, arom., v$_B$=7.44, 2H, J=8 Hz), 5.43 (d, 1H, H-14, J=6.4 Hz), 1.34 (s, 3H, H-15), 0.92 (s, 3H, H-18), 0.81 (d, 3H, H-17, J=5.4 Hz), 0.55 (d, 3H, H-16, J=5.4 Hz)
MS m/e: 623 [M$^-$+Cl]

Preparation of the intermediate
(4-Hydroxymethyl-2-mercapto-phenyl)-methanol

Step a: 2-Chlorosulfonylterephthalic acid 15.3 g of 2-sulfoterephthalic acid sodium salt and 49 g of phosphorous pentachloride were mixed and the mixture was heated to 80° C. over night, cooled to rt and poured onto ice followed by extraction with diethyl ether. The organic phase obtained was washed successively with ice water until pH=4, and optionally with brine, dried over Na$_2$SO$_4$ and evaporated to dryness. The product was obtained in the form of colourless crystals.

Step b: 2-Mercaptoterephthalic acid 19 g of 2-chlorosulfonylterephthalic acid was dissolved in 200 mL of THF and with external cooling 66 g of triphenylphosphine was added, followed by 1 mL of water and heating to reflux for 1 h. The mixture obtained was cooled to rt and poured onto 2N NaOH. The mixture obtained was washed twice with EtOAc; the aqueous phase obtained was acidified with 36% HCl, extracted with EtOAc, the organic phase obtained dried over Na$_2$SO$_4$ and evaporated to dryness yielding the title compound in the form of colourless crystals.

Step c:
(4-Hydroxymethyl-2-mercapto-phenyl)-methanol 11.5 g (303 mmol) of LAH was slurried in 100 mL of dry THF and brought to reflux. To that mixture 4.4 g of 2-mercaptoterephthalic acid, dissolved in 100 mL of dry THF, was added slowly and after complete addition the mixture obtained was refluxed overnight. The mixture obtained was cooled in an ice bath and rendered acidic by the cautious addition of conc. HCl. The acidic mixture obtained was extracted with EtOAc, the organic phase obtained was stirred with solid NaHCO$_3$, the mixture obtained was decanted, the organic phase obtained was dried over Na$_2$SO$_4$, evaporated to dryness and dried in high vacuum overnight yielding the title compound.

According, e.g. analogously, to a method as set out under Example 123 above, but using appropriate starting materials, the compound of formula I$_{EX}$, wherein R$_{1EX}$ and R$_{2EX}$ are as defined in Table 13 is prepared. Chemical characterisation data are also set out in Table 13.

TABLE 13

| Example | | R$_{2EX}$ | R$_{1EX}$ |
|---|---|---|---|
| 124 | 12-epi-12-desvinyl-14-O-[(3,5-Bis-aminomethyl-phenylsulfanyl)-acetyl]-12-[(3-amino-propylamino)-methyl] mutilin tetrahydrochloride<br>$^1$H-NMR (200 MHz, DMSO-d$_6$): 7.58 (s, 2H, H-2, H-6, arom.), 7.37 (s, 1H, H-4, arom.), 5.48 (d, 1H, H-14, J = 6.2 Hz), 1.33 (s, 3H, H-15), 0.96 (s, 3H, H-18), 0.81 (d, 3H, H-17, J = 5.6 Hz), 0.62 (d, 3H, H-16, J = 5 Hz)<br>MS m/e: 589 [M$^+$ + H] | 3,5-bis(aminomethyl)phenyl | 3-aminopropylaminoethyl |

EXAMPLE 125

12-epi-12-desvinyl-14-O-{[(3-Amino-propylcarbamoyl)-phenylsulfanyl]-acetyl}-12-[(2-guanidino-ethyl] mutilin dihydrochloride Step 1: 4-epi-12-epi-12-(2-Amino-ethyl)-14-O-{{4-[(3-tert-butoxycarbonylamino-propylcarbamoyl)-methyl]-phenylsulfanyl}-acetyl}-3-deoxo-11-deoxy-12-desvinyl-3-methoxy-11-oxo mutilin 305 mg of 4-epi-12-epi-12-(2-Allylamino-ethyl)-14-O-{{4-[(3-tert-butoxycarbonylamino-propylcarbamoyl)-methyl]-phenylsulfanyl}-acetyl}-3-deoxo-11-deoxy-12-desvinyl-3-methoxy-11-oxo mutilin (prepared from the intermediate of step 4, Example 52, via reductive amination with allylamine in analogy to Example 1, step 4) in 10 mL of DCM was degassed in an ultrasonic bath for 10 min and then added to a mixture of 382 mg of N,N'-dimethylbarbituric acid and 19 mg of tetrakis(triphenylphosphino) palladium (0) under an argon atmosphere. The mixture obtained was stirred at rt for 14 h. Since the reaction was not complete, the same amount of reagents was added and stirring was continued for another 24 h. The mixture obtained was diluted with DCM, washed with 10% K$_2$CO$_3$ solution (2×), the combined aqueous phases were washed with DCM, the combined organic layers were dried over Na$_2$SO$_4$ and evaporated to dryness. The residue in the form of orange foamy crystals was subjected to silica gel chromatography (eluent: EtOAc/Et$_3$N=100:1, 80:1, 60:1 and finally MeOH/Et$_3$N=10:1). The title compound of formula

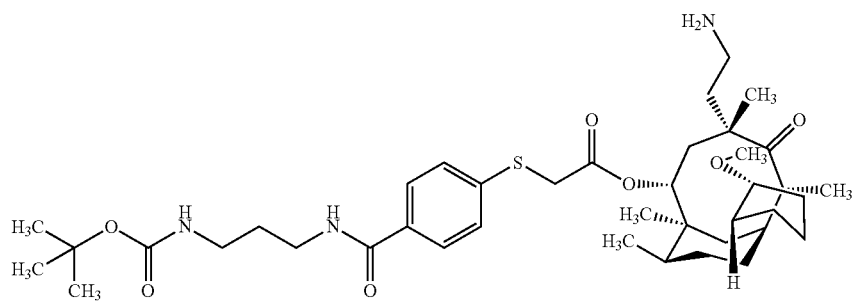

was obtained in the form of an orange-red semicrystalline oil.

Step 2: 4-epi-12-epi-12-(2-guanidino-ethyl)-14-O-{{4-[(3-tert-butoxycarbonylamino-propylcarbamoyl)-methyl]-phenylsulfanyl}-acetyl}-3-deoxo-11-deoxy-12-desvinyl-3-methoxy-11-oxo mutilin

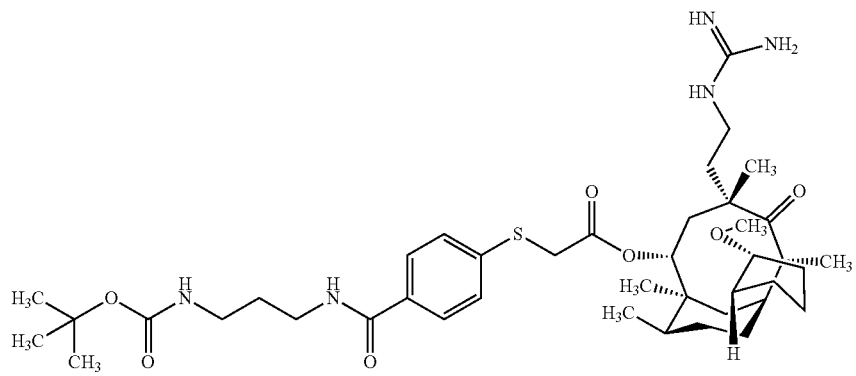

192 mg of 4-epi-12-epi-12-(2-Amino-ethyl)-14-O-{{4-[(3-tert-butoxycarbonylamino-propylcarbamoyl)-methyl]-phenylsulfanyl}-acetyl}-3-deoxo-11-deoxy-12-desvinyl-3-methoxy-11-oxo mutilin and 75 mg of S-methylisothiuronium iodide was dissolved in 10 mL of THF and the mixture obtained was stirred for 14 h at rt. Then again 75 mg of isothiuronium iodide was added and the mixture obtained was stirred for another 4 d, diluted with EtOAc, washed with 5% $NaHCO_3$ (2×), dried over $Na_2SO_4$ and brought to dryness. The title compound was obtained in the form of pale orange crystals which were used without purification in the next step.

Step 3: 12-epi-12-desvinyl-14-O-{[(3-Amino-propylcarbamoyl)-phenylsulfanyl]-acetyl}-12-[(2-guanidino-ethyl] mutilin dihydrochloride

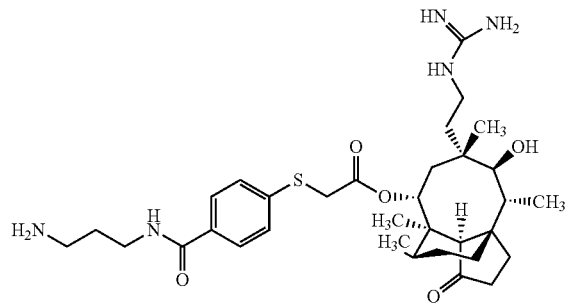 [SMILES: C[C@@H]1CC[C@@]23CCC(=O)[C@H]2[C@]1(C)[C@H](OC(=O)CSc1ccc(C(=O)NCCCN)cc1)C[C@](C)(CCNC(=N)N)[C@@H](O)[C@@H]3C]

174 mg of 4-epi-3-Methoxy-12-epi-12-desvinyl-14-O-{[4-(3-tert-butoxycarbonylamino-propylcarbamoyl)-phenylsulfanyl]-acetyl}-12-(2-guanidino-ethyl) mutilin was dissolved in 0.5 mL of DCM, 2 mL of 4N HCl in dioxane was added and after 15 min 5 mL of diethyl ether. The mixture obtained was stirred for 1 h and the formed precipitate was filtered off with suction, washed 5× with ether and dried in a rotovap bulb under vacuum without heating for 1 h. The crude product (brown crystals) was subjected to reverse chromatography (LiChroprep RP-18 (40-63 μm)) with $CH_3CN/H_2O$=0-30%. The title compound was obtained in the form of colourless crystals after lyophilisation.

MS m/e: 630 [M$^+$+H].

According, e.g. analogously, to a method as set out under Examples 1 and 23 above, but using appropriate starting materials, the compounds of formula $I_{EX}$, wherein $R_{1EX}$ and $R_{2EX}$ are as defined in Table 14 are prepared. Chemical characterisation data are also set out in Table 14.

TABLE 14

| Example | | $R_{2EX}$ | $R_{1EX}$ |
|---|---|---|---|
| 126 | 12-epi-12-desvinyl-14-O-{[4-(3-Hydroxy-propylcarbamoyl)-phenylsulfanyl]-acetyl}-12-[(6-amino-hexylamino)-methyl] mutilin dihydrochloride<br>$^1$H-NMR (200 MHz, DMSO-d$_6$): 8.57 (t, 1H, —CO—NH, J = 6 Hz), 7.82 (d, 2H, arom., J = 8 Hz), 7.38 (d, 2H, arom., J = 8 Hz), 5.46 (d, 1H, H-14, J = 6.8 Hz), 5.38 (bs, 1H, 11-OH), 3.96 (s, 2H, H-22), 1.36 (s, 3H, H-15), 0.87 (s, 3H, H-18), 0.80 (d, 3H, H-17, J = 6.4 Hz), 0.59 (d, 3H, H-16, J = 5.6 Hz)<br>MS m/e: 674 [M$^+$ + H] | *(4-carboxamide-phenyl linked to N-(3-hydroxypropyl)amide)* | *(6-aminohexylamino-methyl)* |
| 127 | 12-epi-12-desvinyl-14-O-[(2-Hydroxy-ethylsulfanyl)-acetyl]-12-[(6-amino-hexylamino)-methyl] mutilin dihydrochloride<br>$^1$H-NMR (200 MHz, DMSO-d$_6$): 5.48 (d, 1H, H-14, J = 7.6 Hz), 1.41 (s, 3H, H-15), 0.99 (s, 3H, H-18), 0.83 (d, 3H, H-17, J = 6 Hz), 0.65 (d, 3H, H-16, J = 5.2 Hz)<br>MS m/e: 541 [M + H] | *(2-hydroxyethyl)* | *(6-aminohexylamino-methyl)* |

EXAMPLE 128

12-epi-12-desvinyl-14-O-{[3-(2,2-Difluoro-ethyl-amino)-cyclohexylsulfanyl]-acetyl}-12-[(6-amino-hexylamino)-methyl] mutilin trihydrochloride

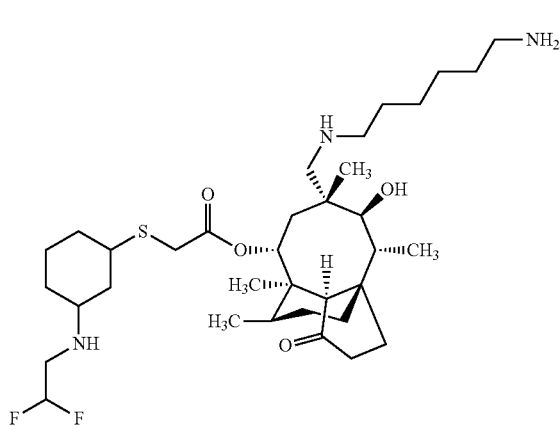 [SMILES: C[C@@H]1CC[C@@]23CCC(=O)[C@H]2[C@]1(C)[C@H](OC(=O)CSC1CCCC(NCC(F)F)C1)C[C@](C)(CNCCCCCCN)[C@@H](O)[C@@H]3C]

was obtained similarly and in analogy to a method as set out in Example 1, but using appropriate starting materials.

$^1$H-NMR (200 MHz, DMSO-d$_6$): 5.48 (d, 1H, H-14, J=6.8 Hz), 1.40 (s, 3H, H-15), 0.98 (s, 3H, H-18), 0.82 (d, 3H, H-17, J=6 Hz), 0.65 (d, 3H, H-16, J=5 Hz)

MS m/e: 658 [M+H].

Preparation of thioacetic acid S-[3-(2,2-difluoro-ethylamino)-cyclohexyl] ester

Step a: Thioacetic acid S-(3-oxocyclohexyl) ester

A mixture of 2.45 mL of 2-cyclohexene-1-one, 1.96 mL of thioacetic acid and 11 mL of water was stirred vigorously over 5 h at rt, extracted with DCM (2×); the combined organic phases were washed successively with 5% NaHCO$_3$, 2N HCl and brine, dried over Na$_2$SO$_4$ and evaporated to dryness. The evaporation residue obtained was subjected to chromatography over silica gel (eluent: cyclohexane/EtOAc=30:1). The title compound was obtained in the form of a pale yellow oil.

Step b: Thioacetic acid S-[3-(2,2-difluoroethylamino)cyclohexyl] ester 1 g of thioacetic acid S-(3-oxocyclohexyl) ester and 470 mg of 2,2-difluoroethylamine were dissolved with stirring in 20 mL of dichloroethane; 2.7 g of sodium triacetoxyborohydride and 498 μL of acetic acid was added and the mixture obtained was stirred overnight at rt followed by neutralisation with 5% aqueous NaHCO$_3$ solution and extraction with EtOAc (2×). The combined organic phases obtained were dried over Na$_2$SO$_4$ and brought to dryness. The residue obtained was subjected to chromatography over silica gel (eluent: toluene/acetone=8:1) to obtain the title compound in the form of a yellow oil.

Accordingly, e.g. analogously, to a method as set out under Example 1 above, but using appropriate starting materials, the compound of formula I$_{EX}$, wherein R$_{1EX}$ and R$_{2EX}$ are as defined in Table 15 is prepared. Chemical characterisation data are also set out in Table 15.

TABLE 15

| Example | | $R_{2EX}$ | $R_{1EX}$ |
|---|---|---|---|
| 129 | 12-epi-12-desvinyl-14-O-[(2-Amino-7H-purin-6-ylsulfanyl)-acetyl]-12-[(6-amino-hexylamino)-methyl] mutilin dihydrochloride<br>$^1$H-NMR (200 MHz, DMSO-d$_6$): 8.53 (s, 1H, arom.), 5.46 (d, 1H, H-14, J = 6.8 Hz), AB (2H, H-22, v$_A$ = 4.23, v$_B$ = 4.13, J = 16 Hz), 1.35 (s, 3H, H-15), 0.90 (s, 3H, H-18), 0.79 (d, 3H, H-17, J = 6 Hz), 0.61 (d, 3H, H-16, J = 5 Hz).<br>[0306] MS m/e: 630 [M + H] | | |

EXAMPLE 130

12-epi-12-desvinyl-14-O-[(Azepan-4-ylsulfanyl)-acetyl]-12-[(6-amino-hexylamino)-methyl] mutilin trihydrochloride

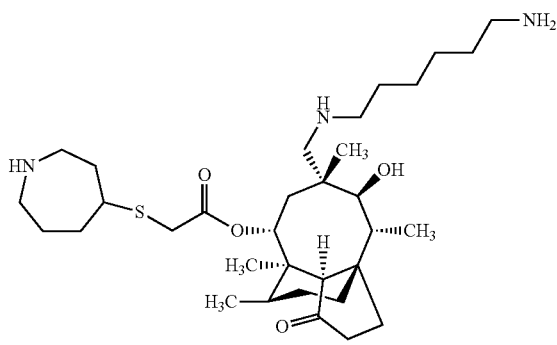 [SMILES: C[C@@H]1CC[C@@]23CCC(=O)[C@H]2[C@]1(C)[C@H](OC(=O)CSC1CCCNCC1)C[C@](C)(CNCCCCCCN)[C@@H](O)[C@@H]3C]

was obtained similarly and in analogy to a method as set out in Example 1, but using appropriate starting materials.

$^1$H-NMR (200 MHz, DMSO-d$_6$): 5.47 (d, 1H, H-14, J=7 Hz), 5.35 (bs, 1H, 11-OH), 1.40 (s, 3H, H-15), 0.97 (s, 3H, H-18), 0.82 (d, 3H, H-17, J=5.8 Hz), 0.64 (d, 3H, H-16, J=5.2 Hz).

MS m/e: 594 [M+H]

Preparation of the intermediate tert-butyl 4-acetylsulfanyl-azepane-1-carboxylate Step a: 4-Oxo-azepane-1-carboxylic acid tert-butyl ester 2.5 g of 4-Oxo-piperidine-1-carboxylic acid tert-butyl ester was dissolved in diethyl ether, cooled to −35° C., 2 mL of diazoacetic acid diethyl ester and 2.15 mL of borontrifluoride diethyl ether complex were added simultaneously and stirring at −35° C. was continued for one h. The mixture obtained was allowed to warm to rt and was rendered alkaline with 30% K$_2$CO$_3$ solution. The mixture obtained was extracted with EtOAc, the organic phase obtained was dried over Na$_2$SO$_4$, evaporated to dryness and the residue was dried in high vacuum leaving a yellow oil. The oil was taken up in 12 mL of THF, treated with 1.8 g of LiOH in 4 mL of water and the mixture obtained was refluxed overnight, cooled to rt and partitioned between brine and EtOAC. The phases obtained were separated and the organic phase obtained was dried over Na$_2$SO$_4$, brought to dryness and dried in high vacuum. The title compound was obtained in the form of colourless crystals.

Step b: 4-Hydroxy-azepane-1-carboxylic acid tert-butyl ester 2.06 g of 4-Oxo-azepane-1-carboxylic acid tert-butyl ester was dissolved in 20 mL of THF/MeOH 4:1, treated with external cooling with 370 mg of sodium borohydride and stirred with cooling for 1 h. The cold solution obtained was quenched with 10 mL of MeOH/H$_2$O 1:1, the organic solvents were removed in vacuo and the residue obtained was partitioned between DCM and water; the organic phase was separated, dried over Na$_2$SO$_4$ and evaporated to dryness. The title compound in the form of a colourless oil was obtained.

Step c: tert-Butyl 4-methylsulfonyloxy-azepane-1-carboxylate 2.08 g of 4-Hydroxy-azepane-1-carboxylic acid tert-butyl ester, dissolved in 10 mL of DCM, was treated with external ice cooling with 2.02 g of methanesulfonic anhydride followed by 2.02 mL of TEA and stirred for one h. The phases obtained were separated, the organic phase obtained was washed with brine, dried over Na$_2$SO$_4$ and brought to dryness. The title compound in the form of a semicrystalline oil was obtained.

Step d: tert-Butyl 4-acetylsulfanyl-azepane-1-carboxylate 2.75 g of tert-Butyl 4-methylsulfonyloxy-azepane-1-carboxylate and 2.14 g of potassium thioacetate was dissolved in 10 mL of DMF and warmed to 70° C. for 3 h. From the mixture obtained the solvent was partially removed in vacuo, the residue partitioned between EtOAc/n-heptane=3:1 and water, the organic phase was separated, dried over Na$_2$SO$_4$ and evaporated to dryness. The title compound in the form of a dark orange oil was obtained.

According, e.g. analogously, to a method as set out under Examples 1 and 130 above, but using appropriate starting materials, the compounds of formula I$_{EX}$, wherein R$_{1EX}$ and R$_{2EX}$ are as defined in Table 16 are prepared. Chemical characterisation data are also set out in Table 16.

TABLE 16

| Example | | $R_{2EX}$ | $R_{1EX}$ |
|---|---|---|---|
| 131 | 12-epi-12-desvinyl-14-O-[(Azepan-4-ylsulfanyl)-acetyl]-12-[(6-guanidino-hexylamino)-methyl] mutilin trihydrochloride<br>$^1$H-NMR (200 MHz, DMSO-d$_6$): 5.47 (d, 1H, H-14, J = 7.6 Hz), 5.37 (bs, 1H, 11-OH), 1.40 (s, 3H, H-15), 0.98 (s, 3H, H-18), 0.82 (d, 3H, H-17, J = 6.4 Hz), 0.64 (d, 3H, H-16, J = 4.8 Hz)<br>MS m/e: 637 [M$^+$ + H] | 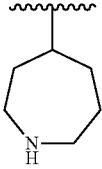 | 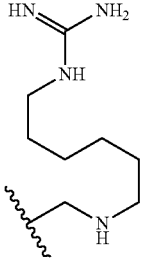 [SMILES: *CNCCCCCCNC(=N)N] |
| 132 | 12-epi-12-desvinyl-14-O-[(Azepan-4-ylsulfanyl)-acetyl]-12-[(4-aminomethyl-benzylamino)-methyl] mutilin trihydrochloride<br>$^1$H-NMR (200 MHz, DMSO-d$_6$): 7.68 (d, 2H, arom., J = 8 Hz), 7,53 (d, 2H, arom., J = 8 Hz), 5.45 (d, 1H, H-14, J = 7.2 Hz), 5.30 (bs, 1H, 11-OH), 1.39 (s, 3H, H-15), 0.92 (s, 3H, H-18), 0.80 (d, 3H, H-17, J = 6.4 Hz), 0.63 (d, 3H, H-16, J = 5 Hz)<br>MS m/e: 615 [M$^+$ + H] | 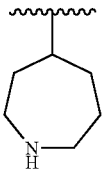 | 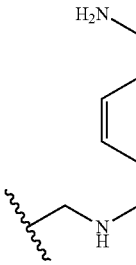 |
| 133 | 12-epi-12-desvinyl-14-O-[(Azepan-4-ylsulfanyl)-acetyl]-12-[(6-amino-octylamino)-methyl] mutilin trihydrochloride<br>$^1$H-NMR (200 MHz, DMSO-d$_6$): 5.45 (d, 1H, H-14, J = 5 Hz), 5.36 (bs, 1H, 11-OH), 1.39 (s, 3H, H-15), 0.96 (s, 3H, H-18), 0.81 (d, 3H, H-17, J = 5 Hz), 0.63 (d, 3H, H-16, J = 3.8 Hz)<br>MS m/e: 622 [M$^+$ + H]<br>The reductive amination was done as described in Example 1, step 4 using 10 eq of 1,8-diaminooctane | 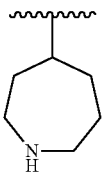 | 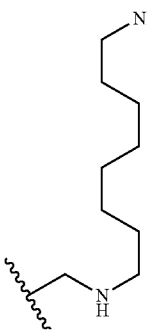 |

According, e.g. analogously, to a method as set out under Example 52, but with altered order of events (step 2→step 4→step 5→step 3→step 6, cf. Reaction Scheme 2) and using appropriate starting materials, the compounds of formula $I_{EX}$, wherein $R_{1EX}$ and $R_{2EX}$ are as defined in Table 17 are prepared. Chemical characterisation data are also set out in Table 17.

TABLE 17

| Example | | $R_{2EX}$ | $R_{1EX}$ |
|---|---|---|---|
| 134 | 12-epi-12-desvinyl-14-O-{[1-(2-Amino-acetyl)-piperidin-4-yl-sulfanyl)]-acetyl}-12-[(6-amino-hexylamino)-ethyl] mutilin trihydrochloride<br>$^1$H-NMR (200 MHz, DMSO-d$_6$): 5.47 (d, 1H, H-14, J = 7.8 Hz), 1.40 (s, 3H, H-15), 0.98 (s, 3H, H-18), 0.82 (d, 3H, H-17, J = 5.8 Hz), 0.64 (d, 3H, H-16, J = 5 Hz)<br>MS m/e: 608 [M$^+$ + H] | 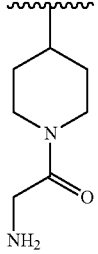 | 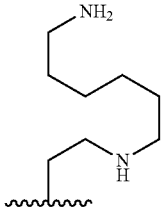 [SMILES: *CCNCCCCCCN] |

TABLE 17-continued

| Example | | R$_{2EX}$ | R$_{1EX}$ |
|---|---|---|---|
| 135 | 12-epi-12-desvinyl-14-O-{[1-(2-Amino-acetyl)-piperidin-4-yl-sulfanyl)]-acetyl}-12-[(4-aminomethyl-benzylamino)-ethyl] mutilin trihydrochloride<br>$^1$H-NMR (200 MHz, DMSO-d$_6$): 7.61 (d, 2H, arom., J = 8 Hz), 7.52 (d, 2H, arom., J = 8 Hz), 5.48 (d, 1H, H-14, J = 5 Hz), 4.77 (bs, 1H, 11-OH), 1.38 (s, 3H, H-15), 0.92 (s, 3H, H-18), 0.82 (d, 3H, H-17, J = 6 Hz), 0.64 (d, 3H, H-17, J = 5.2 Hz),<br>MS m/e: 671 [M$^+$ + H] | | |
| 136 | 12-epi-12-desvinyl-14-O-[5-Hydroxymethyl-pyridin-2-yl-sulfanylacetyl]-12-[(4-aminomethyl-3-fluoro-benzylamino)-ethyl] mutilin tetrahydrochloride<br>MS m/e: 655 [M$^+$ + H] | | |
| 137 | 12-epi-12-desvinyl-14-O-{4-[(2-Amino-acetylamino)-cyclohexylsulfanyl]-acetyl}-12-[(4-aminomethyl-3-fluoro-benzylamino)-ethyl] mutilin trihydrochloride<br>$^1$H-NMR (200 MHz, DMSO-d$_6$): 7.66-7.53 (m, 2H, arom.), 7.44 (d, 1H, arom., J = 7.6 Hz), 5.48 (d, 1H, H-14, J = 7.2 Hz), 4.72 (d, 1H, 11-OH, J = 5.8 Hz), 1.38 (s, 3H, H-15), 1.37 (s, 3H, H-15), 0.92 (s, 3H, H-18), 0.83 (d, 2H, H-17, J = 6.4 Hz), 0.65 (d, 3H, H-16, J = 5.4 Hz)<br>MS m/e: 703 [M$^+$ + H]<br>The required Thioacetic acid S-[4-(2-tert-butoxycarbonylamino-acetylamino)-cyclohexyl] ester was prepared in analogy to the procedure described in Example 78 using the appropriate starting materials | | |
| 138 | 12-epi-12-desvinyl-14-O-{[1-(2-Amino-acetyl)-piperidin-4-yl-sulfanyl]-acetyl}-12-[(4-aminomethyl-3-fluoro-benzylamino)-ethyl] mutilin trihydrochloride<br>MS m/e: 689 [M$^+$ + H] | | |
| 139 | 12-epi-12-desvinyl-14-O-[(5-Aminomethyl-pyridin-2-yl-sulfanyl)-acetyl]-12-[(4-aminomethyl-2,5-difluoro-benzylamino)-ethyl] mutilin tetrahydrochloride<br>MS m/e: 673 [M$^+$ + H] | | |

TABLE 17-continued

| Example | | $R_{2EX}$ | $R_{1EX}$ |
|---|---|---|---|
| 140 | 12-epi-12-desvinyl-14-O-{[1-(2-Amino-acetyl)-piperidin-4-yl-sulfanyl]-acetyl}-12-[(4-aminomethyl-2,5-difluoro-benzylamino)-ethyl] mutilin trihydrochloride<br>MS m/e: 707 [M⁺ + H] | | |
| 141 | 12-epi-12-desvinyl-14-O-{[1-(2-Amino-acetyl)-piperidin-4-yl-sulfanyl]-acetyl}-12{2-[4-(2-amino-ethoxy)-benzylamino]-ethyl} mutilin trihydrochlorid<br>MS m/e: 701 [M⁺ + H] | | |
| 142 | 12-epi-12-desvinyl-14-O-{{4-[(2-Amino-acetylamino)-methyl]-cyclohexylsulfanyl}-acetyl}-12-[(4-aminomethyl-3-fluoro-benzylamino)-ethyl] mutilin trihydrochloride<br>MS m/e: 717 [M⁺ + H]<br>The required Thioacetic acid S-{4-[(2-tert-butoxycarbonylamino-acetylamino)-methyl]-cyclohexyl} ester was prepared in analogy to the procedure described in Example 78 using the appropriate starting materials | | |

EXAMPLE 143

12-epi-12-desvinyl-14-O-[(Azepan-4-ylsulfanyl)-acetyl]-12-[(4-aminomethyl-phenylamino)-ethyl] mutilin trihydrochloride Step 1: 4-epi-12-epi-3-deoxo-11-deoxy-12-desvinyl-3-methoxy-11-oxo-12-(2-oxo-ethyl)-14-O-[(toluene-4-sulfonyloxy)-acetyl] mutilin

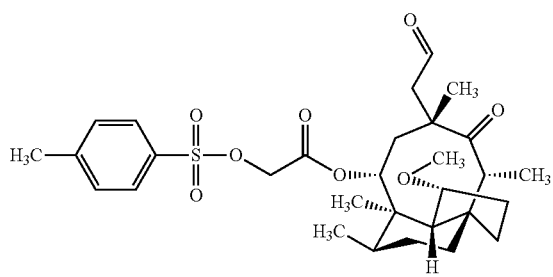

was prepared by Dess-Martin oxidation from 4-epi-12-epi-3-deoxo-11-deoxy-12-desvinyl-12-(2-hydroxy-ethyl)-3-methoxy-11-oxo-14-O-[(toluene-4-sulfonyloxy)-acetyl] mutilin (Example 52, step 2) in analogy to the procedure described in Example 52, step 4.

Step 2: 4-epi-12-epi-3-deoxo-11-deoxy-12-desvinyl-3-methoxy-11-oxo-14-O-[(toluene-4-sulfonyloxy)-acetyl]-12-(2-{4-[(2,2,2-trifluoro-acetylamino)-methyl]-phenylamino}-ethyl) mutilin

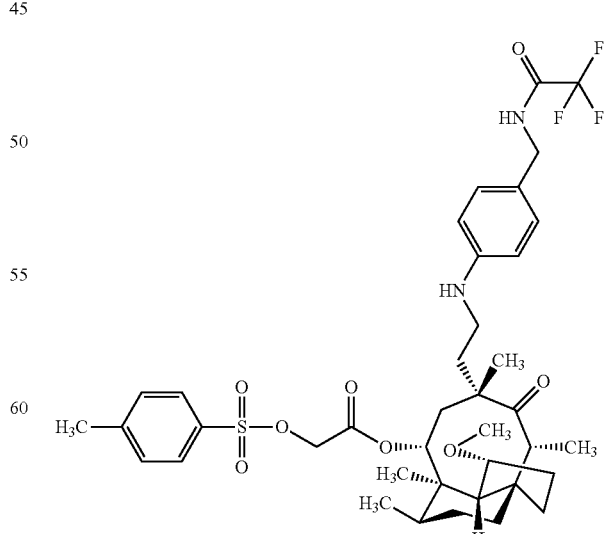

was prepared by reductive amination of 4-epi-12-epi-3-deoxo-11-deoxy-12-desvinyl-3-methoxy-11-oxo-12-(2-oxo-ethyl)-14-O-[(toluene-4-sulfonyloxy)-acetyl] mutilin with N-(4-Amino-benzyl)-2,2,2-trifluoro-acetamide according to the procedure described in Example 1, step 4.

Step 3: 12-epi-12-desvinyl-14-O-[(Toluene-4-sulfonyloxy)-acetyl]-12-(2-{4-[(2,2,2-trifluoro-acetylamino)-methyl]-phenylamino}-ethyl) motilin

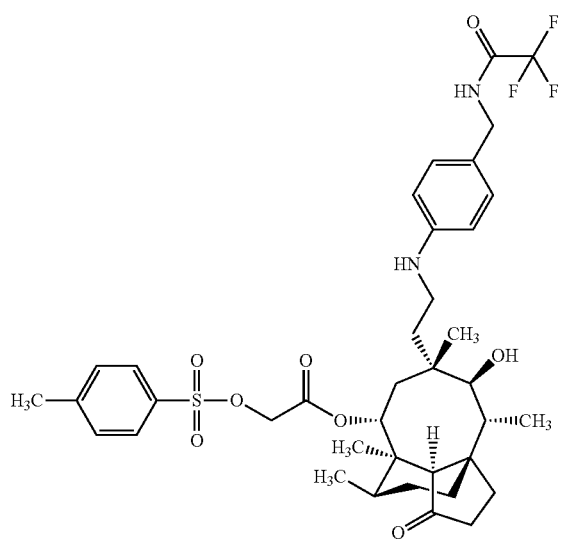 [SMILES: Cc1ccc(S(=O)(=O)OCC(=O)O[C@@H]2C[C@](C)(CCNc3ccc(CNC(=O)C(F)(F)F)cc3)[C@@H](O)[C@H](C)[C@]34CCC(=O)[C@H]3[C@@]2(C)[C@H](C)CC4)cc1]

1.36 g of 4-epi-12-epi-3-deoxo-11-deoxy-12-desvinyl-3-methoxy-11-oxo-14-O-[(toluene-4-sulfonyloxy)-acetyl]-12-(2-{4-[(2,2,2-trifluoro-acetylamino)-methyl]-phenylamino}-ethyl) mutilin was dissolved in 10 mL of 1,4 dioxane and 2.5 mL of Lucas reagent was added. The mixture was stirred at ambient temperature for 2 h, diluted with EtOAc and washed with 2× water, NaHCO₃ and brine, dried over Na₂SO₄ and evaporated to dryness. The product was obtained as colorless foam and used for the next step without further purification.

Step 4: 12-epi-12-desvinyl-4-O-[(Azepan-4-ylsulfanyl)-acetyl]-12-[2-(4-aminomethyl-phenylamino)-ethyl] mutilin trihydrochloride

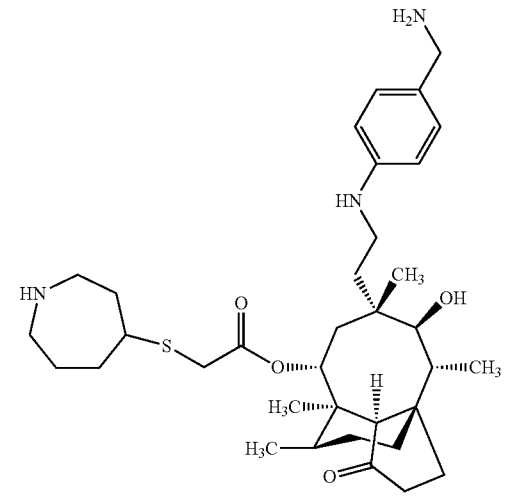 [SMILES: C[C@@H]1CC[C@@]23CCC(=O)[C@H]2[C@]1(C)[C@H](OC(=O)CSC1CCCNCC1)C[C@](C)(CCNc1ccc(CN)cc1)[C@@H](O)[C@@H]3C]

was prepared in analogy to Example 1, step 5 and 6 and Example 82 from 12-epi-2-desvinyl-14-O-[(toluene-4-sulfonyloxy)-acetyl]-12-(2-{4-[(2,2,2-Trifluoro-acetylamino)-methyl]-phenylamino}-ethyl) mutilin and Thioacetic acid S-azepan-4-yl ester. In order to ensure complete cleavage of the N-trifluoroacetyl group the reaction mixture was stirred an additional 20 min. at 40° C. The intermediate free amine was obtained as an off-white foam and converted into the hydrochloride salt without further purification.

$^1$H-NMR (200 MHz, DMSO-d$_6$): 7.47 (m, 2H, arom.), 5.46 (d, 1H, H-14, J=6.6 Hz), 1.38 (s, 3H, H-15), 0.91 (s, 3H, H-18), 0.81 (d, 3H, H-17, J=6 Hz), 0.63 (d, 3H, H-16, J=5.2 Hz)

MS m/e: 614 [M$^-$+Cl]

Preparation of the required
N-(4-Amino-benzyl)-2,2,2-trifluoro-acetamide

To 1 g of 4-(aminomethyl)-aniline in 50 mL of ethanol was slowly added 1.16 g of ethyl 2,2,2-trifluoroacetate at 4° C. The reaction mixture was allowed to warm to ambient temperature, diluted with EtOAc, washed with semi-saturated NaHCO₃ solution and dried over Na₂SO₄. After evaporation the product was obtained as yellow crystals.

Preparation of the required Thioacetic acid
S-azepan-4-yl ester

Tert-Butyl 4-acetylsulfanyl-azepane-1-carboxylate (intermediate of Example 130, step d) was deprotected in analogy to Example 1, step 6 to give the title compound.

According, e.g. analogously, to a method as set out under Example 143, but using appropriate starting materials, the compounds of formula $I_{EX}$, wherein $R_{1EX}$ and $R_{2EX}$ are as defined, in Table 18 are prepared. Chemical characterisation data are also set out in Table 18.

TABLE 18

| Example | | $R_{2EX}$ | $R_{1EX}$ |
|---|---|---|---|
| 144 | 12-epi-12-desvinyl-14-O-{{4-[(2-Amino-acetylamino)]-cyclohexylsulfanyl}-acetyl}-12-[(4-aminomethyl-phenylamino)-ethyl] mutilin trihydrochloride<br>$^1$H-NMR (200 MHz, DMSO-d$_6$): 5.48 (d, 1H, H-14, J = 4.6 Hz), 1.38 (s, 3H, H-15), 0.91 (s, 3H, H-18), 0.82 (d, 3H, H-17, J = 6.6 Hz), 0.64 (d, 3H, H-16, J = 5 Hz)<br>MS m/e: 705 [M$^-$ + Cl]<br>Thioacetic acid S-[4-(2-amino-acetylamino)-cyclohexyl] ester (prepared byreaction of the corresponding intermediate of Example 137 with TFA in DCM) was used as intermediate in step 4 | (structure) | (structure) |
| 145 | 12-epi-12-desvinyl-14-O-{[1-(2-Amino-acetyl)-piperidin-4-yl-methylsulfanyl]-acetyl}-12-[(4-aminomethyl-phenylamino)-ethyl] mutilin trihydrochloride<br>$^1$H-NMR (200 MHz, DMSO-d$_6$): 5.49 (d, 1H, H-14, J = 7.6 Hz), 1.38 (s, 3H, H-15), 0.92 (s, 3H, H-18), 0.82 (d, 3H, H-17, J = 6.6 Hz), 0.65 (d, 3H, H-16, J = 4.4 Hz)<br>MS m/e: 705 [M$^-$ + Cl]<br>Thioacetic acid S-[1-(2-amino-acetyl)-piperidin-4-ylmethyl] ester (prepared byreaction of the corresponding intermediate of Example 81 with TFA in DCM) was used as intermediate in step 4 | (structure) | (structure) |

EXAMPLE 146

12-epi-12-desvinyl-14-O-{[1-(2-Amino-acetyl)-piperidin-4-yl-sulfanyl]-acetyl}-2-(8-amino-octyl) mutilin dihydrochloride Step 1; 4-epi-12-epi-12-(8-Azido-oct-2-enyl)-3-deoxo-11-deoxy-12-desvinyl-3-methoxy-11-oxo-14-O-triethylsilyl mutilin

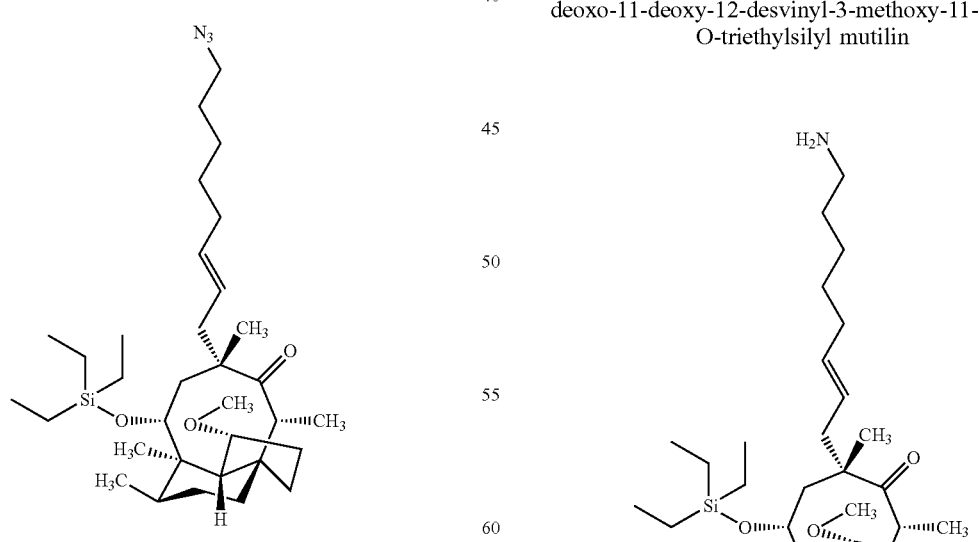

5.95 g of 6-Azidohexyl-triphenylphosphonium iodide was dissolved in 90 mL THF, 25 mL of 0.5M potassium hexamethyldisilazide in THF was added dropwise under argon at −78° C. After stirring at this temperature for 30 minutes 4.47 g of 4-epi-12-epi-3-deoxo-11-deoxy-12-desvinyl-3-methoxy-11-oxo-12-(2-oxo-ethyl)-14-O-triethylsilyl mutilin in 20 mL THF was added dropwise, the reaction mixture was left in the cooling bath and allowed to warm to ambient temperature overnight. The suspension was poured into 500 mL water/20 mL 2N HCl, extracted 3× with EtOAc, the combined organic layers were washed with 5% sodium bicarbonate solution, dried over Na$_2$SO$_4$ and evaporated to dryness, leaving a beige semi crystalline residue. Purification over silica gel (toluene/EtOAc=20:1) yielded the product as pale yellow oil.

Step 2: 4-epi-12-epi-12-(8-Amino-oct-2-enyl)-3-deoxo-11-deoxy-12-desvinyl-3-methoxy-11-oxo-14-O-triethylsilyl mutilin 4.31 g of 4-epi-12-epi-12-(8-Azido-oct-2-enyl)-3-deoxo-11-deoxy-12-desvinyl-3-methoxy-11-oxo-14-O-triethylsilyl mutilin was hydrogenated in an H-cube apparatus at 50 bar over 10% Pd/C (flow 1 mL/min). After evaporation of the solvent the title compound was isolated.

Step 3: 4-epi-12-epi-12-(8-Amino-octyl)-3-deoxo-11-deoxy-12-desvinyl-3-methoxy-11-oxo-14-O-triethylsilyl mutilin

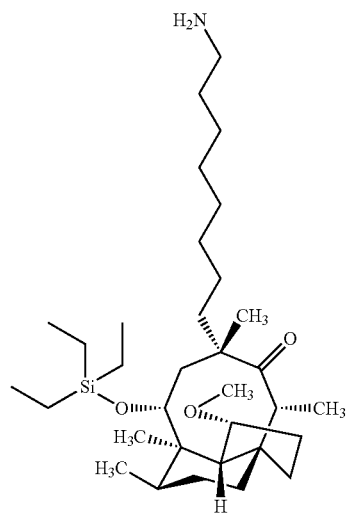

2.9 g (5.29 mmol) of 4-epi-12-epi-12-(8-Amino-oct-2-enyl)-3-deoxo-11-deoxy-12-desvinyl-3-methoxy-11-oxo-14-O-triethylsilyl mutilin was dissolved in 200 mL THF/MeOH 1+1 and hydrogenated (balloon) over 290 mg of 10% Pd/C for 16 hours. The catalyst was filtered off and the solvent evaporated yielding the product as yellow oil containing some residual solvent.

Step 4: 4-epi-12-epi-3-deoxo-11-deoxy-12-desvinyl-3-methoxy-11-oxo-14-O-triethylsilyl-12-[8-(2,2,2-trifluoro-acetylamino)-octyl] mutilin

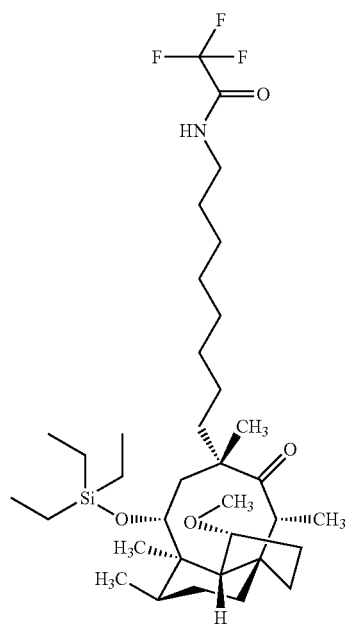

2.88 g of 4-epi-12-epi-12-(8-amino-octyl)-3-deoxo-11-deoxy-12-desvinyl-3-methoxy-11-oxo-14-O-triethylsilyl mutilin and 637 mg of triethylamine were dissolved in 25 mL dichloromethane, cooled in an ice bath, treated dropwise with 1.15 g of trifluoroacetic acid anhydride in 15 mL dichloromethane and then stirred at ambient temperature for 1 hour. The reaction mixture was washed with 1N HCl (20 mL), 5% sodium bicarbonate solution, dried over Na₂SO₄ and evaporated to dryness. The product was obtained as yellow oil.

Step 5: 4-epi-12-epi-3-deoxo-11-deoxy-12-desvinyl-3-methoxy-11-oxo-12-[8-(2,2,2-trifluoro-acetylamino)-octyl] mutilin

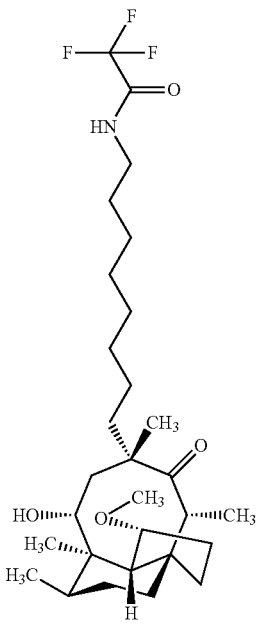

3.26 g of 4-epi-12-epi-3-deoxo-11-deoxy-12-desvinyl-3-methoxy-11-oxo-14-O-triethylsilyl-12-[8-(2,2,2-trifluoro-acetylamino)-octyl] mutilin was suspended in 65 mL ethanol containing 2 wt. % hydrochloric acid (aq) and stirred at ambient temperature. After 3 hours the mixture was partitioned between 5% sodium bicarbonate solution and EtOAc, the aqueous phase washed with EtOAc, the combined organic layers were dried over Na₂SO₄ and evaporated to dryness to give a pale yellow oil which was chromatographed over silica gel (DCM/tert-butyl methyl ether=40:1) to give a colorless oil.

Step 6: 4-epi-12-epi-14-O-Bromoacetyl-3-deoxo-11-deoxy-12-desvinyl-3-methoxy-11-oxo-12-[8-(2,2,2-trifluoro-acetylamino)-octyl] mutilin

Step 7: 4-epi-12-epi-14-O-{[1-(2-tert-Butoxycarbonylamino-acetyl)-piperidin-4-ylsulfanyl]-acetyl}-3-deoxo-11-deoxy-12-desvinyl-3-methoxy-11-oxo-12-[8-(2,2,2-trifluoro-acetylamino)-octyl] mutilin

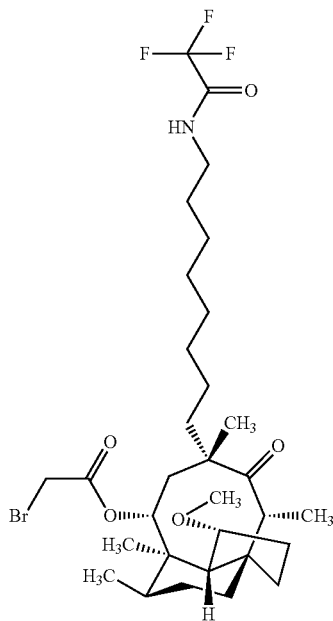

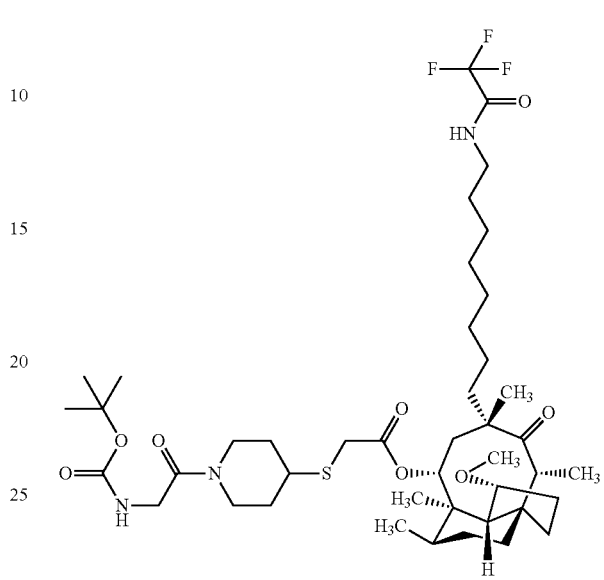

320 mg of 4-epi-12-epi-14-O-Bromoacetyl-3-deoxo-11-deoxy-12-desvinyl-3-methoxy-11-oxo-12-[8-(2,2,2-trifluoro-acetylamino)-octyl] mutilin and 233 mg of Thioacetic acid S-[1-(2-tert-butoxycarbonylamino-acetyl)-piperidin-4-yl] ester was dissolved in 10 mL methanol and treated with 294 μl 5M aqueous potassium carbonate solution, stirred 15 minutes at ambient temperature and 30 minutes in an ultrasonic bath. The reaction mixture was diluted with EtOAc, washed with 1N HCl, 2N NaOH, 5% sodium bicarbonate solution, dried over Na$_2$SO$_4$ and brought to dryness; the crude product was obtained as an orange oil.

750 mg (1.41 mmol) of 4-epi-12-epi-3-deoxo-11-deoxy-12-desvinyl-3-methoxy-11-oxo-12-[8-(2,2,2-trifluoro-acetylamino)-octyl] mutilin was dissolved in 10 mL EtOAc, treated with 571 mg of triethylamine, 52 mg of 4-dimethylaminopyridine and warmed with stirring to 50° C. 854 mg of bromoacetic acid bromide in 10 mL EtOAc was added dropwise over 20 minutes, during which time the reaction mixture turned dark brown. After 15 minutes 0.79 mL of Et$_3$N followed by 854 mg of bromoacetic acid bromide in 5 mL EtOAc and after further 15 minutes the same amount of Et$_3$N and bromoacetic acid bromide was added after which no starting material could be detected by TLC (toluene/EtOAc 5:1). 1 mL methanol was added to destroy residual acid bromide and stirring was continued for 45 minutes. Then the reaction solution was shaken with 1N HClmL, filtered over celite biphasically, the organic layer washed with 5% sodium bicarbonate solution, dried over Na$_2$SO$_4$ and evaporated to dryness. The crude product (black oil) was purified by chromatography over silica gel (eluant: DCM) and yielded the title compound as yellow oil.

Step 8: 4-epi-12-epi-12-(8-Amino-octyl)-14-O-{[1-(2-tert-Butoxycarbonylamino-acetyl)-piperidin-4-ylsulfanyl]-acetyl}-3-deoxo-11-deoxy-12-desvinyl-3-methoxy-11-oxo mutilin

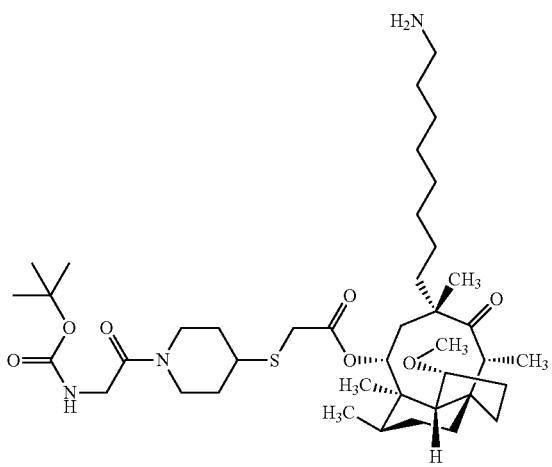

134 mg of 4-epi-12-epi-14-O-{[1-(2-tert-Butoxycarbonylamino-acetyl)-piperidin-4-ylsulfanyl]-acetyl}-3-deoxo-11-deoxy-12-desvinyl-3-methoxy-11-oxo-12-[8-(2,2,2-trifluoro-acetylamino)-octyl] mutilin was dissolved in 10 mL methanol, treated with 1.6 mL 1N sodium hydroxide solution and stirred at ambient temperature. After 1 hour 1.6 mL 1N sodium hydroxide solution was added and stirring was continued for 1 h. The solution was diluted with EtOAc and washed 2× with water; the combined aqueous layers were washed with EtOAc, the organic phases dried over $Na_2SO_4$ and evaporated to dryness to give a light yellow oil containing some residual solvent.

Step 9: 12-epi-12-desvinyl-14-O-{[1-(2-Amino-acetyl)-piperidin-4-ylsulfanyl]-acetyl}-12-(8-amino-octyl)-mutilin dihydrochloride

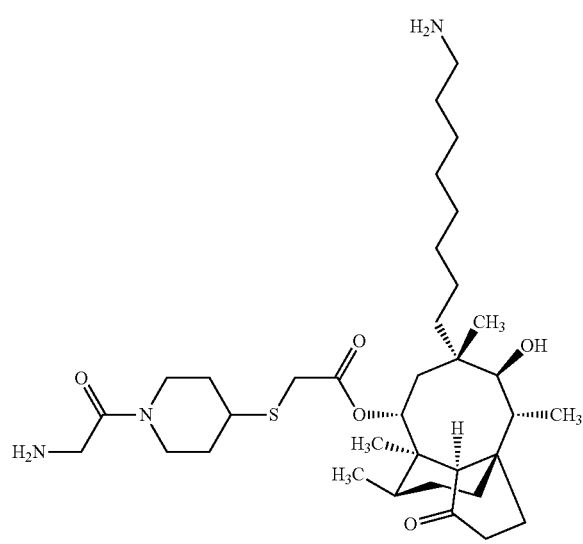 [SMILES: C[C@@H]1CC[C@@]23CCC(=O)[C@H]2[C@]1(C)[C@H](OC(=O)CSC1CCN(C(=O)CN)CC1)C[C@](C)(CCCCCCCCN)[C@@H](O)[C@@H]3C]

129 mg of 4-epi-12-epi-12-(8-Amino-octyl)-14-O-{[1-(2-tert-Butoxycarbonylamino-acetyl)-piperidin-4-ylsulfanyl]-acetyl}-3-deoxo-11-deoxy-12-desvinyl-3-methoxy-11-oxo mutilin was dissolved in 0.5 mL dioxane, treated with 2 mL 4N HCl in dioxane and the homogeneous solution was stirred at ambient temperature overnight. Then the volatiles were removed in vacuo and the residue (yellow oil) was purified by reversed phase chromatography (eluant: acetonitrile in water 0-35%). The title compound was obtained as colourless crystals.

$^1$H-NMR (200 MHz, DMSO-$d_6$): 5.46 (d, 1H, H-14, J=7.4 Hz), 1.33 (s, 3H, H-15), 0.83-0.77 (m, 6H, H-18, H-17), 0.62 (d, 3H, H-16, J=5.4 Hz)

MS m/e: 636 [M$^+$+H]

Preparation of the required
6-Azidohexyl-triphenylphosphonium iodide

Step a: 6-Hydroxyhexyl-triphenylphosphonium iodide 7.97 g of 6-iodohexanol and 9.17 g of triphenylphosphine was dissolved in 10 mL of acetonitrile and refluxed for 20 hours. The mixture was cooled to ambient temperature, treated with 150 mL diethyl ether, stirred for about 4 hours and left standing overnight. The resulting precipitate was filtered off, washed five times with diethyl ether and dried in high vacuum overnight; the product was obtained as colorless powder.

Step b: 6-Bromohexyl-triphenylphosphonium iodide 7.97 g of 6-iodohexanol and 9.17 g of triphenylphosphine was dissolved in 10 mL of acetonitrile and refluxed for 20 hours. The mixture was cooled to ambient temperature, treated with 150 mL diethyl ether, stirred for about 4 hours and left standing overnight. The resulting precipitate was filtered off, washed five times with diethyl ether and dried in high vacuum overnight; the product was obtained as colorless powder.

Step c: 6-Azidohexyl-triphenylphosphonium iod 10.4 g of 6-Bromohexyl-triphenylphosphonium iodide was dissolved in 25 mL ethanol, 1.83 g of sodium azide in 25 mL water was added and the mixture was refluxed for ca. 16 hours. The volatiles were almost completely removed and the residue was stirred with 50 mL dichloromethane and 20 mL water for 30 minutes. After phase separation the aqueous layer was extracted with 3× dichloromethane, the combined organic layers were dried over $Na_2SO_4$ and brought to dryness yielding the title compound as a light brown resin Preparation of the required 4-epi-12-epi-3-deoxo-11-deoxy-12-desvinyl-3-methoxy-11-oxo-12-(2-oxo-ethyl)-14-O-triethylsilyl mutilin Step a: 4-epi-12-epi-3-deoxo-11-deoxy-3-methoxy-11-oxo mutilin 53 g of Sodium hydroxide was dissolved in 500 mL of methanol with boiling. The temperature was lowered by 5° C. and then 240 g of 4-epi-12-epi-3-deoxo-11-deoxy-3-methoxy-11-oxo-14-O-[(toluene-4-sulfonyloxy)-acetyl] mutilin was charged and the mixture was refluxed for 1 hour. Almost 90% of the solvent was removed in vacuo, the residue was diluted with external cooling with water, and then extracted with EtOAc. The combined organic phases were washed with brine, dried over $Na_2SO_4$ and concentrated to give the title compound as yellow solid.

Step b: 4-epi-12-epi-3-deoxo-11-deoxy-3-methoxy-11-oxo-14-O-triethylsilyl mutilin 140 g of 4-epi-12-epi-3-deoxo-11-deoxy-3-methoxy-11-oxo mutilin 57 g of imidazole and 26 g of DMAP was dissolved in 2 L of DCM, then 126 g of $Et_3SiCl$ was added and the mixture stirred at rt overnight. The reaction was quenched with water, extracted with EtOAc, the organic phases were combined, dried over $Na_2SO_4$ and concentrated. The residue was purified by chromatography (PE/EtOAc=10/1) to give the title compound as yellow solid.

Step c: 4-epi-12-epi-3-deoxo-11-deoxy-12-desvinyl-12-(2-hydroxy-ethyl)-3-methoxy-11-oxo-14-O-triethylsilyl mutilin 140 g of 4-epi-12-epi-3-deoxo-11-deoxy-3-methoxy-11-oxo-14-O-triethylsilyl mutilin was dissolved in 1 L of THF, then 1.25 L of 9-BBN (0.5 m in THF) was added and the reaction refluxed for 2 h. The reaction is cooled in an ice-bath, slowly 350 g of $H_2O_2$ (30%) and 310 mL of 2N NaOH) were added and stirred for 30 min. After warming to room temperature water and EtOAc were added, the organic phase was washed with brine, dried over Na$_2$SO$_4$, concentrated and the residue was purified by chromatography (PE/EtOAc=15/1) to give the title compound as white solid.

Step d: 4-epi-12-epi-3-deoxo-11-deoxy-12-desvinyl-3-methoxy-11-oxo-12-(2-oxo-ethyl)-14-O-triethylsilyl mutilin 70 g of 4-epi-12-epi-3-deoxo-11-deoxy-12-desvinyl-12-(2-hydroxy-ethyl)-3-methoxy-11-oxo- 14-O-triethylsilyl mutilin was dissolved in 1 L of DCM, then 64 g of Dess-Martin reagent was added and the reaction stirred at rt.

After 2 h the reaction was quenched by addition of sat. NaHCO3 solution, the organic phase was separated, dried over Na$_2$SO$_4$, concentrated and the residue was purified by chromatography (PE/EtOAc=8/1) to give the title compound as white solid.

According, e.g. analogously, to a method as set out under Example 1 and 146, but using appropriate starting materials, the compounds of formula I$_{EX}$, wherein R$_{1EX}$ and R$_{2EX}$ are as defined in Table 19 are prepared. Chemical characterisation data are also set out in Table 19.

TABLE 19

| Example | | R$_{2EX}$ | R$_{1EX}$ |
|---|---|---|---|
| 147 | 12-epi-12-desvinyl-14-O-{[1-(2-Amino-acetyl)-piperidin-4-yl-sulfanyl]-acetyl}-12-[3-(4-aminomethyl-phenyl)-propyl] mutilin dihydrochloride<br>$^1$H-NMR (200 MHz, DMSO-d$_6$): 7.39 (d, 2H, arom., J = 8 Hz), 7.21 (d, 2H, arom., J = 8 Hz), 5.47 (d, 1H, H-14, J = 7 Hz), 4.48 (bs, 1H, 11-OH), 1.35 (s, 3H, H-15), 0.84 (m, 6H, H-18, H-17), 0.63 (d, 3H, H-16, J = 5.2 Hz)<br>MS m/e: 656 [M$^+$ + H]<br>Azidomethyl-phenyl-methyl-triphosphonium bromide was used as intermediate in step 1 | | |
| 148 | 12-epi-12-desvinyl-14-O-[(Azepan-4-yl-sulfanyl)-acetyl]-12-[3-(4-aminomethyl-phenyl)-propyl] mutilin trihydrochloride<br>$^1$H-NMR (200 MHz, DMSO-d$_6$): 7.38 (d, 2H, arom., J = 8 Hz), 7.22 (d, 2H, arom., J = 8 Hz), 5.46 (d, 1H, H-14, J = 5.6 Hz), 3.96 (bs, 1H, 11-OH), 1.35 (s, 3H, H-15), 0.81 (m, 6H, H-18, H-17), 0.62 (d, 3H, H-16, J = 4.2 Hz)<br>MS m/e: 613 [M$^+$ + H] | | |
| 149 | 12-epi-12-desvinyl-14-O-[(Azepan-4-yl-sulfanyl)-acetyl]-12-(6-amino-hexyl) mutilin dihydrochloride<br>$^1$H-NMR (200 MHz, DMSO-d$_6$): 5.48 (d, 1H, H-14, J = 7.6 Hz), 4.33 (d, 1H, 11-OH, J = 5.8 Hz), 1.36 (s, 3H, H-15), 0.84-0.79 (m, 4H, H-18, H-17), 0.64 (d, 3H, H-16, J = 5.6 Hz)<br>MS m/e: 565 [M$^+$ + H] | | |
| 150 | 12-epi-12-desvinyl-14-O-[(Azepan-4-yl-sulfanyl)-acetyl]-12-(8-amino-octyl) mutilin dihydrochloride<br>$^1$H-NMR (200 MHz, DMSO-d$_6$): 5.48 (d, 1H, H-14, J = 7.6 Hz), 4.40 (d, 1H, 11-OH, J = 5.38 Hz), 3.88 (s, 2H, H-22), 1.36 (s, 3H, H-15), 0.84-0.79 (m, 6H, H-18, H-17), 0.64 (d, 3H, H-16, J = 5.6 Hz)<br>MS m/e: 593 [M$^+$ + Cl] | | |

EXAMPLE 151

12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethenyl) mutilin trihydrochloride Step 1: 12-epi-14-O-{4-[(2-tert-Butoxycarbonylamino-acetylamino)-methyl]-cyclohexylsulfanyl}-acetyl mutilin

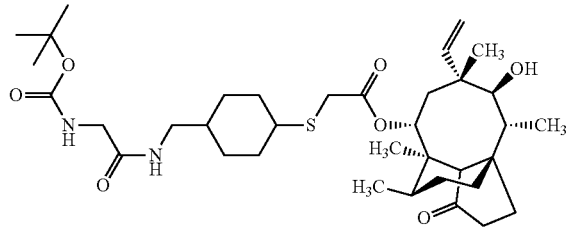 [SMILES: C=C[C@@]1(C)C[C@@H](OC(=O)CSC2CCC(CNC(=O)CNC(=O)OC(C)(C)C)CC2)[C@@]2(C)C3C(=O)CC[C@@]3(CC[C@H]2C)[C@@H](C)[C@@H]1O]

2.5 g of 12-epi-Pleuromutilintosylate was coupled with thioacetic acid S-{4-[(2-tert-butoxycarbonylamino-acetylamino)-methyl]-cyclohexyl} ester (Example 84) following the general procedure as described in Example 1, step 5. The title compound was obtained as colorless foam.

Step 2: 12-epi-12-desvinyl-14-O-{{4-[(2-tert-Butoxycarbonylamino-acetylamino)-methyl]-cyclohexylsulfanyl}-acetyl}-12-[(E)-2-(4-{[tert-butoxycarbonyl-(2-tert-butoxycarbonylamino-ethyl)-amino]-methyl}-phenyl)-ethenyl] mutilin

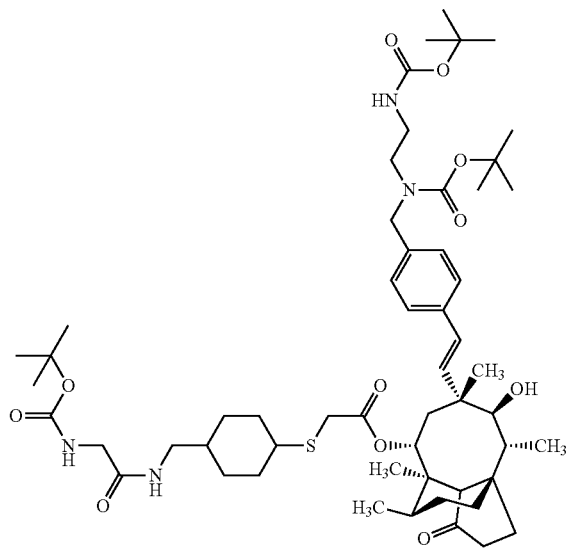 [SMILES: C[C@@H]1CC[C@@]23CCC(=O)C2[C@]1(C)[C@H](OC(=O)CSC1CCC(CNC(=O)CNC(=O)OC(C)(C)C)CC1)C[C@](C)(/C=C/c1ccc(CN(CCNC(=O)OC(C)(C)C)C(=O)OC(C)(C)C)cc1)[C@@H](O)[C@@H]3C]

3.5 g of 12-epi-14-O-{4-[(2-tert-Butoxycarbonylamino-acetylamino)-methyl]-cyclohexylsulfanyl}-acetyl mutilin was dissolved in 20 mL of DMA, 5 g of (2-tert-Butoxycarbonylamino-ethyl)-(4-iodo-phenyl)-carbamic acid tert-butyl ester, 1.1 g of NMM and 223 mg of bis-(benzonitrile)-palladium(II)-chloride was added and the reaction mixture stirred at 100° C. for 20 h in a microwave synthesizer (Biotage). The reaction mixture was poured into water, extracted with EtOAc, washed with brine and water and concentrated to give the title product as colorless foam.

Step 3: 12-epi-12-desvinyl-14-O-{{4-[(2-Aminoacetylamino)-methyl]-cyclohexylsulfanyl}-acetyl}-12-[2-{4-[(2-amino-ethylamino)-methyl]-phenyl}-ethenyl) mutilin trihydrochloride The title compound was obtained following the general procedure as described in Example 1, step 6. The product was purified by reversed phase chromatography (eluant: acetonitrile in water 0-35%).
$^1$H-NMR (200 MHz, DMSO-$d_6$): 7.39 (d, 2H, arom., J=8 Hz), 7.49 (d, 2H, arom., J=8 Hz), 6.55 (d, 2H, J=16 Hz), 6.30 (d, 2H, J=17 Hz), 5.57 (d, 1H, H-14, J=7 Hz), 1.41 (s, 3H, H-15), 1.19 (s, 3H, H-18), 0.88 (bs, 6H, H-17), 0.68 (bs, 3H, H-16)

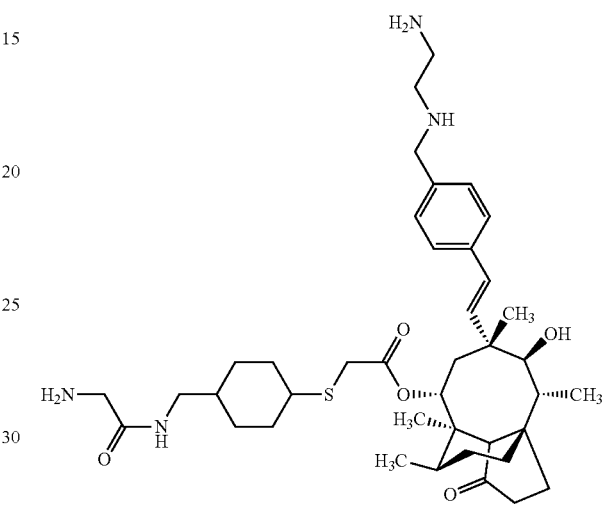

MS m/e: 711 [M$^+$+H]

EXAMPLE 152

12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethyl) mutilin trihydrochloride Step 1: 12-epi-12-desvinyl-14-O-{{4-[(2-tert-Butoxycarbonylamino-acetylamino)-methyl]-cyclohexylsulfanyl}-acetyl}-12-[(E)-2-(4-{[tert-butoxycarbonyl-(2-tert-butoxycarbonylamino-ethyl)-amino]-methyl}-phenyl)-ethyl] mutilin

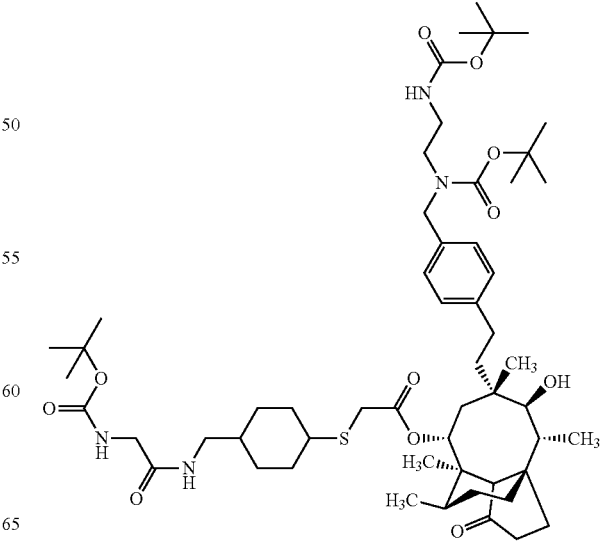

2 g of 12-epi-12-desvinyl-14-O-{{4-[(2-tert-Butoxycarbonylamino-acetylamino)-methyl]-cyclohexylsulfanyl}-acetyl}-12-[(E)-2-(4-{[tert-butoxycarbonyl-(2-tert-butoxycarbonylamino-ethyl)-amino]-methyl}-phenyl)-ethenyl]] mutilin was dissolved in 1250 mL of MeOH and hydrogenated in an H-Cube apparatus using 10% Pd/C as catalyst (50° C., 1 mL/min, 60 bar). After concentration the product was obtained as yellow foam.

Step 2: 12-epi-12-desvinyl-14-O-{{4-[(2-Aminoacetylamino)-methyl]-cyclohexylsulfanyl}-acetyl}-12-[2-{4-[(2-amino-ethylamino)-methyl]-phenyl}-ethyl) mutilin trihydrochloride

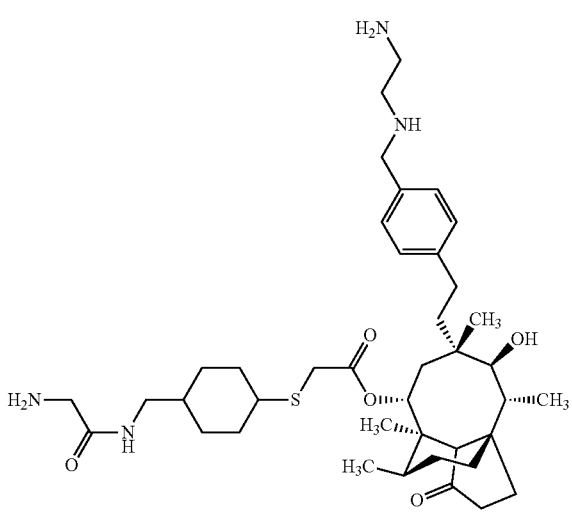 [SMILES: C[C@@H]1CC[C@@]23CCC(=O)C2[C@]1(C)[C@H](OC(=O)CSC1CCC(CNC(=O)CN)CC1)C[C@](C)(CCc1ccc(CNCCN)cc1)[C@@H](O)[C@@H]3C]

The product was obtained following the general procedure as described in Example 1, step 6. The product was purified by reversed phase chromatography (eluant: acetonitrile in water 0-35%).

$^1$H-NMR (200 MHz, DMSO-d$_6$): 7.45 (m, 2H, arom.), 7.22 (m, 2H, arom.), 5.51 (d, 1H, H-14, J=5.8 Hz), 1.40 (s, 3H, H-15), 0.91 (s, 3H, H-18), 0.85 (bs, 3H, H-17), 0.66 (bs, 3H, H-16)

MS m/e: 713 [M$^+$+H]

Preparation of the required (2-tert-Butoxycarbonylamino-ethyl)-(4-iodo-phenyl)-carbamic acid tert-butyl ester Step a [2-(4-Iodo-phenylamino)-ethyl]-carbamic acid tert-butyl ester To 10.5 g of 4-Iodobenzyl bromide in 100 mL of THF was added 11.4 g of (2-amino-ethyl)-carbamic acid tert-butyl ester and the reaction mixture was stirred for 12 h at rt. The reaction mixture was poured into water, extracted with EtOAc, washed with brine and water, dried over Na$_2$SO$_4$, concentrated and chromatographed on silica using DCM/MeOH=30:1. The title compound was obtained as yellow oil.

Step b: (2-tert-Butoxycarbonylamino-ethyl)-(4-iodo-phenyl)-carbamic acid tert-butyl ester 8.6 g of [2-(4-Iodo-phenylamino)-ethyl]-carbamic acid tert-butyl ester was dissolved in 200 mL of DCM, 5.4 g of BOC$_2$O and 4.81 g of TEA was added and the reaction mixture stirred at rt for 16 h. The reaction mixture was poured into water, extracted with EtOAc, washed with 1n HCl and water. After concentration the title compound was obtained as colorless crystals.

According, e.g. analogously, to a method as set out under Example 1, 151 and 152, but using appropriate starting materials, the compounds of formula I$_{EX}$, wherein R$_{1EX}$ and R$_{2EX}$ are as defined in Table 20 are prepared. Chemical characterisation data are also set out in Table 20.

TABLE 20

| Example | | R$_{2EX}$ | R$_{1EX}$ |
|---|---|---|---|
| 153 | 12-epi-12-desvinyl-14-O-[(Azepan-4-ylsulfanyl)-acetyl]-12-[2-(4-Aminomethyl-phenyl)-ethyl]-mutilin dihydrochloride<br>$^1$H-NMR (200 MHz, DMSO-d$_6$): 7.41 (bs, 2H, arom.), 7.23 (bs, 2H, arom.), 5.52 (bs, 1H, H-14), 4.63 (bs, 1H, 11-OH), 1.40 (s, 3H, H-15), 0.91 (s, 3H, H-18), 0.84 (bs, 3H, H-17), 0.65 (bs, 3H, H-16)<br>MS m/e: 599 [M$^+$ + H]<br>1-Azidomethyl-4-iodo-benzene (prepared from 1-Bromomethyl-4-iodo-benzene) was used as intermediate in step 1 | azepane | H$_2$N-CH$_2$-phenyl-CH$_2$CH$_2$- |
| 154 | 12-epi-12-desvinyl-14-O-[(Azepan-4-ylsulfanyl)-acetyl]-12-((E)-2-pyridin-3-yl-ethenyl) mutilin hydrochloride<br>$^1$H-NMR (200 MHz, DMSO-d$_6$): 8.88 (m, 1H, arom.), 8.67 (m, 1H, arom.), 8.45 (m, 1H, arom.), 7.91 (m, 1H, arom.), 6.81 (d, 2H, J = 17 Hz), 6.48 (d, 2H, J = 17 Hz), 5.52 (d, 1H, H-14, J = 7.4 Hz), 1.38 (s, 3H, H-15), 1.17 (s, 3H, H-18), 0.83 (d, 3H, H-17, J = 6.6 Hz), 0.65 (d, 3H, H-16, J = 4.6 Hz),<br>MS m/e: 569 [M$^+$ + H]<br>3-Bromo-pyridine was used as intermediate in step 1 | azepane | pyridin-3-yl-CH=CH- |

TABLE 20-continued

| Example | | $R_{2EX}$ | $R_{1EX}$ |
|---|---|---|---|
| 155 | 12-epi-12-desvinyl-14-O-[(Azepan-4-ylsulfanyl)-acetyl]-12-((E)-2-{4-[(2-Amino-ethylamino)-methyl]-phenyl}-ethenyl) mutilin trihydrochloride<br>$^1$H-NMR (200 MHz, DMSO-d$_6$): 7.5 (d, 2H, arom., J = 8.2 Hz), 7.42 (d, 2H, arom., J = 8.2 Hz), 6.52 (d, 2H, J = 16.4 Hz), 6.29 (d, 2H, J = 16.4 Hz), 5.54 (d, 1H, H-14, J = 7.2 Hz), 4.46 (bs, 1H, 11-OH), 1.39 (s, 3H, H-15), 1.16 (s, 6H, H-18), 0.84 (d, 3H, H-16, J = 5.8 Hz), 0.67 (bs, 3H, H-16)<br>MS m/e: 640 [M$^+$ + H] | azepan-4-yl | 4-[(2-aminoethylamino)methyl]phenyl-ethenyl group |
| 156 | 12-epi-12-desvinyl-14-O-[(Azepan-4-ylsulfanyl)-acetyl]-12-[2-{4-[(2-amino-ethylamino)-methyl]-phenyl}-ethyl) mutilin trihydrochloride<br>MS m/e: 642 [M$^+$ + H] | azepan-4-yl | 4-[(2-aminoethylamino)methyl]phenyl-ethyl group |
| 157 | 12-epi-12-desvinyl-14-O-[(Azepan-4-ylsulfanyl)-acetyl]-12-((E)-2-{4-[(2-amino-ethylamino)-methyl]-3-fluoro-phenyl}-ethenyl) mutilin trihydrochlorid<br>$^1$H-NMR (200 MHz, DMSO-d$_6$): 7.68-7.6 (m, 1H, arom.), 7.34-7.26 (m, 2H, arom.), AB (2H, CH=CH, v$_A$ = 6.59, v$_B$ = 6.30, J = 16 Hz), 5.53 (d, 1H, H-14, J = 5.2 Hz), 1.39 (s, 3H, H-15), 1.08 (s, 3H, H-18), 0.84 (d, 3H, H-17, J = 6.4 Hz), 0.66 (d, 3H, H-16, J = 4.4 Hz)<br>MS m/e: 658 [M$^+$ + H]<br>The required 1 Bromomethyl 2 fluoro 4 iodo benzene is described in: PCT Int. Appl., 2011132051, 27 Oct. 2011 | azepan-4-yl | 4-[(2-aminoethylamino)methyl]-3-fluoro-phenyl-ethenyl group |

TABLE 20-continued

| Example | | R$_{2EX}$ | R$_{1EX}$ |
|---|---|---|---|
| 158 | 12-epi-14-O-{[1-(2-Amino-acetyl)-piperidin-4-yl-sulfanyl]-acetyl}-12-((E)-2-{4-[(2-amino-ethylamino)-methyl]-phenyl}-ethenyl) mutilin trihydrochloride<br>MS m/e: 683 [M⁺ + H] | piperidine with 2-amino-acetyl | 4-[(2-aminoethylamino)methyl]phenyl ethenyl |
| 159 | 12-epi-14-O-{[1-(2-Amino-acetyl)-piperidin-4-yl-sulfanyl]-acetyl}-12-[2-{4-[(2-amino-ethylamino)-methyl]-phenyl}-ethyl] mutilin trihydrochloride<br>MS m/e: 685 [M⁺ + H] | piperidine with 2-amino-acetyl | 4-[(2-aminoethylamino)methyl]phenyl ethyl |

EXAMPLE 160

12-epi-12-desvinyl-14-O-[(5-Aminomethyl-pyridin-2-ylsulfanyl)-acetyl]-12-[2-(4-aminomethyl-benzoylamino)-ethyl] mutilin trihydrochloride Step 1: 4-epi-12-epi-3-deoxo-11-deoxy-12-desvinyl-12-(hydroxyimino-ethyl)-3-methoxy-11-oxo-14-O-[(toluene-4-sulfonyloxy)-acetyl] mutilin 617 mg of NH$_2$OH.HCl and 355 mg of NaOH was dissolved in 60 mL MeOH, the mixture was stirred at 25° C. for 1 h, then 5.0 g of 4-epi-12-epi-3-deoxo-11-deoxy-12-desvinyl-3-methoxy-11-oxo-12-(2-oxo-ethyl)-14-O-[(toluene-4-sulfonyloxy)-acetyl] mutilin (Example 143, step 1) was added and the mixture stirred at 25° C. for 12 hours. The mixture was concentrated and the residue purified by chromatography (PE/EtOAc=3:1) to give the title compound as colorless oil.

Step 2: 4-epi-12-epi-12-(2-Amino-ethyl)-3-deoxo-11-deoxy-12-desvinyl-3-methoxy-11-oxo-14-O-[(toluene-4-sulfonyloxy)-acetyl] mutilin

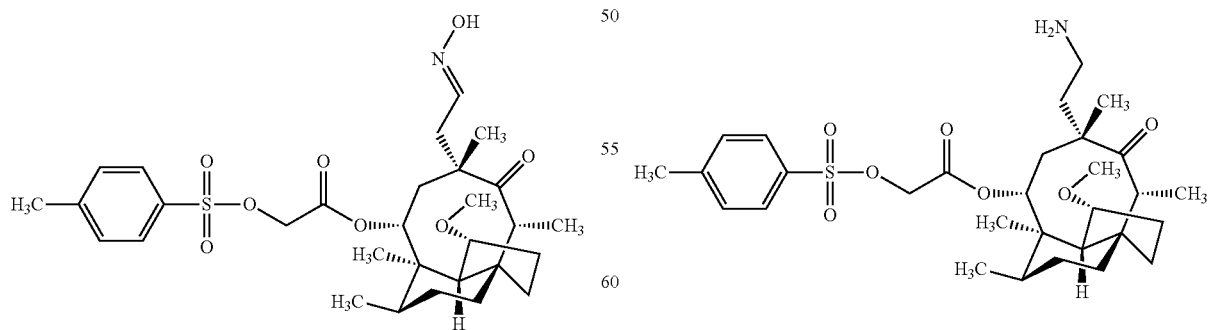

2.9 g of 4-epi-12-epi-3-deoxo-11-deoxy-12-desvinyl-12-(hydroxyimino-ethyl)-3-methoxy-11-oxo-14-O-[(toluene-4-sulfonyloxy)-acetyl] mutilin was dissolved in 50 mL of MeOH, then 672 mg of NiCl$_2$ and 196 mg of NaBH$_4$ was added at −78° C., afterwards stirred at −78° C. for 2 h, warmed to 25° C. and stirred for 2 h. The reaction was filtered, concentrated, the residue was dissolved in DCM, washed with water, the organic phase was separated, dried over Na₂SO₄, concentrated to give the title compound as colorless oil.

Step 3: 4-epi-12-epi-12-{2-[4-(tert-Butoxycarbonylamino-methyl)-benzoylamino]-ethyl}-3-deoxo-11-deoxy-12-desvinyl-3-methoxy-11-oxo-14-O-[(toluene-4-sulfonyloxy)-acetyl] mutilin Step 4: 4-epi-12-epi-12-{2-[4-(tert-Butoxycarbonylamino-methyl)-benzoylamino]-ethyl}-14-O-{[5-(tert-Butoxycarbonylamino-methyl)-pyridin-2-ylsulfanyl]-acetyl}-3-deoxo-11-deoxy-12-desvinyl-3-methoxy-11-oxo mutilin

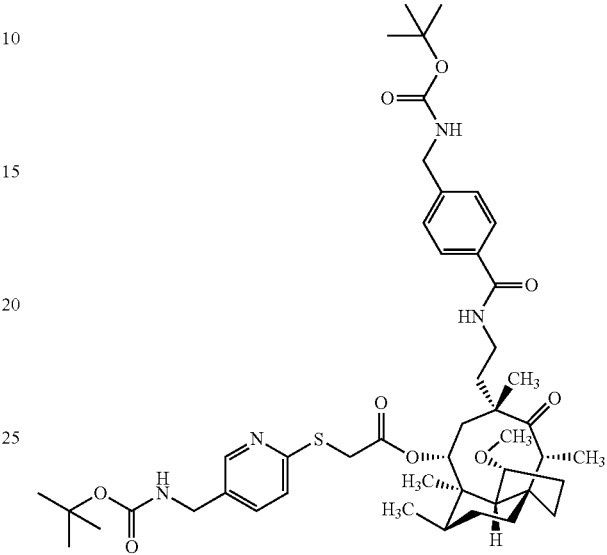

was prepared following the general procedure as described in Example 1, step 5. After chromatography (PE/EtOAc=2:1) the title compound was obtained as white solid.

Step 5: 12-epi-12-desvinyl-14-O-[(5-Aminomethyl-pyridin-2-ylsulfanyl)-acetyl]-12-[2-(4-aminomethyl-benzoylamino)-ethyl] mutilin trihydrochloride

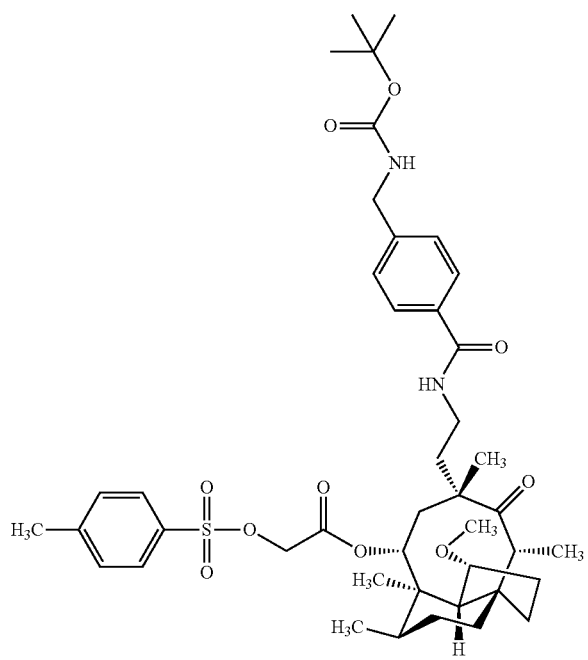

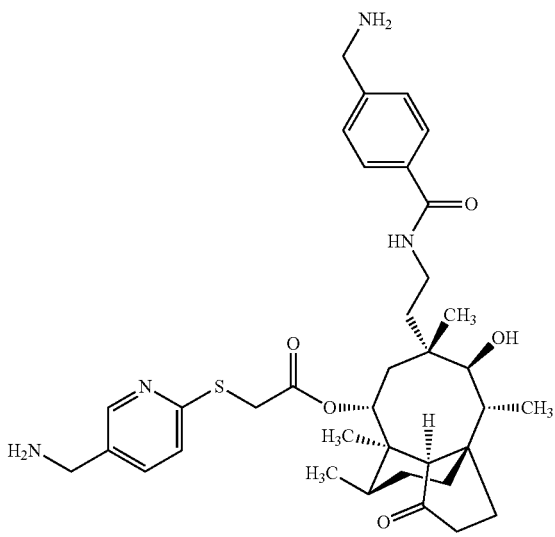 [SMILES: C[C@@H]1CC[C@@]23CCC(=O)[C@H]2[C@]1(C)[C@H](OC(=O)CSc1ccc(CN)cn1)C[C@](C)(CCNC(=O)c1ccc(CN)cc1)[C@@H](O)[C@@H]3C]

440 mg of 4-epi-12-epi-12-(2-Amino-ethyl)-3-deoxo-11-deoxy-12-desvinyl-3-methoxy-11-oxo-14-O-[(toluene-4-sulfonyloxy)-acetyl] mutilin was dissolved in 10 mL of DCM, then 240 mg of 4-(tert-Butoxycarbonylamino-methyl) benzoic acid, 364 mg of HATU and 242 mg of TEA was added and the mixture was stirred at 25° C. for 12 hours. Then the mixture was quenched with water, extracted with DCM, the organic phase was separated, dried over Na₂SO₄, concentrated and the residue was purified by chromatography (PE/EtOAc=3:1) to give the title compound as white solid.

The product was obtained following the general procedure as described in Example 1, step 6.

MS m/e: 651 [M⁺+H]

Comparator Compounds

According to a method as described in Monatshefte für Chemie 117, 1073 (1986) and a method as described in the examples, in particular in Examples 1 and 62 above, but using appropriate starting materials, compounds of formula IV are obtained

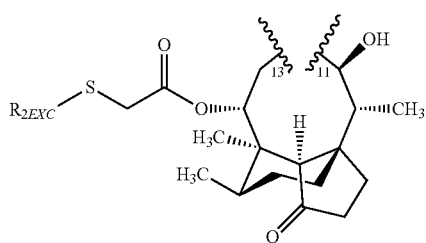

IV wherein $R_{EX2C}$ and the substituent and its stereospecity at position C-12 of the mutilin ring are as defined in table 21 below.

Antimicrobial Activity of Pleuromutilin Derivatives of Present Invention

The antibacterial activity expressed as minimal inhibitory concentration (MIC) was determined according to the approved standard reference recommendations of CLSI (former NCCLS) as described in the description of the application.

Compounds of the present invention exhibit very good activity against the clinical relevant bacterial pathogens *Staphylococcus aureus* and *Escherichia coli*. Surprisingly, the activity against *Escherichia coli* is significantly improved by introduction of C-12 substituents with inverted stereochemistry of the methyl group in position 12 of the mutilin ring (12-epi mutilins) according to the present invention compared with compounds wherein the stereochemistry of the methyl substituent in position 12 of the mutilin ring is as in the naturally occurring pleuromutilin. The in vitro activity against *Escherichia coli* of a compound of the present invention is significantly and surprisingly better than that of the comparator compound as set out in Table 22 below.

TABLE 21

| Example | | $R_{2EXC}$ | C-12 substitution |
|---|---|---|---|
| C1 | 12-epi-14-O-{[(5-Amino-4H-1,2,4-triazol-3-yl)-sulfanyl]-acetyl} mutilin hydrochloride (comparator compound) ¹H-NMR (200 MHz, DMSO-d₆): 5.91 (dd, 1H, H-19, $J_E$ = 18 Hz, $J_Z$ = 12 Hz), 5.48 (d, 1H, H-14, J = 7.6 Hz), 4.96-4.84 (m, 2H, H-20), AB (2H, H-22, $v_A$ = 3.99, $v_B$ = 3.89, J = 16 Hz), 3.46 (d, 1H, H-11, J = 5.4 Hz), 1.32 (s, 3H, H-15), 0.99 (s, 3H, H-18), 0.80 (d, 3H, H-17, J = 6.6 Hz), 0.59 (d, 3H, H-16, J = 6 Hz) MS m/e: 477 [M⁺ + H] | (triazole-NH₂ structure) | (vinyl C-12 structure) |
| C2 | 14-O-{{4-[(2-Amino-propylcarbamoyl)-methyl]-phenylsulfanyl}-acetyl} mutilin hydrochloride (comparator compound) ¹H-NMR (200 MHz, DMSO-d₆): 8.35 (t, 1H, —CO—NH, J = 6 Hz), 8.01 (bs, 3H, NH₃⁺), 7.27 (d, 2H, arom., J = 8 Hz), 7.18 (d, 2H, arom., J = 8 Hz), 6.04 (dd, 1H, H-19, $J_E$ = 18 Hz, $J_Z$ = 10 Hz), 5.50 (d, 1H, H-14, J = 7.6 Hz), 5.09-4.92 (m, 2H, H-20), AB (2H, H-22, $v_A$ = 3.82, $v_B$ = 3.72, J = 16 Hz), 1.31 (s, 3H, H-15), 0.99 (s, 3H, H-18), 0.79 (d, 3H, H-17, J = 6.8 Hz), 0.55 (d, 3H, H-16, J = 5.8 Hz) MS m/e: 585 [M⁺ + H] | (phenyl-CH₂-C(O)-NH-CH₂CH₂CH₂-NH₂ structure) | (vinyl C-12 structure) |
| C3 | 14-O-{[(1R,2R,4R)-4-Amino-2-hydroxy-cyclohexylsulfanyl]-acetyl}-12-desvinyl-12-[(3-amino-propylamino)-methyl] mutilin trihydrochlorid (comparator compound) MS m/e: 568 [M⁺ + H] | (aminocyclohexyl-OH structure) | (CH₂-NH-CH₂CH₂CH₂-NH₂ at C-12 structure) |

TABLE 22

Antimicrobial activity of the compound of
Example 1 and of the comparator compound C2

| | | MIC [µg/mL] | |
|---|---|---|---|
| Species | ATCC number | Compound of Example 1 | Comparator Compound C2 |
| Staphylococcus aureus | ATCC 49951 | ≤0.03 | ≤0.03 |
| Escherichia coli | ATCC25922 | 0.5 | 32 |

Table 23 below presents the in vitro activity of further of compounds described in the present invention comprising surprising activity against *Staphylococcus aureus* and even more surprising activity against *Escherichia coli*.

TABLE 23

Antimicrobial activity of the compounds of further
examples described in the present invention

| | MIC [µg/mL] | |
|---|---|---|
| Compound of Example | S. aureus ATCC 49951 | E. coli ATCC25922 |
| 9 | ≤0.03 | 0.5 |
| 11 | ≤0.03 | 0.25 |
| 23 | ≤0.03 | 1 |
| 47 | ≤0.03 | 0.5 |
| 48 | ≤0.03 | 0.25 |
| 52 | ≤0.03 | 0.5 |
| 54 | 0.125 | 4 |
| 64 | 0.5 | 4 |
| 65 | 0.5 | 2 |
| 68 | 0.25 | 4 |
| 78 | 0.5 | 2 |
| 81 | 0.125 | 8 |
| 83 | 0.25 | 1 |
| 86 | 0.06 | 0.5 |
| 98 | 0.125 | 0.5 |
| 99 | 0.25 | 0.5 |
| 103 | 0.5 | 4 |
| 115 | ≤0.03 | 0.25 |
| 130 | ≤0.03 | 0.5 |
| 131 | 0.06 | 0.125 |
| 143 | 0.125 | 4 |
| 146 | ≤0.03 | 8 |
| 152 | 0.25 | 4 |
| 157 | 0.25 | 4 |

Table 24 below presents the in vitro activity of the 12-epi-mutilin compound known from prior art (H. Berner et al, Monatshefte fir Chemie, 1986, 117, 1073-1080) (compound of Example C1) with the naturally occurring vinyl group at position C-12 and the methyl group in epi position, and the C-12-epi substituted compound of Example 66 with identical side chain at position C-14 of the mutilin ring as the compound of Example C1. Evidently the replacement of the naturally occurring vinyl group by a group according to the present invention in a compound having the methyl group in position C-12 of the mutilin ring inverted, namely contrary to the stereochemistry of the methyl group in position 12 in the natural occurring pleuromutilin ring, significantly and surprisingly improves the activity against *Escherichia coli*.

TABLE 24

Antimicrobial activity of the compound of Example
66 and comparator of the compound of Example C1

| | | MIC [µg/mL] | |
|---|---|---|---|
| Species | ATCC number | Compound of Example 66 | Compound C1 |
| Staphylococcus aureus | ATCC 49951 | 0.5 | 0.5 |
| Escherichia coli | ATCC25922 | 4 | 128 |

Table 25 below presents the in vitro activity of two compounds which are identical in structure with the only exception that the stereochemistry of the methyl substituent in position C-12 of the mutilin ring in a compound of the present invention is inverted whereas in the comparator compound the stereochemistry of said methyl group is the same as in the naturally occurring pleuromutilin. Thus, the C-12 epi compound of Example 62 exhibits significantly improved activity against *Staphylococcus aureus* and *Escherichia coli* compared to the comparator compound of Example C3 having the natural stereochemistry of the methyl group in position C-12 and otherwise is identical.

TABLE 25

Antimicrobial activity of the compound of
Example 62 and comparator compound C3

| | | MIC [µg/mL] | |
|---|---|---|---|
| Species | ATCC number | Compound of Example 62 | Compound C3 |
| Staphylococcus aureus | ATCC 49951 | 0.25 | 16 |
| Escherichia coli | ATCC25922 | 4 | >32 |

Table 26 below shows the activity of tiamulin, econor and retapamulin against *Staphylococcus aureus* and *Escherichia coli*. Whilst retaining good activity against *Staphylococcus aureus* the activity against *Escherichia coli* is significantly reduced with MIC >16 µg/ml.

TABLE 26

Antimicrobial activity of tiamulin, econor and retapamulin

| | | MIC [µg/mL] | | |
|---|---|---|---|---|
| Species | ATCC number | Tiamulin | Econor | Retapamulin |
| Staphylococcus aureus | ATCC 49951 | 0.5 | ≤0.03 | ≤0.03 |
| Escherichia coli | ATCC25922 | >32 | 32 | 32 |

The invention claimed is:

1. A compound selected from 14-O-[((Alkyl-, cycloalkyl-, heterocycloalkyl-, heteoroaryl-, or aryl)-sulfanyl)-acetyl]-12-epi-mutilins, or
   14-O-[((Alkyl-, cycloalkyl-, heterocycloalkyl-, heteoro-aryl-, or aryl)-oxy)-acetyl]-12-epi-mutilins,
   wherein 12-epi-mutilin is characterized in that
   the mutilin ring at position 12 is substituted by two substituents,
   the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom, and all other substituents of the mutilin ring having the same stereochemistry compared with the stereochemistry of the substituents at the corresponding positions in the naturally occurring pleuromutilin ring;

optionally in the form of a salt and/or solvate, wherein the naturally occurring pleuromutilin is of formula

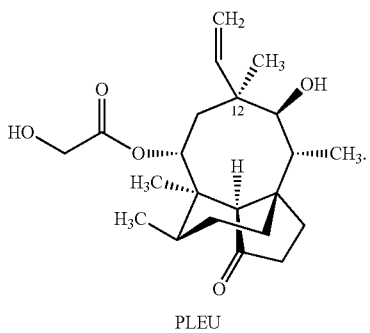

PLEU

2. The compound according to claim 1 of formula

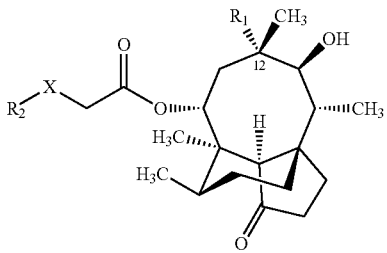

wherein the methyl group at position 12 of the mutilin ring has the inverse stereochemistry compared with the stereochemistry of the methyl group at position 12 of the naturally occurring pleuromutilin ring, all other substituents of the mutilin ring having the same stereochemistry compared with the stereochemistry of the substituents at the corresponding positions in the naturally occurring pleuromutilin ring, $R_1$ is a hydrocarbon group comprising 1 to 16, in particular 1 to 12 carbon atoms comprising one N atom, optionally comprising one or more additional heteroatoms selected from N, O, S, halogen, in particular N, X is sulfur or oxygen, in particular sulfur, and $R_2$ is a hydrocarbon group comprising 1 to 22 carbon atoms, optionally comprising heteroatoms selected from N, O, S, halogen, in particular N or O.

3. The compound according to claim 2, wherein $R_1$ is either $(C_{1-16})$alkyl or $(C_{2-16})$alkenyl, substituted by heterocyclyl, including aliphatic heterocyclyl and aromatic heterocyclyl comprising 1 to 4 heteroatoms selected from N, O, S, with the proviso that at least one heteroatom is a nitrogen atom, or $R_1$ is a group of formula

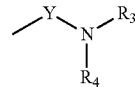

wherein $Y—N(R_3R_4)$ is $(C_{1-16})$alkyl-$N(R_3R_4)$,
$(C_{1-16})$alkyl-$(C_{6-14})$aryl-$N(R_3R_4)$,
$(C_{1-16})$alkyl-$(C_{6-14})$aryl-$(C_{1-16})$alkyl-$N(R_3R_4)$,
$(C_{1-16})$alkyl-$(C_{1-13})$heterocyclyl —$N(R_3R_4)$,
$(C_{1-16})$alkyl-$(C_{1-13})$heterocyclyl-$(C_{1-16})$alkyl-$N(R_3R_4)$,
carbonyl-$N(R_3R_4)$,
$(C_{1-4})$alkyl-carbonyl-$N(R_3R_4)$,
$(C_{2-16})$alkenyl-$N(R_3R_4)$,
$(C_{2-16})$alkenyl-$(C_{6-14})$aryl-$N(R_3R_4)$,
$(C_{2-16})$alkenyl-$(C_{6-14})$aryl-$(C_{1-16})$alkyl-$N(R_3R_4)$,
$(C_{2-16})$alkenyl-$(C_{1-13})$heterocyclyl-$N(R_3R_4)$,
$(C_{2-16})$alkenyl-$(C_{1-13})$heterocyclyl-$(C_{1-16})$alkyl-$N(R_3R_4)$, wherein heterocyclyl includes aliphatic and aromatic heterocyclyl comprising at least one heteroatom selected from N, O, S and wherein alkyl, aryl, heterocyclyl or alkenyl is optionally substituted comprising substituents which optionally having heteroatoms selected from O, N, S, halogen;

$R_3$ and $R_4$ independently of each other are hydrogen,
$(C_{1-16})$alkyl,
$(C_{2-16})$alkenyl,
hydroxy$(C_{1-16})$alkyl,
amino-$(C_{1-16})$alkyl,
mono or di-$(C_{1-6})$alkylamino-$(C_{1-16})$alkyl,
guanidino$(C_{1-16})$alkyl, ureido$(C_{1-16})$alkyl or thioureido $(C_{1-16})$alkyl,
amino$(C_{1-6})$alkyl-$(C_{6-14})$aryl-$(C_{1-6})$alkyl,
amino$(C_{1-6})$alkyl-$(C_{6-14})$aryl,
guanidino$(C_{1-6})$alkyl-$(C_{6-14})$aryl-$(C_{1-6})$alkyl,
amino-$(C_{1-6})$alkyloxy-$(C_{1-6})$alkyl,
amino$(C_{3-8})$cycloalkyl,
amino$(C_{1-6})$alkyl-$(C_{3-8})$cycloalkyl,
amino$(C_{3-8})$cycloalkyl-$(C_{1-6})$alkyl,
amino$(C_{1-6})$alkyl-$(C_{3-8})$cycloalkyl-$(C_{1-6})$alkyl,
$(C_{1-13})$heterocyclyl-$(C_{1-16})$alkyl,
$(C_{6-14})$aryl-$(C_{1-6})$alkyl,
$(C_{1-13})$heterocyclyl,
amino-$(C_{6-14})$aryl-$(C_{1-16})$alkyl,
amino-$(C_{1-6})$alkyloxy-$(C_{6-14})$aryl-$(C_{1-16})$alkyl,
amino$(C_{1-6})$alkyl-$(C_{6-12})$aryl-carbonyl,
amino$(C_{1-6})$alkyl-amido-$(C_{6-12})$aryl$(C_{1-6})$alkyl,
$(C_{1-4})$alkylcarbonyl,
carbamimidoyl, carbamoyl, thiocarbamoyl, wherein heterocyclyl includes aliphatic and aromatic heterocyclyl comprising at least one heteroatom selected from N, O, S, and wherein alkyl, cycloalkyl, heterocyclyl, alkenyl or aryl is optionally further substituted, by amino$(C_{1-4})$alkyl, amido, mono or di-$(C_{1-4})$alkyl-amido, $(C_{1-6})$alkyloxy-carbonyl, halogen, oxo, hydroxy.

4. The compound according to claim 2, wherein $R_2$ is $(C_{1-16})$alkyl,
$(C_{3-12})$cycloalkyl, $(C_{1-13})$heterocyclyl,
$(C_{6-14})$aryl,
wherein heterocyclyl includes aliphatic and aromatic heterocyclyl comprising at least one heteroatom selected from N, O, S, and wherein alkyl, cycloalkyl, aryl, heterocyclyl is unsubstituted or substituted by substituents optionally having a heteroatom selected from O, N, S, and halogen.

5. The compound according to claim 4,
wherein $R_2$ is
alkyl,
optionally substituted by
hydroxy or amino,
$(C_{3-12})$cycloalkyl wherein the cycloalkyl group is optionally further substituted by amino or amino$(C_{1-4})$alkyl wherein the amino or aminoalkyl group is optionally further substituted by amino$(C_{1-6})$alkylcarbonyl and optionally $(C_{1-4})$alkyl,
$(C_{2-11})$heterocyclyl, wherein a nitrogen in the ring as a heteroatom optionally is further substituted by amino $(C_{1-6})$alkylcarbonyl,
cycloalkyl,
optionally substituted by
amino$(C_{1-4})$alkyl, wherein the amino group is optionally further substituted by amino$(C_{1-6})$alkylcarbonyl,
hydroxy,
amino, wherein the amino group is optionally further substituted by amino$(C_{1-6})$alkylcarbonyl and optionally $(C_{1-4})$alkyl,
amino and hydroxy, wherein the amino group is optionally further substituted by amino$(C_{1-6})$alkylcarbonyl and optionally $(C_{1-4})$alkyl,
$(C_{1-4})$alkylamino, wherein alkyl is optionally further substituted by one or more halogen atoms;
aliphatic $(C_{2-11})$heterocyclyl,
comprising 1 to 4 heteroatoms selected from N, O, S, wherein a nitrogen in the ring as heteroatom is optionally further substituted by
$(C_{1-4})$alkyl,
amino$(C_{1-6})$alkylcarbonyl,
aryl,
optionally substituted by
hydroxy, halogen, amino, hydroxy$(C_{1-4})$alkyl, bis-(hydroxy$(C_{1-4})$alkyl), amino$(C_{1-4})$alkyl, bis-(amino$(C_{1-4})$alkyl), wherein the amino group in amino$(C_{1-4})$alkyl optionally is further substituted,
aminocarbonyl, wherein the nitrogen optionally is substituted by
amino$(C_{1-12})$alkyl, bis-(amino$(C_{1-12})$alkyl), hydroxy$(C_{1-6})$alkyl, bis-(hydroxy$(C_{1-6})$alkyl) or diamino$(C_{1-6})$alkyl,
$(C_{1-12})$alkyl, which alkyl optionally is substituted by
amino, which amino optionally is acylated, particularly amino is substituted by formyl, $(C_{1-4})$alkylcarbonyl, saturated or unsaturated heterocyclyl comprising 1 to 3 heteroatoms, particularly N, and 4 to 8, particularly 5 to 6 ring members $(C_{6-14})$aryl, particularly phenyl, which aryl optionally is substituted by amino$(C_{1-4})$alkyl,
or
the nitrogen of the aminocarbonyl group is part of $(C_{3-8})$ heterocyclyl, including aliphatic and aromatic heterocyclyl, comprising one or more heteroatoms selected from N, O, S preferably N, wherein the heterocycle is optionally further substituted by amino$(C_{1-4})$alkyl;
$(C_{1-6})$alkyl, which $(C_{1-6})$alkyl group is optionally substituted by aminocarbonyl, wherein the nitrogen of the aminocarbonyl group is optionally further substituted by amino$(C_{1-12})$alkyl, diamino-$(C_{1-12})$alkyl, bis-(amino$(C_{1-12})$alkyl), hydroxy$(C_{1-6})$alkyl, bis-(hydroxy$(C_{1-6})$alkyl),
acylated amino$(C_{1-4})$alkyl,
aromatic $(C_{1-13})$heterocyclyl, comprising 1 to 4 heteroatoms,
wherein the aromatic heterocyclyl is optionally substituted by $(C_{1-6})$alkyl, amino or hydroxy wherein the alkyl group is optionally further substituted by halogen or amino or the aromatic heterocyclyl is optionally substituted by aminocarbonyl wherein the amino group is optionally further substituted by amino$(C_{1-12})$alkyl, bis-(amino$(C_{1-12})$alkyl), hydroxy$(C_{1-6})$alkyl, bis-(hydroxy$(C_{1-6})$alkyl) or diamino$(C_{1-6})$alkyl.

6. The compound according to claim 2, wherein
$R_2$ is amido-phenyl, amido$(C_{1-4})$alkyl-phenyl, wherein the nitrogen of the amido group is unsubstituted or substituted by amino$(C_{1-8})$alkyl, in which alkyl optionally is further substituted.

7. The compound according to claim 2, wherein
$R_2$ is
amino$(C_{3-12})$cycloalkyl,
amino$(C_{1-4})$alkyl$(C_{3-12})$cycloalkyl,
amino$(C_{3-12})$cycloalkyl$(C_{1-4})$alkyl, or
amino$(C_{1-4})$alkyl$(C_{3-12})$cycloalkyl$(C_{1-4})$alkyl,
wherein the amino group is unsubstituted or substituted by amino$(C_{1-6})$alkylcarbonyl, or amino$(C_{1-6})$alkylcarbonyl and $(C_{1-4})$alkyl.

8. The compound according to claim 2, wherein
$R_2$ is $(C_{2-11})$heterocyclyl comprising 1 to 4 heteroatoms selected from N, O, S, wherein, if a nitrogen in the ring as a heteroatom is present, said nitrogen is unsubstituted or optionally further substituted by
$(C_{1-4})$alkyl,
amino$(C_{1-6})$alkylcarbonyl.

9. The compound according to claim 2, wherein
X is S,
and $R^2$ is
aminoethyl-amidomethyl-phenyl, aminopropyl-amidomethyl-phenyl, hydroxyphenyl-(amino)ethyl-amidomethyl-phenyl, aminomethyl-phenyl-(amino)ethyl-amidomethyl-phenyl, aminopropyl-amidophenyl, aminomethyl-phenylmethyl-amido-phenyl, aminomethyl-phenyl, aminoacetyl-aminomethyl-phenyl, bis(aminomethyl)phenyl, bisaminopropyl-amidomethyl-phenyl, (2-amino)-aminopropyl-amidomethyl-phenyl, aminoethyl-aminomethyl-phenyl, aminopropyl-aminomethyl-phenyl, allyl-aminomethyl-phenyl, aminomethyl-phenylmethyl-aminomethyl-phenyl, hydroxymethyl-phenyl, bis(hydroxymethyl)-phenyl, (tetrafluorohydroxymethyl)-phenyl, amino-hydroxy-cyclohexyl, hydroxyethyl, aminoethyl, piperazinocarbonyl-phenyl, aminomethyl-piperidine-carbonyl-phenyl,
piperidine-ylmethyl-amido-phenyl, pyridine-ylmethyl-amido-phenyl, acetyl-aminopropyl-amido-phenyl, formyl-aminopropyl-amido-phenyl, amido-phenyl, aminohexyl-amidophenyl, aminoethyl-amidophenyl, (5-Amino)-4H-[1,2,4]triazol-3-yl, pyridinyl, hydroxyphenyl, fluorophenyl, purinyl, aminophenyl, acetyl-aminomethyl-phenyl, cyclopropyl-aminomethyl-phenyl, aminopropyl-amidopyridinyl, hydroxypropyl-amidophenyl, amino-purinyl, difluoroethylaminocyclohexyl, amino-hydroxy-cyclohexyl, azepanyl, aminomethylcyclohexylmethyl, N-methyl-piperidinyl, piperidinyl, aminomethylcyclohexyl, aminopropylphenyl, phenyl, N-aminomethylcarbonyl-piperidinyl, N-aminoethylcarbonyl-piperidinyl, N-aminomethylcarbonyl-piperidinylmethyl, aminomethylamidomethylcyclohexyl, aminomethyl-pyridinyl, aminomethyl-amidocyclohexyl.

10. The compound according to claim 2, which is of formula

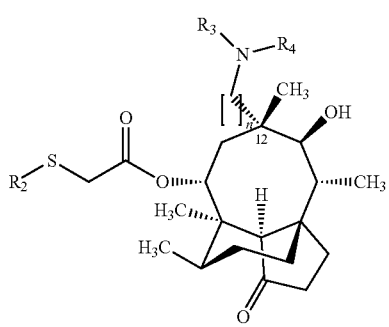

wherein
n is 1 to 12
$R_3$ is H, aminoethyl, aminopropyl, aminobutyl, aminopentyl, aminohexyl, aminooctyl, aminodecyl, dimethylaminopropyl, dimethylamidopentyl, guanidinobutyl, guanidinohexyl, carbamimidoyl, aminomethylcylcohexylmethyl, aminopropoxypropyl, aminocyclohexyl, hydroxyhexyl, dihydroxypropyl, aminomethylphenylmethyl, guanidinomethylphenylmethyl, phenylmethyl, morpholinopropyl, piperidinyl, hexyl, pyridinylethyl, allyl, amido-benzyl, aminopropyl-amidobenzyl, (2-amino)-amidoethyl-benzyl, (2-amino)-dimethylamidoethyl-benzyl, 2-amino-1-aminomethyl-ethyl, 5-amino-5-ethoxycarbonyl-pentyl, aminomethylphenylpropyl, aminomethylphenyl, aminophenymethyl, aminoethoxyphenylmethyl, aminomethyl-fluorophenyl-methyl, aminomethyl-difluorophenyl-methyl, and
$R_4$ is H($C_{1-4}$)alkylcarbonyl or aminomethylphenylcarbonyl.

11. The compound according to claim 2, wherein
$R_1$ is aminomethylphenylpropyl, aminoethylaminomethylphenylethenyl, aminoethylaminomethylphenyl ethyl, aminomethylphenylethyl, aminomethylphenylethyl, pyridinylethenyl, aminoethylamino-fluorophenyl-ethenyl.

12. The compound according to claim 1, selected from the group consisting of
12-epi-12-desvinyl-14-O-{{4-[(3-Amino-propylcarbamoyl)-methyl]-phenylsulfanyl}-acetyl}-12-[(3-aminopropylamino)-methyl] mutilin,
12-epi-12-desvinyl-14-O-{{4-[(2-Amino-ethylcarbamoyl)-methyl]-phenylsulfanyl}-acetyl}-12-[(3-aminopropylamino)-methyl] mutilin,
12-epi-12-desvinyl-14-O-{{4-([Bis-(3-amino-propyl)-carbamoyl]-methyl})-phenylsulfanyl)-acetyl}-12-[(3-amino-propylamino)-methyl] mutilin,
12-epi-12-desvinyl-14-O-{{4-[(2,3-Diamino-propylcarbamoyl)-methyl]-phenylsulfanyl}-acetyl}-12-[(3-amino-propylamino)-methyl] mutilin,
12-epi-12-desvinyl-14-O-{4-[(2-Amino-ethylcarbamoyl)-methyl]-phenylsulfanyl}-acetyl}-12-[(2-aminoethylamino)-methyl] mutilin,
12-epi-12-desvinyl-14-O-{4-[(3-Amino-propylcarbamoyl)-methyl]-phenylsulfanyl}-acetyl}-12-[(2-aminoethylamino)-methyl] mutilin,
12-epi-12-desvinyl-14-O-{{4-[(3-Amino-propylcarbamoyl)-methyl]-phenylsulfanyl}-acetyl}-12-[(4-aminobutylamino)-methyl] mutilin,
12-epi-12-desvinyl-14-O-{{4-[(3-Amino-propylcarbamoyl)-methyl]-phenylsulfanyl}-acetyl}-12-[(5-aminopentylamino)-methyl] mutilin,
12-epi-12-desvinyl-14-O-{{4-[(3-Amino-propylcarbamoyl)-methyl]-phenylsulfanyl}-acetyl}-12-[(4-aminomethyl-benzylamino)-methyl] mutilin,
12-epi-12-desvinyl-14-O-{{4-[(3-Amino-propylcarbamoyl)-methyl]-phenylsulfanyl}-acetyl}-12-[(6-aminohexylamino)-methyl] mutilin,
12-epi-12-desvinyl-14-O-{{4-[(3-Amino-propylcarbamoyl)-methyl]-phenylsulfanyl}-acetyl}-12-[(6-guanidino-hexylamino)-methyl] mutilin,
12-epi-12-desvinyl-14-O-{{4-[(3-Amino-propylcarbamoyl)-methyl]-phenylsulfanyl}-acetyl}-12-[(4-guanidino-butylamino)-methyl] mutilin,
12-epi-12-desvinyl-14-O-{{4-[(3-Amino-propylcarbamoyl)-methyl]-phenylsulfanyl}-acetyl}-12-[(allylamino)-methyl] mutilin,
12-epi-12-desvinyl-14-O-{{4-[(3-Amino-propylcarbamoyl)-methyl]-phenylsulfanyl}-acetyl}-12-aminomethyl mutilin,
12-epi-12-desvinyl-14-O-{{4-[(3-Amino-propylcarbamoyl)-methyl]-phenylsulfanyl}-acetyl}-12-[(benzylamino)-methyl] mutilin,
12-epi-12-desvinyl-14-O-{{4-[(3-Amino-propylcarbamoyl)-methyl]-phenylsulfanyl}-acetyl}-12-[(4-guanidinomethyl-benzylamino)-methyl] mutilin,
12-epi-12-desvinyl-14-O-{{4-[(3-Amino-propylcarbamoyl)-methyl]-phenylsulfanyl}-acetyl}-12-[(6-hydroxyhexylamino)-methyl] mutilin,
12-epi-12-desvinyl-14-O-{{4-[(3-Amino-propylcarbamoyl)-methyl]-phenylsulfanyl}-acetyl}-12-[(2,3-dihydroxypropylamino)-methyl] mutilin,
12-epi-12-desvinyl-14-O-{{4-[(3-Amino-propylcarbamoyl)-methyl]-phenylsulfanyl}-acetyl}-12-[(4-piperidylamino)-methyl] mutilin,
12-epi-12-desvinyl-14-O-{{4-[(3-Amino-propylcarbamoyl)-methyl]-phenylsulfanyl}-acetyl}-12-[(3-morpholin-4-yl-propylamino)-methyl] mutilin,
12-epi-12-desvinyl-14-O-{{4-[(3-Amino-propylcarbamoyl)-methyl]-phenylsulfanyl}-acetyl}-12-[(3-dimethylamino-propylamino)-methyl] mutilin,
12-epi-12-desvinyl-14-O-{{4-[(3-Amino-propylcarbamoyl)-methyl]-phenylsulfanyl}-acetyl}-12-[(S)-5-amino-5-ethoxycarbonyl-pentylamino-methyl] mutilin,
12-epi-12-desvinyl-14-O-{4-(4-Aminomethyl-benzylcarbamoyl)-phenylsulfanyl]-acetyl}-12-[(6-aminohexylamino)-methyl] mutilin,
12-epi-12-desvinyl-14-O-{4-(4-Aminomethyl-benzylcarbamoyl)-phenylsulfanyl]-acetyl}-12-[(6-guanidinohexylamino)-methyl] mutilin,
12-epi-12-desvinyl-14-O-{[(4-Piperazinylcarbamoyl)-phenylsulfanyl]-acetyl})-12-[(6-guanidino-hexylamino)-methyl] mutilin,
12-epi-12-desvinyl-14-O-{[4-(4-Aminomethyl-piperidine-1-carbonyl)-phenylsulfanyl]-acetyl}-12-[(6-guanidino-hexylamino)-methyl] mutilin,
12-epi-12-desvinyl-14-O-{(4-[(Piperidin-4-ylmethyl)-carbamoyl]-phenylsulfanyl)-acetyl}-12-[(6-guanidinohexylamino)-methyl] mutilin,
12-epi-12-desvinyl-14-O-{(4-[(Pyridin-4-ylmethyl)-carbamoyl]-phenylsulfanyl)-acetyl}-12-[(6-amino-hexylamino)-methyl] mutilin, 12-epi-12-desvinyl-14-O-{[3-(3-Aminopropylcarbamoyl)-phenylsulfanyl]-acetyl})-12-[(6-guanidino-hexylamino)-methyl] mutilin,
12-epi-12-desvinyl-14-O-{[4-(3-Acetylamino-propylcarbamoyl)-phenylsulfanyl]-acetyl}-12-[(3-amino-propylamino)-methyl] mutilin,
12-epi-12-desvinyl-14-O-{[4-(3-Formylamino-propylcarbamoyl)-phenylsulfanyl]-acetyl}-12-[(3-amino-propylamino)-methyl] mutilin,
12-epi-12-desvinyl-14-O-{[4-(3-Amino-propylcarbamoyl)-phenylsulfanyl]-acetyl}-12-[(3-amino-propylamino)-methyl] mutilin,
12-epi-12-desvinyl-14-O-{(4-[(3-Aminopropylcarbamoyl)-phenylsulfanyl)-acetyl}-12-[(4-aminomethyl-benzylamino)-methyl] mutilin,
12-epi-12-desvinyl-14-O-{(4-[(3-Aminopropylcarbamoyl)-phenylsulfanyl)-acetyl}-12-[(6-amino-hexylamino)-methyl] mutilin,
12-epi-12-desvinyl-14-O-{[4-(3-Aminopropylcarbamoyl)-phenylsulfanyl]-acetyl}-12-[(6-guanidino-hexylamino)-methyl] mutilin,
12-epi-12-desvinyl-14-O-{[4-(3-Aminopropylcarbamoyl)-phenylsulfanyl]-acetyl}-12-[(8-amino-octylamino)-methyl] mutilin,
12-epi-12-desvinyl-14-O-{[4-(3-Aminopropylcarbamoyl)-phenylsulfanyl]-acetyl}-12-[(10-amino-decylamino)-methyl] mutilin,
12-epi-12-desvinyl-14-O-{(4-Carbamoyl-phenylsulfanyl)-acetyl}-12-[(6-guanidino-hexylamino)-methyl] mutilin,
12-epi-12-desvinyl-14-O-{[4-(3-Amino-propylcarbamoyl)-phenylsulfanyl]-acetyl}-12-{[3-(3-amino-propoxy)-propylamino)]-methyl} mutilin,
12-epi-12-desvinyl-14-O-{[4-(3-Amino-propylcarbamoyl)-phenylsulfanyl]-acetyl}-12 [(2-pyridin-4-yl-ethyl amino)-methyl] mutilin,
12-epi-12-desvinyl-14-O-{[4-(6-Amino-hexylcarbamoyl)-phenylsulfanyl]-acetyl}-12-[(6-guanidino-hexylamino)-methyl] mutilin,
12-epi-12-desvinyl-14-O-{[4-(2-Amino-ethylcarbamoyl)-phenylsulfanyl]-acetyl}-12-[(6-guanidino-hexylamino)-methyl] mutilin,
12-epi-12-desvinyl-14-O-{[4-(3-Aminopropylcarbamoyl)-phenylsulfanyl]-acetyl}-12-{[3-(4-aminomethyl-phenyl)-propylamino)]-methyl} mutilin,
12-epi-12-desvinyl-14-O-{[(4-Aminomethyl-cyclohexyl)-methylsulfanyl]-acetyl}-12-[(6-amino-hexylamino)-methyl] mutilin,
12-epi-14-O-[(1-Methyl-piperidin-4-ylsulfanyl)-acetyl}-12-[(6-guanidino-hexylamino)-methyl] mutilin,
12-epi-14-O-[(Piperidin-4-ylsulfanyl)-acetyl]-12-[(6-amino-hexylamino)-methyl]mutilin,
12-epi-12-desvinyl-14-O-{[(4-Aminomethyl-cyclohexyl)-sulfanyl]-acetyl}-12-[(6-amino-hexylamino)-methyl] mutilin,
12-epi-12-desvinyl-14-O-{[4-(3-Amino-propyl)-phenylsulfanyl]-acetyl}-12-[(6-amino-hexylamino)-methyl] mutilin,
12-epi-12-desvinyl-14-O-{(4-[(3-Amino-propylcarbamoyl)-methyl]-phenylsulfanyl)-acetyl}-12-{[(3-amino-propyl)-acetylamino]-methyl} mutilin,
12-epi-12-desvinyl-14-O-{(4-[(3-Amino-propylcarbamoyl)-methyl]-phenylsulfanyl)-acetyl}-12-(3-amino-propylcarbamoyl) mutilin,
12-epi-12-desvinyl-14-O-{[4-(3-Amino-propylcarbamoyl)-phenylsulfanyl]-acetyl}-12-(4-aminomethyl-benzylcarbamoyl) mutilin, 12-epi-12-desvinyl-14-O-{{4-[(3-Amino-propylcarbamoyl)-methyl]-phenylsulfanyl}-acetyl}-12-[2-(3-amino-propylamino)-ethyl] mutilin,
12-epi-12-desvinyl-14-O-[(3-Hydroxymethyl-phenylsulfanyl)-acetyl]-12-[(3-amino-propylamino)-methyl] mutilin,
12-epi-12-desvinyl-14-O-[(3-Hydroxymethyl-phenylsulfanyl)-acetyl]-12-[(6-amino-hexylamino)-methyl] mutilin,
12-epi-12-desvinyl-14-O-[(3-Hydroxymethyl-phenylsulfanyl)-acetyl]-12-[(4-aminomethyl-benzylamino)-methyl] mutilin,
12-epi-12-desvinyl-14-O-[(3-Hydroxymethyl-phenylsulfanyl)-acetyl]-12-[(6-guanidino-hexylamino)-methyl] mutilin,
12-epi-12-desvinyl-14-O-[(4-Hydroxymethyl-phenylsulfanyl)-acetyl]-12-[(3-amino-propylamino)-methyl] mutilin,
12-epi-12-desvinyl-14-O-[(4-Hydroxymethyl-phenylsulfanyl)-acetyl]-12-[(4-aminomethyl-benzylamino)-methyl] mutilin,
12-epi-12-desvinyl-14-O-[(4-Hydroxymethyl-phenylsulfanyl)-acetyl]-12-[(6-amino-hexylamino)-methyl] mutilin,
12-epi-12-desvinyl-14-O-[(3,5-Bis-hydroxymethyl-phenylsulfanyl)-acetyl]-12-[(3-amino-propylamino)-methyl] mutilin,
12-epi-12-desvinyl-14-O-{[(2,3,5,6-Tetrafluoro-4-hydroxymethyl)-phenylsulfanyl]-acetyl}-12-[(4-aminomethyl-benzylamino)-methyl]-mutilin,
12-epi-12-desvinyl-14-O-{[(1R,2R,4R)-4-Amino-2-hydroxy-cyclohexylsulfanyl]-acetyl}-12-[(3-amino-propylamino)-methyl] mutilin,
12-epi-12-desvinyl-14-O-{[(1R,2R,4R)-4-Amino-2-hydroxy-cyclohexylsulfanyl]-acetyl}-12-[(4-aminomethyl-benzylamino)-methyl] mutilin,
12-epi-12-desvinyl-14-O-[(2-Hydroxy-ethylsulfanyl)-acetyl]-12-[(4-aminomethyl-benzylamino)-methyl] mutilin,
12-epi-12-desvinyl-14-O-[(2-Amino-ethylsulfanyl)-acetyl]-12-[(4-aminomethyl-benzylamino)-methyl] mutilin,
12-epi-12-desvinyl-14-O-{[(5-Amino-4H-1,2,4-triazol-3-yl)-sulfanyl]-acetyl}-12-[(6-amino-hexylamino)-methyl] mutilin,
12-epi-12-desvinyl-14-O-[(2-Amino-ethylsulfanyl)-acetyl]-12-[(6-amino-hexylamino)-methyl] mutilin,
12-epi-12-desvinyl-14-O-[(Pyridin-4-ylsulfanyl)-acetyl]-12-[(6-amino-hexylamino)-methyl] mutilin,
12-epi-12-desvinyl-14-O-[(Pyridin-4-ylsulfanyl)-acetyl]-12-[(6-guanidino-hexylamino)-methyl] mutilin,
12-epi-12-desvinyl-14-O-[(3-Hydroxy-phenylsulfanyl)-acetyl]-12-[(6-amino-hexylamino)-methyl] mutilin,
12-epi-12-desvinyl-14-O-[(4-Fluoro-phenylsulfanyl)-acetyl]-12-[(6-amino-hexylamino)-methyl] mutilin,
12-epi-12-desvinyl-14-O-{[(7H-Purin-6-yl)-sulfanyl]-acetyl}-12-[(6-amino-hexylamino)-methyl] mutilin,
12-epi-12-desvinyl-14-O-[(3-Amino-phenylsulfanyl)-acetyl]-12-[(3-amino-propylamino)-methyl] mutilin,
12-epi-12-desvinyl-14-O-(Phenylsulfanyl-acetyl)-12-[(4-aminomethyl-benzylamino)-methyl] mutilin,
12-epi-12-desvinyl-14-O-[(4-Fluoro-phenylsulfanyl)-acetyl]-12-[(4-aminomethyl-benzylamino)-methyl] mutilin,
12-epi-12-desvinyl-14-O-[(Pyridin-2-ylsulfanyl)-acetyl]-12-[(4-aminomethyl-benzylamino)-methyl] mutilin, 12-epi-12-desvinyl-14-O-[(Pyridin-4-ylsulfanyl)-acetyl]-12-[(4-aminomethyl-benzylamino)-methyl] mutilin,
12-epi-12-desvinyl-14-O-{[1-(2-Amino-acetyl)-piperidin-4-yl-sulfanyl)]-acetyl})-12-[(4-aminomethyl-benzylamino)-methyl] mutilin,
12-epi-12-desvinyl-14-O-{[1-(3-Amino-propionyl)-piperidin-4-yl-sulfanyl)]-acetyl}-12-[(4-aminomethyl-benzylamino)-methyl] mutilin,
12-epi-12-desvinyl-14-O-{[1-(3-Amino-propionyl)-piperidin-4-yl-sulfanyl]-acetyl}-12-[(6-amino-hexylamino)-methyl] mutilin,
12-epi-12-desvinyl-14-O-{[1-(2-Amino-acetyl)-piperidin-4-yl-methylsulfanyl]-acetyl}-12-[(4-aminomethyl-phenylamino)-methyl] mutilin,
12-epi-12-desvinyl-14-O-{[1-(2-Amino-acetyl)-piperidin-4-yl-methylsulfanyl]-acetyl}-12-[(4-amino-benzylamino)-methyl] mutilin,
12-epi-12-desvinyl-14-O-{[1-(2-Amino-acetyl)-piperidin-4-yl-sulfanyl]-acetyl}-12{2-[4-(2-amino-ethoxy)-benzylamino]-methyl} mutilin,
12-epi-12-desvinyl-14-O-{{4-[(2-Amino-acetylamino)-methyl]-cyclohexylsulfanyl}-acetyl}-12-[{4-[(2-amino-ethoxy)-benzylamino]-methyl} mutilin,
12-epi-12-desvinyl-14-O-[(4-Aminomethyl-phenylsulfanyl)-acetyl]-12-[(3-amino-propylamino)-methyl] mutilin,
12-epi-12-desvinyl-14-O-[(3-Aminomethyl-phenylsulfanyl)-acetyl]-12-[(3-amino-propylamino)-methyl] mutilin,
12-epi-12-desvinyl-14-O-[(3-Aminomethyl-phenylsulfanyl)-acetyl]-12-[(6-guanidino-hexylamino)-methyl] mutilin,
12-epi-12-desvinyl-14-O-[(4-Aminomethyl-phenylsulfanyl)-acetyl]-12-[(4-aminomethyl-benzylamino)-methyl] mutilin,
12-epi-12-desvinyl-14-O-[(4-Aminomethyl-phenylsulfanyl)-acetyl]-12-[(6-amino-hexylamino)-methyl] mutilin,
12-epi-12-desvinyl-14-O-[(3-Aminomethyl-phenylsulfanyl)-acetyl]-12-[((4-aminomethyl-cyclohexyl)-methyl-amino)-methyl] mutilin,
12-epi-12-desvinyl-14-O-[(4-Aminomethyl-phenylsulfanyl)-acetyl]-12-{[(4-aminocyclohexyl)-amino]-methyl} mutilin,
12-epi-12-desvinyl-14-O-[(4-Aminomethyl-phenylsulfanyl)-acetyl]-12-[(hexylamino)-methyl] mutilin,
12-epi-12-desvinyl-14-O-[(4-Aminomethyl-phenylsulfanyl)-acetyl]-12-[(4-carbamoylphenyl)-methylamino)-methyl] mutilin,
12-epi-12-desvinyl-14-O-[(4-Aminomethyl-phenylsulfanyl)-acetyl]-12-{[4-(3-amino-propylcarbamoyl)-benzylamino]-methyl} mutilin,
12-epi-12-desvinyl-14-O-[(4-Aminomethyl-phenylsulfanyl)-acetyl]-12-[(5-dimethylcarbamoyl-pentyl amino)-methyl] mutilin,
12-epi-12-desvinyl-14-O-[(4-Aminomethyl-phenylsulfanyl)-acetyl]-12-{[4-(2-amino-2-carbamoyl-ethyl)-benzylamino]-methyl} mutilin,
12-epi-12-desvinyl-14-O-[(4-Aminomethyl-phenylsulfanyl)-acetyl]-12-{[4-(2-amino-2-dimethylcarbamoyl-ethyl)-benzylamino]-methyl} mutilin,
12-epi-12-desvinyl-14-O-{[5-Aminomethyl-pyridin-2-yl-sulfanyl)]-acetyl}-12-[(4-aminomethyl-benzylamino)-methyl] mutilin,
12-epi-12-Desvinyl-14-O-{[5-aminomethyl-pyridin-2-yl-sulfanyl)]-acetyl}-12-[(4-aminomethyl-3-fluoro-benzyl amino)-methyl] mutilin,
12-epi-12-desvinyl-14-O-{[(4-Aminomethyl-cyclohexyl)-methylsulfanyl]-acetyl}{[(4-Aminomethyl-cyclohexyl)-methyl sulfanyl]-acetyl}-12-[(4-aminomethyl-benzylamino)-methyl] mutilin,
12-epi-12-desvinyl-14-O-{1-(2-Amino-acetyl)-piperidin-4-yl-sulfanyl]-acetyl}-12-[(4-aminomethyl-3-fluoro-benzylamino)-methyl] mutilin,
12-epi-12-Desvinyl-14-O-{{4-[(2-Amino-acetylamino)-methyl]-cyclohexylsulfanyl)}-acetyl}-12-[(4-aminomethyl-3-fluoro-benzylamino)-methyl] mutilin,
12-epi-12-desvinyl-14-O-{[5-Aminomethyl-pyridin-2-yl-sulfanyl]-acetyl}-12-[(4-aminomethyl-2,5-difluoro-benzylamino)-methyl] mutilin,
12-epi-12-desvinyl-14-O-[(4-Aminomethyl-phenylsulfanyl)-acetyl]-12-[(2-amino-1-aminomethyl-ethyl-amino)-methyl] mutilin,
12-epi-12-Desvinyl-14-O-[(5-aminomethyl-pyridin-2-yl-sulfanyl)-acetyl]-12-[(6-amino-hexylamino)-methyl] mutilin,
12-epi-12-desvinyl-14-O-{(4-[(2-Amino-acetylamino)-methyl]-phenylsulfanyl)-acetyl}-12-[(3-amino-propylamino)-methyl] mutilin,
12-epi-12-desvinyl-14-O-{(4-[(2-Amino-3-(4-hydroxy-phenyl)-propionylamino)-methyl]-phenylsulfanyl)-acetyl}-12-[(3-amino-propylamino)-methyl] mutilin,
12-epi-12-desvinyl-14-O-{(4-[(3-Amino-propionylamino)-methyl]-phenylsulfanyl)-acetyl}-12-[(3-amino-propylamino)-methyl] mutilin,
12-epi-12-desvinyl-14-O-{(4-[(2-Amino-acetylamino)-methyl]-phenylsulfanyl)-acetyl}-12-[4-aminomethyl-benzylamino-methyl] mutilin,
12-epi-12-desvinyl-14-O-{(4-[(2-Amino-acetylamino)-methyl]-phenylsulfanyl)-acetyl}-12-(6-amino-hexylamino-methyl) mutilin,
12-epi-12-desvinyl-14-O-{[(3-Acetylamino-methyl)-phenylsulfanyl]-acetyl}-12-[(3-amino-propyl amino)-methyl] mutilin,
12-epi-12-desvinyl-14-O-{(4-{[2-Amino-3-(4-aminomethyl-phenyl)-propionylamino]-methyl}-phenylsulfanyl)-acetyl}-12-[(3-amino-propylamino)-methyl]mutilin,
12-epi-12-desvinyl-14-O-{{4-[(3-Amino-propylamino)-methyl]-phenylsulfanyl}-acetyl}-12-[(3-amino-propylamino)-methyl] mutilin,
12-epi-12-desvinyl-14-O-{{3-[(3-Amino-propylamino)-methyl]-phenylsulfanyl}-acetyl}-12-[(3-amino-propylamino)-methyl] mutilin,
12-epi-12-desvinyl-14-O-{{4-[(4-Aminomethyl-benzylamino)-methyl]-phenylsulfanyl}-acetyl}-12-[(3-amino-propylamino)-methyl] mutilin,
12-epi-12-desvinyl-14-O-[(3-Allylaminomethyl-phenylsulfanyl)-acetyl]-12-[(3-amino-propylamino)-methyl] mutilin,
12-epi-12-desvinyl-14-O-{{4-[(3-Amino-propylamino)-methyl]-phenylsulfanyl}-acetyl}-12-{[3-(3-amino-propoxy)-propylamino]-methyl} mutilin,
12-epi-12-desvinyl-14-O-[(4-Cyclopropylaminomethyl-phenylsulfanyl)-acetyl]-12-[(3-amino-propylamino)-methyl] mutilin,
12-epi-12-desvinyl-14-O-[(4-Cyclopropylaminomethyl-phenylsulfanyl)-acetyl]-12-[(6-amino-hexylamino)-methyl] mutilin,
12-epi-12-desvinyl-14-O-{{4-[(4-Aminomethyl-benzylamino)-methyl]-phenylsulfanyl}-acetyl}-12-[(6-amino-hexylamino)-methyl] mutilin, 12-epi-12-desvinyl-14-O-{{4-[(4-Aminomethyl-benzylamino)-methyl]-phenylsulfanyl}-acetyl}-12-[(4-aminomethyl-benzylamino)-methyl]-mutilin, 12-epi-12-desvinyl-14-O-[5-(3-Amino-propylcarbamoyl)-pyridin-2-ylsulfanyl]-acetyl-12-[(6-amino-hexylamino)-methyl] mutilin, 12-epi-12-desvinyl-14-O-[(2,5-Bis-aminomethyl-phenylsulfanyl)-acetyl]-12-[(3-amino-propylamino)-methyl] mutilin, 12-epi-12-desvinyl-14-O-[(3,5-Bis-aminomethyl-phenylsulfanyl)-acetyl]-12-[(3-amino-propylamino)-methyl] mutilin, 12-epi-12-desvinyl-14-O-{[(3-Amino-propylcarbamoyl)-phenylsulfanyl]-acetyl}-12-[(2-guanidino-ethyl] mutilin, 12-epi-12-desvinyl-14-O-{[4-(3-Hydroxy-propylcarbamoyl)-phenylsulfanyl]-acetyl}-12-[(6-amino-hexylamino)-methyl] mutilin, 12-epi-12-desvinyl-14-O-[(2-Hydroxy-ethylsulfanyl)-acetyl]-12-[(6-amino-hexylamino)-methyl] mutilin, 12-epi-12-desvinyl-14-O-{[3-(2,2-Difluoro-ethylamino)-cyclohexylsulfanyl]-acetyl}-12-[(6-amino-hexylamino)-methyl] mutilin, 12-epi-12-desvinyl-14-O-[(2-Amino-7H-purin-6-ylsulfanyl)-acetyl]-12-[(6-amino-hexylamino)-methyl] mutilin, 12-epi-12-desvinyl-14-O-[(Azepan-4-ylsulfanyl)-acetyl]-12-[(6-amino-hexylamino)-methyl] mutilin, 12-epi-12-desvinyl-14-O-[(Azepan-4-ylsulfanyl)-acetyl]-12-[(6-guanidino-hexylamino)-methyl] mutilin, 12-epi-12-desvinyl-14-O-[(Azepan-4-ylsulfanyl)-acetyl]-12-[(4-aminomethyl-benzylamino)-methyl] mutilin, 12-epi-12-desvinyl-14-O-[(Azepan-4-ylsulfanyl)-acetyl]-12-[(6-amino-octylamino)-methyl] mutilin, 12-epi-12-desvinyl-14-O-{[1-(2-Amino-acetyl)-piperidin-4-yl-sulfanyl)]-acetyl}-12-[(6-amino-hexylamino)-ethyl] mutilin, 12-epi-12-desvinyl-14-O-{[1-(2-Amino-acetyl)-piperidin-4-yl-sulfanyl)]-acetyl}-12-[(4-aminomethyl-benzylamino)-ethyl] mutilin, 12-epi-12-desvinyl-14-O-[5-Hydroxymethyl-pyridin-2-yl-sulfanylacetyl]-12-[(4-aminomethyl-3-fluoro-benzyl amino)-ethyl] mutilin, 12-epi-12-desvinyl-14-O-{4-[(2-Amino-acetylamino)-cyclohexylsulfanyl]-acetyl}-12-[(4-aminomethyl-3-fluoro-benzylamino)-ethyl] mutilin, 12-epi-12-desvinyl-14-O-{[1-(2-Amino-acetyl)-piperidin-4-yl-sulfanyl]-acetyl}-12-[(4-aminomethyl-3-fluoro-benzylamino)-ethyl] mutilin, 12-epi-12-desvinyl-14-O-[(5-Aminomethyl-pyridin-2-yl-sulfanyl)-acetyl]-12-[(4-aminomethyl-2,5-difluoro-benzylamino)-ethyl] mutilin, 12-epi-12-desvinyl-14-O-{[1-(2-Amino-acetyl)-piperidin-4-yl-sulfanyl]-acetyl}-12-[(4-aminomethyl-2,5-difluoro-benzylamino)-ethyl] mutilin, 12-epi-12-desvinyl-14-O-{[1-(2-Amino-acetyl)-piperidin-4-yl-sulfanyl]-acetyl}-12{2-[4-(2-amino-ethoxy)-benzylamino]-ethyl} mutilin, 12-epi-12-desvinyl-14-O-{{4-[(2-Amino-acetylamino)-methyl]-cyclohexylsulfanyl}-acetyl}-12-[(4-aminomethyl-3-fluoro-benzylamino)-ethyl] mutilin, 12-epi-12-desvinyl-14-O-[(Azepan-4-ylsulfanyl)-acetyl]-12-[(4-aminomethyl-phenylamino)-ethyl] mutilin, 12-epi-12-desvinyl-14-O-{{4-[(2-Amino-acetylamino)]-cyclohexylsulfanyl})-acetyl})-12-[(4-aminomethyl-phenylamino)-ethyl] mutilin, 12-epi-12-desvinyl-14-O-{[1-(2-Amino-acetyl)-piperidin-4-yl-methylsulfanyl]-acetyl})-12-[(4-aminomethyl-phenylamino)-ethyl] mutilin, 12-epi-12-desvinyl-14-O-{[1-(2-Amino-acetyl)-piperidin-4-yl-sulfanyl]-acetyl})-12-(8-amino-octyl) mutilin, 12-epi-12-desvinyl-14-O-{[1-(2-Amino-acetyl)-piperidin-4-yl-sulfanyl]-acetyl})-12-[3-(4-aminomethyl-phenyl)-propyl] mutilin, 12-epi-12-desvinyl-14-O-[(Azepan-4-yl-sulfanyl)-acetyl]-12-[3-(4-aminomethyl-phenyl)-propyl] mutilin, 12-epi-12-desvinyl-14-O-[(Azepan-4-yl-sulfanyl)-acetyl]-12-(6-amino-hexyl) mutilin, 12-epi-12-desvinyl-14-O-[(Azepan-4-yl-sulfanyl)-acetyl]-12-(8-amino-octyl) mutilin, 12-epi-12-desvinyl-14-O-{{4-[(2-Amino-acetylamino)-methyl]-cyclohexylsulfanyl}-acetyl})-12-[2-{4-[(2-amino-ethylamino)-methyl]-phenyl}-ethenyl) mutilin, 12-epi-12-desvinyl-14-O-{{4-[(2-Amino-acetylamino)-methyl]-cyclohexylsulfanyl}-acetyl})-12-[2-{4-[(2-amino-ethylamino)-methyl]-phenyl}-ethyl) mutilin, 12-epi-12-desvinyl-14-O-[(Azepan-4-ylsulfanyl)-acetyl]-12-[2-(4-Aminomethyl-phenyl)-ethyl]-mutilin, 12-epi-12-desvinyl-14-O-[(Azepan-4-ylsulfanyl)-acetyl]-12-((E)-2-pyridin-3-yl-ethenyl) mutilin, 12-epi-12-desvinyl-14-O-[(Azepan-4-ylsulfanyl)-acetyl]-12-((E)-2-{4-[(2-Amino-ethylamino)-methyl]-phenyl}-ethenyl) mutilin, 12-epi-12-desvinyl-14-O-[(Azepan-4-ylsulfanyl)-acetyl]-12-[2-{4-[(2-amino-ethylamino)-methyl]-phenyl}-ethyl) mutilin, 12-epi-12-desvinyl-14-O-[(Azepan-4-ylsulfanyl)-acetyl]-12-((E)-2-{4-[(2-amino-ethylamino)-methyl]-3-fluoro-phenyl}-ethenyl) mutilin, 12-epi-14-O-{[1-(2-Amino-acetyl)-piperidin-4-yl-sulfanyl]-acetyl}-12-((E)-2-{4-[(2-amino-ethylamino)-methyl]-phenyl}-ethenyl) mutilin, 12-epi-14-O-{[1-(2-Amino-acetyl)-piperidin-4-yl-sulfanyl]-acetyl}-12-[2-{4-[(2-amino-ethylamino)-methyl]-phenyl}-ethyl) mutilin, 12-epi-12-desvinyl-14-O-[(5-Aminomethyl-pyridin-2-yl-sulfanyl)-acetyl]-12-[2-(4-aminomethyl-benzoylamino)-ethyl] mutilin.

13. The compound according to claim 12, in the form of a salt and/or solvate.

14. The compound according to claim 1, optionally in the form of a pharmaceutically acceptable salt, for use as a pharmaceutical drug substance, in particular for use in the treatment of diseases mediated by Gram negative bacteria, in particular *Escherichia coli*.

15. A pharmaceutical composition comprising a compound according to claim 1 optionally in the form of a pharmaceutically acceptable salt, in association with at least one pharmaceutical excipient, optionally further comprising another pharmaceutically active agent.

16. The compound according to claim 12, optionally in the form of a pharmaceutically acceptable salt, for use as a pharmaceutical drug substance, in particular for use in the treatment of diseases mediated by Gram negative bacteria, in particular *Escherichia coli*.

17. A pharmaceutical composition comprising a compound according to claim 12, optionally in the form of a pharmaceutically acceptable salt, in association with at least one pharmaceutical excipient, optionally further comprising another pharmaceutically active agent.

* * * * *